United States Patent
Dawson et al.

(10) Patent No.: US 9,623,039 B2
(45) Date of Patent: Apr. 18, 2017

(54) TREATMENT AND PREVENTION OF PATHOLOGICAL CONDITIONS USING IDUNA RELATED TECHNIQUES AND COMPOSITIONS

(75) Inventors: Ted M. Dawson, Baltimore, MD (US); Valina L. Dawson, Baltimore, MD (US); Shaida A. Andrabi, Baltimore, MD (US); Ho Chul Kang, Parkville, MD (US)

(73) Assignee: VALTED, LLC, Baltimore, MD (US)

( * ) Notice: Subject to any disclaimer, the term of this patent is extended or adjusted under 35 U.S.C. 154(b) by 75 days.

(21) Appl. No.: 13/294,884

(22) Filed: Nov. 11, 2011

(65) Prior Publication Data

US 2012/0121559 A1 May 17, 2012

Related U.S. Application Data

(60) Provisional application No. 61/412,423, filed on Nov. 11, 2010.

(51) Int. Cl.
| | |
|---|---|
| *A61K 48/00* | (2006.01) |
| *A61K 31/7088* | (2006.01) |
| *A61K 31/7105* | (2006.01) |
| *C12N 9/00* | (2006.01) |
| *C12N 15/113* | (2010.01) |

(52) U.S. Cl.
CPC ...... *A61K 31/7088* (2013.01); *A61K 31/7105* (2013.01); *C12N 9/93* (2013.01); *A61K 48/005* (2013.01); *C12N 15/1137* (2013.01); *C12N 2310/14* (2013.01); *C12Y 603/02019* (2013.01)

(58) Field of Classification Search
CPC ............ A61K 31/7088; A61K 31/8105; A61K 48/005; C12N 9/93
See application file for complete search history.

(56) References Cited

U.S. PATENT DOCUMENTS

2010/0068813 A1   3/2010   Li et al.

FOREIGN PATENT DOCUMENTS

WO   2010030355 A2   3/2010

OTHER PUBLICATIONS

David et al (2009, Frontiers in Bioscience, 2009, 14:1116-1128).*
Saleh, 2009,Brain Research, 1247:212-220.*
Lorenzo, et al., "Therapeutic Potential of AIF-Mediated Caspase-Independent Programmed Cell Death," Drug Resist Update, Dec. 2007, vol. 10, No. 6, pp. 235-255, p. 244, left col, para 1, 3; p. 244, right col, para 1; p. 245, left col, para 2, 4; p. 246, left col, para 2, 4.
Dawson, S14-03 Ischemic Preconditioning, "Symposium S14: Stroke: Inflammation in the Neurovascular Unit," Jounal of Neurochemistry, Aug. 2004, vol. 90, Supplement 1, p. 80.
Andrabi, et al., Iduna Protects the Brain from Glutamate Excitotoxicity and Stroke by Interfering with Poly(ADP-ribose) Polymer-Induced Cell Death, Nat. Med., May 22, 2011, vol. 17, No. 6, pp. 692-699.
Kang, et al., "Iduna is a Poly(ADP-Ribose) (PAR)-dependent E3 Ubiquitin Ligase that Regulates DNA Damage." Proc. National Acad., Sci. USA, Aug. 23, 2011, vol. 108, No. 34, pp. 14103-14108.
International Search Report mailed Mar. 29, 2012, corresponding to International Application No. PCT/US11/60441.
Dawson, "Molecular Mechanisms in Neuronal and Axonal Apoptosis and Necrosis." Advanced Studies in Medicine, Apr. 2005, vol. 5, No. 4D, pp. S387-S391.

* cited by examiner

*Primary Examiner* — Valarie Bertoglio
(74) *Attorney, Agent, or Firm* — Hogan Lovells US LLP

(57) ABSTRACT

Research into neuroprotective mechanisms has at its heart the goal of developing new therapeutic strategies to treat patients. For example, the compositions and induction strategies disclosed herein have use for acute injuries such as stroke or trauma, and would be extremely useful in treating patients undergoing cardiac bypass surgery, neurosurgery or other surgical cohorts where ischemia is a risk. Further, patients with subarachnoid hemorrhage, transient ischemic attacks, soldiers at risk for blast injury or patients suffering from chronic neurodegenerative diseases would also benefit from enhanced neuronal survival based upon the techniques and compositions disclosed herein. In addition, protecting against cell death by, for example, interfering with PAR polymer signaling via the compositions and processes disclosed herein, offers new therapeutic strategies for the treatment of neurologic disorders.

1 Claim, 107 Drawing Sheets

Figure 1

TREATMENT AND PREVENTION OF PATHOLOGICAL CONDITIONS USING IDUNA RELATED TECHNIQUES AND COMPOSITIONS

CROSS-REFERENCE TO RELATED APPLICATIONS

This application claims priority to provisional application No. 61/412,423, filed on Nov. 11, 2010, which is incorporated herein in its entirety by reference thereto.

STATEMENT REGARDING FEDERALLY SPONSORED RESEARCH OR DEVELOPMENT

This invention was made with government support under grant award numbers NIH/NINDS NS039148, NS067525, NIDA DA000266, and NS051764. The government has certain rights in the invention.

FIELD OF THE INVENTION

The present invention relates to the treatment and prevention of neurological disorders, cancer, diabetes, cardiac conditions and the like.

BACKGROUND OF THE INVENTION

Glutamate is the major excitatory neurotransmitter regulating normal physiologic activity in the brain. Excessive glutamate release leads to excitotoxicity, which plays a prominent role in many disorders of the nervous system, including trauma and ischemic brain injury. Further, dysfunctional glutamate neurotransmission contributes to seizures and neurodegenerative disorders. Glutamate excitotoxicity is mediated largely through influx of calcium through the N-methyl-D-aspartate (NMDA) receptor leading to activation of PAR polymerases (PARP) and generation of Poly(ADP-ribose) (PAR) polymer, a newly described death signal that kills cells through apoptosis inducing factor (AIF). Genetic deletion of PARP-1 or drug inhibition results in profound neuroprotection. This form of cell death has recently been designated parthanatos to distinguish it from apoptosis, autophagy and necrosis. Parthanatos is prominently implicated in models of diabetes, inflammation, MPTP toxicity, myocardial infarction and cerebral ischemia.

Under physiologic conditions, normal bursts of excitatory activity result in synaptic transmission and the expression of molecular substrates of long-term plasticity, growth and survival. The activation of NMDA receptors in glutamatergic neurons plays a prominent role in inducing these long-lasting synaptic changes through multiple downstream signaling molecules and changes in gene expression. NMDA receptor stimulation may also be important for long-term changes that lead to neuronal survival.

Protein ubiquitination is a major regulatory process that controls a variety of cellular functions. Covalent modifications of proteins by ubiquitin can either mediate protein interactions or target the proteins for degradation depending on the nature of the ubiquitin modification. Conjugation of ubiquitin to a substrate uses a complex of proteins composed of an E1 ubiquitin activating enzyme, an E2 ubiquitin conjugating enzyme and an E3 ubiquitin ligase. E3 ligases are involved in substrate recognition and transfer of the ubiquitin molecule to the lysine residue on the substrate. Ubiquitin conjugation is activated and regulated by a few cellular signals. Phosphorylation is a well-studied intracellular signaling motif that marks proteins for the ubiquitination machinery. SUMOylation of proteins also appears to be a signal for ubiquitin modification and proteasomal modification. Other mechanisms of substrate recognition are not as well characterized.

PAR modification (PARsylation) of proteins is as an important cellular signaling mechanism. Proteins are PARsylated by PARPs. PARsylation regulates the function of a variety of nuclear proteins. Proteins can be covalently modified by PARP with PAR of different size and complexity, but proteins can also bind PAR non-covalently at specific PAR binding sites to regulate cellular signaling. For instance, PAR can act as a cytosolic signaling molecule during parthanatos.

RNF146 is a RING (really interesting new gene) finger protein that contains a WWE domain. This protein has been identified as a NMDA glutamate-receptor inducible gene in a genetic screen as clone PLING932.

SUMMARY OF THE INVENTION

We disclose herein the identification and characterization of Iduna [MGI: 1915281 (RNF 146)], a novel NMDA-induced cell survival molecule that protects against NMDA excitotoxicity and stroke through binding poly (ADP-ribose) (PAR) polymer and blocking parthanatos. The nucleotide and amino acid sequences encoding for Iduna are also disclosed. Iduna is a PAR-dependent E3 ligase that binds and ubiquitinates both PARsylated and PAR binding proteins via its PBM, marking these proteins for ubiquitin proteasomal degradation. Moreover, Iduna plays a prominent role in DNA repair through its PAR-dependent E3 ligase activity. Iduna is the first endogenous inhibitor of parthanatos. Protecting against cell death by, for example, interfering with PAR polymer signaling via the compositions and processes disclosed herein, offers new therapeutic strategies for the treatment of neurologic disorders. One aspect of the invention comprises methods for overexpressing human Iduna in a cell.

In certain embodiments, the present invention comprises methods for treating diseases or conditions that result from parathanatos cell death. In particular, conditions such as neurodegenerative disorders, or conditions caused by surgical trauma, ischemic attacks, or subarachnoid hemorrhage are disclosed. The present invention also may comprise methods whereby the activity levels of Iduna are increased in cells, such as through gene therapy, or whereby excess Iduna is externally administered to cells, such as through injection or some other sort of ingestion mechanism.

In further embodiments of the invention, cell death is prevented, minimized or treated by administration of one or more of; a novel NMDA-induced cell survival molecule that protects against NMDA excitotoxicity and stroke through binding poly (ADP-ribose); and/or a therapy that induces activity of Iduna.

In certain embodiments, enhancing the actions of Iduna via overexpression, inducers, potentiators or allosteric modulators could be used to treat diseases such as the following: Diabetes; Diabetes Mellitus; Diabetic Retinopathy; Diabetic Endovascular Disease; Diabetic Nephropathy; Diabetic Neuropathy; Cardiac; Acute Myocardial Infarction; Heart Disease; Cardiac Allograft Rejection; Cardiac Bypass Surgery; Postoperative Complications, Cardiac Myocarditis; Heart Failure; Circulatory Shock; Stroke; Ischemia Reperfusion Injury to, for exmaple, the brain, spinal cord, Retina, Muscle, Kidney, and/or Heart; Postoperative Complications involving, for example, the central nervous system; Traumatic Brain Injury; Spinal Cord Injury; Parkinson's disease; Alzheimer's disease; Multiple Sclerosis; Retinopathy; Macular Degeneration; neurodegenerative and related neurologic diseases such as Alexander's disease, Alper's disease, Alzheimer's disease, amyotrophic lateral sclerosis, ataxia telangiectasia, Batten disease, bovine spongiform encephalopathy, Canavan disease, Cockayne syndrome, corticobasal degeneration, Creutzfeldt-Jakob disease, Huntington's disease, HIVassociated dementia, Kennedy's disease, Krabbe's disease, lewy body dementia, Machado-Joseph disease, multiple sclerosis, multiple system atrophy, narcolepsy, neuroborreliosis, Parkinson's disease, Pelizaeus-Merzbacher Disease, Pick's disease, primary lateral sclerosis, prion diseases, Refsum's disease, Sandhoff's disease, Schilder's disease, subacute combined degeneration of spinal cord secondary to pernicious anaemia, schizophrenia, spinocerebellar ataxia, spinal muscular atrophy, Steele-Richardson-Olszewski disease, and tabes dorsalis; Atherosclerosis; Arthritis; Colitis; and/or Vascular hyporeactivity in Sepsis.

Further disclosed herein are compositions and methods for treating cancers using small molecule inhibitors. For example, small molecule inhibitors of Iduna may be used to treat a variety of cancers including Solid Tumors; Hepatocellular Carcinoma; Prostate Cancer; Colorectal Cancer; Colorectal Cancer; Ovarian Cancer; Breast Cancer; BRCA-1 or -2 Associated Breast Cancer; Triple Negative Breast Cancer; Skin Cancer; Metastatic Melanoma; Advanced Solid Tumors; Non-hematologic Malignancies; Brain Neoplasms; Pancreatic; Advanced Tumors; Pancreatic Neoplasms; Colorectal Cancer; Gastric Cancer; Melanoma Neoplasms; Breast Neoplasms; Ovarian Neoplasm; Neoplasm Metastasis; Glioblastoma Multiforme; Lymphoma; and/or Squamous Cell Lung Cancer. In addition, the techniques and compositions disclosed herein may be used to identify effective inhibitors of Iduna, such as shRNA, antisense, and microRNA based inhibitors.

Research into neuroprotective mechanisms has at its heart the goal of developing new therapeutic strategies to treat patients. For example, the compositions and induction strategies disclosed herein have use for acute injuries such as stroke or trauma, and would be extremely useful in treating patients undergoing cardiac bypass surgery, neurosurgery or other surgical cohorts where ischemia is a risk. Further, patients with subarachnoid hemorrhage, transient ischemic attacks, soldiers at risk for blast injury or patients suffering from chronic neurodegenerative diseases would also benefit from enhanced neuronal survival based upon the techniques and compositions disclosed herein.

BRIEF DESCRIPTION OF THE DRAWINGS

FIGS. 1, 2 and 5-9—Illustrate, among other features, that Iduna is an NMDA induced neuroprotective protein.

FIG. 1—Amino acid sequences of Iduna proteins are conserved among different species [*Mus musculus* (SEQ. ID. NO.: 24), *Rattus norvegicus* (SEQ. ID. NO.: 25), *Homo sapiens* (SEQ. ID. NO.: 26), *Danio rerio* (SEQ. ID. NO.: 27) and *Caenorhabditis elegans* (SEQ. ID. NO.: 28)].

FIG. 2—Northern analysis of Iduna (arrow) in mouse tissue. β-actin and GAPDH are loading controls.

FIG. 3—Characterization of Iduna polyclonal antibody. Primary cortical cultures were treated with a neuroprotective dose of NMDA (50 μM for 5 min) and harvested 24 h after treatment. To test the specificity of the antibody, endogenous Iduna was pre-adsorbed from the lysate by immunoprecipitation with anti-Iduna antibody. Samples were analyzed by 8-16% SDS-PAGE. Following immunoblotting, the membranes were probed with anti-Iduna and anti-β-actin antibodies. Mouse brain lysate was used as a control. Time course of this experiment is indicated at top of the figure.

FIG. 4—The Iduna antibody recognizes both human Iduna (hIduna) and mouse Iduna (mIduna) equally. Mouse cortical neurons were transduced with a lentivirus expressing hIduna, and a plasmid expressing mIduna was transfected to human MCF7 cells. Following SDS-PAGE of the lysates and immunoblotting, nitrocellulose membranes were probed with anti-Iduna antibody. Cell lysates from both mock infected cortical neurons and mock transfected MCF7 cells were used as control to detect endogenous Iduna.

FIG. 5—Immunoblot analysis of Iduna protein expression in different regions of brain. β-actin is a loading control. Data were repeated with similar results.

FIG. 6—Induction of Iduna mRNA by 50 μM NMDA detected by RT-PCR in primary neuronal cultures over time. Data are the mean±SEM from two experiments.

FIG. 7-Immunoblot of Iduna induced by 50 μM NMDA (upper panel). These data were normalized to β-actin and quantified by optical density (bottom panel). Data are the mean±SEM from three experiments.

FIG. 8—Immunoblots of Iduna expression following an excitotoxic 500 μM dose of NMDA in primary cortical neurons. The data were normalized to β-actin and quantified by optical density (side panel). Data are the mean±SEM from two experiments.

FIG. 9—Immunoblot of Iduna expression over time following induction by 20 min of oxygen glucose deprivation (OGD) in primary cortical cultures. Experiments were repeated three times.

FIG. 12—Primary cortical neurons expressing GFP or Iduna-GFP were exposed to excitotoxic NMDA (500 μM, 5 min). Sister cultures expressing shRNA to Iduna (shRNA-Iduna) or dsRed (shRNA dsRed) were exposed to 50 μM NMDA and then 500 μM NMDA. Abbreviation: NT, not transduced. Data represent mean±SEM, n=5 from two experiments; *p<0.05.

FIG. 13—Immunoblot of Iduna expression in cortical cultures expressing shRNA Iduna or shRNA dsRed exposed to 50 μM NMDA.

FIG. 14—Quantification of the data in FIG. 3 normalized to β-actin. Data are the mean±SEM from three experiments, *p<0.05 vs control, **p<0.05 vs. NT.

FIG. 15—Primary cortical cultures expressing shRNA Iduna or shRNA dsRed were challenged with 500 μM NMDA. Data are the mean±SEM of at least two experiments.

FIG. 16—Immunoblot of Iduna expression in primary cortical cultures exposed to 50 μM NMDA in the presence of shRNA to mouse Iduna and expression of human Iduna (hIduna).

FIG. 17—Quantification of FIG. 16 normalized to β-actin. Data represent mean±SEM, n=4; *p<0.05.

FIG. 18—Primary cortical cultures expressing lentivirus shIduna±human Iduna (hIduna), which is resistant to mouse Iduna shRNA were exposed to NMDA as indicated. Data represent mean±SEM, n=4 from 4 experiments; *p<0.05. Experimental schedule is indicated above panels and treatment conditions are indicated by horizontal bars. Significance determined by ANOVA with Tukey-Kramer's posthoc test.

FIG. 19—Dot blot of immunoprecipitated GFP-Iduna and GFP with biotin-labeled PAR polymer and detected with anti-biotin antibody. Data were reproduced with similar results.

FIG. 20—Far western analysis of Iduna PAR binding activity. Arrows indicate GFP-Iduna fusion protein and bracket indicates PAR binding proteins. Asterisk indicates a IgG heavy chain signal recognized by polyclonal antibodies including the GFP or PAR antibodies. Data were reproduced with similar results.

FIG. 21—Immunoprecipitated GFP-Iduna, GFP or recombinant Histone 3 (H3) were incubated with synthesized [$^{32}$P]-PAR polymer and the amount of bound PAR polymer was measured by scintillation counting. Data are the mean±S.E.M. from two experiments. *p<0.05 by ANOVA with Tukey-Kramer's posthoc test.

FIG. 22—[$^{32}$P]-PAR polymer bound to GFP-Iduna or GFP analyzed in Tris-borate-EDTA PAGE. Values represent ADP-ribose units in the PAR polymer. Asterisk indicates non-specific PAR polymer binding.

FIG. 23—Immunoblot of endogenous Iduna and PAR from cortical neurons treated with 50 μM NMDA. These experiments were repeated at least two times with similar results.

FIG. 24—Alignment of the PAR binding motif in Iduna and Histone 3. The Iduna Y156A/R157A PAR binding mutant (red) is indicated. Schematic of Iduna functional domains and deletion mutants. Ring finger (RF) domain (AA 35-77) [pink bar], WWE domain (AA 91-167) [blue bar] and the PAR binding domain (144-167) [green triangle] are highlighted. Full-length Iduna, and RF (IdunaΔRF) and WWE (IdunaΔWWE) domain deletion mutants of Iduna are shown. [Histone 3 (SEQ ID NO: 29), Iduna 144-16 (SEQ ID NO: 30), Iduna Y156A/R157A (SEQ ID NO: 31), Consensus (SEQ ID NO: 32)].

FIG. 25—Far western analysis of PAR binding activity of Iduna and Iduna deletion mutants. Arrows indicate GFP-Iduna fusion proteins and bracket indicates PAR binding proteins. IgG heavy chain (IgG Hc) is indicated by arrow. n=2

FIG. 26—Far western analysis of PAR binding activity of Iduna and Iduna-YRRA mutant. Arrows indicate GFP-Iduna fusion proteins and bracket indicates PAR binding proteins.

FIG. 27—Histone 3, Iduna 144-167 wild type peptide and Iduna 144-167 YRAA (YRAA) mutant peptide (top panel), and PAR binding activity of recombinant GST, GST-Iduna-YRAA, GST-Iduna and Histone 3 (bottom panel) were analyzed for PAR binding activity by a biotin-labeled-PAR probe and subjected to immunoblot analysis with antibodies to PAR using a dot blot. Ponceau S stain of blotted proteins and peptides served to confirm that an equal amount was blotted onto nitrocellulose.

FIG. 28-PAR binding activity of GST-Iduna-YRAA, GST-Iduna, GST and Histone 3 were analyzed by electrophoretic gel mobility shift assay (EMSA) of [$^{32}$P]PAR polymer.

FIG. 29—Analysis of PAR binding properties of wild type Iduna (•) and Iduna-YRAA mutant (○).

FIG. 30—Chemiluminescent activity of PARP-1 in the presence of Iduna or the PARP-1 inhibitor 3-aminobenzamide (3-AB). Data represent two separate experiments. *p<0.05

FIG. 31—Quantification of [$^{32}$P]-PAR polymers synthesized by PARP-1 in the presence of GST, GST-Iduna or PARG (which catalytically degrades PAR), respectively. Data represent mean±SEM, n=3 *p<0.05 by ANOVA with Tukey-Kramer's posthoc test.

FIG. 32—Quantification of 500 μM NMDA induced cell death in primary cortical neurons transiently transfected to express GFP, GFP-Iduna, GFP-Iduna-YRAA, GFP-IdunaΔRF or GFP-IdunaΔWWE. Cells with fragmented processes were considered dead. Data represent mean±SEM, n=6 from two independent experiments, *p<0.05 by ANOVA with Tukey-Kramer's posthoc test.

FIG. 33—Representative photomicrographs of lentiviral expression of GFP, GFP-Iduna or GFP-Iduna-YRAA in primary cortical neurons. n=4, scale bar=50 μm.

FIG. 34—Lentiviral transduction in mouse cortical neurons. Primary cortical neuronal cultures were transduced with GFP, GFP-Iduna or GFP-Iduna-YRAA lentiviruses on DIV 10. On DIV 14, the cultures were fixed in 4% PFA and stained with NeuN and GFP. Following secondary antibody staining (red-NeuN, green-GFP), images were taken on a Zeiss 710 confocal microscope. Scale bar=50 μm.

FIG. 35—Numbers of NeuN-positive and GFP-positive neurons were quantified to evaluate the transduction efficiency of the lentiviral particles. Percent GFP-positive neurons were evaluated by subtracting the number of GFP-positive neurons to the total number of neurons (NeuN-positive cells). All GFP, GFP-Iduna, GFP-Iduna-YRAA viruses have greater than 95% neuronal transduction efficiency. There is no significant difference in expression between GFP, GFP-Iduna, GFP-Iduna-YRAA transduced neurons. Data represent mean±S.E.M., n=3.

FIG. 36—Immunoblots of lentiviral expression of GFP, GFP-Iduna or GFP-Iduna-YRAA in primary cortical neurons. No signal is seen in control cultures (*) non-specific band. Data were repeated three times with similar results.

FIG. 37—Subcellular fractionation shows cytosolic and nuclear localization of GFP-Iduna or GFP-Iduna-YRAA. Western blots showing lentiviral-mediated expression of GFP-Iduna or GFP-Iduna-YRAA or GFP in cytosolic fractions of mouse cortical neurons 2 h following NMDA (500 μM for 5 min) excitotoxicity. NT is non-transduced cultures. GAPDH and PARP-1 serve as cytosolic and nuclear markers, respectively. CSS treated cultures were treated with CSS alone for 5 min. GFP-Iduna or GFP-YRAA are predominantly localized to the cytosol, whereas only a small amount is in the nuclear fraction. Time course of this experiment is indicated at top of the figure.

FIG. 38—Cortical Neurons were treated with NMDA (50 μM for 5 min). 24 hours later, the cells were treated with toxic dose of NMDA (500 μM for 5 min) to assess the localization of endogenous Iduna. Following NMDA toxicity, endogenous Iduna is mainly localized to cytosol (post-nuclear fractions) with a small fraction in the nucleus. These experiments were repeated two times with similar results. The time course of this experiment is indicated at the top of the figure.

FIG. 39—Quantification of 500 µM NMDA induced cell death in primary cortical neurons with lentiviral expression of GFP, GFP-Iduna or GFP-Iduna-YRAA. Control cultures were treated with control salt solution (CSS) alone. NT, non-transduced. n=12-20 from two experiments. *p<0.05

FIG. 40—Quantification of cell death in cortical neurons treated in an identical manner to panel 4d but cell death was assessed via AlamarBlue® reduction assay. Data represents mean±SEM, n=5, *p<0.05 by ANOVA with Tukey-Kramer's posthoc test.

FIG. 41—Quantification of cell death due to DNA damage by MNNG in primary neuronal cultures expressing GFP, GFP-Iduna or GFP-Iduna YRAA. Data represent mean±SEM, n=5 of two experiments. *p≤0.05 by ANOVA with Tukey-Kramer's posthoc test.

FIG. 42—Neuronal cultures expressing lenti-viral mediated GFP, GFP-Iduna or GFP-Iduna-YRAA were treated with camptothecin (CPT, 20 µM) and cell death assessed 24 h later using PI and Hoechst staining. No protection was observed GFP-Iduna expressing neurons. The pan-caspase inhibitor, Z-VAD provides protection confirming the cell death is caspase dependent. Data represent the mean±SEM, n=4 of two independent experiments. *p<0.05 by ANOVA with Tukey-Kramer's posthoc test.

FIG. 43—Neuronal cultures expressing lenti-viral mediated GFP, GFP-Iduna or GFP-Iduna-YRAA were treated with staurosporine (STS, 500 nM) and cell death assessed 24 h later using PI and Hoechst staining. No protection was observed in GFP-Iduna expressing neurons. The pan-caspase inhibitor, Z-VAD provides protection confirming the cell death is caspase dependent. Data represent the mean±SEM, n=4 of two independent experiments. *p<0.05 by ANOVA with Tukey-Kramer's posthoc test.

FIG. 44—GFP-Iduna expressing neurons are significantly protected against 100 µM H2O2 toxicity in a manner similar to the PARP inhibitor, DPQ.

FIG. 45—Neither GFP-Iduna nor DPQ protect against 500 µM H2O2. Data represent the mean±SEM, n=4 of two experiments. *p≤0.05 by ANOVA with Tukey-Kramer's posthoc test.

FIG. 46—$Ca^{2+}$ influx imaged in primary cortical neurons expressing GFP, GFP-Iduna or GFP-Iduna-YRAA assessed by the $Ca^{2+}$-sensitive fluorochrome fluo-5F (2.0 µM) over time. Intensity gain in these neurons was reduced to avoid saturation effects because of the spectral overlap between GFP and fluo-5F.

FIG. 47-Graphic representation of $Ca^{2+}$ influx before and after 500 µM NMDA. *p<0.05 by ANOVA with Tukey-Kramer's posthoc test.

FIG. 49—Assessment of mitochondrial $Ca^{2+}$ uptake in isolated mitochondria incubated with or without recombinant Iduna protein (top panels) or digitonin permeabilized MCF7 cells expressing GFP-Iduna or GFP-Iduna-YRAA (bottom panels), using Calcium green-5N as an indicator of free $Ca^{2+}$. Experiments were repeated twice with similar results FIG. 50—Representative confocal photomicrographs of NMDA-induced AIF translocation in cortical neurons expressing GFP, GFP-Iduna or GFP-Iduna-YRAA. AIF immunoreactivity (red), DAPI (blue) scale bar=20 µm FIG. 51—Immunoblot analysis of subcellular fractionations from cortical cultures treated as indicated in (d) for AIF. PARP-1, nuclear fraction, COX IV post-nuclear mitochondrial fraction. Data were repeated three times with similar results.

FIG. 52—Quantification of AIF immunoblot analysis in (e). Data are the mean±SEM from three experiments, *p<0.05 vs NT after NMDA treatment by ANOVA with Tukey-Kramer's posthoc test.

FIG. 53—Immunoblot showing release of CYT C. Mouse cortical neurons over-expressing GFP, GFP-Iduna or GFP-Iduna-YRAA were subjected to NMDA-excitotoxicity (500 µM for 5 min) on DIV 14. Following subcellular fractionation into mitochondrial and cytosolic (post-mitochondrial) fractions, CYT C release was monitored 4 hrs following NMDA stimulation. COX IV was used as a marker for mitochondria and GAPDH was used a marker for cytosol. Data were repeated three times with similar results.

FIG. 54—Quantification of cytochrome c release from mitochondria following NMDA-toxicity. Iduna significantly (*p<0.05) reduces CYT C release monitored 4 hrs following NMDA-stimulation. Values of optical density were quantified using Image J software and the data were normalized to the values of GAPDH in the cytosol.

FIG. 55—Analysis of $\Delta\psi_m$ using TMRM live imaging in primary cortical neurons expressing GFP, GFP-Iduna or GFP-Iduna-YRAA. Neurons were treated with either 500 µM NMDA or CSS, *p<0.05

FIG. 56—Graph shows loss of $\Delta\psi_m$ (TMRM fluorescence) before and after 20 min of NMDA application. *p<0.05. Significance determined by ANOVA with Tukey-Kramer's posthoc test.

FIG. 58—Targeting strategy for ROSA26-Iduna conditional transgenic (Tg) mouse.

FIG. 59—Immunoblot of Iduna expression in wild type (WT) and Iduna-Tg mice.

FIG. 60—Quantification of FIG. 59. Data represent mean±SEM, n=6; *p<0.05 by Student's t-test.

FIG. 61—Representative coronal sections stained with nissl to reveal lesions in control (left) and Iduna-Tg (right) mice 48 h after intrastriatal injections with NMDA (20 nmoles).

FIG. 62—Quantification of the lesion-volume. Data represent mean±SEM, n=4; *p<0.05 by Student's t-test.

FIG. 63—Stereological counts of GFP-positive neurons from mouse brain injected with GFP, GFP-Iduna or GFP-Iduna-YRAA lentivirus followed by NMDA (20 nmoles) or normal saline. Quantification of GFP-positive surviving neurons. Data represent mean±SEM, n=4 from two experiments; *p<0.05 by ANOVA with Tukey-Kramer's posthoc test.

FIG. 65—Laser-Doppler flux measured over the lateral parietal cortex in the core of the ischemic region in WT (n=10) and Iduna-Tg (n=11) mice. Values are mean±SEM, expressed as a percent of the pre-ischemic baseline values.

FIG. 66—Brain infarct volume after 60 min of middle cerebral artery occlusion in WT (n=10) and Iduna Tg (n=11) mice. Left panel, *two-way analysis of variance indicated a significant overall effect of genotype among the five coronal levels (level 1 is most anterior), and the Holm-Sidak multiple comparison procedure indicated significant differences at coronal levels 3 and 4 where infarct volume was greatest. Mean±S.E.M. Right panel, total infarct volume expressed as a percent of the entire ischemic hemisphere. * $p<0.05$ from WT Student's t-test. The time course of the various experiments are indicated at top of the panels.

FIG. 67—Neurological deficit was evaluated on a scale of 0-4 (0 no neurological deficit, 4 severe neurological deficit) by the following criteria: 0=mice appeared normal, explored the cage environment and moved around in the cage freely; 1=mice hesitantly moved in cage and didn't approach all sides of the cage, 2=mice showed postural and movement abnormalities and had difficulty to approach the walls of the cage, 3=mice with postural abnormalities tried to move in the cage but did not approach to the wall of the cage, 4=mice were unable to move in the cage and stayed at the center. Recordings were scored by an observer blind to the treatment and genotype. Data represent the mean±SEM, n=5. *p<0.05 by ANOVA with Tukey-Kramer's posthoc test.

FIG. 68—Forelimb use of the mouse was recorded for 10 minutes in a glass cylinder and analyzed according to the following criteria: Ipsilateral (right) forelimb use (number of touches to the cylinder wall) independent of the left limb, contralateral (left) forelimb use (number of touches to the cylinder wall) independent of the right limb and simultaneous use of both limbs. The percent use of the contralateral (left) limb was quantified by subtracting contralateral forepaw touches from the total number of touches made by the mouse during the period of observation. Recordings were scored by an observer blind to the treatment and genotype. Data represent mean±SEM, n=5. *p<0.05 by ANOVA with Tukey-Kramer's posthoc test.

FIG. 69—Screening of UbcHE2 enzymes of Iduna. Either immunoprecipitated GFP-Iduna (left panel) or endogenous Iduna (right panel) was subjected into an in vitro ubiquitination assay (IVUA) along with recombinant E1, ubiquitin and UbcHE2 enzymes as indicated. Samples were resolved in 8-16% SDS-PAGE and then immunoblotted by anti-Iduna or anti-ubiquitin antibody. Protein samples were visualized by coomassie staining, separately. (*) indicates unmodified GFP-Iduna or Iduna.

FIG. 70—GFP interacting proteins do not have ubiquitin E3 ligase activity. Immunoprecipitated GFP was used as a negative control for the in vitro ubiquitination assay. All experiments were repeated three times.

FIG. 71—Screening of UbcH E2 enzymes for Iduna via an in vitro ubiquitination assay (IVUA) with GST-Iduna (left panel) or GST free Iduna (right panel). Samples were resolved in 8-16% SDS-PAGE and either stained with coomassie or immunoblotted by anti-Iduna or anti-ubiquitin antibody. (*) indicates unmodified GST-Iduna or GST-free Iduna.

FIG. 72—Identification of potential Iduna substrates. TAP purification of SK-N-SH cells stably transfected with pNTAP or pNATP-Iduna were resolved in 8-16% SDS-PAGE and silver stained. Mass spectrometric analysis identified sixteen proteins as indicated.

FIG. 73—Iduna interacts with its potential substrates in a PAR dependent manner. MCF7 cells were preincubated with DMSO or PARP1 inhibitors as indicated, and then harvested and lysed. Endogenous Iduna was immunoprecipitated by anti-Iduna antibody from each cell lysate, and subjected into immunoblot with appropriate antibodies. IgG was used as a negative control.

FIG. 74—Iduna strongly binds to PARsylated proteins. TAP or TAP-Iduna pull down samples were analyzed by immunoblot with anti-PAR antibody. Abbreviations: Ub (n), polyubiquitin chains; Ub-Iduna, poly ubiquitinated Iduna. All experiments were repeated two to three times.

FIG. 75—In vitro ubiquitination assay of immunoprecipitated GFP-Iduna and different UbcHE2 enzymes in presence or absence of DTT as indicated. Samples were analyzed by immunoblot with anti-PAR, anti-GFP and anti-ubiquitin antibodies. White or black arrows head indicate the immunoglobulin heavy or light chains, respectively.

FIG. 76—In vitro ubiquitination assay of recombinant PARP1 or PARsylated PARP1 (R-PARP1) by GST-Iduna subjected to immunoblot analysis with indicated antibodies.

FIG. 77—Iduna binds and/or ubiquitinates PARP1 in a PARsylation dependent manner. PARP1 or R-PARP1 were incubated with GST-Iduna, followed by GST pull down and subjected to the in vitro ubiquitination assay (left panel) and analyzed by immunoblot (right panel).

FIG. 78—Iduna is a PAR dependent ubiquitin E3 ligase. In vitro ubiquitination assay of immnuoprecipitated GFP, GFP-Iduna, GFP-Iduna YRAA and GFP-Iduna C60A analyzed by immunoblot with anti-GFP, anti-ubiquitin, anti-PAR, anti-PARP1 and anti-ubiquitin antibodies. Abbreviations: Rb-P, PARsylated proteins; Rb/Ub-P, PARsylated and polyubiquitinated proteins; Ub (n), polyubiquitin chains; Rb/Ub-PARP1, PARsylated and polyubiquitinated PARP1; Ub-Iduna, poly ubiquitinated Iduna; Rb-PARP1, PARsylated PARP1. All experiments were repeated three times.

FIG. 79—Immunoprecipitated GFP and GFP-Iduna were subjected to 2D analysis and then samples were visualized by silver staining and 2D western blot with anti-GFP. An in vitro ubiquitination assay was performed using an immunoprecipitated GFP-Iduna as indicated, and self-ubiquitination activity of Iduna was measured by 2D western blot with anti-GFP.

FIG. 80—Polyubiquitination of PARP1 was analyzed by 2D western blot with anti-PAPP-1 antibody. White and black arrows indicate the GFP-Iduna and polyubiquitinated PARP1, respectively. White (*), indicates polyubiquitinated GFP-Iduna. All experiments were repeated two times.

FIG. 81—The RING domain is critical for Iduna's activity. Immnuoprecipitated GFP-Iduna, GFP-Iduna C60A and GFP-Iduna H54A were subjected to in vitro ubiquitination assay. Its activity was analyzed by immunoblot with anti-GFP and anti-ubiquitin antibodies. White or black arrows head indicate the immunoglobulin heavy or light chains, respectively. (*) indicates unmodified GFP-Iduna.

FIG. 82—Recombinant GST-Iduna, GST-Iduna C60A and GST-Iduna H54A were purified from IPTG-induced $E$ $coli$ and visualized by coomassie staining (upper panel). In vitro ubiquitination assay was performed as indicated in lower panel. Self-ubiquitination activity was confirmed by anti-ubiquitin and -Iduna antibodies. (*) indicates unmodified GFP-Iduna.

FIG. 83—PAR binding activity of Iduna mutants. Immunoprecipitated GFP-Iduna, GFP-Iduna YRAA and GFP-Iduna C60A were analyzed for PAR binding activity by immunoblot with anti-PAR and anti-GFP antibody. White or black arrows head indicate the immunoglobulin heavy or light chains, respectively. (*) indicates unmodified GFP-Iduna. All experiments were repeated three times.

FIG. 84—Pull-down assay of Iduna or Iduna mutants with [$^{32}$P] labeled PAR. H3 was used as a positive control and PARG enzyme was used for the degradation of PAR. n=3, * P<0.05 by ANOVA with Tukey-Kramer's post hoc test.

FIG. 85—PARG activity was measured by incubation with PARsylated PARP1 as indicated. The level of PARsylated PARP1 (Rb-PARP1) was monitored by immunoblot with anti-PAR antibody. There is a slight difference in the sensitivity of assays used to detect PAR, which accounts for the ability of 1 unit of PARG to eliminate PAR in B, but 1.2 units of PARG is required in A.

FIG. 86—EMSA of Iduna and Iduna mutants with [$^{32}$P] labeled PAR. Histone H3 was used as a positive control. n=3 independent experiments.

FIG. 87—[$^{32}$P]-PAR bound to Iduna or Iduna mutants was analyzed in 20% TBE-PAGE. Values represent ADP-ribose units. H3 was used as a positive control. All experiments were repeated three times.

FIG. 88—Self-ubiquitination activity of Iduna was monitored by incubation with PAR and/or PARG as indicated.

FIG. 89—PAR dependent ubiquitination of PARP1 was analyzed by an in vitro ubiquitination with Iduna or Iduna YRAA mutants as indicated. Total protein level was visualized by coomassie brilliant blue staining. Abbreviations: Ub (n), polyubiquitin chains; Ub-PARP1, polyubiquitinated PARP1; Ub-Iduna, poly ubiquitinated Iduna. All experiments were repeated five times.

FIG. 91—Stable MCF7 cell lines expressing GFP, GFP-Iduna, GFP-Iduna C60A or GFP-Iduna YRAA were exposed to DMSO or MNNG (500 μM) for 15 min with or without MG132. PARP1 was immunoprecipitated at 0 or 1 hr after the MNNG challenge. PARP1 and PARsylated-PARP1 were monitored by immunoblot with anti-PARP1 and anti-PAR antibodies.

FIG. 92—Quantification of PARP1 and PARsylated-PARP1 in the absence of MG132.

FIG. 93—Quantification of PARP1 and PARsylated-PARP1 in presence of MG132. Quantifications were normalized with respect to actin levels.

FIG. 94—Levels of immunoprecipitated PARP1 and PARsylated PARP1 after exposure to DMSO or MNNG (500 μM) for 15 min with or without MG132 GFP in MCF7 cell lines stably expressing GFP-Iduna, shRNA-Iduna or shRNA-Iduna/GFP-mouse Iduna (mIduna) at 0 or 1 hr after the MNNG challenge.

FIG. 95—Quantification of PARP1 and PARsylated PARP1 normalized to actin in absence of MG132.

FIG. 96—Quantification of the PARP1 and PARsylated-PARP1 normalized to actin in presence of MG132. Data represents mean±s.e.m., n=3, * P<0.05 by ANOVA with Tukey-Kramer's post hoc test. All experiments were repeated two to three times.

FIG. 98—Recruitment of stably expressed GFP-Iduna to sites of laser (405 nm) microirradiation induced DNA damage in MCF7 cells. GFP-Iduna YRAA does not translocate to the damage site. The PARP inhibitor AG14361 blocks GFP-Iduna recruitment.

Figure 99:
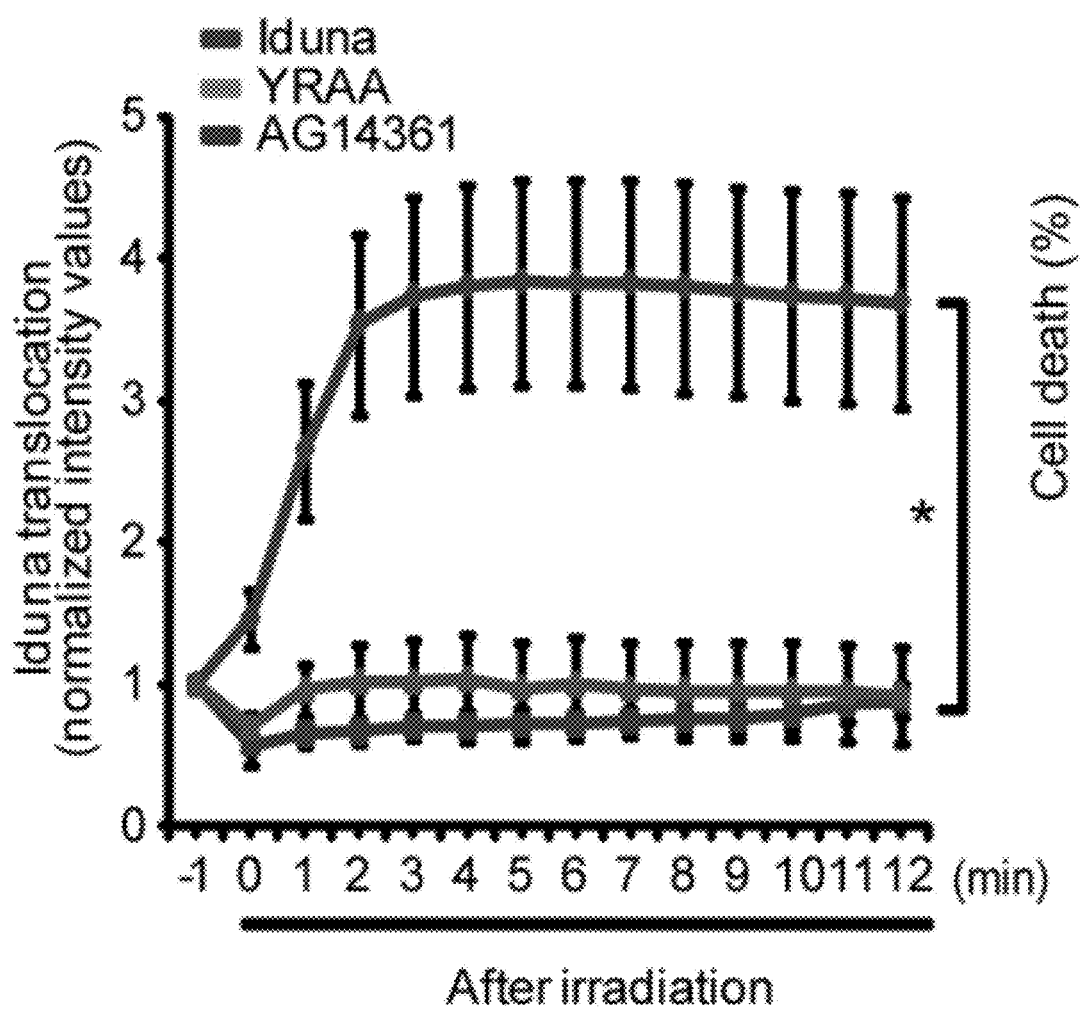

FIG. 99—GFP-Iduna localizes to sites of DNA damage as indicated by co-localization with γH2AX immunostaining.

Figure 100:
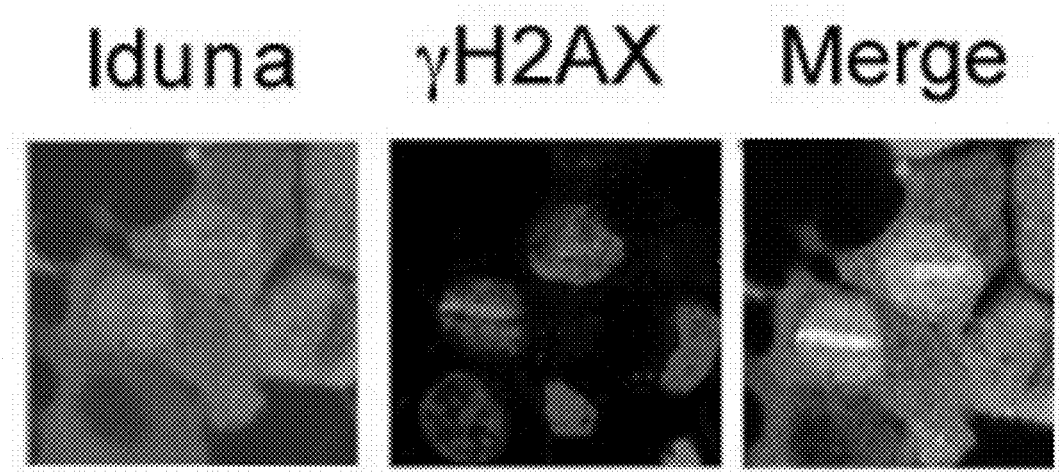

FIG. 100—Comparative quantitative analysis of GFP-Iduna, GFP-Iduna-YRAA and GFP-Iduna plus PARP inhibitor AG14361 kinetics after DNA damage.

Figure 101:
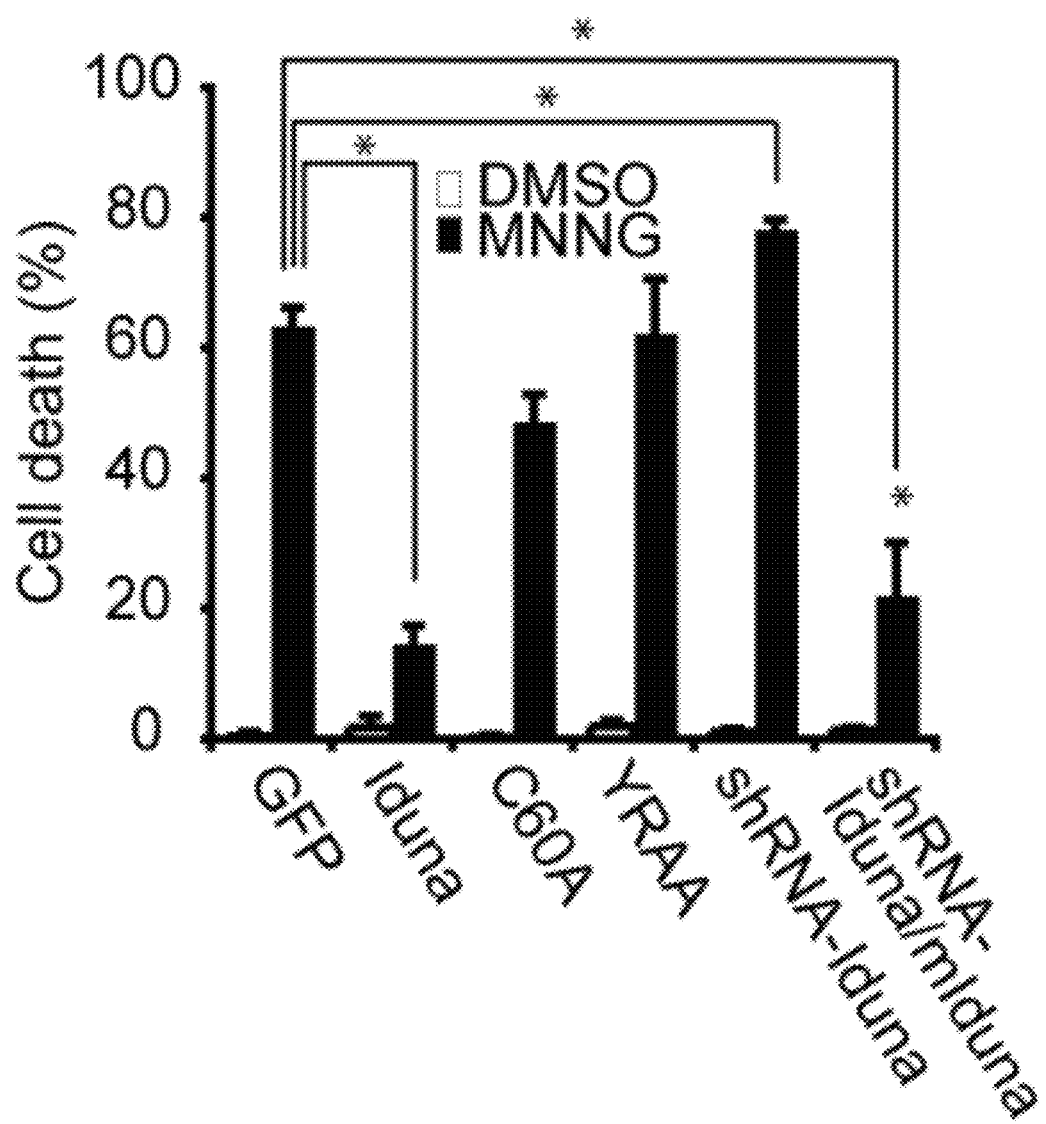

FIG. 101—Stable MCF7 cell lines expressing GFP, GFP-Iduna, GFP-Iduna C60A, GFP-Iduna YRAA, shRNA-Iduna or shRNA-Iduna/GFP-mouse Iduna (mIduna) were treated with DMSO or MNNG (500 µM) for 15 min. After 24 hr, the cells were stained with Hoechst 33342 and propidium iodide (PI), and dead cells were counted by automated computer-assisted program.

Figure 102:
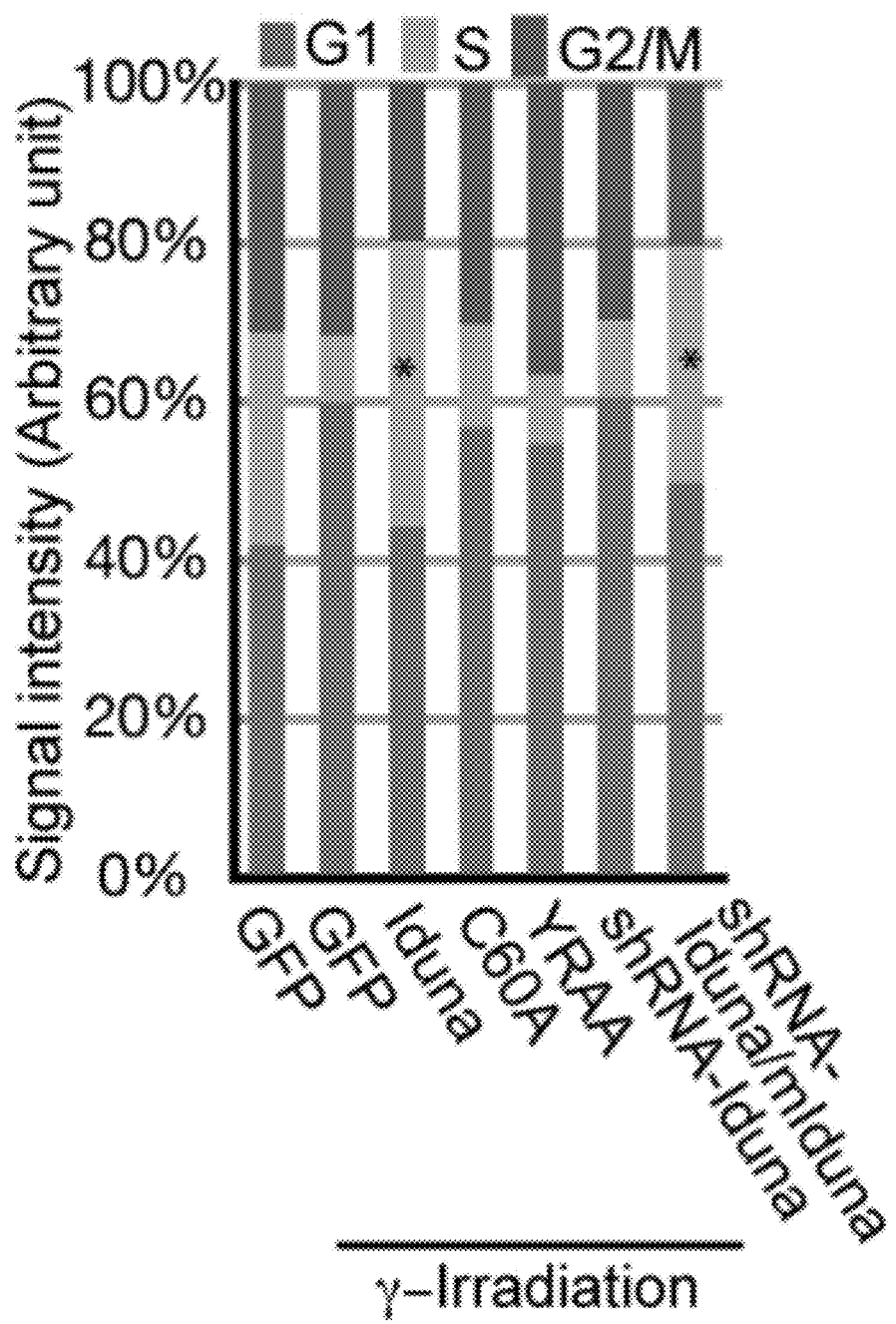

FIG. 102—Stable MCF7 cell lines were γ-irradiated at 2 Gy as indicated. Cells were collected 16 hr after irradiation and then DNA content was measured by flow cytometry. The percentage of each cell cycle phase was measured by FlowJo software using the Dean-Jett-Fox model.

Figure 103:
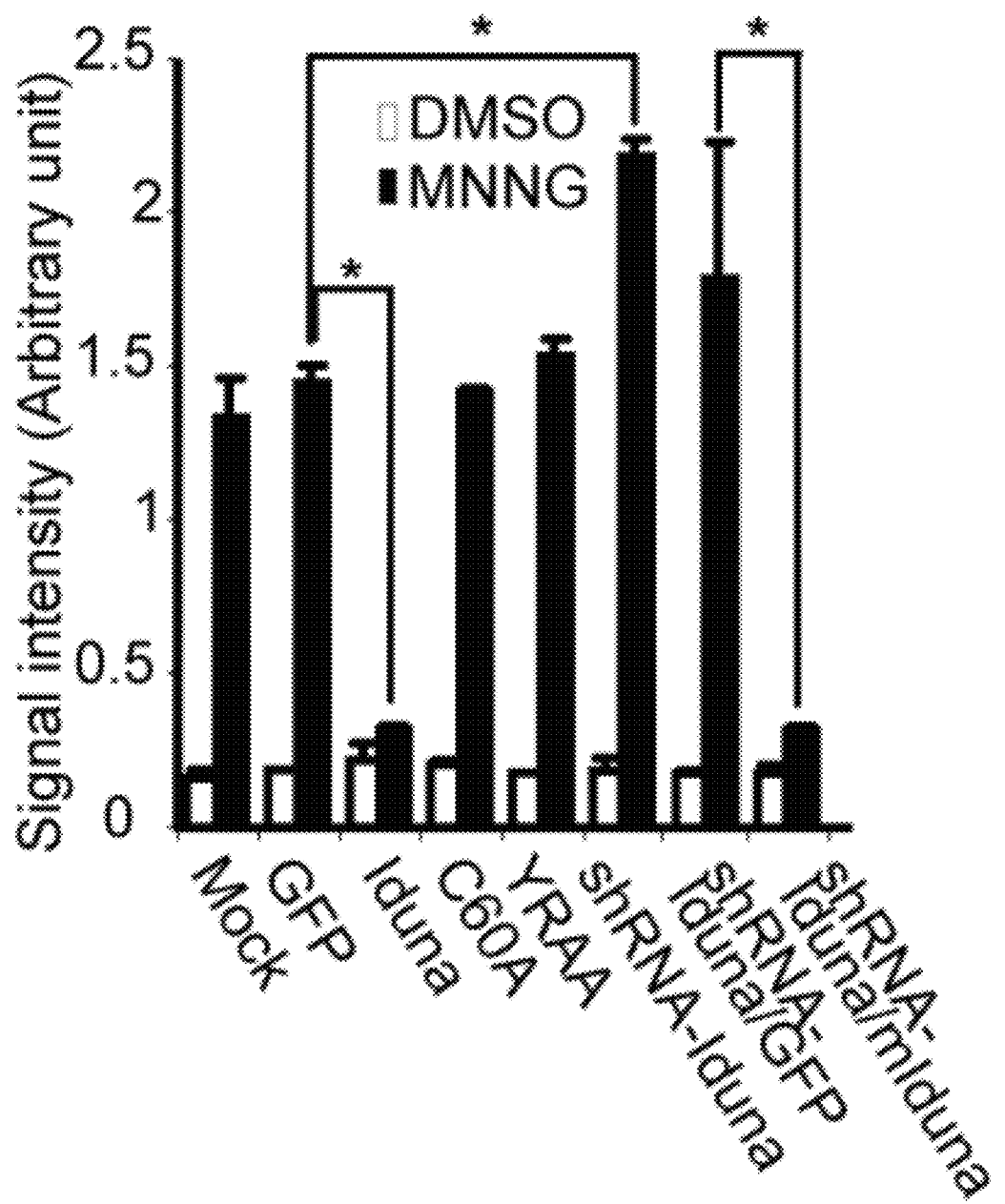

FIG. 103—Stable MCF7 lines as indicated were treated with either DMSO or MNNG. After 1 h, genomic DNA was isolated and then AP sites on genomic DNA were labeled with biotin by Aldehyde Reactive Probe (ARP) reagent. Biotin labeled AP sites were quantified using an avidin-biotin assay.

Figure 104:
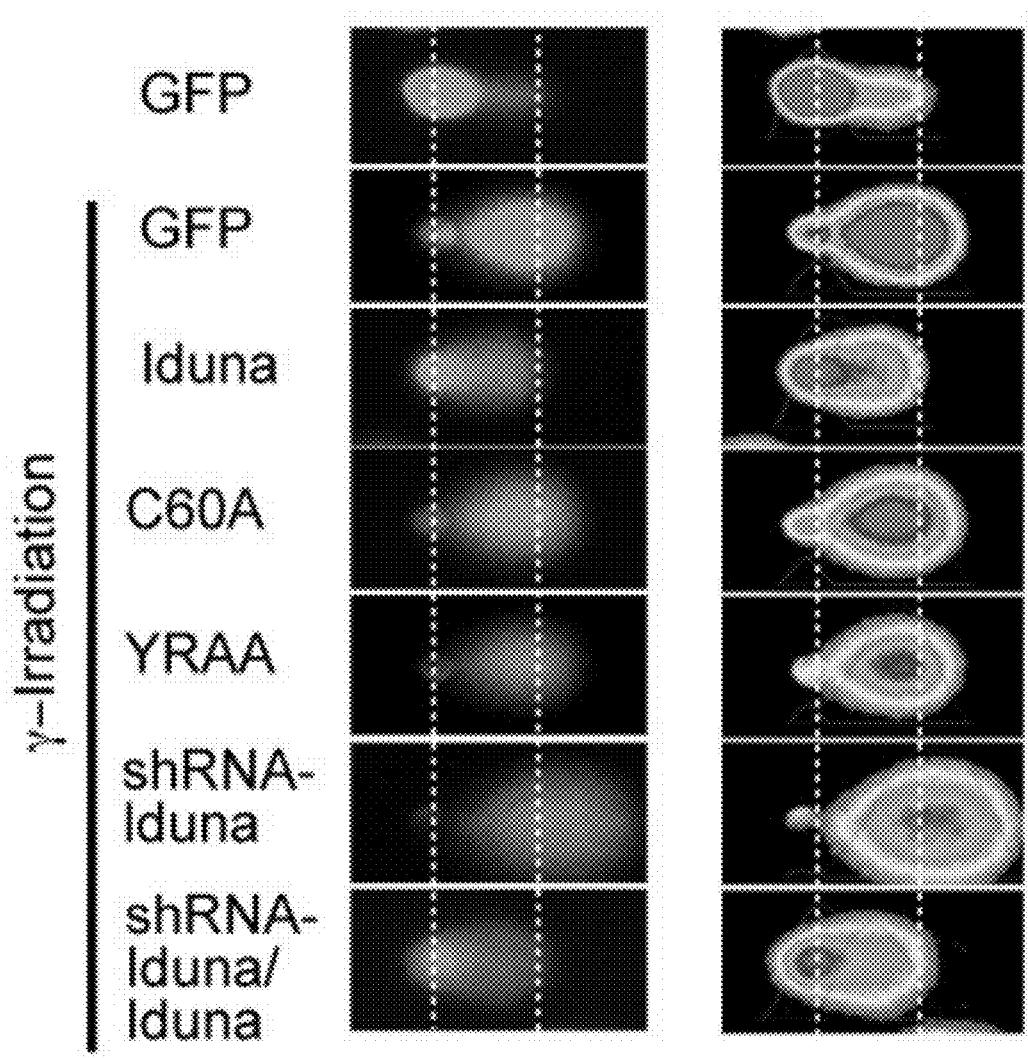

FIG. 104—Stable MCF7 lines were γ-irradiated at 2 Gy as indicated. After 15 min, cells were collected and then subjected to the comet assay.

Figure 105:
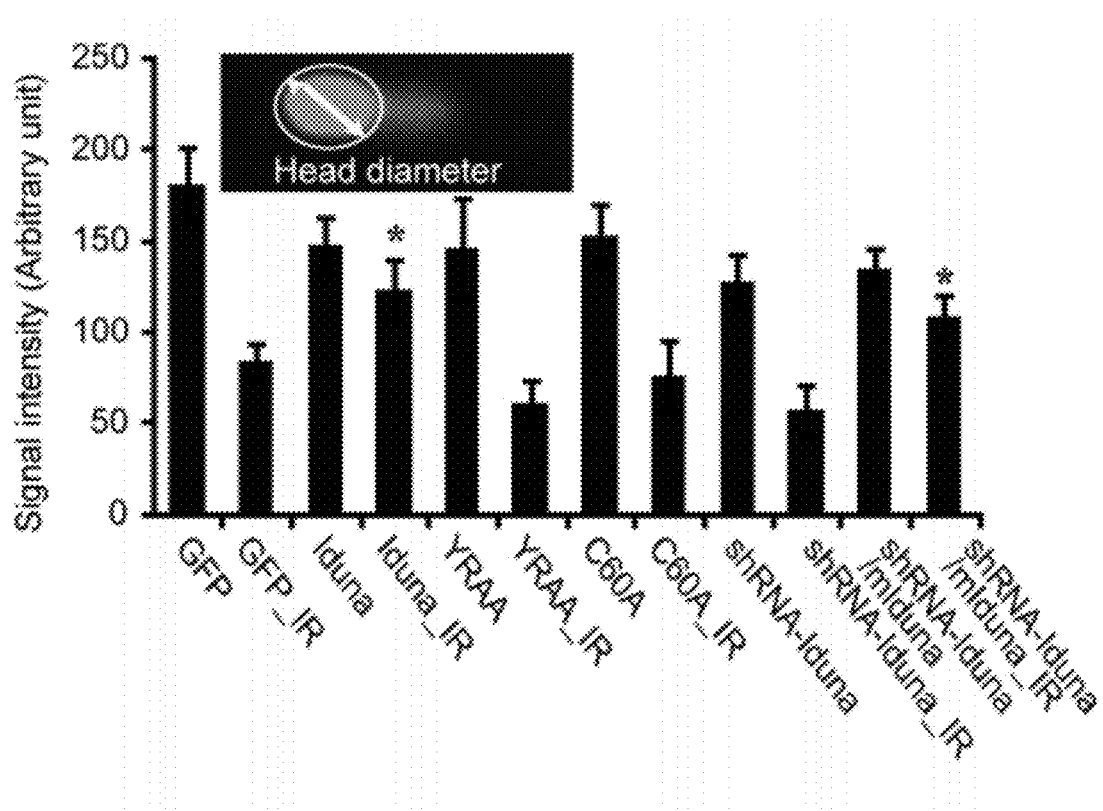

FIG. 105—Quantification of head diameter after comet assay.

Figure 106:
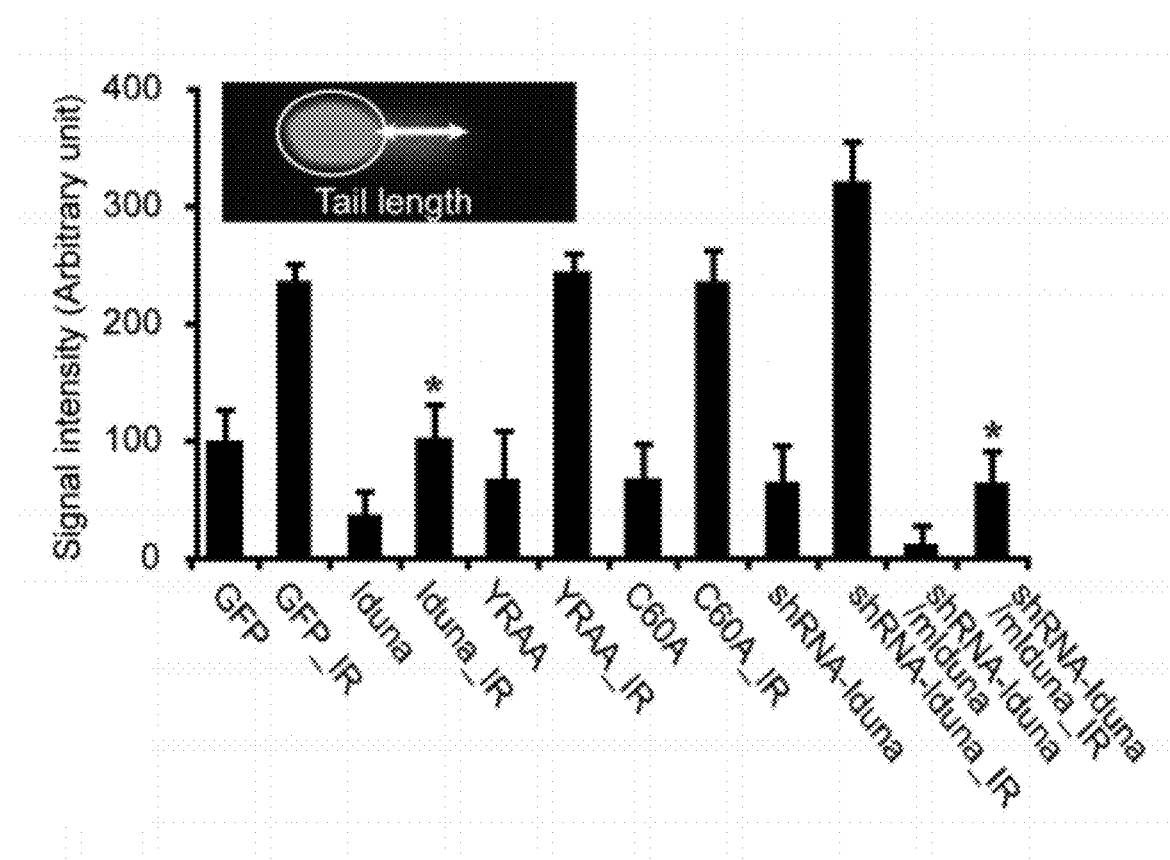

FIG. 106—Quantification of tail length after comet assay. Data represents mean±s.e.m., n=3, * P<0.05 by ANOVA with Tukey-Kramer's post hoc test. All experiments were repeated three to four times.

Figure 107:
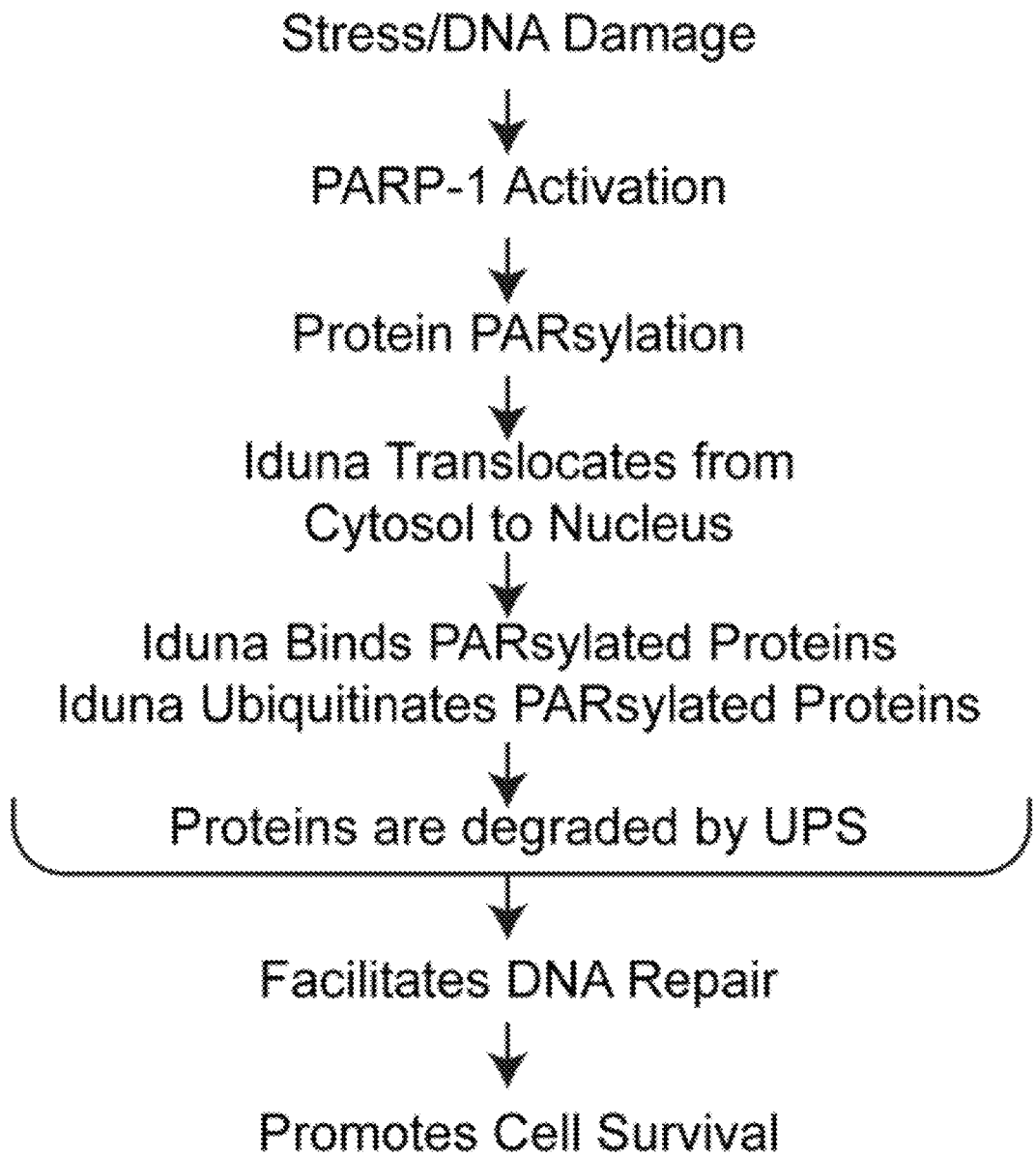

FIG. 107—Summary of Iduna mediated cell survival pathway.

DETAILED DESCRIPTION OF THE EMBODIMENTS

Figure 1:
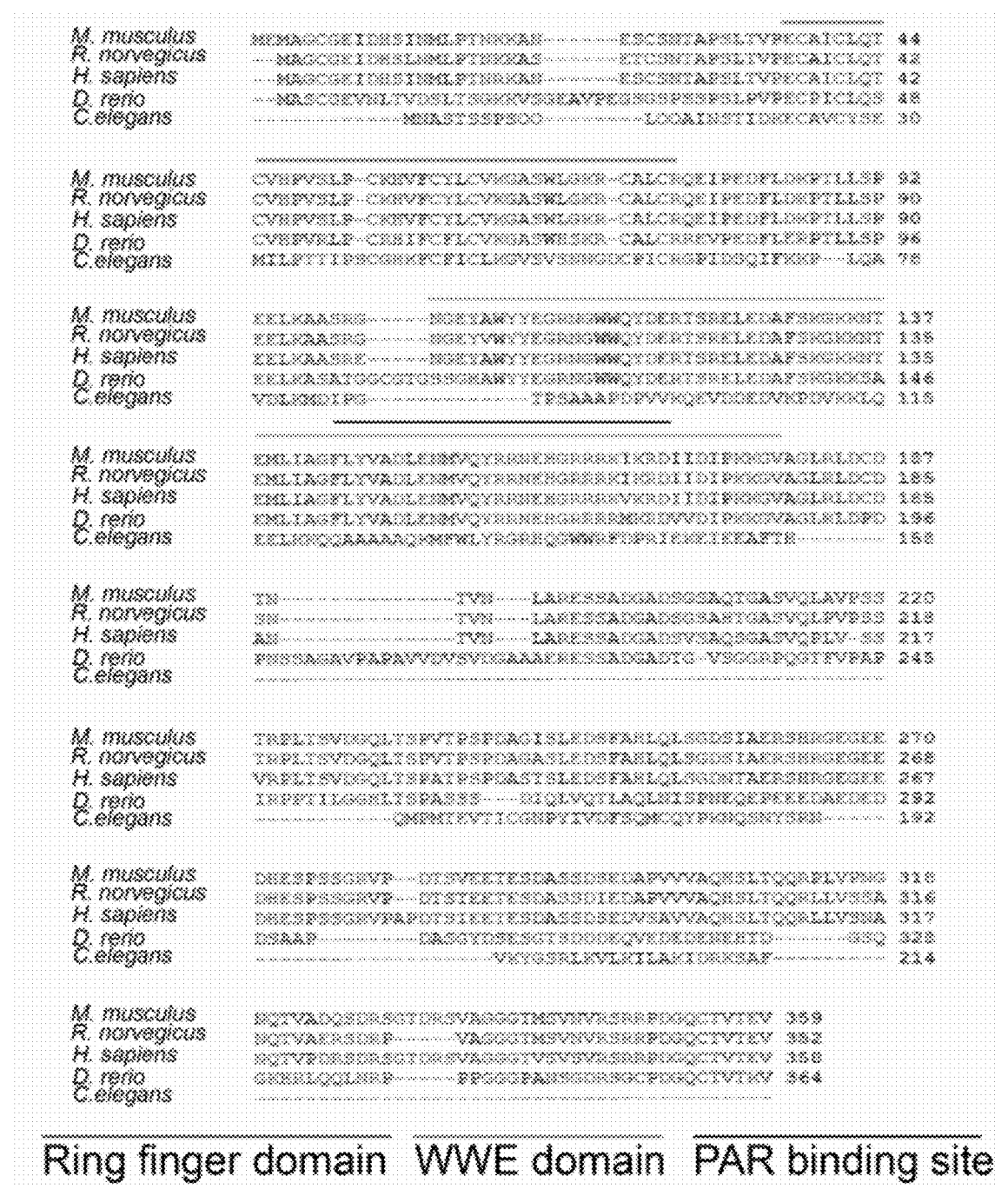

NMDA-induced plasticity late response genes (PLINGS) were identified from cortical neurons by differential analysis of primary cDNA library expression (DAzLE). Of the many genes identified, here we report the characterization of clone 932, named Iduna for the Norse goddess of protection and eternal youth. Iduna encodes for a protein of 359 amino acids with a predicted molecular weight of 39.8 kDa (FIG. 1). There is a high degree of homology with the human (SEQ. ID. NO.: 26), rat (SEQ. ID. NO.: 25) and mouse (SEQ. ID. NO.: 24) Iduna proteins. The evolutionary conserved regions with zebra fish (SEQ. ID. NO.: 27) and nematode (SEQ. ID. NO.: 28) are associated with two domains of Iduna, the Really Interesting New Gene (RING) finger (RF) domain (aa 35-77) and the WWE domain (aa 91-167) (FIG. 1).

Figure 4:
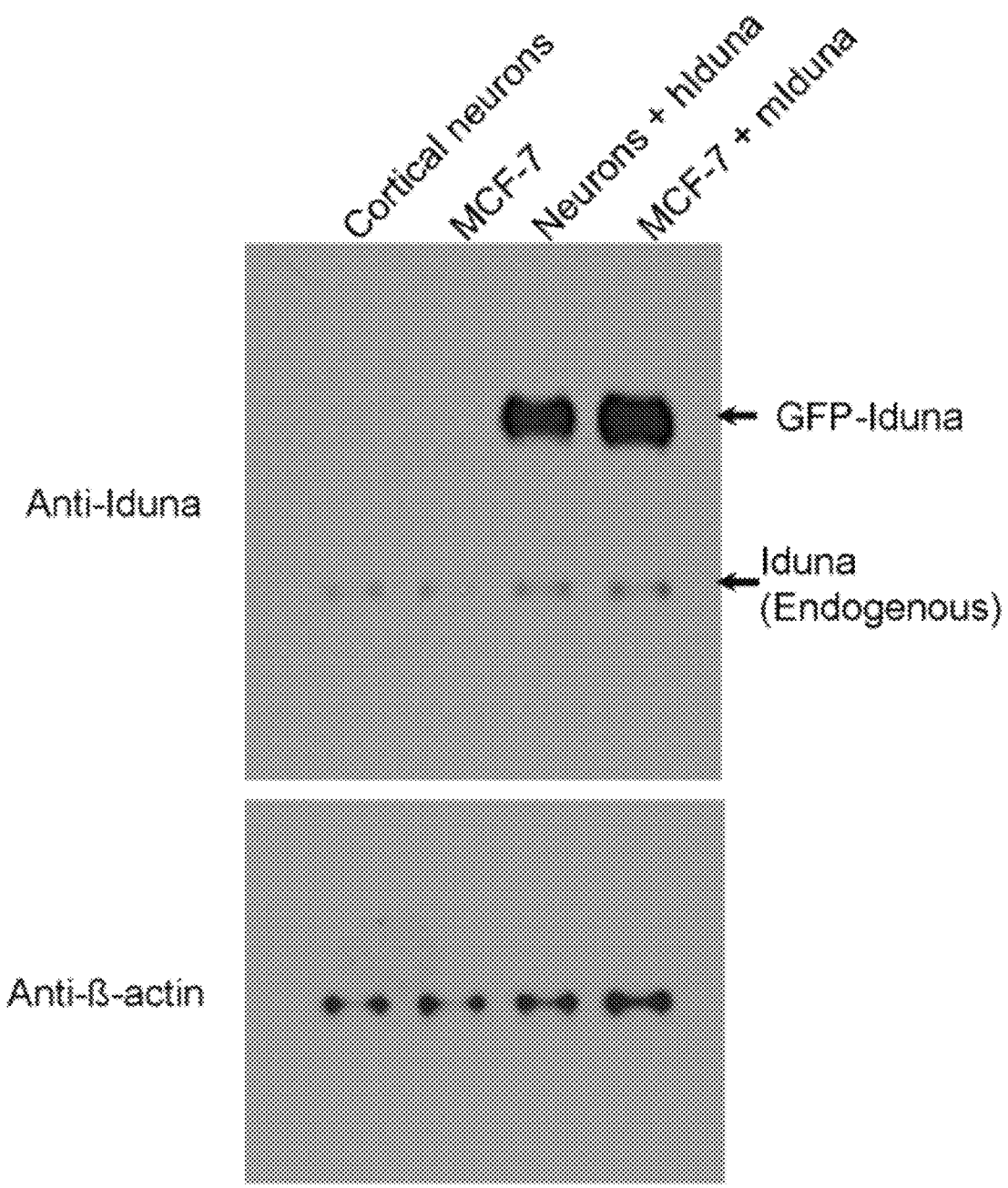
Figure 5:
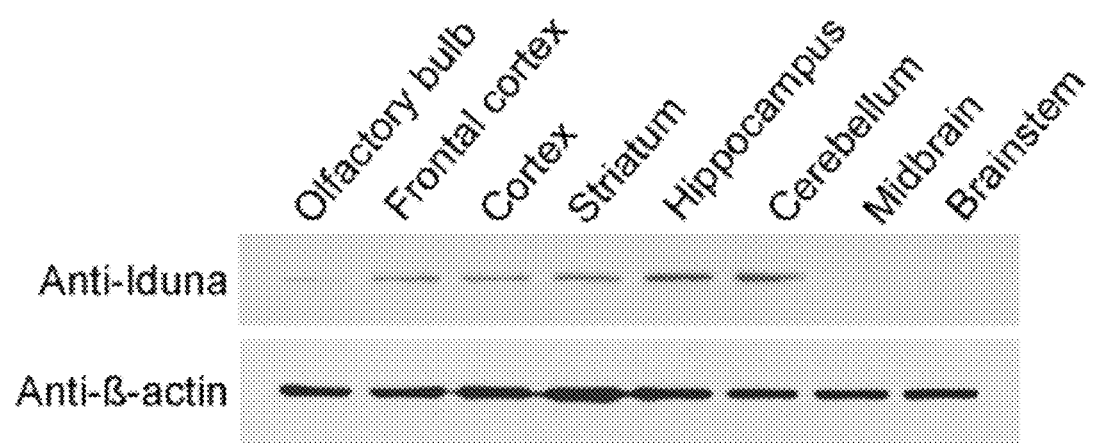

By Northern blot analysis Iduna is expressed at relatively high levels in brain, but is also present in spleen, heart, kidney, testis and liver (FIG. 2), with two Iduna transcripts in the testis. A polyclonal antibody to Iduna, which recognizes a single 40 kDa protein on immunoblot (FIGS. 3 and 4), reveals variable expression of Iduna protein in different brain regions, suggesting a regional diversity in Iduna activity (FIG. 5).

Figure 6:
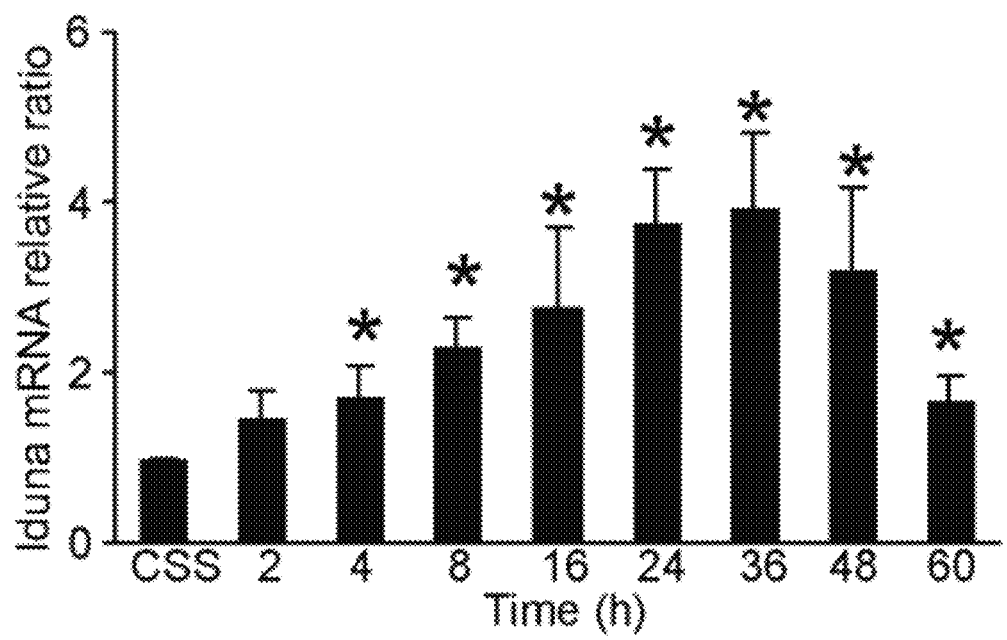
Figure 7:
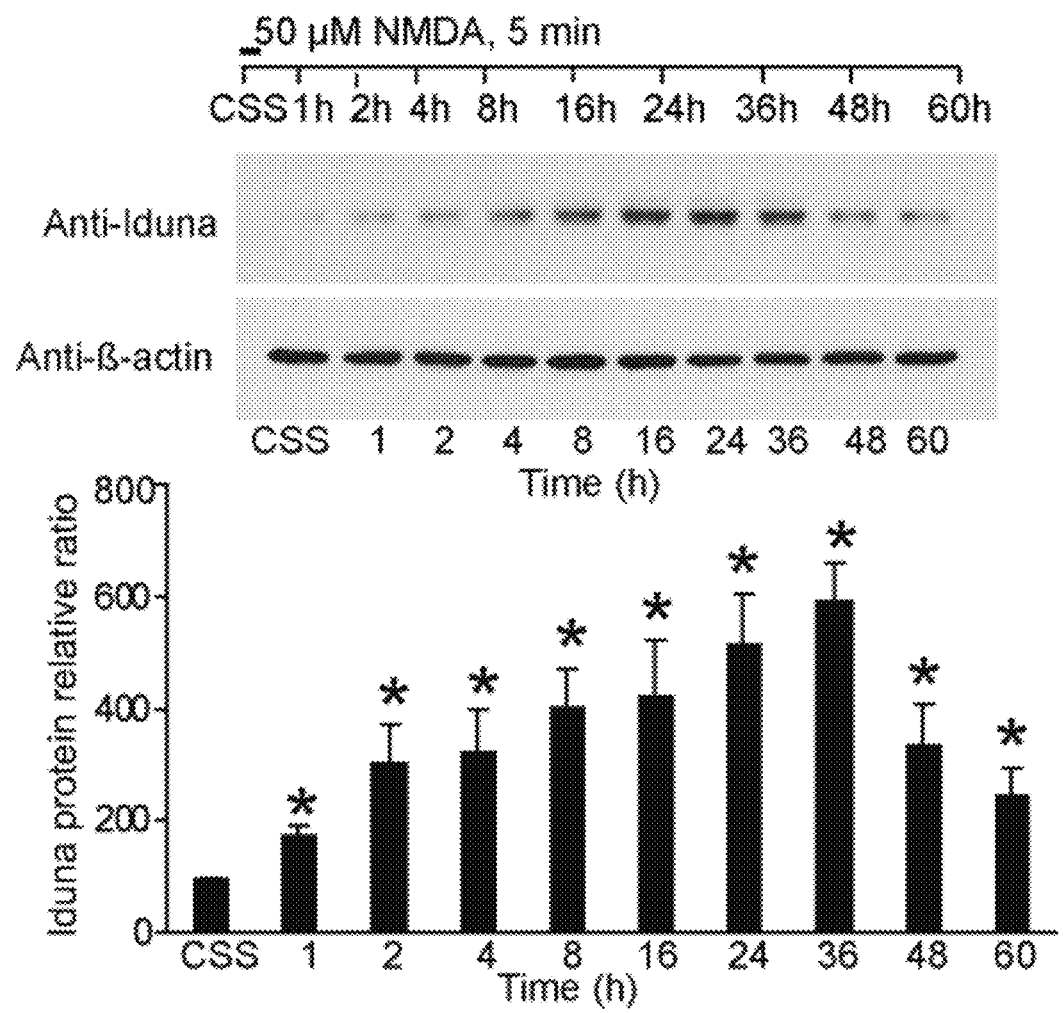
Figure 8:
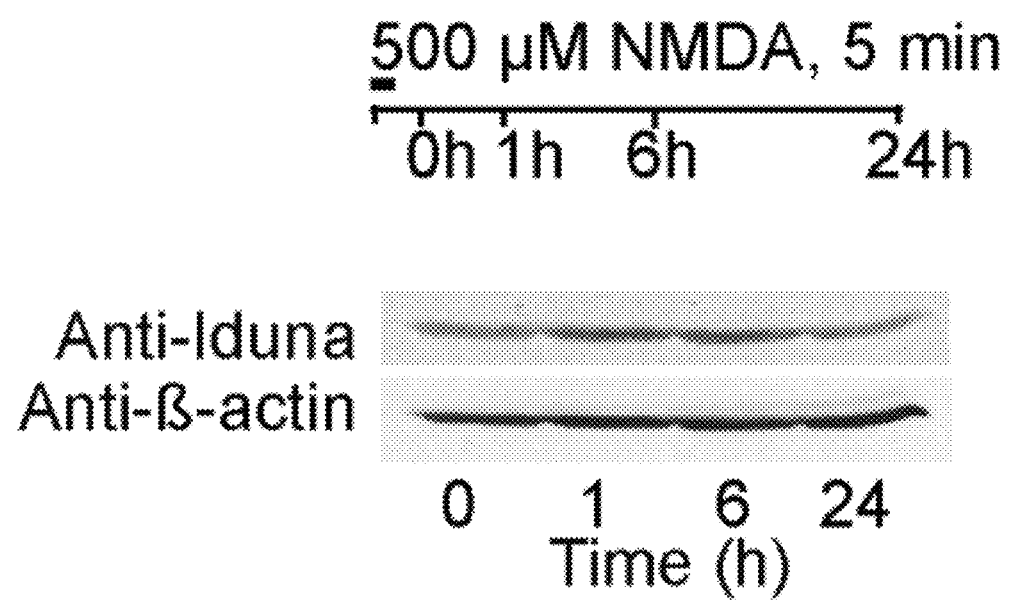
Figure 9:
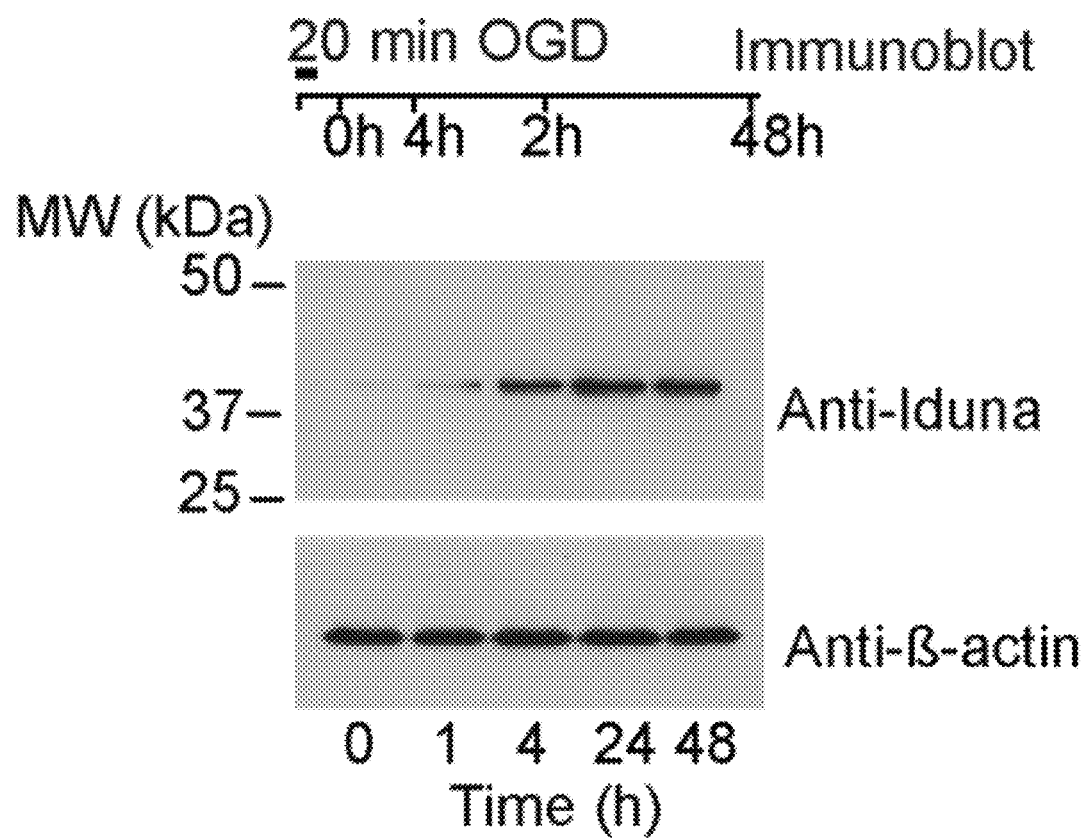
Figure 10:
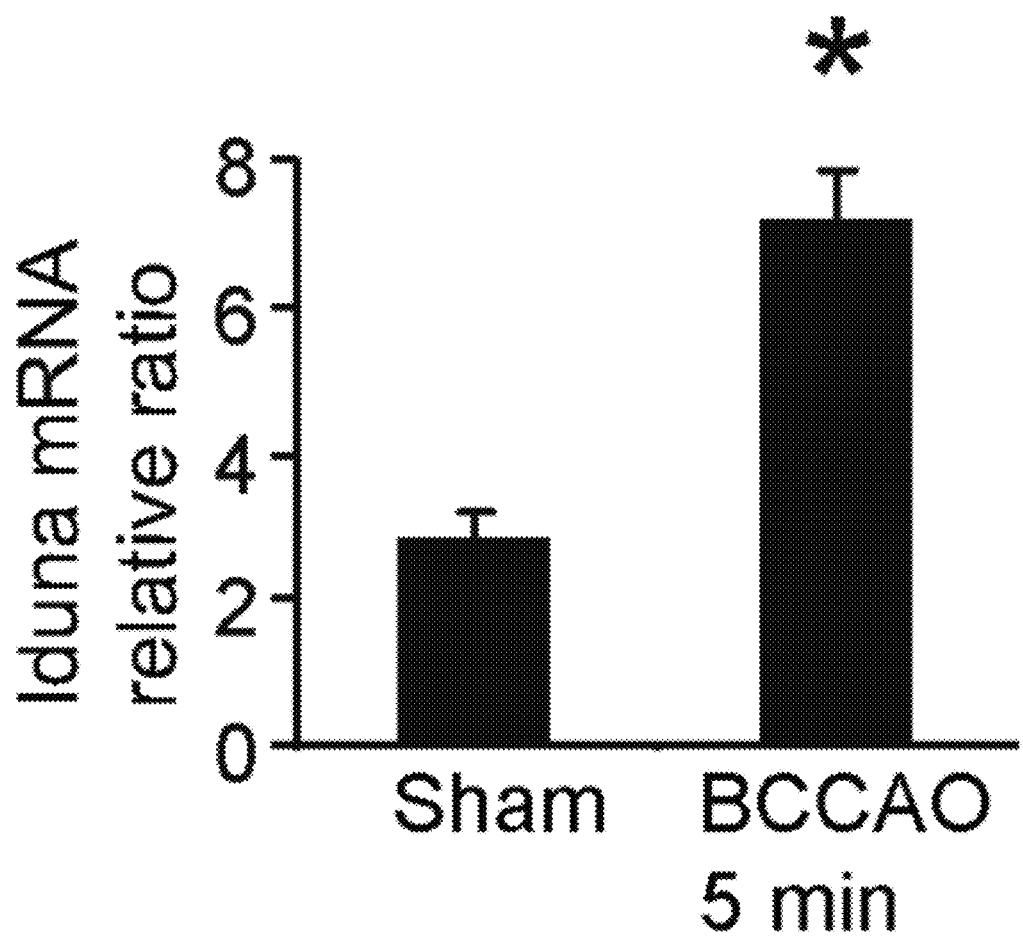
FIG. 10—Iduna mRNA expression in mouse forebrain detected by RT-PCR 48 hr after reperfusion following 5 min bilateral carotid artery occlusion (BCCAO). Data are the mean±SEM, n=4.
Figure 11:
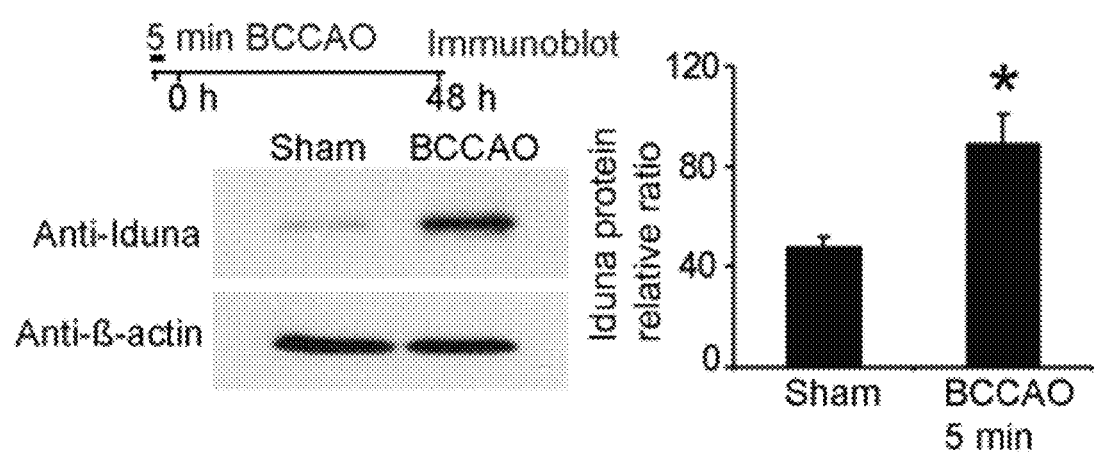
FIG. 11—Immunoblot of Iduna expression in forebrain 48 hr after reperfusion following 5 min BCCAO. Data were normalized to β-actin and quantified by optical density (right panel). Data represents mean±SEM, n=4. Experimental schedule is indicated above panels and treatment conditions are indicated by horizontal bars. Significance determined by by ANOVA with Tukey-Kramer's posthoc test.

Iduna mRNA as assessed by real time PCR increases following 50 µM NMDA (FIG. 6), consistent with our microarray screen. Iduna protein expression also increases following 50 µM NMDA (FIG. 7). Both Iduna mRNA and protein follow a similar pattern of expression, peaking at 36 h after NMDA stimulation (FIGS. 6 and 7). A toxic dose of NMDA (500 µM for 5 min) fails to induce Iduna expression (FIG. 8). Sublethal exposure to oxygen-glucose deprivation (OGD) which induces tolerance to subsequent lethal insults also induces Iduna (FIG. 9). A 5 minute bilateral common carotid artery occlusion (BCCAO) in mice results in resistance to subsequent ischemic injury and induces Iduna mRNA and protein (FIGS. 10 and 11).

Figure 3:
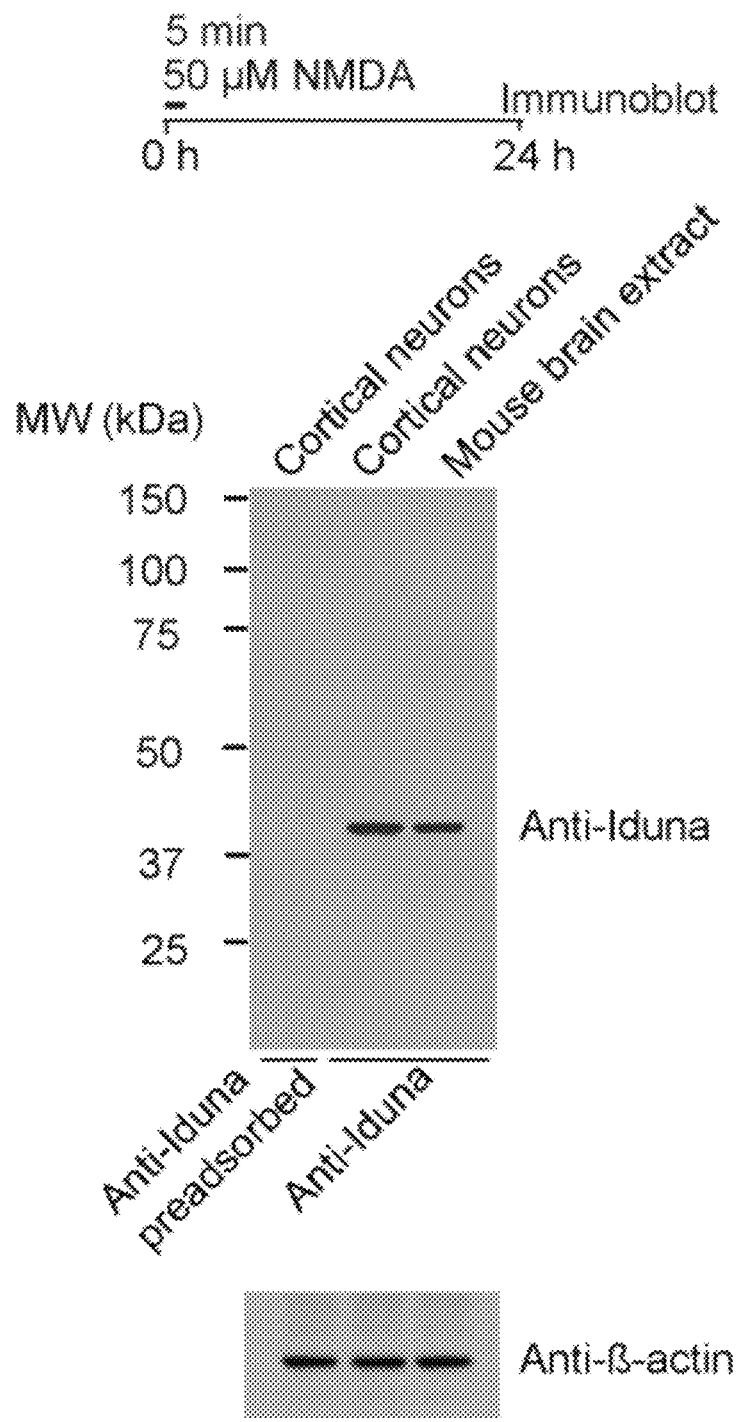
FIGS. 3 and 4—Characterization of Iduna Antibody.
Figure 12:
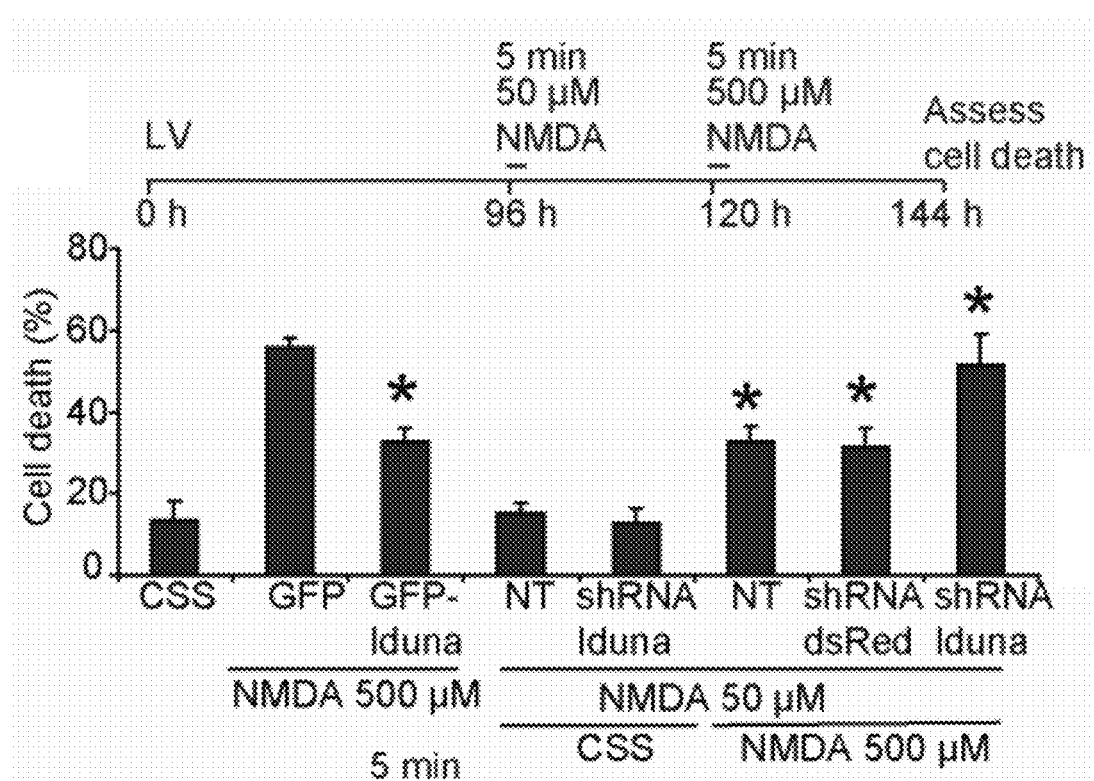
FIG. 12-18—Illustrate that Iduna is neuroprotective.
Figure 13:
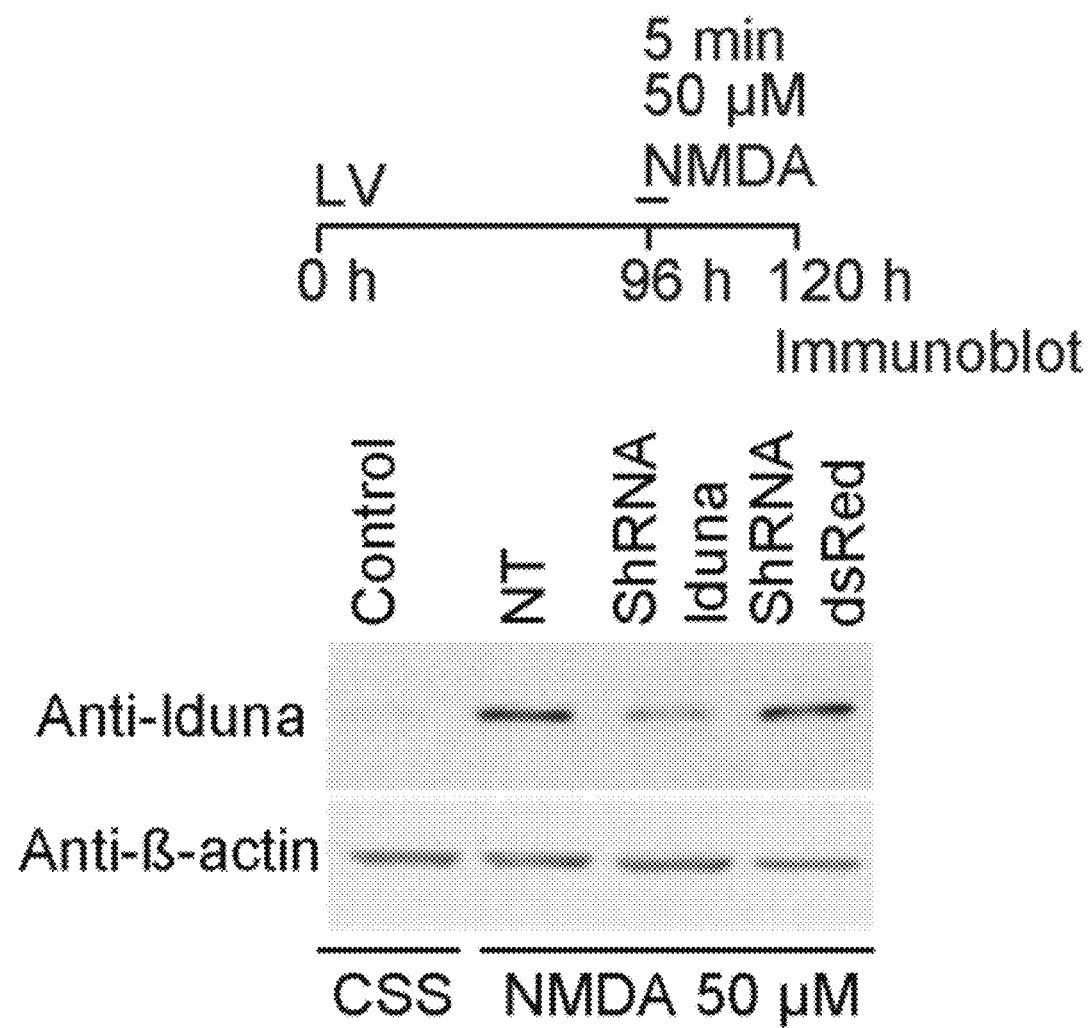
Figure 14:
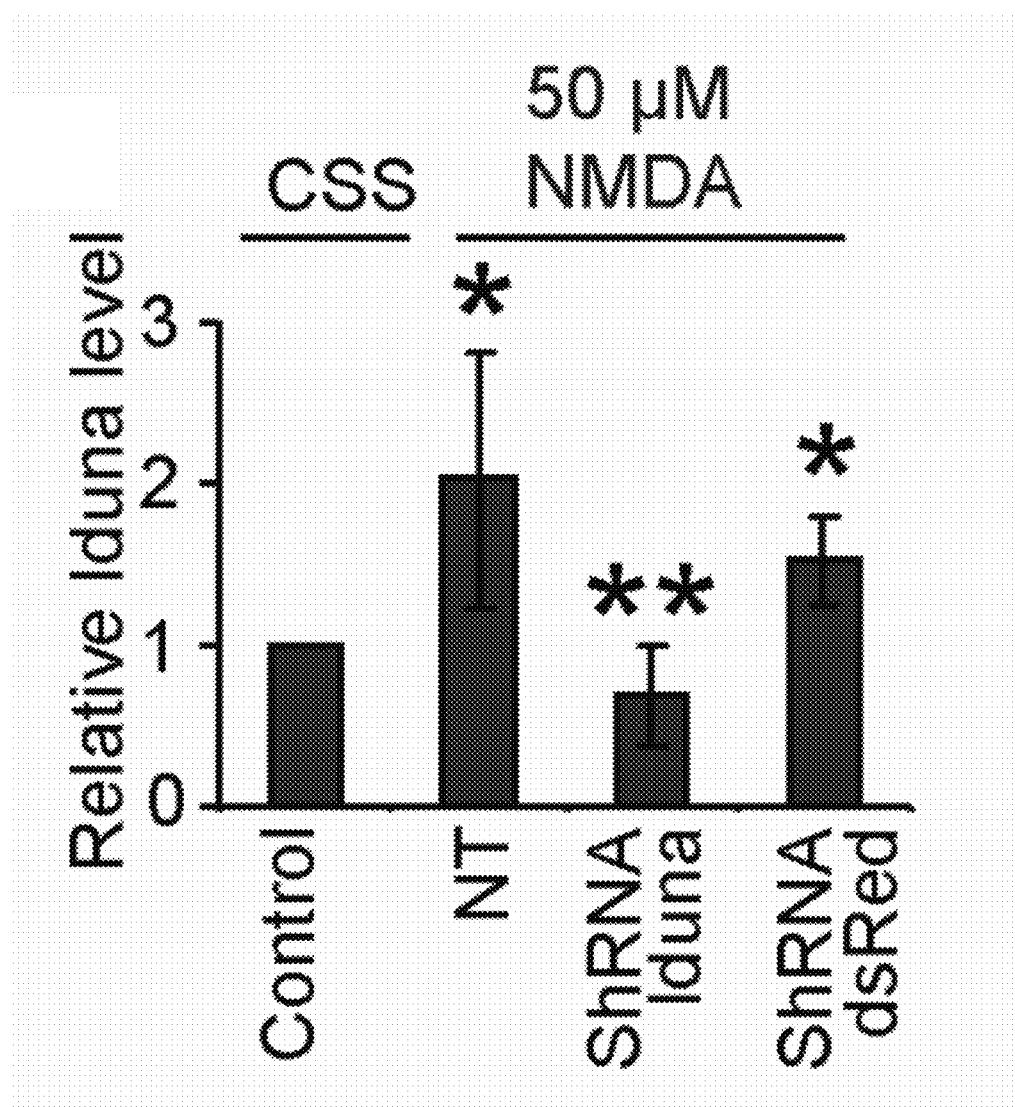
Figure 15:
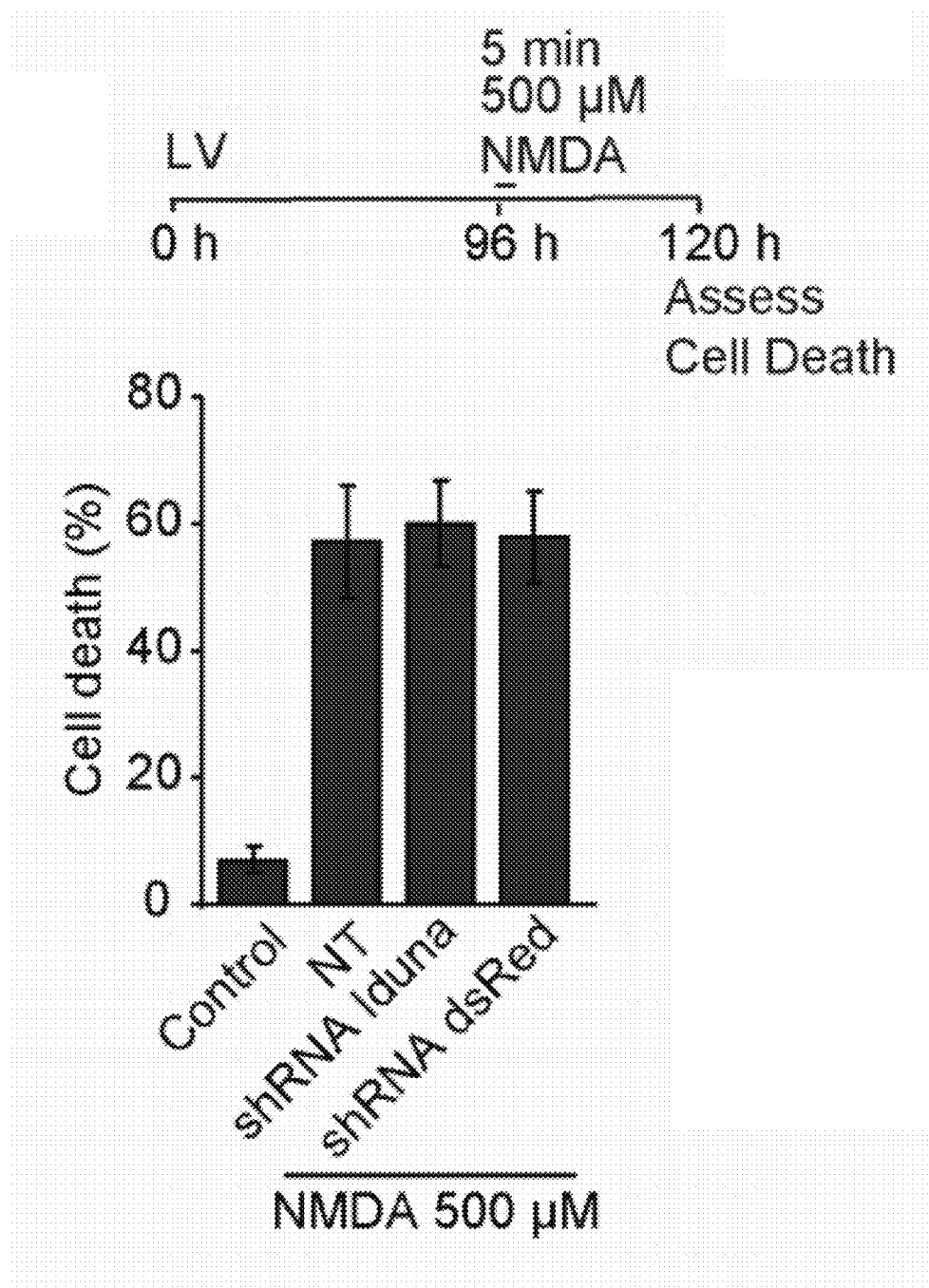
Figure 16:
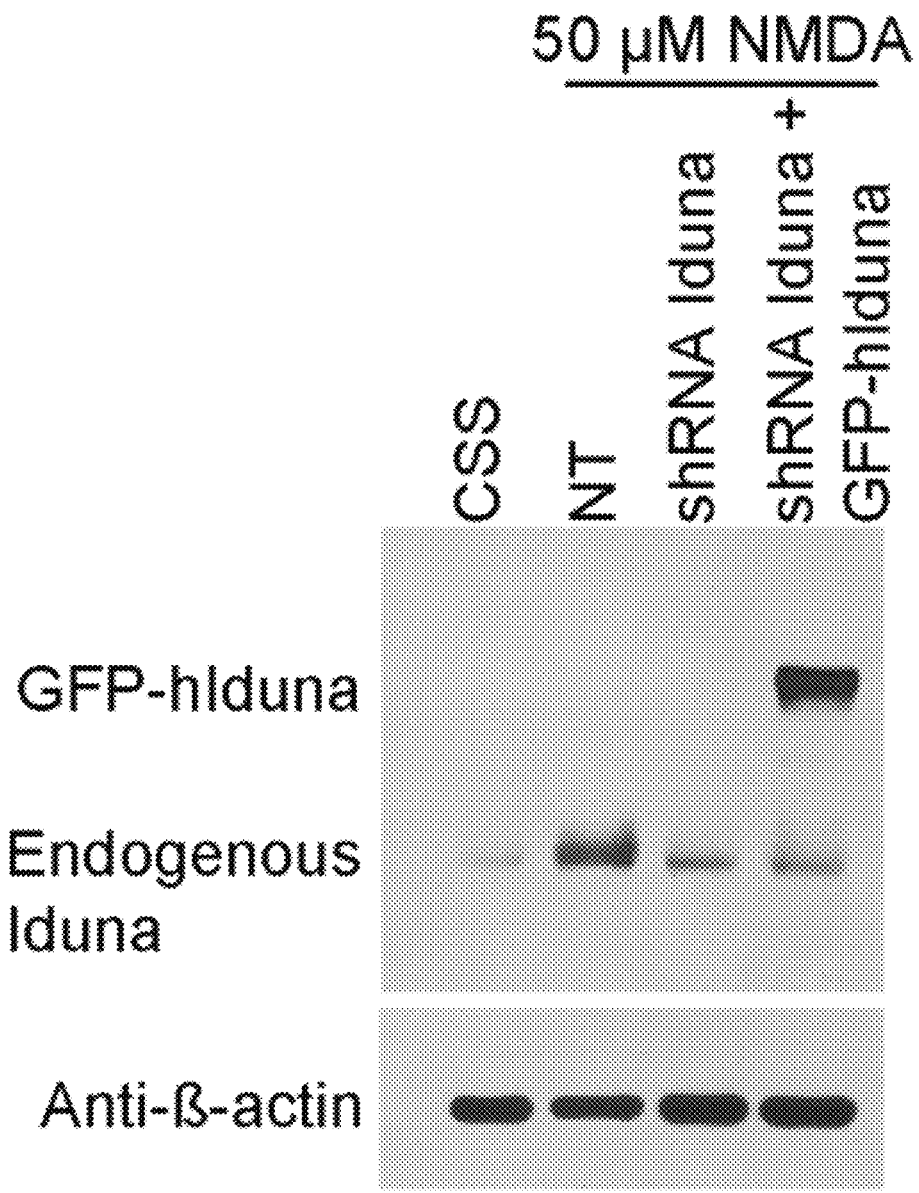
Figure 17:
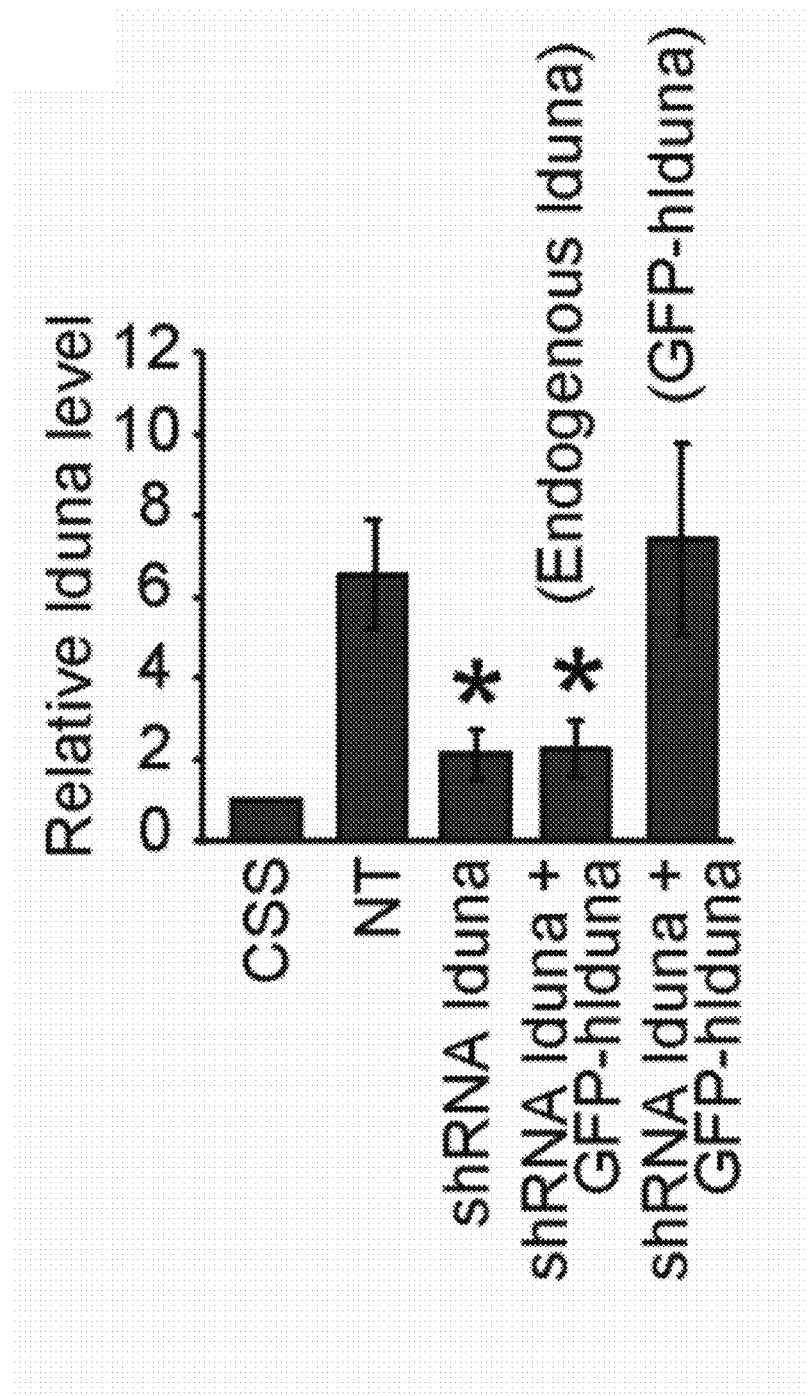
Figure 18:
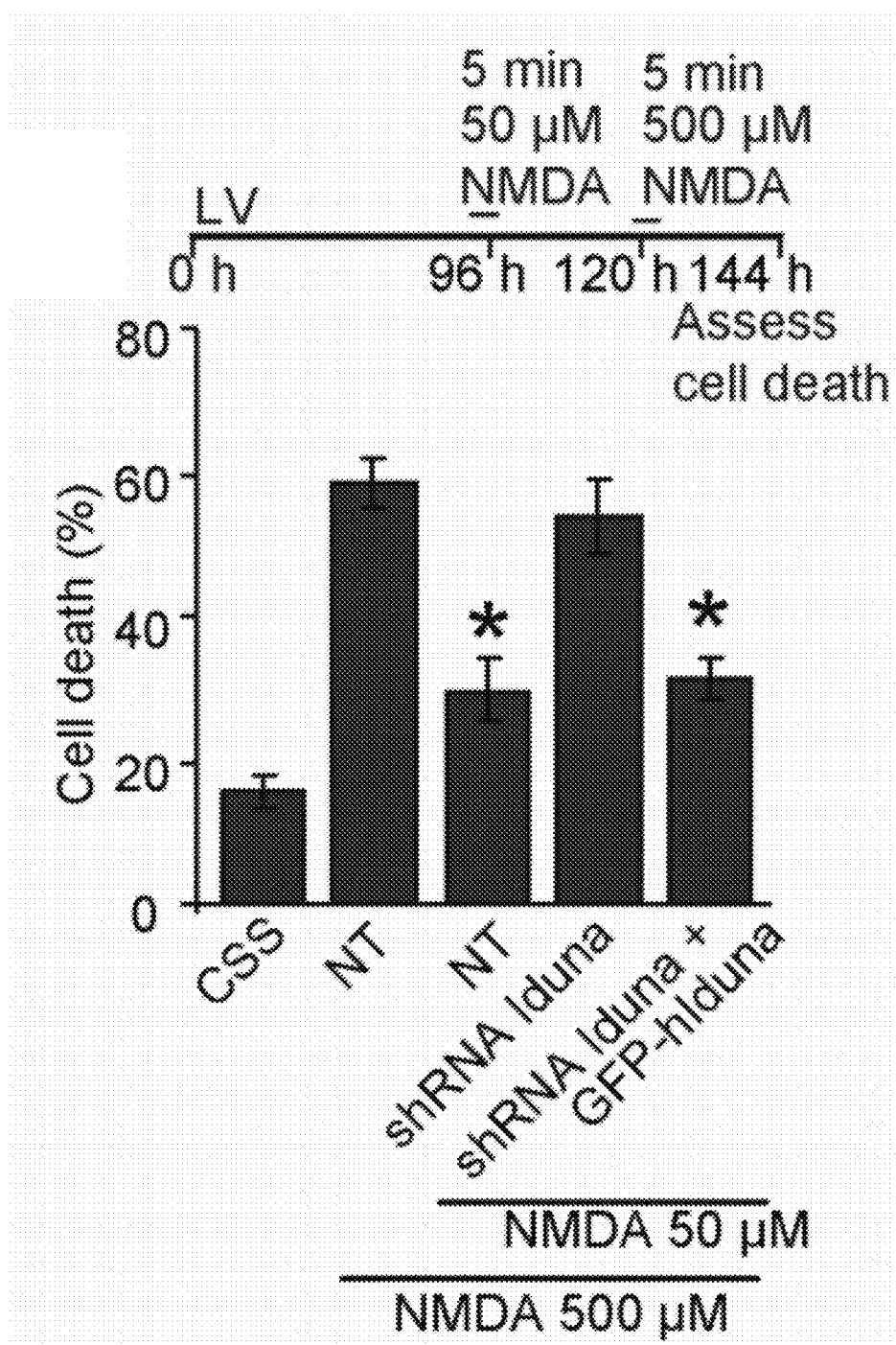

Lentiviral transduction of EGFP-tagged Iduna (GFP-Iduna) in cortical neurons protects against NMDA-induced cell death to a similar degree as the protection afforded by 50 µM NMDA (FIG. 12). Knockdown of Iduna induction by lentiviral shRNA following treatment with 50 µM NMDA (FIGS. 13 and 14) abolishes the NMDA-induced protection (FIG. 12). The control lentiviral shRNA DsRed has no significant effect on NMDA-induced upregulation of Iduna (FIGS. 13 and 14), NMDA-induced cell survival (FIG. 12) or cell death (FIG. 15). Knockdown of Iduna has no effect on cell viability following a toxic 500 µM dose of NMDA (FIG. 15). The Iduna antibody is equally sensitive to human and mouse Iduna detection (FIGS. 3 and 4). Within the DNA sequence of Iduna, between base pairs 556-576, there are five differences between the mouse and human sequence, which is sufficient to render human Iduna resistant to knockdown with the shRNA targeted towards mouse Iduna and thus provide a positive control (FIGS. 16 and 17). Overexpression of human Iduna is protective in the setting of knockdown of induced mouse Iduna (FIG. 18), confirming the specificity of the shRNA knockdown of mouse Iduna. These results taken together indicate that Iduna is an NMDA-induced protective protein.

Figure 2:
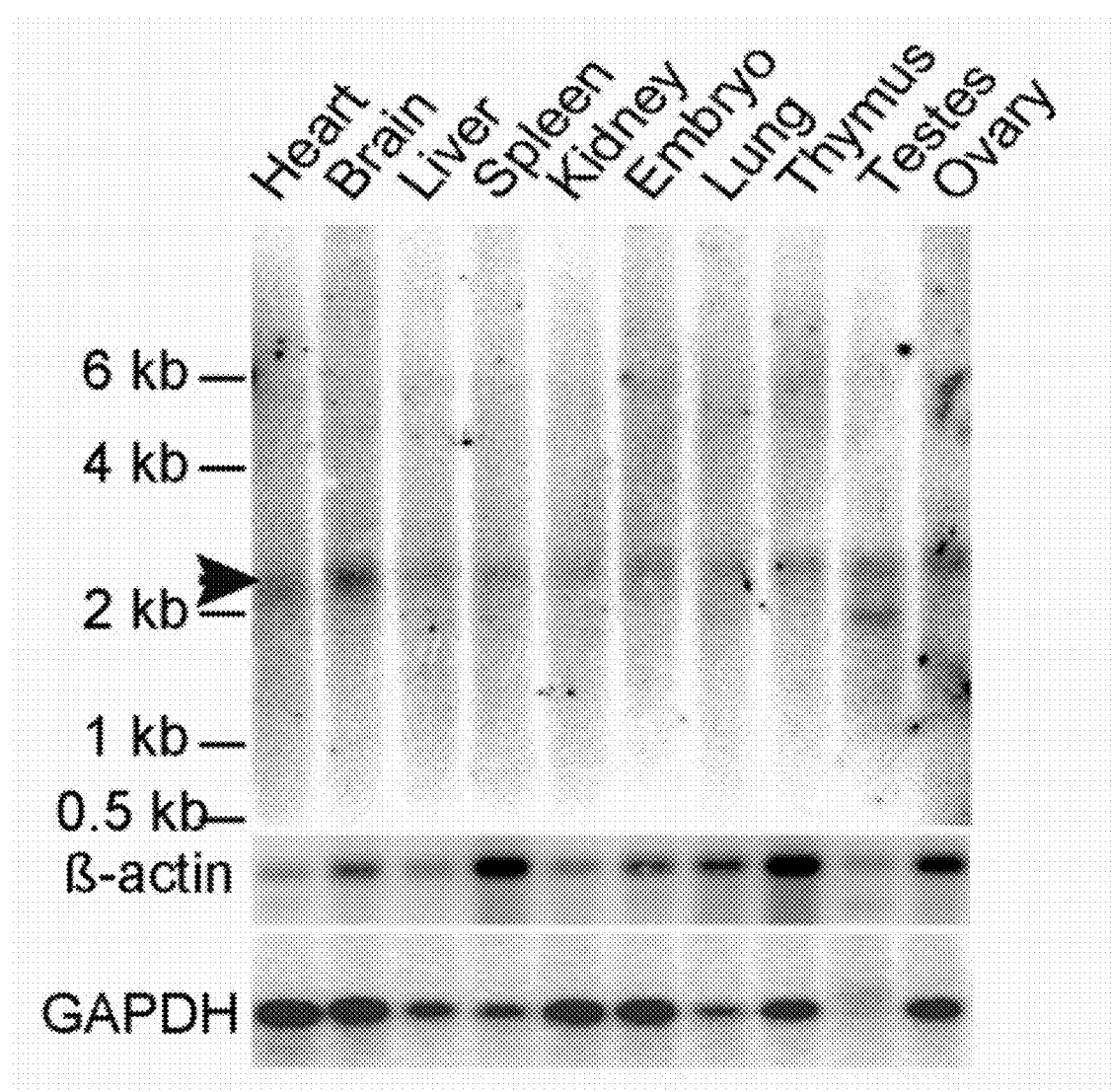
Figure 19:
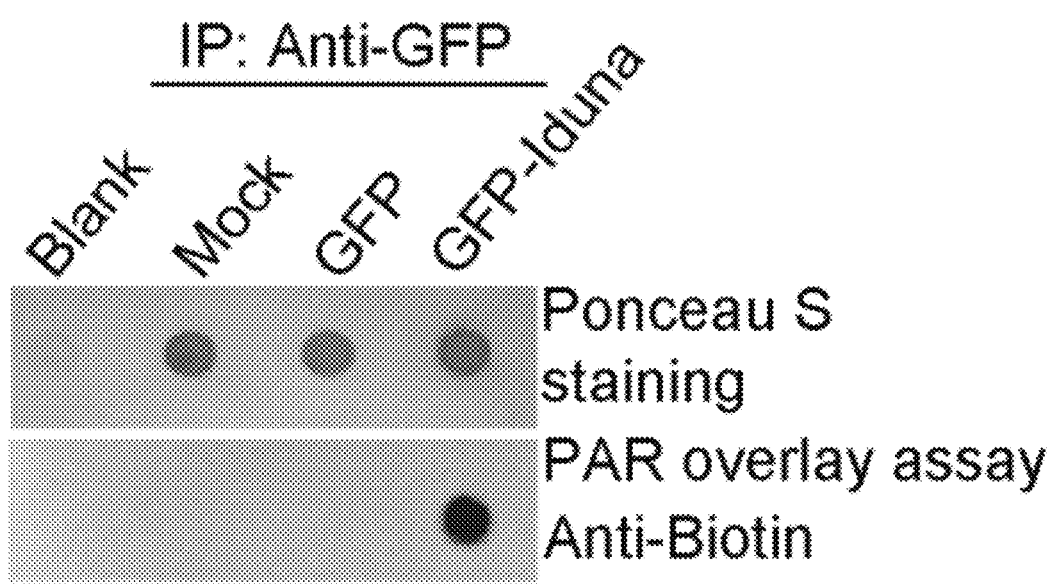
FIGS. 19, 20, 22-26 and 29-31—Illustrate the PAR binding activity of Iduna.
Figure 20:
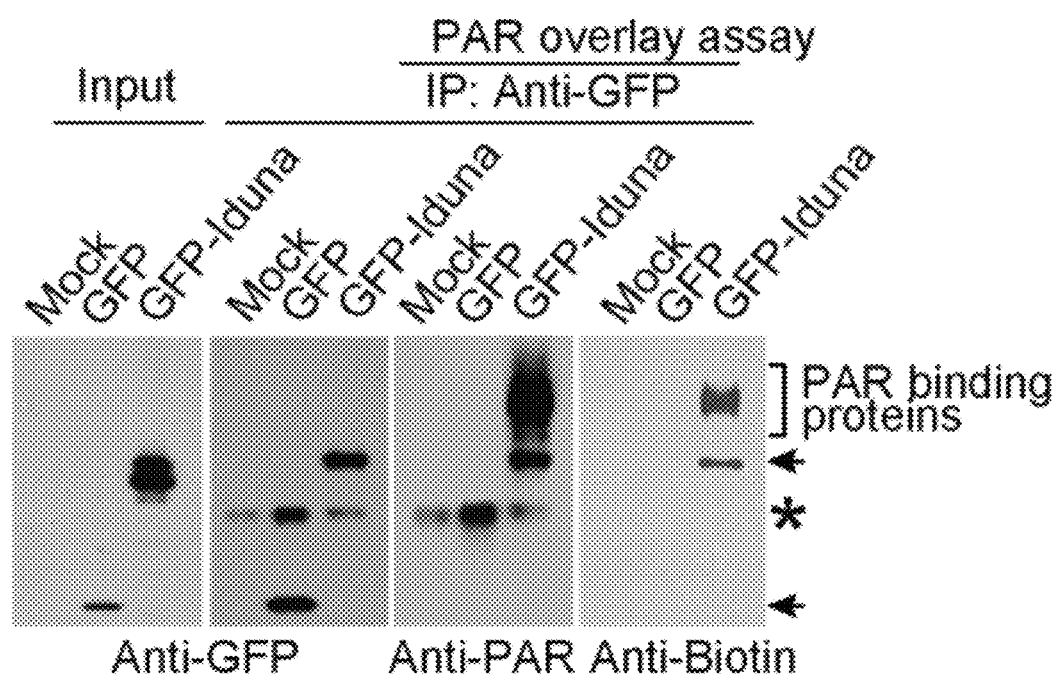
Figure 21:
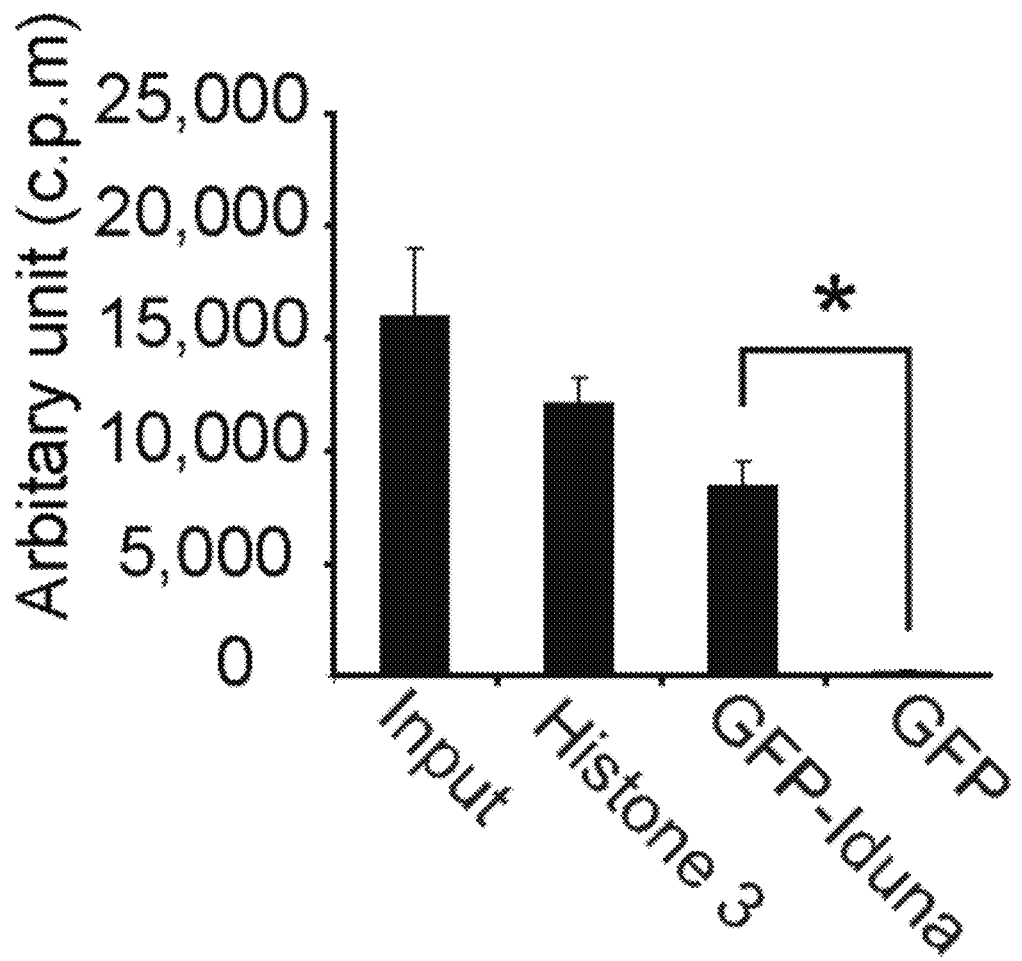
FIGS. 21, 27 and 28—PAR binding activity of Iduna.
Figure 22:
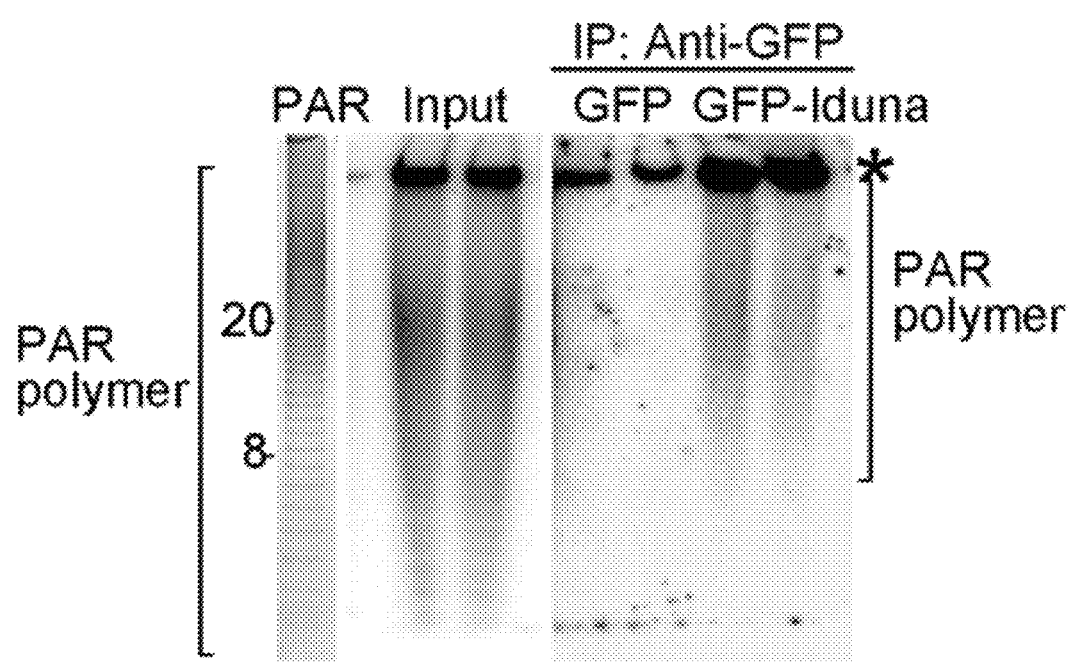
Figure 23:
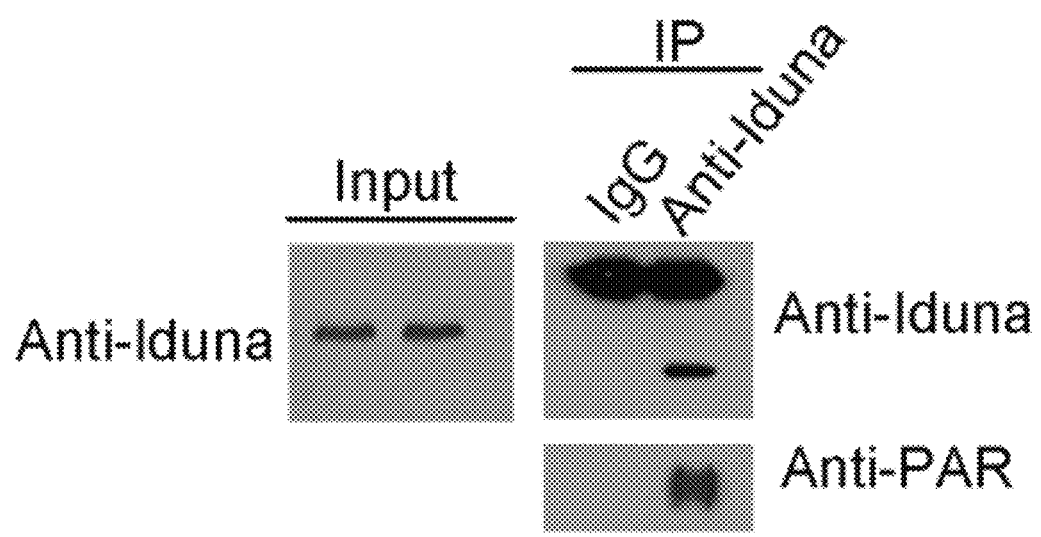

Iduna contains a RING finger domain and a WWE domain. Within the WWE domain there is a putative PAR binding motif (FIGS. 1 and 2). Because PAR is a newly discovered death signal, the ability of Iduna to bind PAR polymer was determined. Dot blots of immunoprecipitated GFP-Iduna incubated with biotin-labeled PAR polymer and probed with an anti-biotin antibody show GFP-Iduna binds to PAR polymer, whereas GFP alone fails to bind (FIG. 19). PAR polymer overlay assays with immunoprecipitated GFP-Iduna reveals PAR polymer specifically binds to GFP-Iduna, but it fails to bind to GFP (FIG. 20). In addition, poly(ADP-ribosyl)ated proteins co-immunoprecipiate with GFP-Iduna (FIG. 20). In a PAR polymer binding assay GFP-Iduna or histone 3 (H3) (a positive control) bind radiolabeled free PAR polymer but GFP does not (FIG. 21). Iduna binds to a range of PAR polymers of varying length as determined by phosphorimager detection of radiolabeled PAR polymer bound to GFP-Iduna following separation by Tris-borate-EDTA PAGE (FIG. 22). In primary neuronal cultures treated with 50 µM NMDA, immunoblot analysis shows that Iduna co-immunoprecipitates with PAR polymer (FIG. 23). Because in resting neurons Iduna is expressed at low levels and there is relatively little PAR polymer, there is no detectable interaction between Iduna and PAR polymer under resting conditions. Taken together, these results indicate that Iduna is a PAR polymer binding protein.

Figure 24:
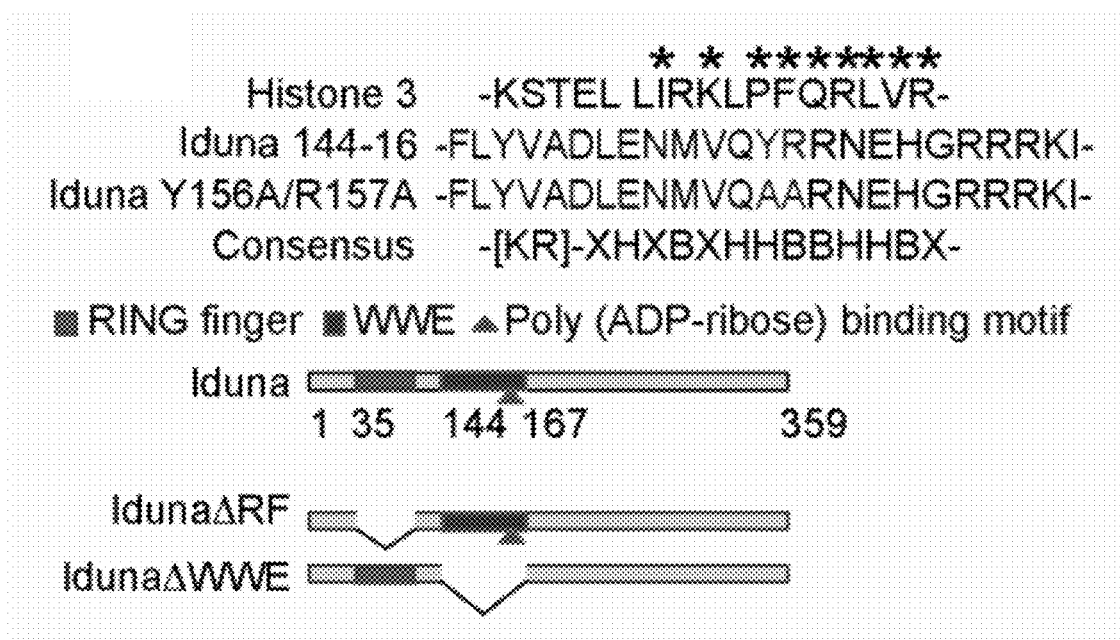
Figure 25:
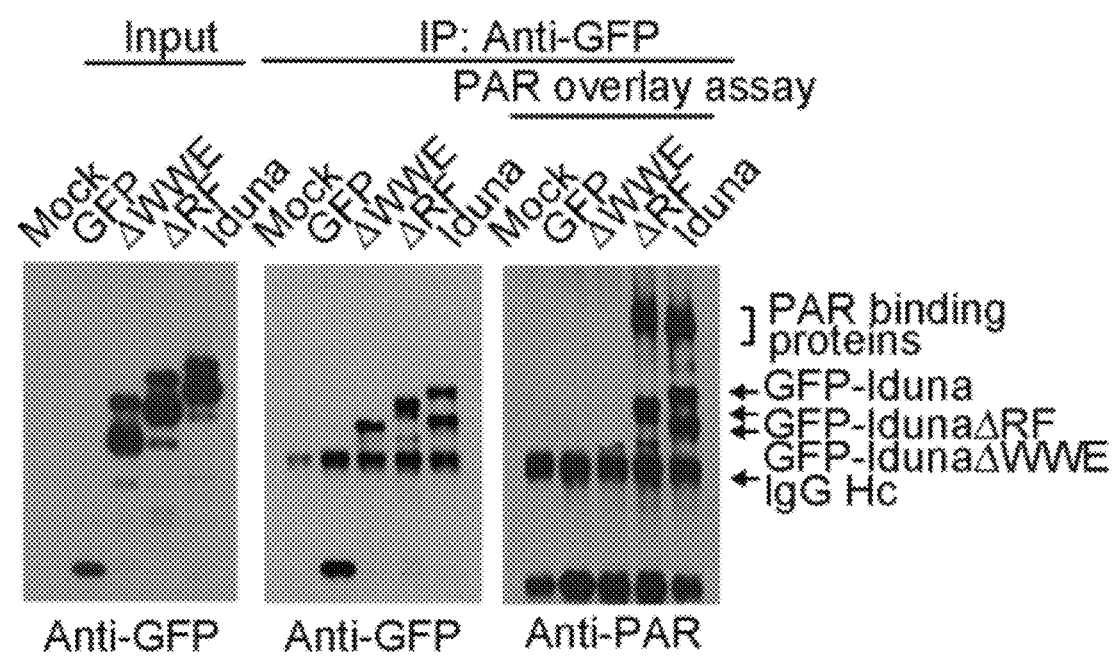
Figure 26:
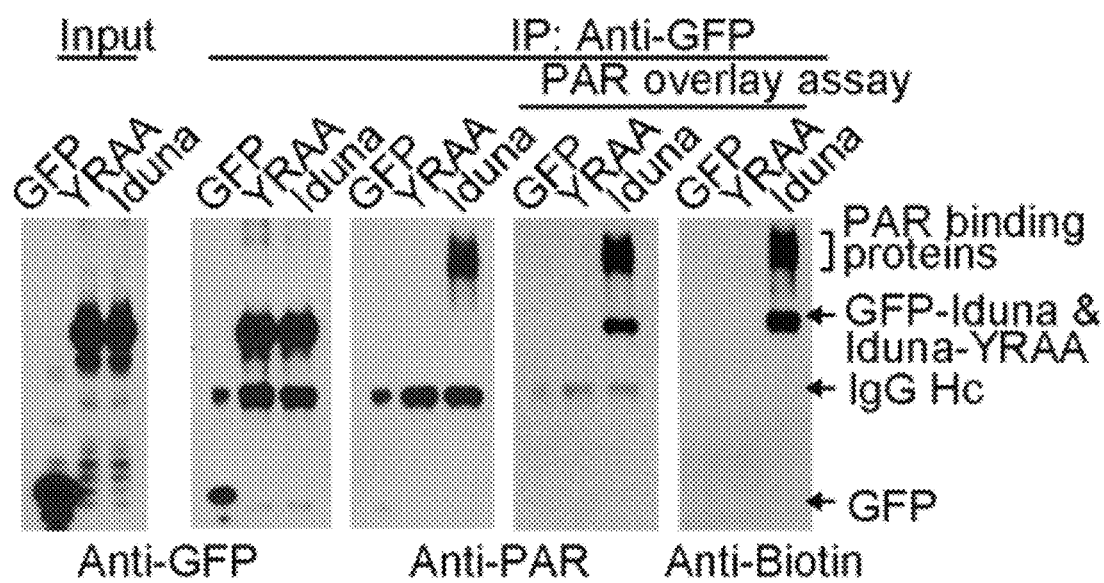
Figure 27:
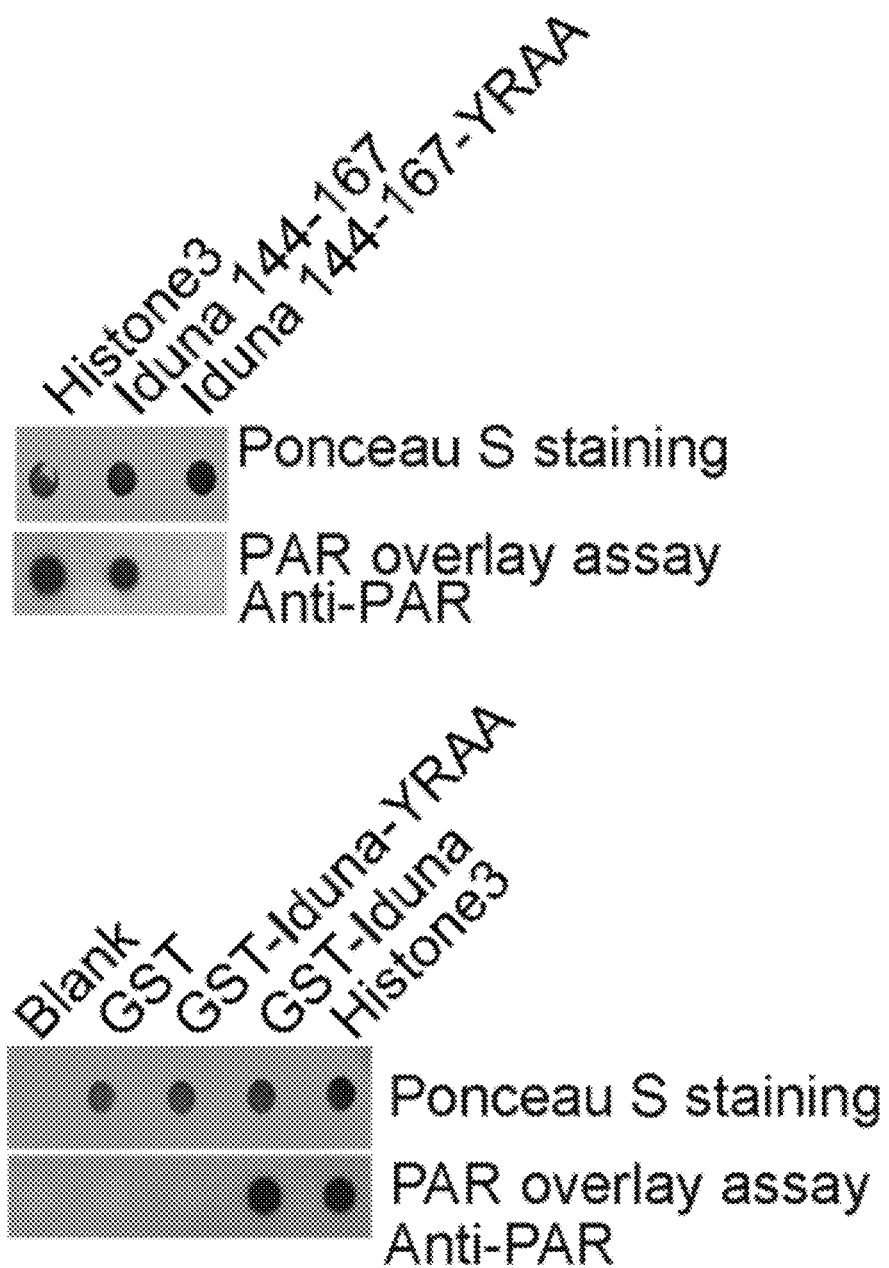
Figure 28:
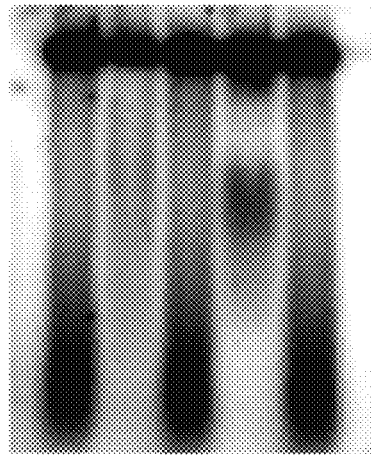

PAR binding is specified by a sequence of approximately 20 amino acids containing N-terminal basic amino acids and a C-terminal region containing alternating hydrophobic and basic amino acids (FIG. 24). Iduna contains a predicted PAR polymer binding sequence within amino acids 144-167 of the WWE domain (FIGS. 1 and 24). The PAR-binding domain was defined by comparing to the consensus sequence for PAR-binding and the known PAR binding domain of Histone 3 (FIG. 24). HEK293 cells were transfected with GFP, GFP-Iduna lacking the WWE domain (GFP-IdunaΔWWE), GFP-Iduna lacking the RF domain (GFP-IdunaΔRF), and full-length GFP-Iduna, followed by immunoprecipitation with a GFP antibody. The PAR polymer overlay assay of the immunoprecipitate shows PAR polymer binds to GFP-IdunaΔRF and full-length GFP-Iduna and co-immunoprecipitated PAR binding proteins, but it fails to bind to GFP and GFP-IdunaΔWWE (FIG. 25). Only GFP-Iduna-ΔRF and full-length GFP-Iduna can co-immunoprecipiate PAR binding proteins (FIG. 25). The critical amino acids in the PAR binding domain, 156Y and 157R, were mutated to 156A and 157A in full length Iduna (Iduna-YRAA). A PAR polymer overlay assay reveals that PAR polymer binds to GFP-Iduna and co-immunoprecipitated PAR binding proteins, but it fails to bind to GFP-Iduna-YRAA and PAR binding proteins fail to co-immunoprecipitate (FIG. 26). Similar results are obtained with a biotin-tagged PAR polymer followed by detection with an anti-biotin antibody (FIG. 26). A synthesized peptide fragment of the predicted PAR polymer binding sequence in Iduna between of amino acids 144-167 of the WWE domain (Iduna 144-167) binds to PAR polymer in a manner comparable to full-length Iduna (FIG. 27). However, when the peptide fragment was synthesized with amino acids 156A and 157A to disrupt the PAR binding site, (Iduna 144-167 YRAA) it fails to bind PAR polymer (FIG. 27). Histone H3 is a known PAR binding protein and was used as a positive control for the PAR overlay assay. Full length GST-Iduna binds to PAR polymer whereas GST alone or GST-Iduna-YRAA fails to bind PAR polymer in the PAR polymer overlay assay (FIG. 27). An assay based on electrophoretic mobility shift (EMSA) for PAR binding was developed to monitor PAR polymer binding to Iduna. Iduna retards the mobility shift of PAR polymer whereas GST or GST-Iduna-YRAA has no effect of PAR polymer mobility shift. Histone 3, a positive control also retards the PAR polymer mobility shift (FIG. 28).

Figure 29:
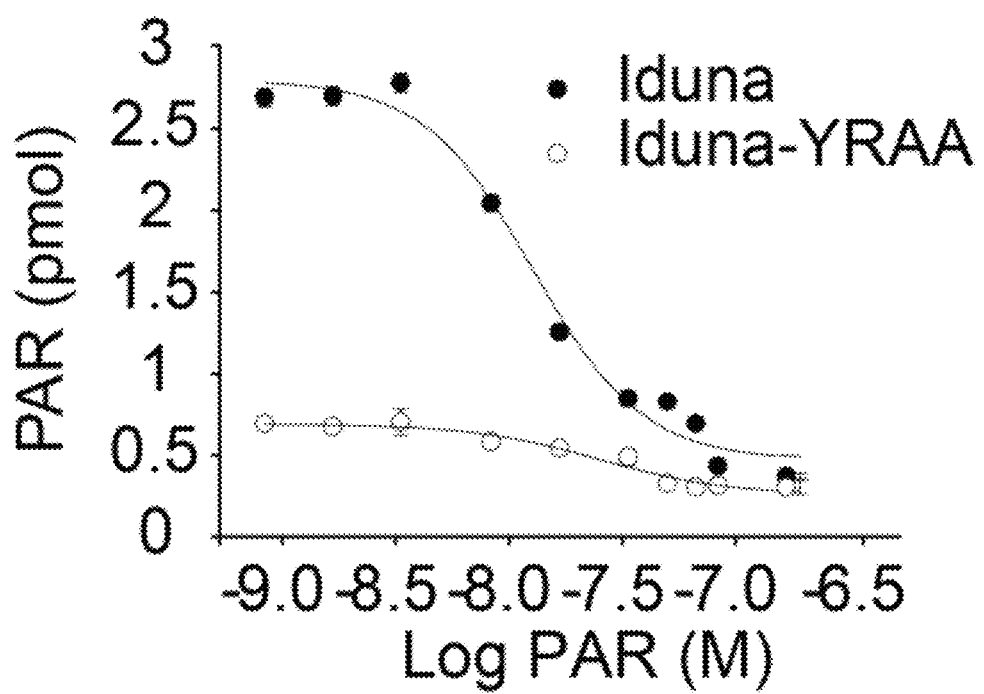

The affinity of Iduna and Iduna-YRAA for PAR binding was determined by a competition assay with increasing concentrations of unlabeled PAR polymer against 2.5 nM [$^{32}$P]-labeled PAR polymer (mean size of 40 ADP-ribose units) (FIG. 29). From the competitive binding curve, the $EC_{50}$ of wild type Iduna for PAR polymer is 14.5±0.13 nM (p>0.001) calculated as a function of PAR polymer concentration, and the maximum binding capacity ($B_{max}$) is 3.04±0.16 µmol. The PAR polymer synthesized by in vitro automodification of PARP-1 has a mean length of 40 ADP-ribose residues and accordingly the concentration of PAR is given as a function of polymer molecules with a mean size of 40 ADP-ribose units. These concentrations of PAR polymers are within the range of polymer concentrations found in intact cells during NMDA excitotoxicity and N-methyl-N-nitro-N-nitrosoguanidine (MNNG) toxicity. PAR polymer fails to bind to Iduna-YRAA (FIG. 29). The homologous competitive binding curve for wild type Iduna analyzed by the Cheng-Prusoff equation provides a dissociation constant ($K_d$) for wild type Iduna of 12.0 nM. The observed $K_d$ is 10 times less than the PAR polymer concentration found after NMDA-induced excitotoxicity in cortical neurons. These results taken together indicate that Iduna is a high affinity and saturable PAR polymer binding protein at its WWE domain, and that the basic and hydrophobic amino acids YR located at position 156 and 157 are critical for PAR polymer binding.

Figure 30:
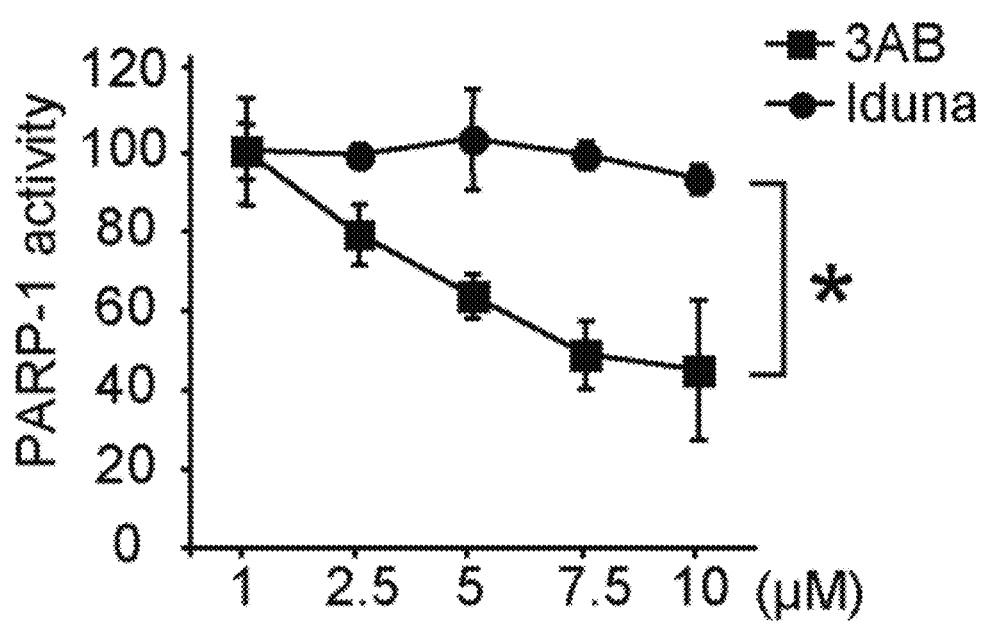
Figure 31:
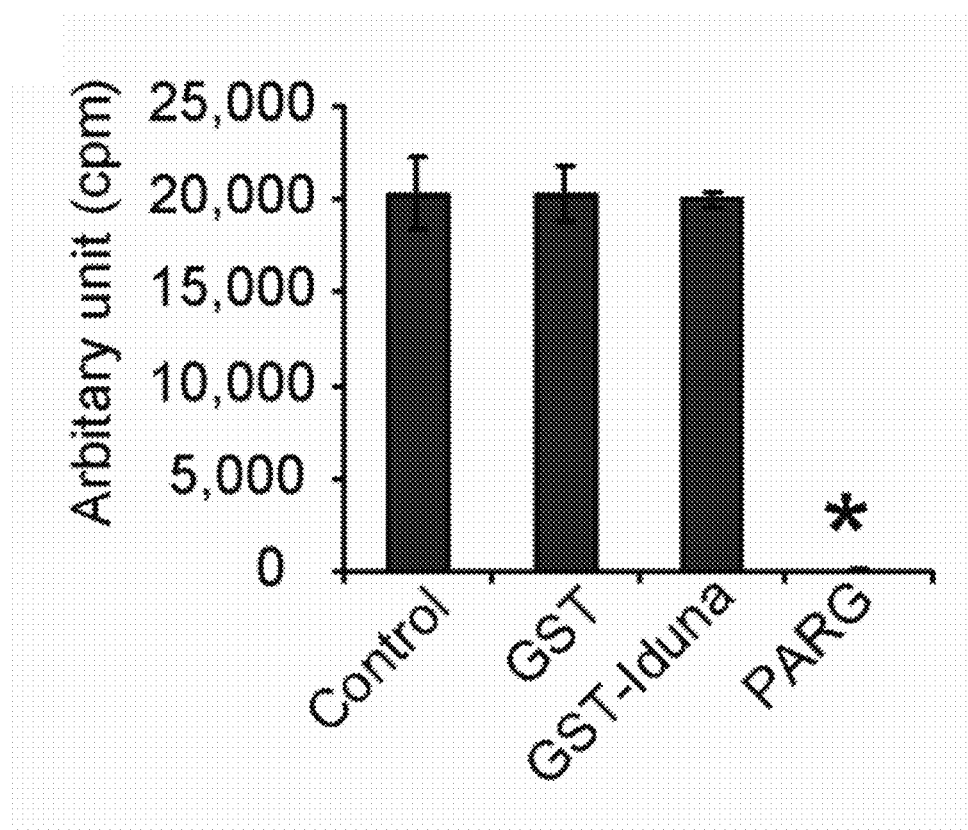

Because PARP-1 activation plays a prominent role in NMDA excitotoxicity we tested whether PARP-1 activity is directly affected by Iduna. PARP-1 activity was assessed by incorporation of biotinylated PAR onto histone proteins. The PARP-1 inhibitor 3-aminobenzamide (3-AB) inhibits PARP-1 activity, but Iduna has no effect (FIG. 30). Iduna also fails to inhibit PARP-1 catalytic activity as assessed by $^{32}$P-NAD incorporation into radiolabeled PAR polymer (FIG. 31). Thus, Iduna does not inhibit PARP-1 catalytic activity, and is a PAR binding protein that acts downstream of PARP-1 activation.

Figure 32:
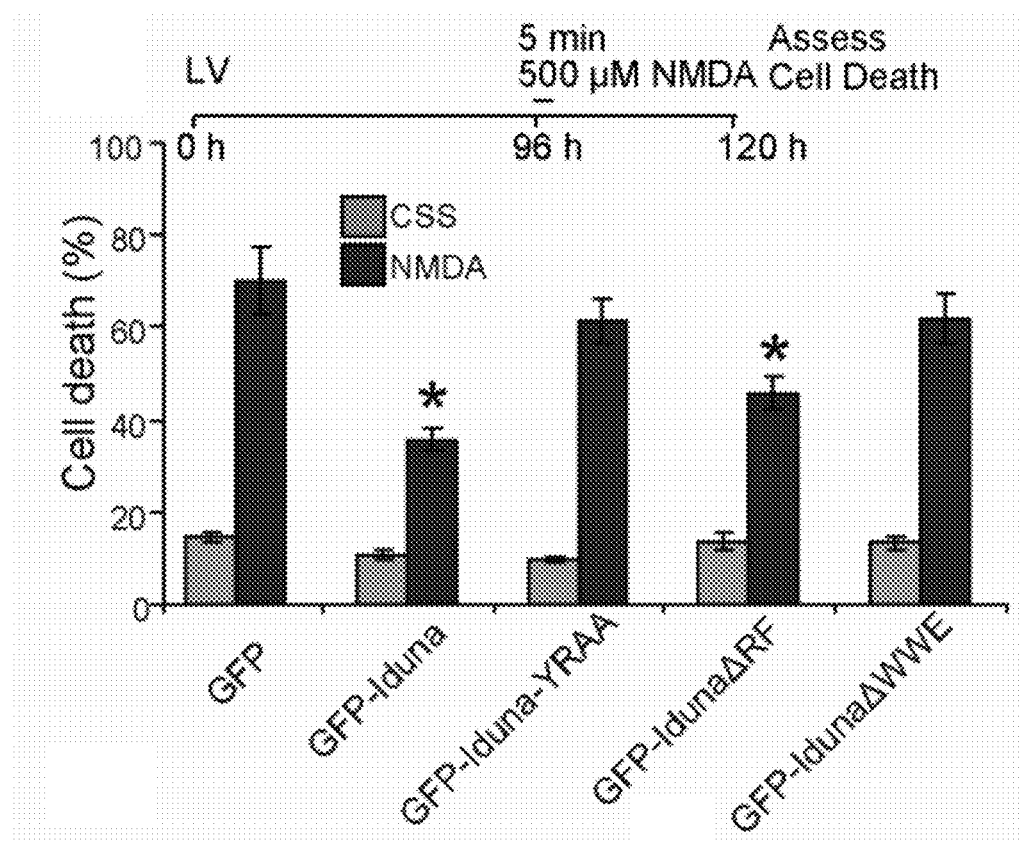
FIGS. 32, 33, 36 and 39-41—Illustrate that the PAR-binding property of Iduna mediates neuroprotection.
Figure 33:
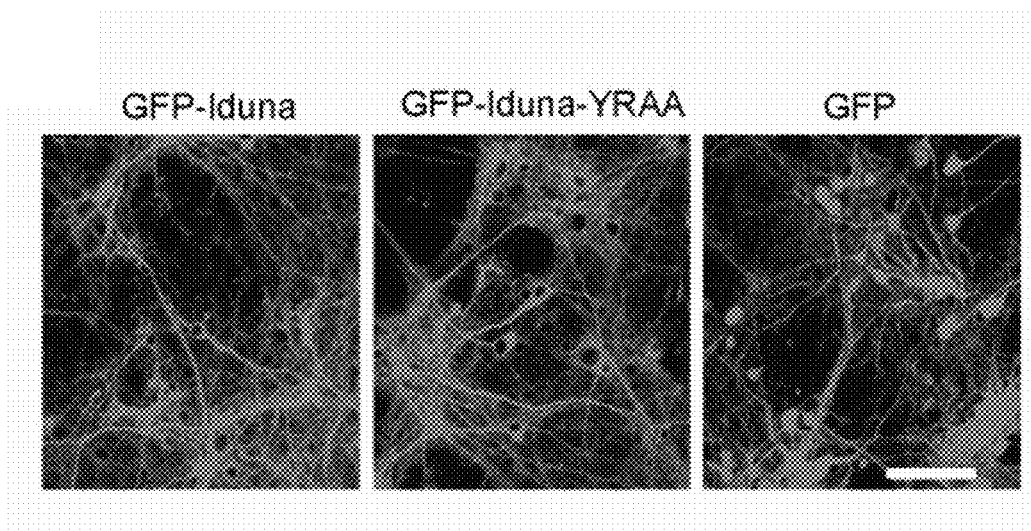
Figure 34:
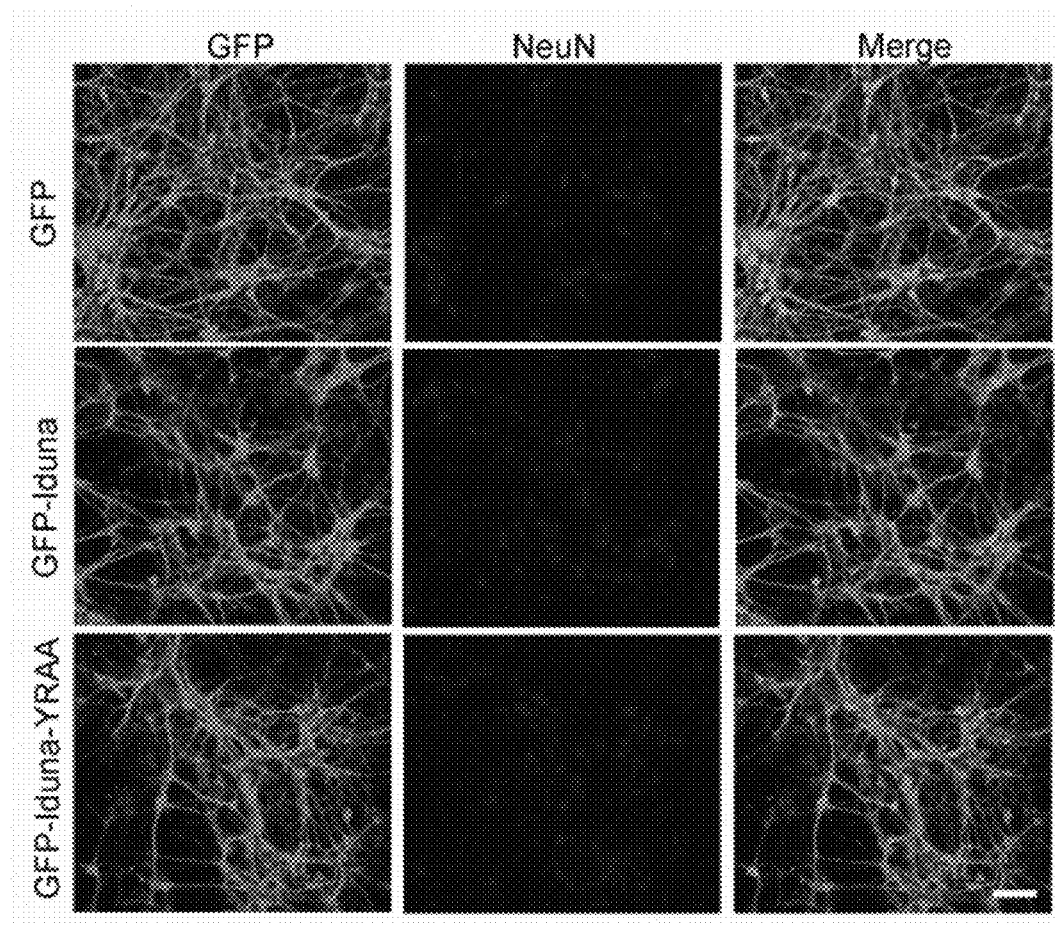
FIGS. 34 and 35—Lentiviral Expression of Iduna.
Figure 35:
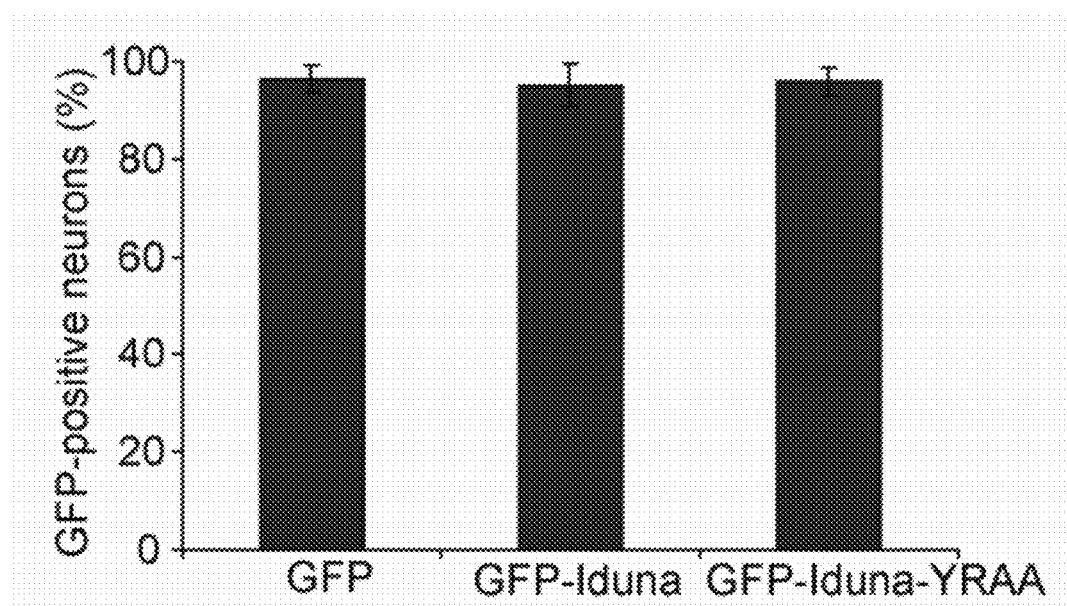
Figure 36:
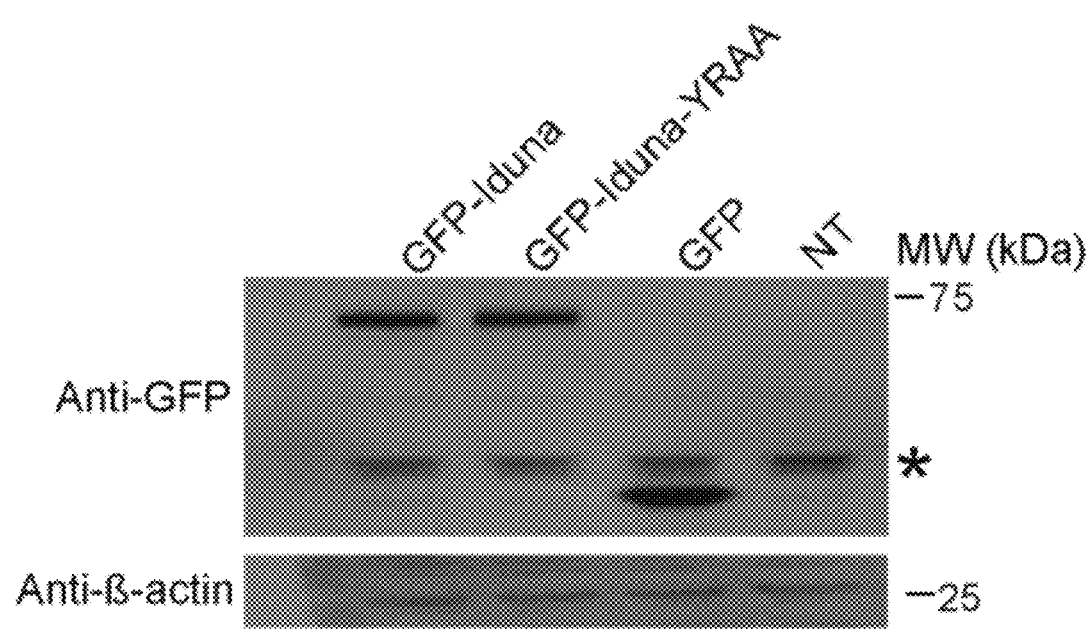
Figure 37:
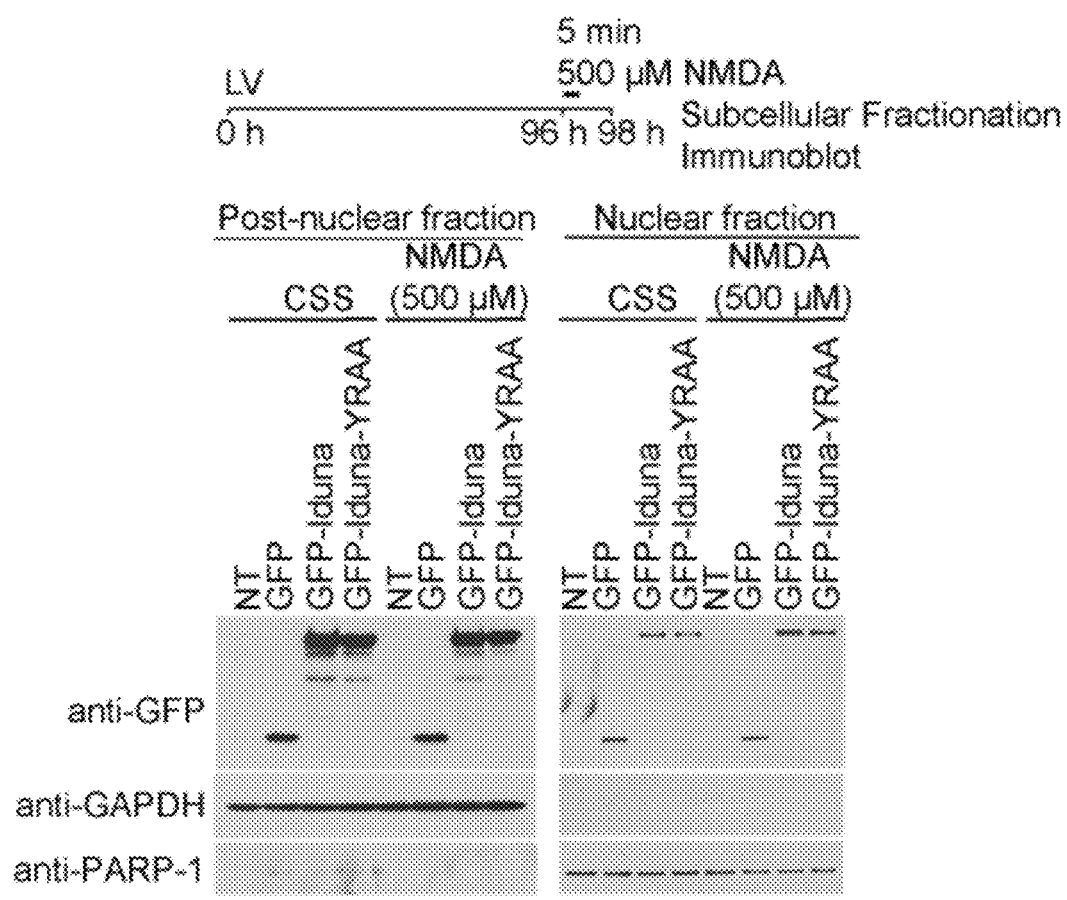
FIGS. 37 and 38—Iduna is predominantly a cytosolic protein.
Figure 38:
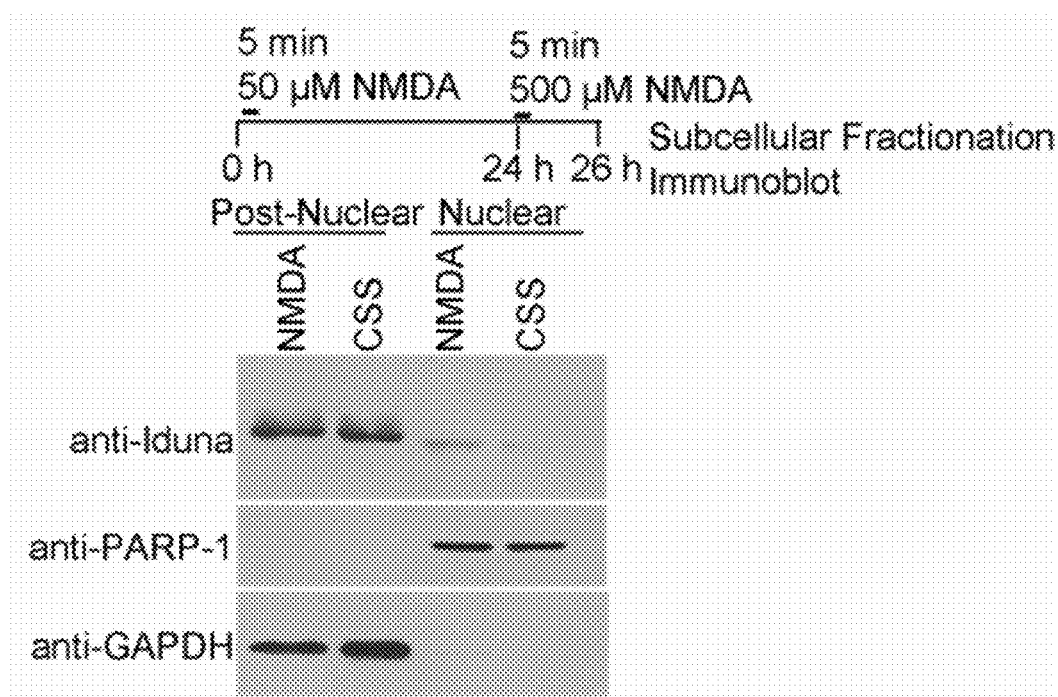
Figure 39:
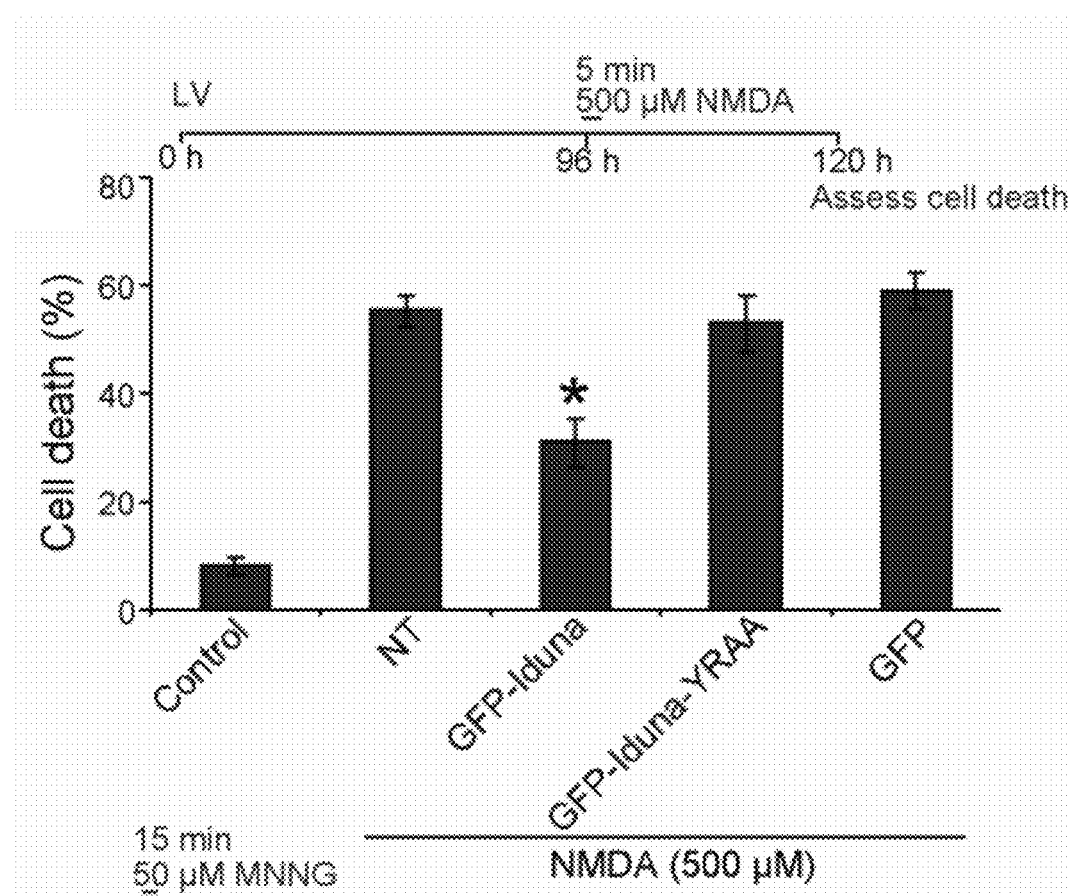
Figure 40:
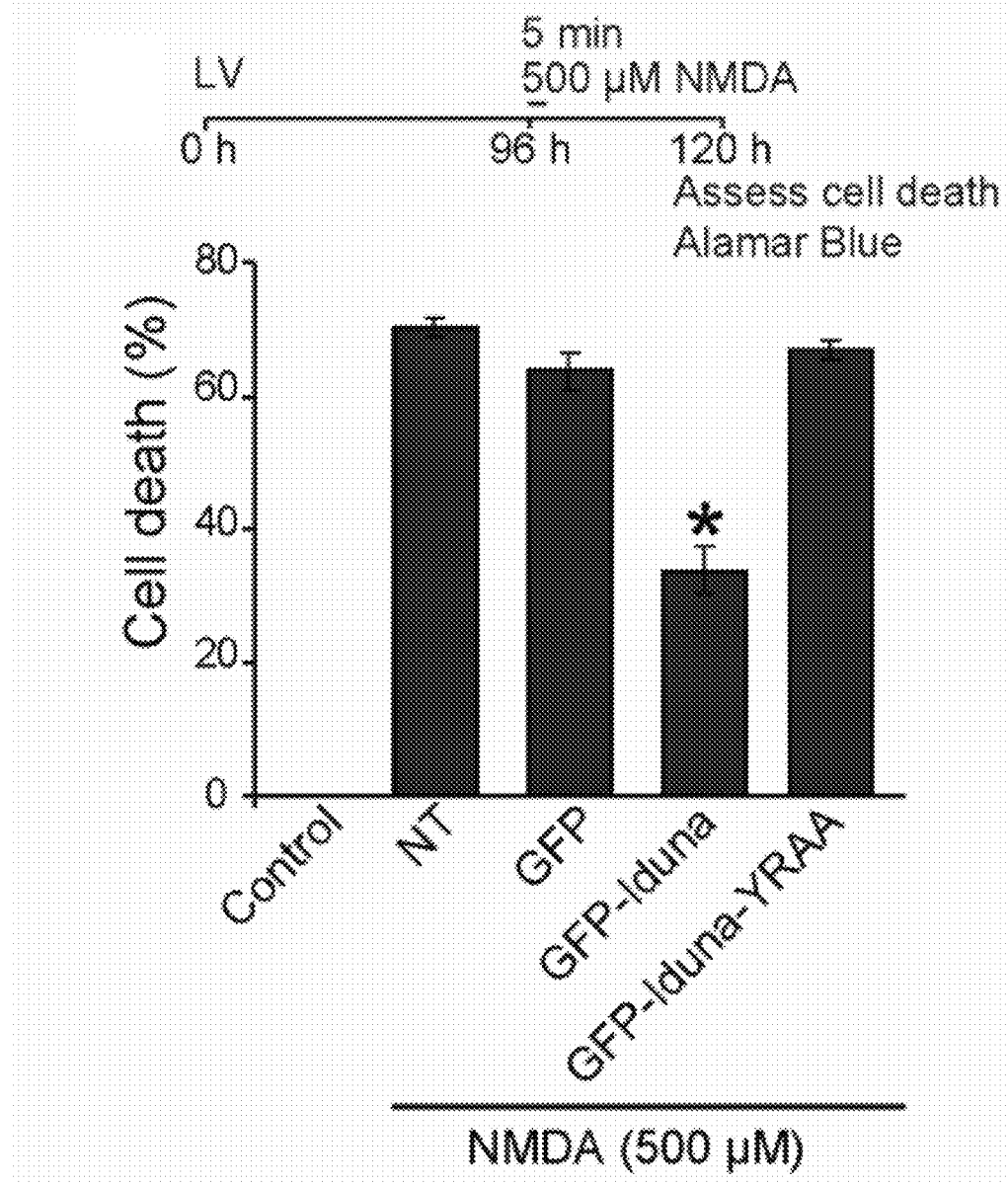
Figure 41:
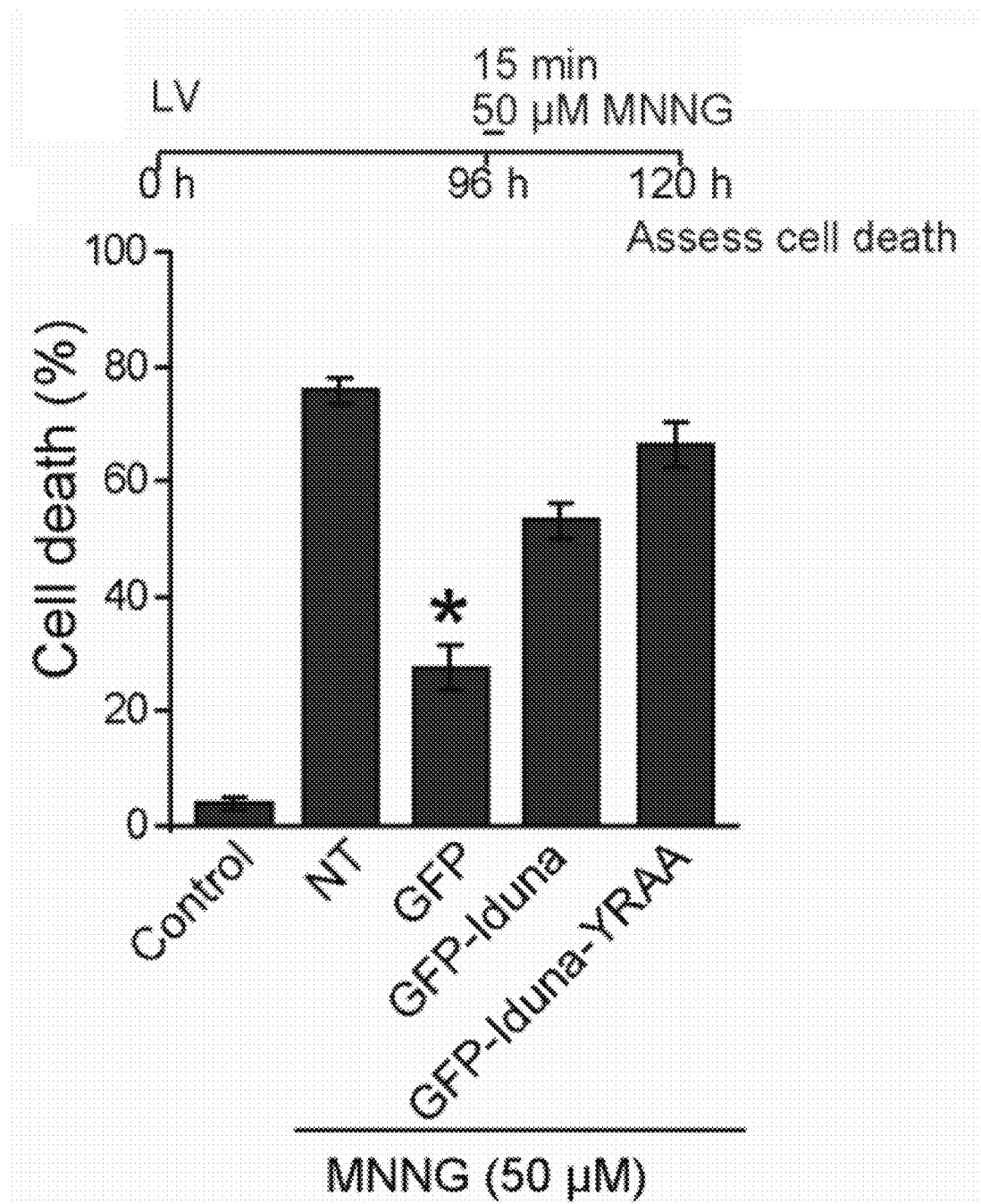
Figure 42:
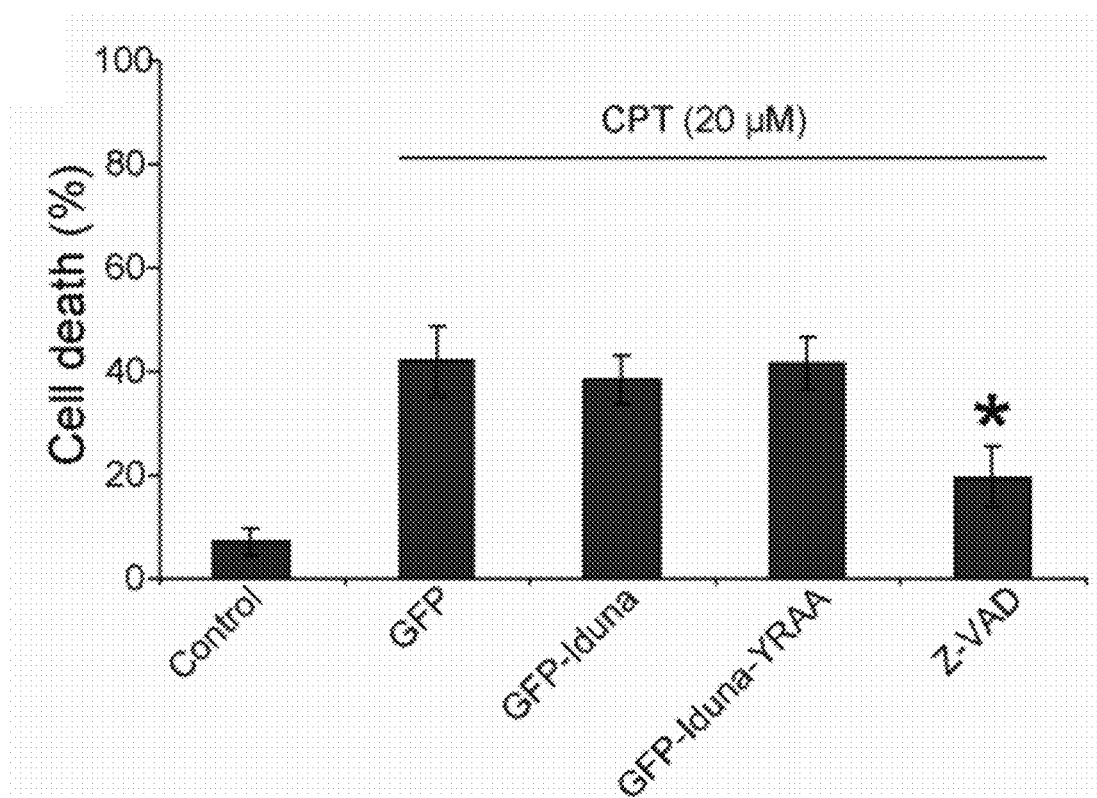
FIGS. 42 and 43—Iduna is ineffective against caspase-dependent cell death.
Figure 43:
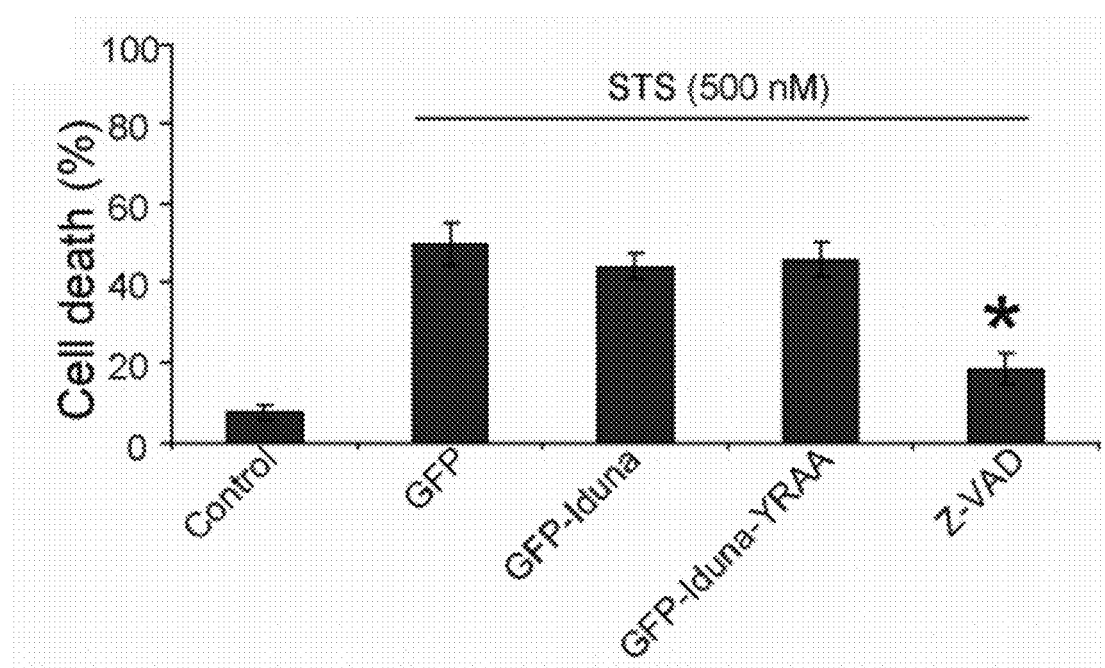
Figure 44:
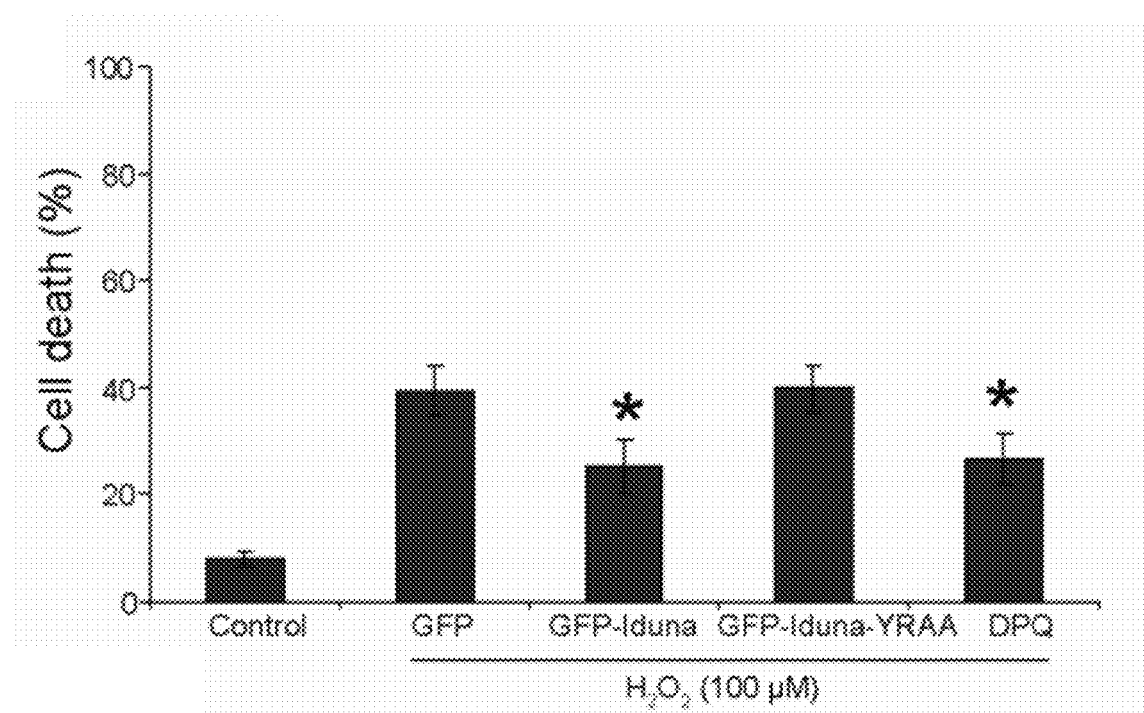
FIGS. 44 and 45—Iduna protects against peroxide-induced cell death in primary neurons. Primary neuronal cultures were transduced with lentiviruses expressing GFP, GFP-Iduna or GFP-Iduna-YRAA. 4 days following lentiviral transduction, cultures were treated with H2O2 (100 µM or 500 µM) and cell death assessed 24 h later using PI and Hoechst staining.
Figure 45:
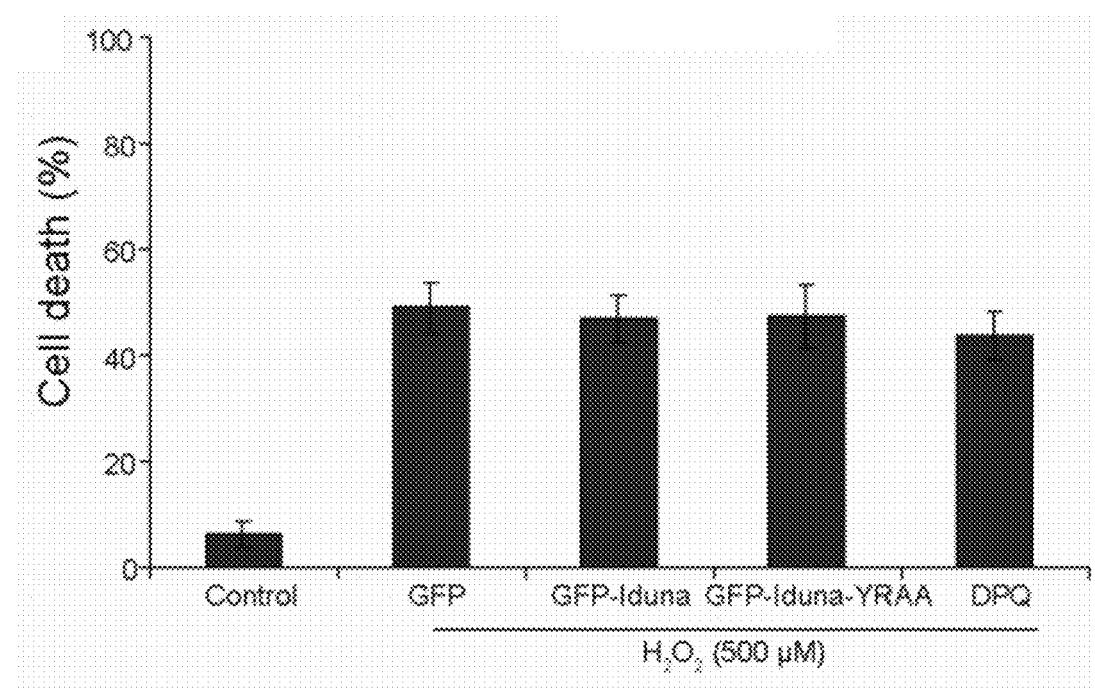

To ascertain whether the binding of Iduna to PAR polymer effects the neuroprotective actions of Iduna against NMDA excitotoxicity and parthanatos, neuronal cultures were transiently transfected with GFP-tagged-Iduna and GFP-tagged-Iduna mutants (FIG. 32). Both GFP-Iduna and GFP-IdunaΔRF, which contain the PAR-binding domain, prevent NMDA excitotoxicity whereas GFP-IdunaΔWWE and GFP-Iduna-YRAA fail to protect against NMDA excitotoxicity (FIG. 32). Because transient transfections are effective in only a small population of neurons, lentiviral expression of GFP, GFP-Iduna or GFP-Iduna-YRAA was used in neuronal culture with an efficiency greater than 95% (FIGS. 33-35). Equivalent levels of GFP-Iduna and GFP-Iduna-YRAA protein are expressed (FIG. 36) with primarily cytoplasmic localizations similar to endogenous Iduna as determined by confocal microscopy and subcellular fractionation (FIGS. 33, 37 and 38). A small amount of endogenous Iduna and lentiviral expressed GFP-Iduna and GFP-Iduna-YRAA seem to translocate to the nucleus after an excitotoxic dose of NMDA (500 µM) (FIGS. 37 and 38). Thus, we cannot exclude the possibility of a contributory effect of Iduna's translocation to the nucleus. However, because Iduna is a primarily a cytosolic protein, and the protective actions of Iduna do not require an interaction with PARP-1 (see FIGS. 30 and 31), it is likely the protective effects occur in the cytoplasm. Because PAR exits the nucleus to mediate its toxicity, the actions of Iduna in the cytoplasm may be important for the regulation of cell viability. Overexpression of GFP-Iduna protects neuronal cultures against NMDA excitotoxicity, whereas GFP-Iduna-YRAA or GFP fail to provide neuroprotection (FIGS. 12 and 39). Similar results were obtained using Alamar Blue reduction to assess cell viability (FIG. 40). Iduna overexpression also protects neuronal cultures against a lower excitotoxic dose of NMDA (100 µM for 5 min) (cell death %: NT 44.2±3.2, Iduna 23.0±1.8). To determine whether Iduna protects against other forms of parthanatos, cortical neurons were exposed to the DNA alkylating agent and PARP-1 activator, MNNG under conditions where MNNG toxicity is PARP-1 dependent (MNNG, 50 µM for 15 min). Iduna protects neuronal cultures against MNNG-induced cell death whereas Iduna-YRAA or GFP fail to provide any protection (FIG. 41). Expression of GFP-Iduna or GFP-Iduna-YRAA has no effect against apoptotic cell death in neuronal cultures treated with staurosporine (STS, 500 nM) or camptothecin (CPT 20 µM). Both STS and CPT induce caspase-dependent cell death as the pan-caspase inhibitor z-VAD fmk inhibited cell death in neuronal cultures (FIGS. 42 and 43). In neuronal cultures treated with 100 µM or 500 µM $H_2O_2$, Iduna protects only against 100 µM $H_2O_2$, further indicating that Iduna-mediated protection is specific for PAR mediated cell death as the PARP inhibitor DPQ only protected against 100 µM $H_2O_2$ toxicity as well (FIGS. 44 and 45).

Figure 46:
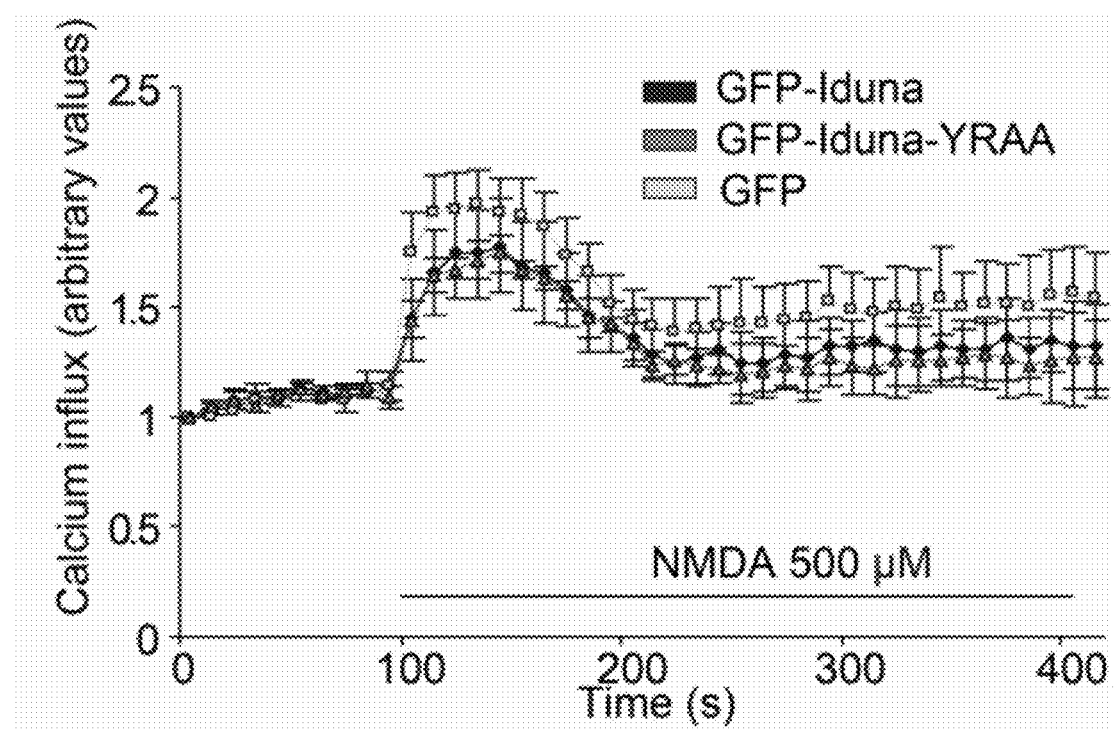
FIGS. 46, 47, 49-52, 55 and 56—Illustrate that Iduna does not interfere with NMDA-induced changes in $Ca^{2+}$ or mitochondrial $Ca^{2+}$ loading, but prevents AIF translocation and reductions in mitochondrial membrane potential ($\Delta\psi_m$).
Figure 47:
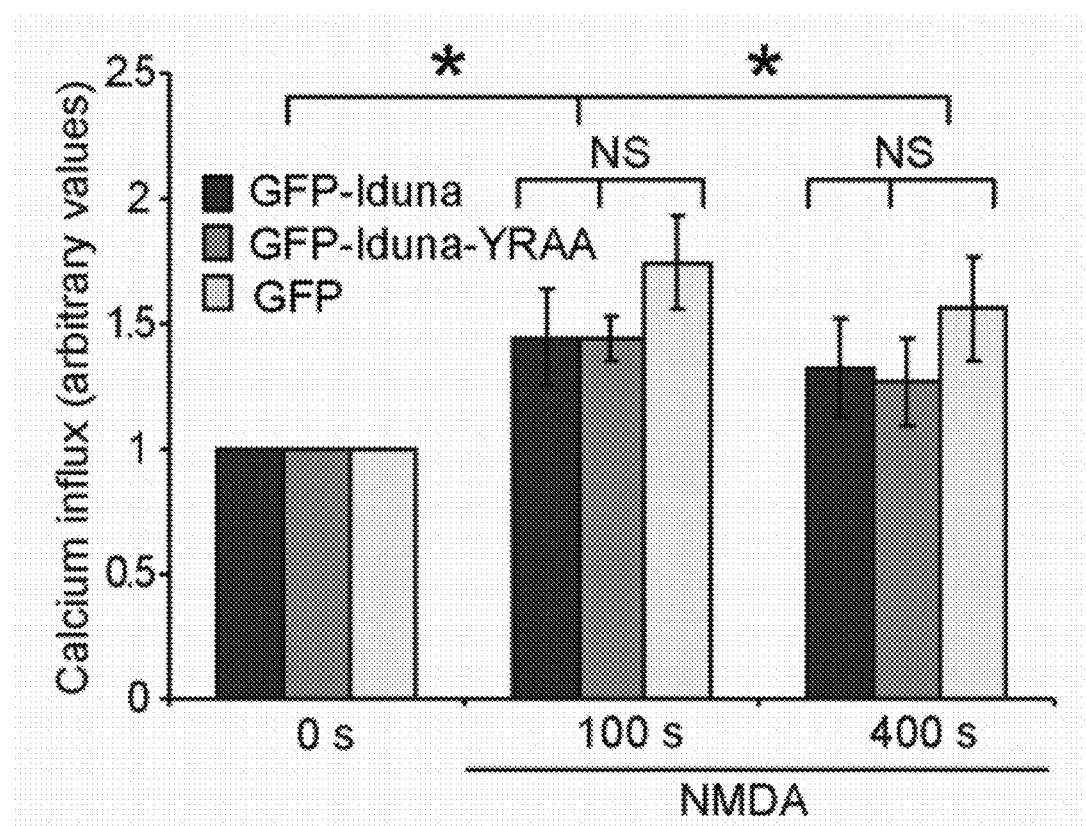
Figure 48:
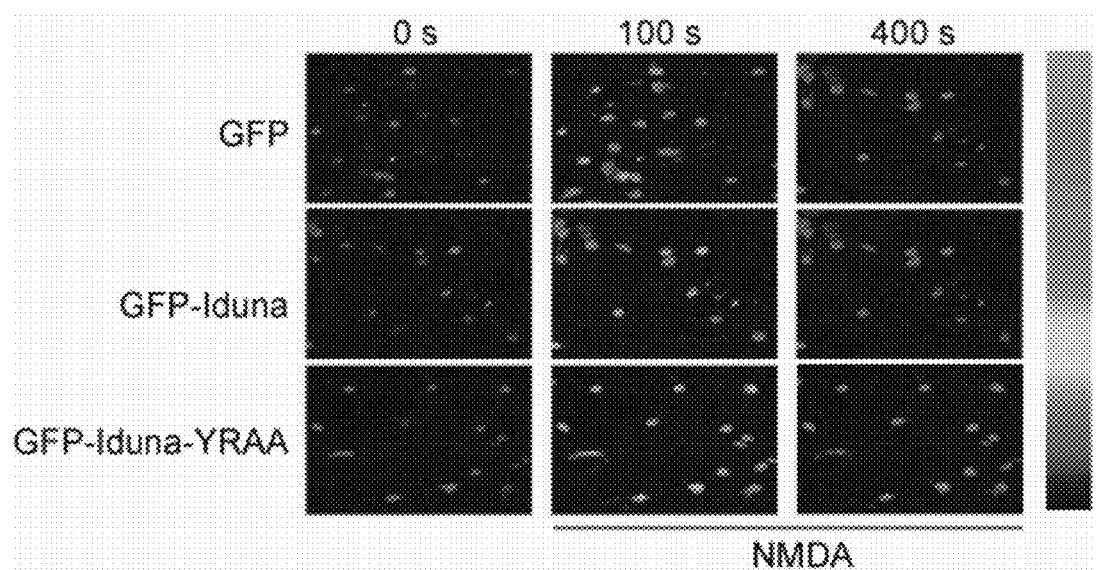
FIG. 48—Iduna does not interfere with NMDA-induced intracellular $Ca^{2+}$ influx. Primary cortical cultures were transduced with GFP, GFP-Iduna or GFP-Iduna-YRAA lentiviruses on DIV 10. On DIV 14, the cultures were loaded with the $Ca^{2+}$-sensitive fluorochrome fluo-5f (2.0 µM final concentration) and a time series of confocal imaging was recorded to monitor the fluorescence intensities. NMDA 500 µM was superfused in CSS for 5 min. Representative images of the fluo-5f-loaded cultures show NMDA-mediated $Ca^{2+}$ influx in cortical neurons. The pictures represent 0 s (before NMDA application), 100 s (at the time of NMDA application) and 400 s (after NMDA application) times points of image acquisition.
Figure 49:
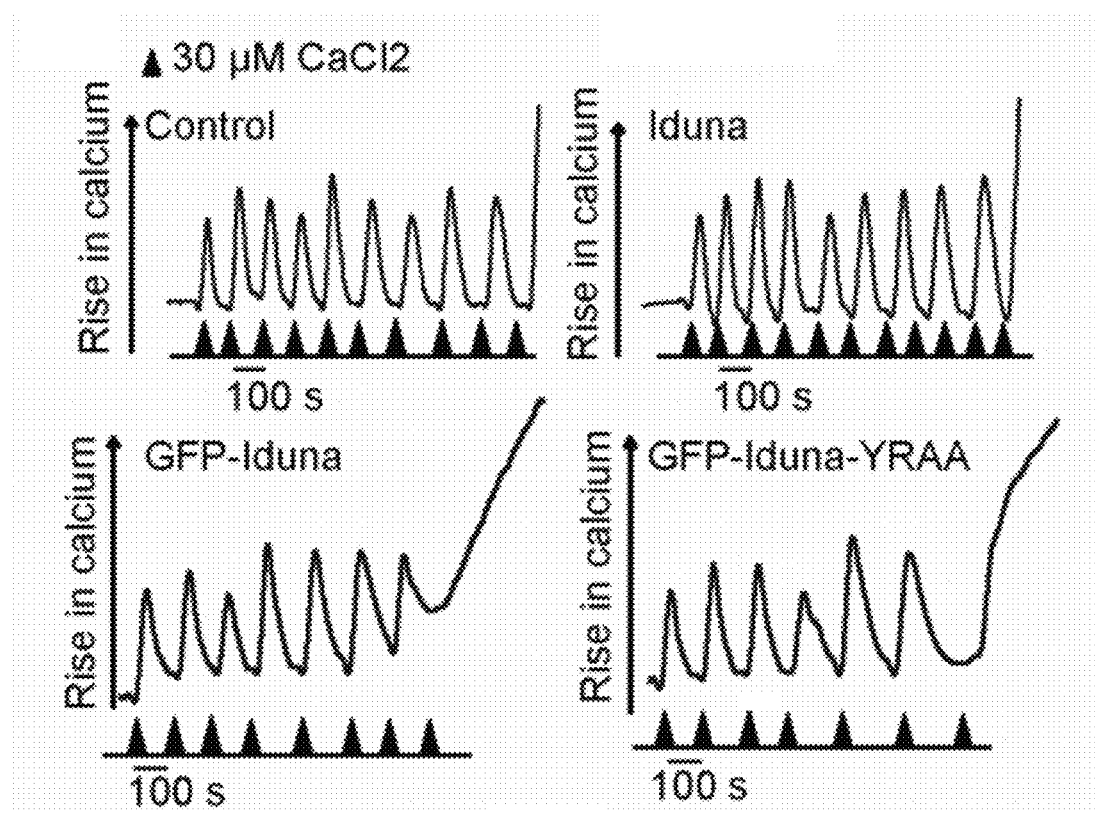

Iduna does not interfere with NMDA-induced intercellular calcium influx determined in neuronal cultures loaded with fluo-5F (Invitrogen). Live-cell calcium imaging captured using a confocal microscope (LSM-710, Carl Zeiss) observed following a 5 min application of NMDA is similar in neurons expressing Iduna, Iduna-YRAA or GFP (FIGS. 46-48). Iduna overexpression does not interfere with mitochondrial calcium uptake (FIG. 49). These results taken together indicate that the neuroprotection elicited by Iduna against NMDA excitotoxcity is not due to interference with NMDA-induced elevations of calcium.

Figure 50:
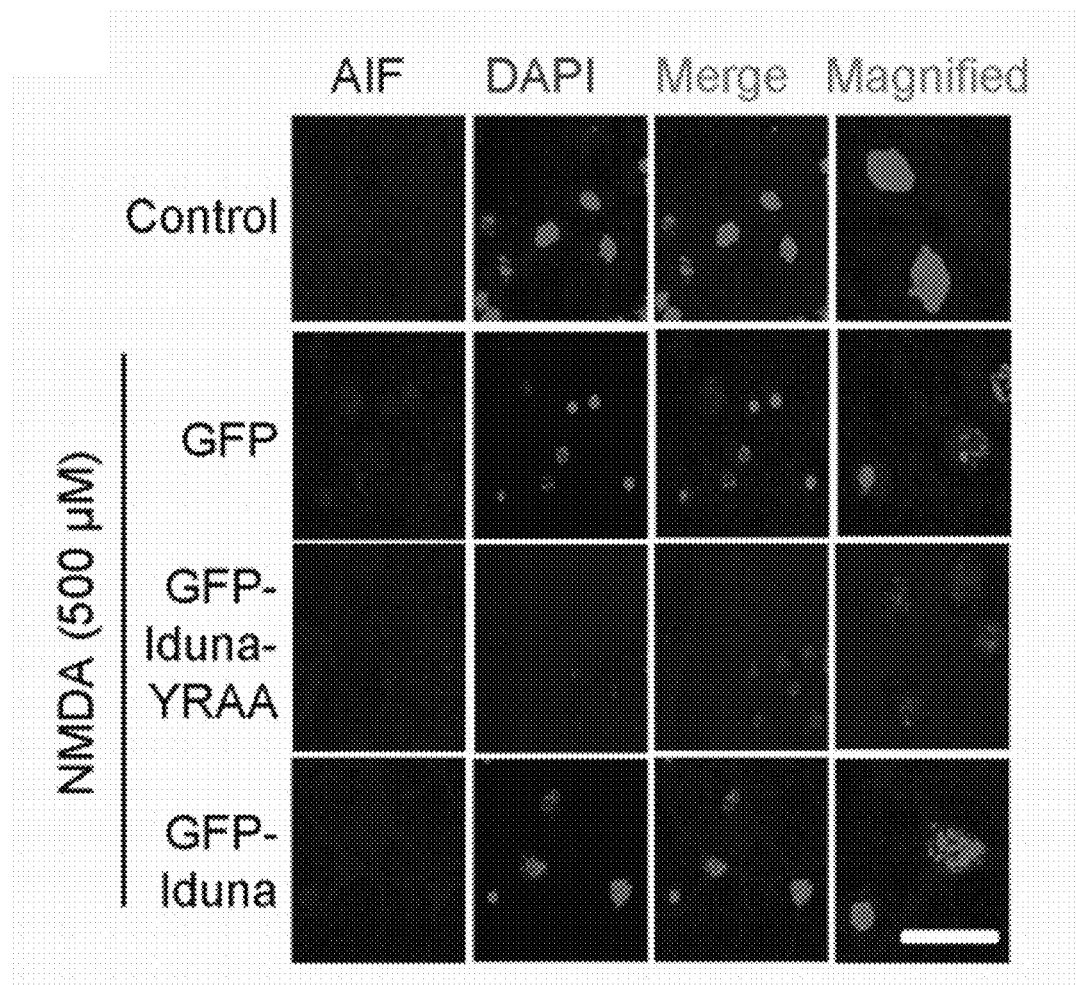
Figure 51:
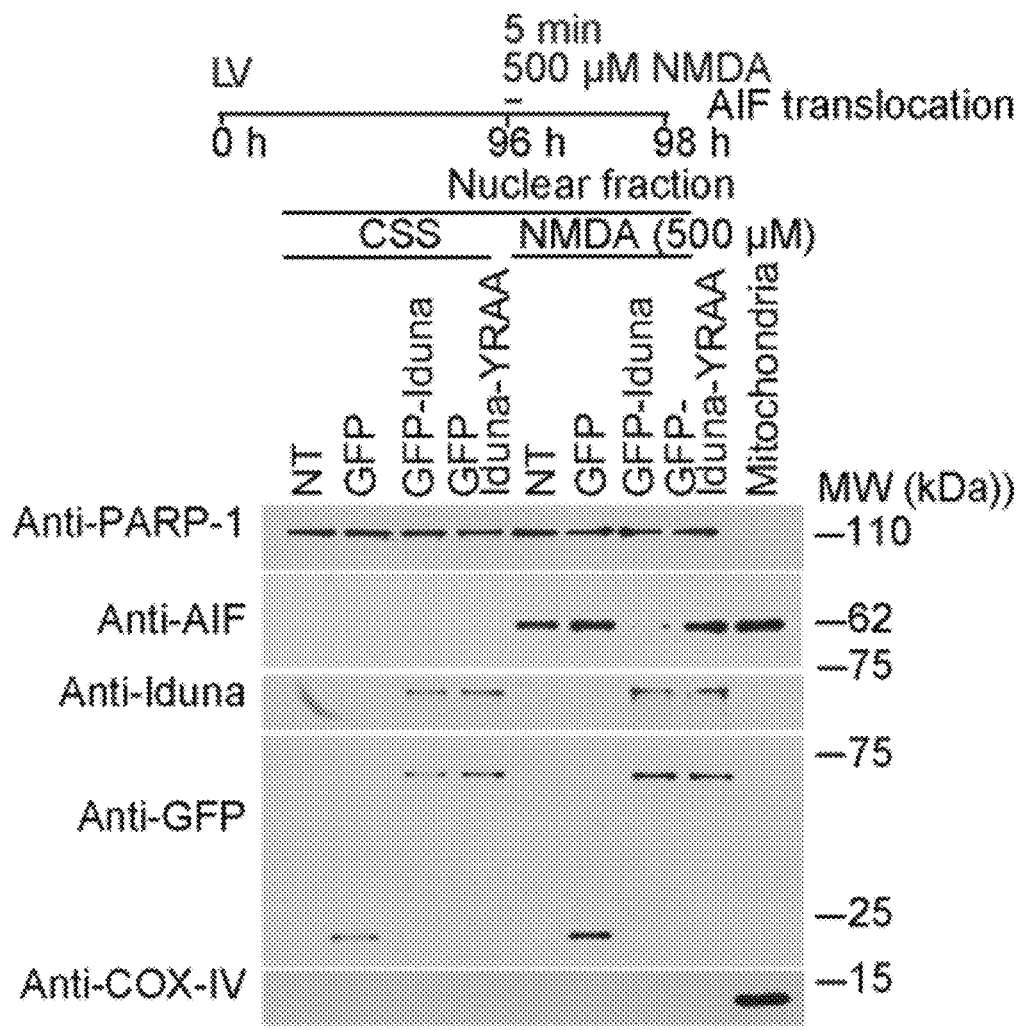
Figure 52:
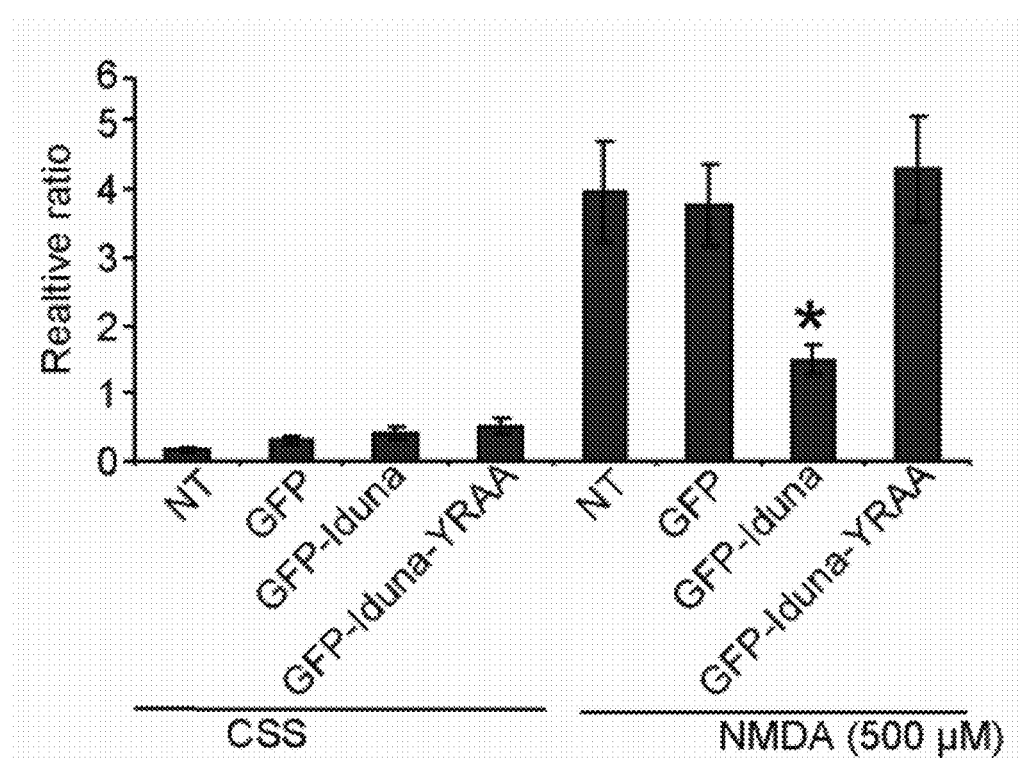
Figure 53:
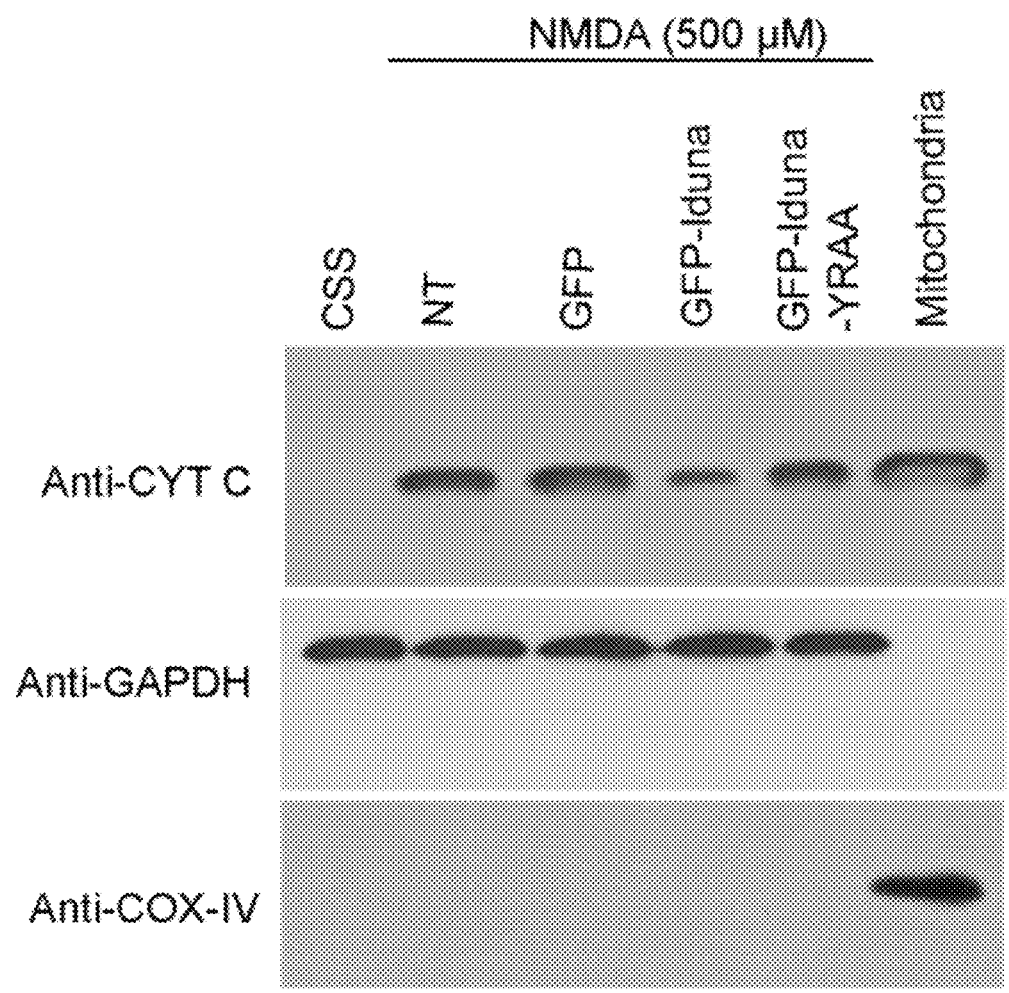
FIG. 53-54—Iduna reduces cytochrome c (CYT C) release after NMDA excitotoxicity.
Figure 54:
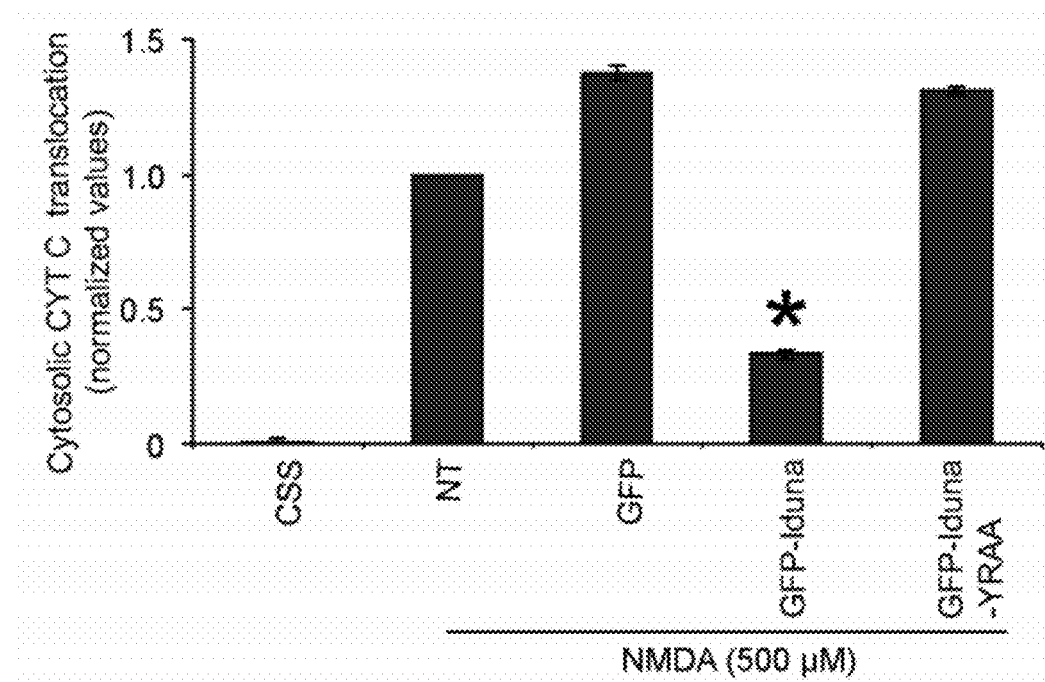

Parthanatos involves the translocation of apoptosis inducing factor (AIF) from the mitochondria to the nucleus following NMDA excitotoxicity. AIF translocation following excitotoxic NMDA treatment was monitored by immunohistochemistry and confocal microscopy (FIG. 50) and by immunoblot analysis of nuclear and mitochondrial subcellular fractions (FIG. 51). AIF translocates to the nucleus in GFP and Iduna-YRAA transduced neurons following NMDA excitotoxicity, whereas Iduna reduces the translocation of AIF (FIG. 52) comparable to the degree of neuroprotection afforded by Iduna overexpression. During parthanatos, cytochrome c is released from mitochondria long after AIF translocates to the nucleus, after 1-2 hours. Consistent with the protective effects of Iduna against parthanatos, we observe a reduction of cytochrome c translocation from mitochondria to the cytoplasm with Iduna overexpression compared to Iduna-YRAA or GFP (FIGS. 53 and 54).

Figure 55:
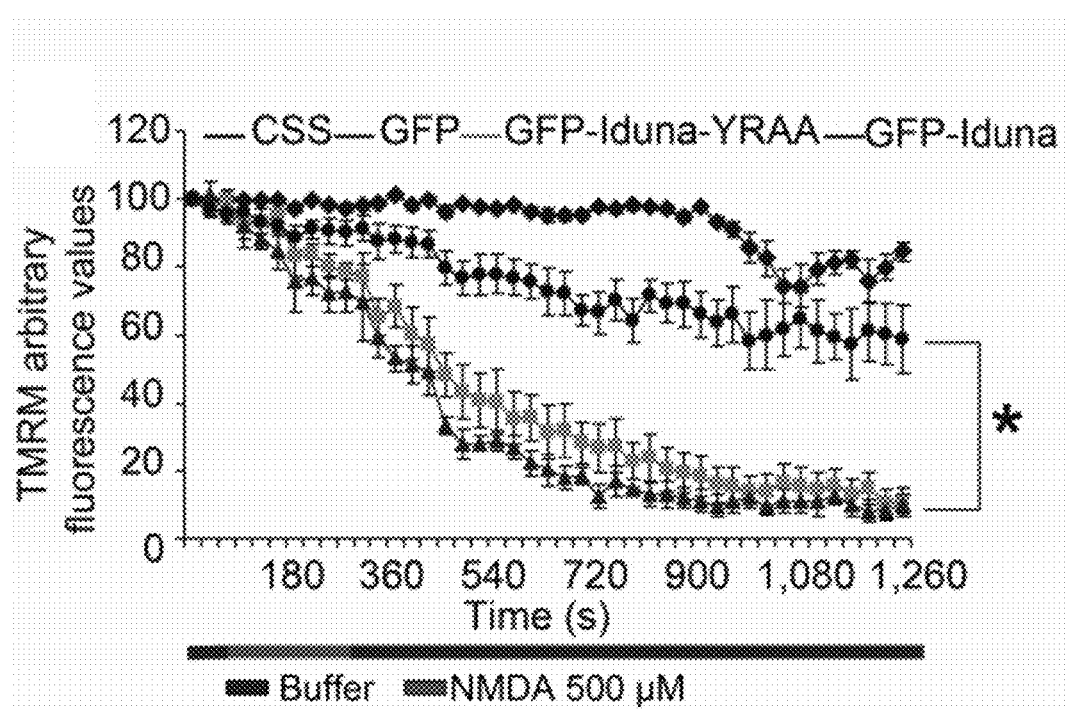
Figure 56:
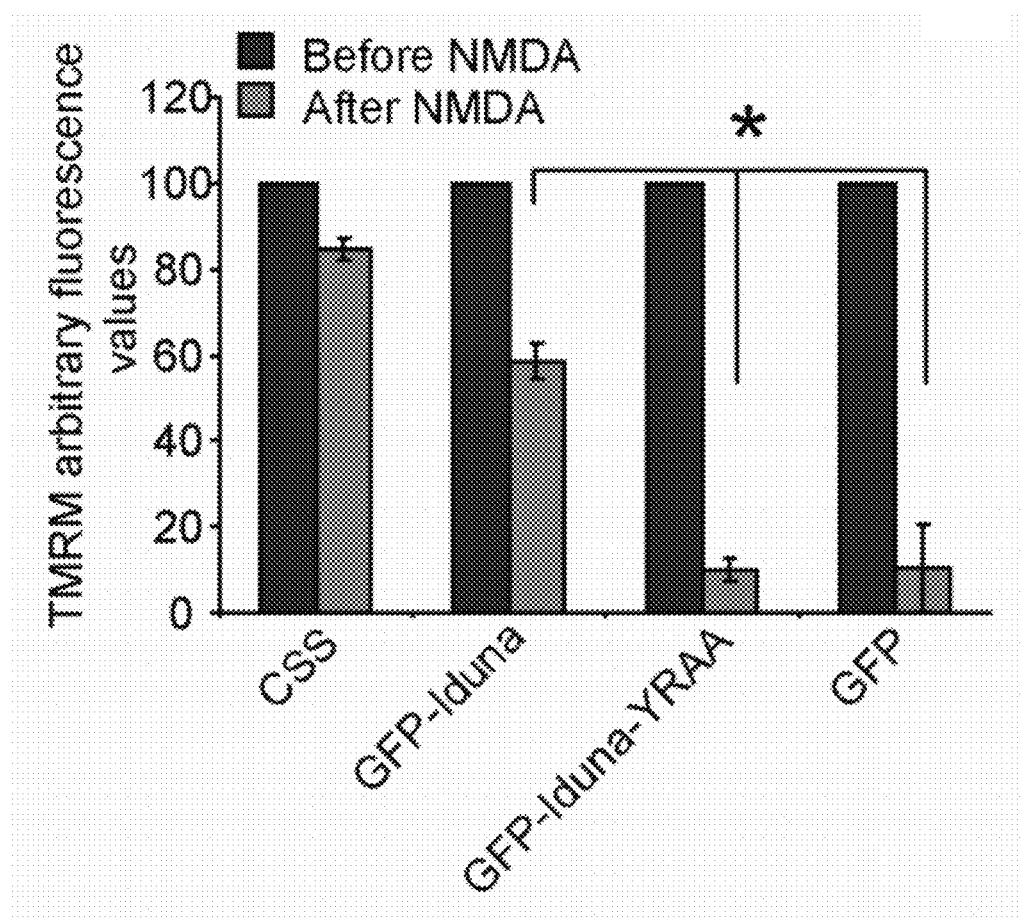
Figure 57:
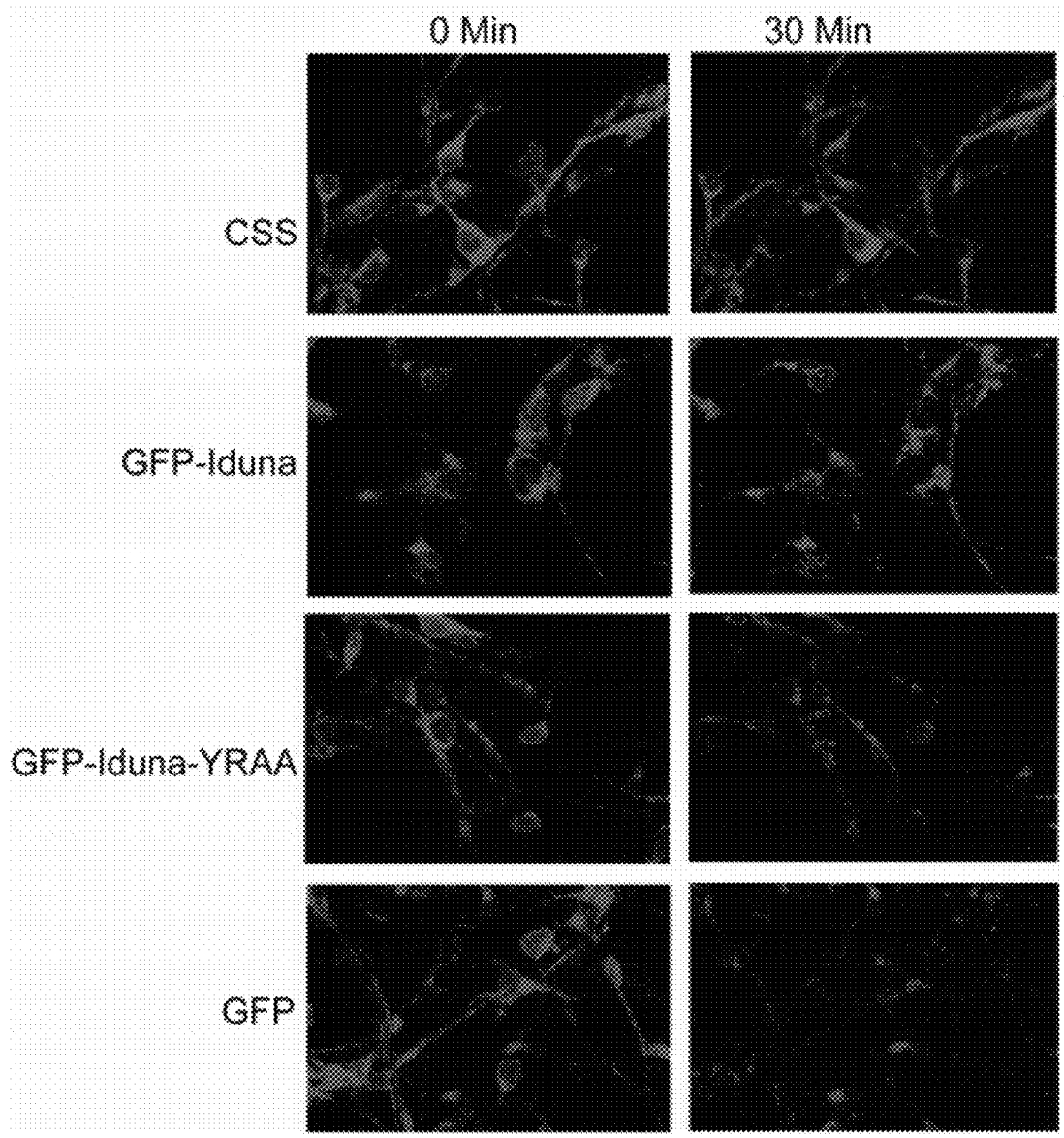
FIG. 57—Iduna protects against NMDA-induced loss of $\Delta\psi_m$ in mouse cortical neurons. Representative images of TMRM fluorescence before and after NMDA-application. Primary cortical neurons expressing GFP, GFP-Iduna or GFP-Iduna-YRAA were loaded with TMRM (100 nM) for 20 min and then live imaging was conducted for 20 min, using an LSM 5 Live confocal microscope (Carl Zeiss, Germany). NMDA-stimulation (500 µM for 5 min) leads to a substantial loss of $\Delta\psi_m$ (TMRM fluorescence) in mitochondria. Overexpression of Iduna in mouse cortical neurons protects against NMDA-induced loss of $\Delta\Psi_m$, whereas no protection was observed in Iduna-YRAA or GFP-expressing neurons.

Mitochondrial membrane potential ($\Delta\psi_m$) reduction accompanies the translocation of AIF during NMDA excitotoxicity. Overexpression of Iduna prevents NMDA induced loss of $\Delta\psi_m$ as monitored by TMRM fluorescence compared to Iduna-YRAA or GFP (FIGS. 55-57) similar to the reduction in AIF nuclear translocation and cell death. Taken together, these results indicate that Iduna prevents AIF translocation and reductions in $\Delta\psi_m$ in a PAR binding dependent manner.

Figure 58:
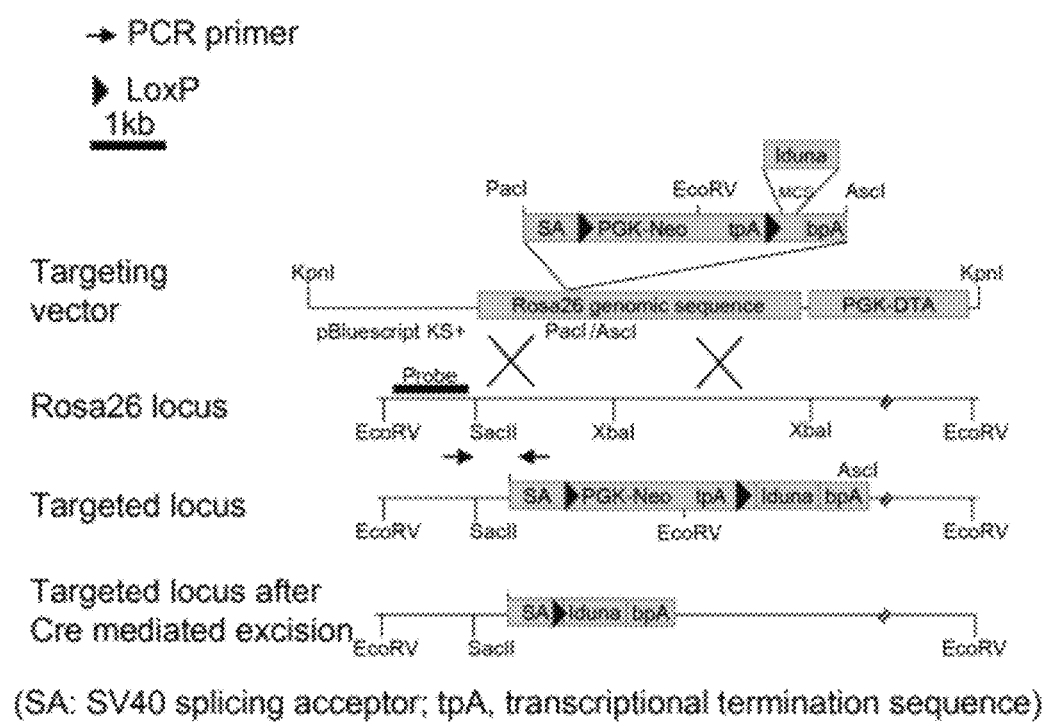
FIGS. 58-63, 65 and 66—Illustrate that Iduna is neuroprotective in vivo.
Figure 59:
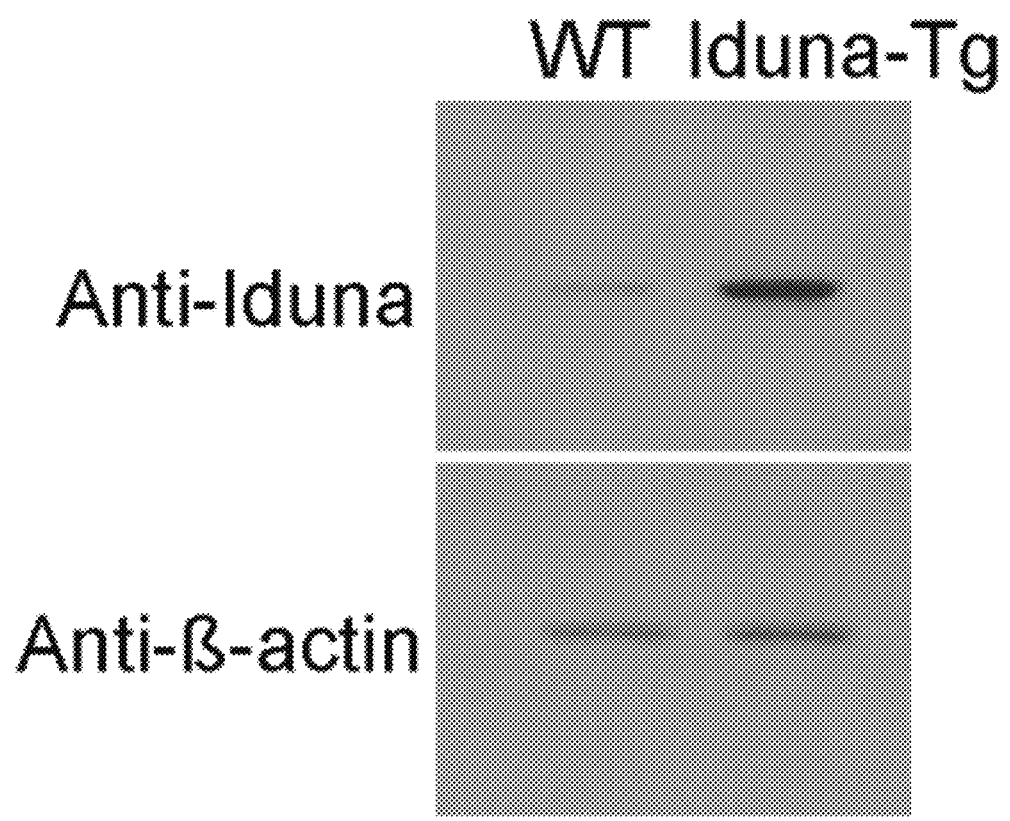
Figure 60:
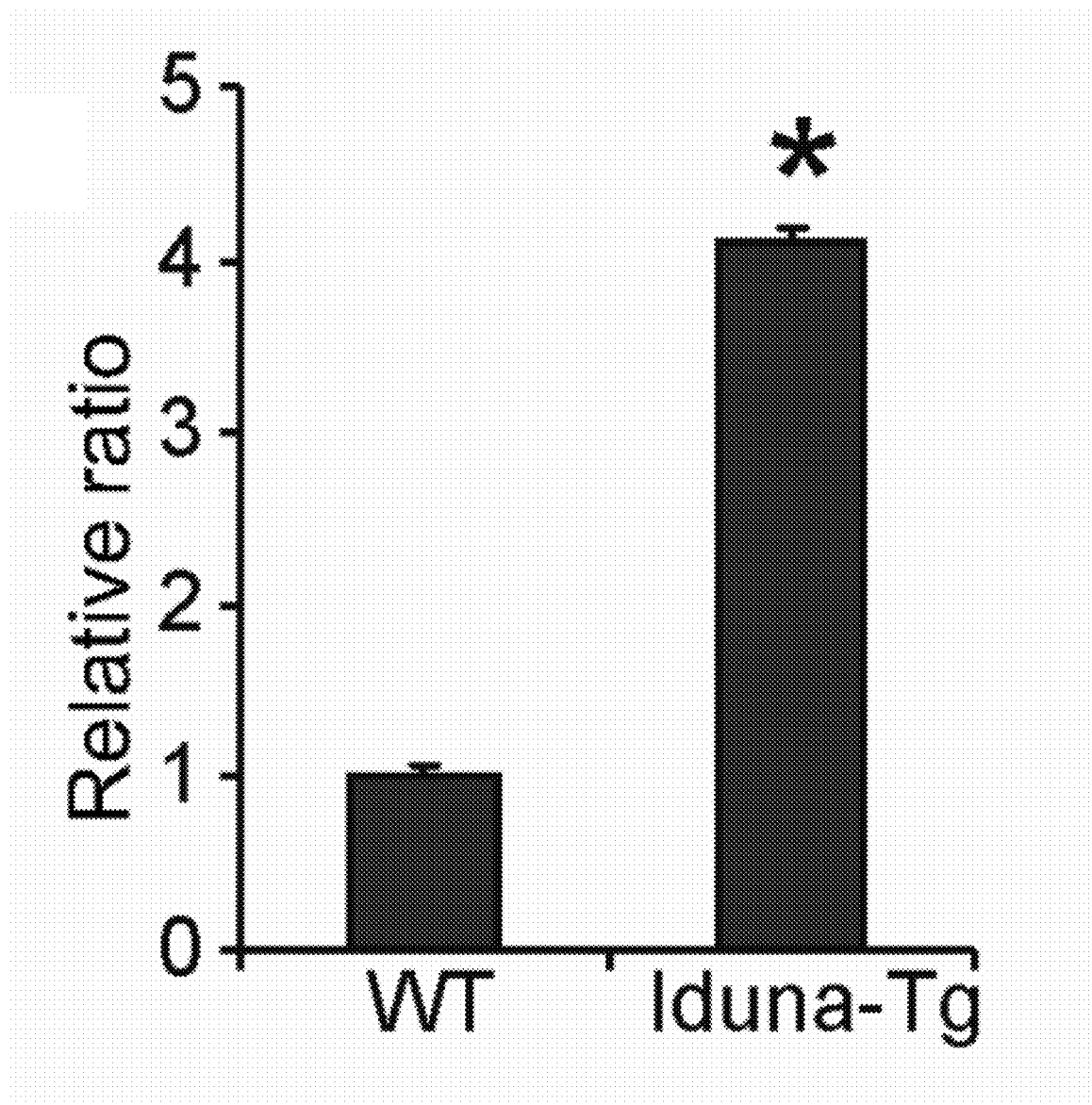
Figure 61:
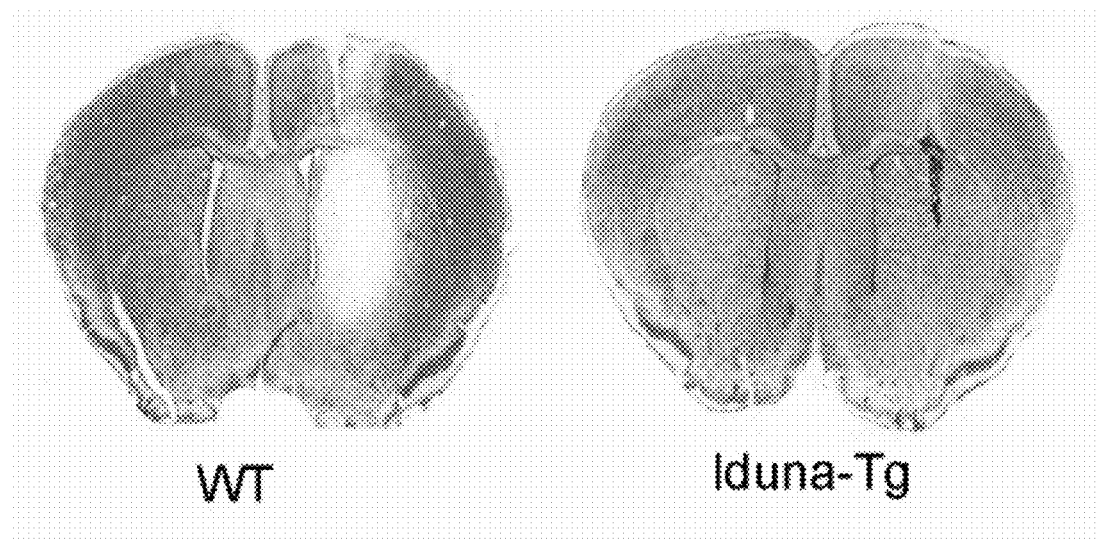
Figure 62:
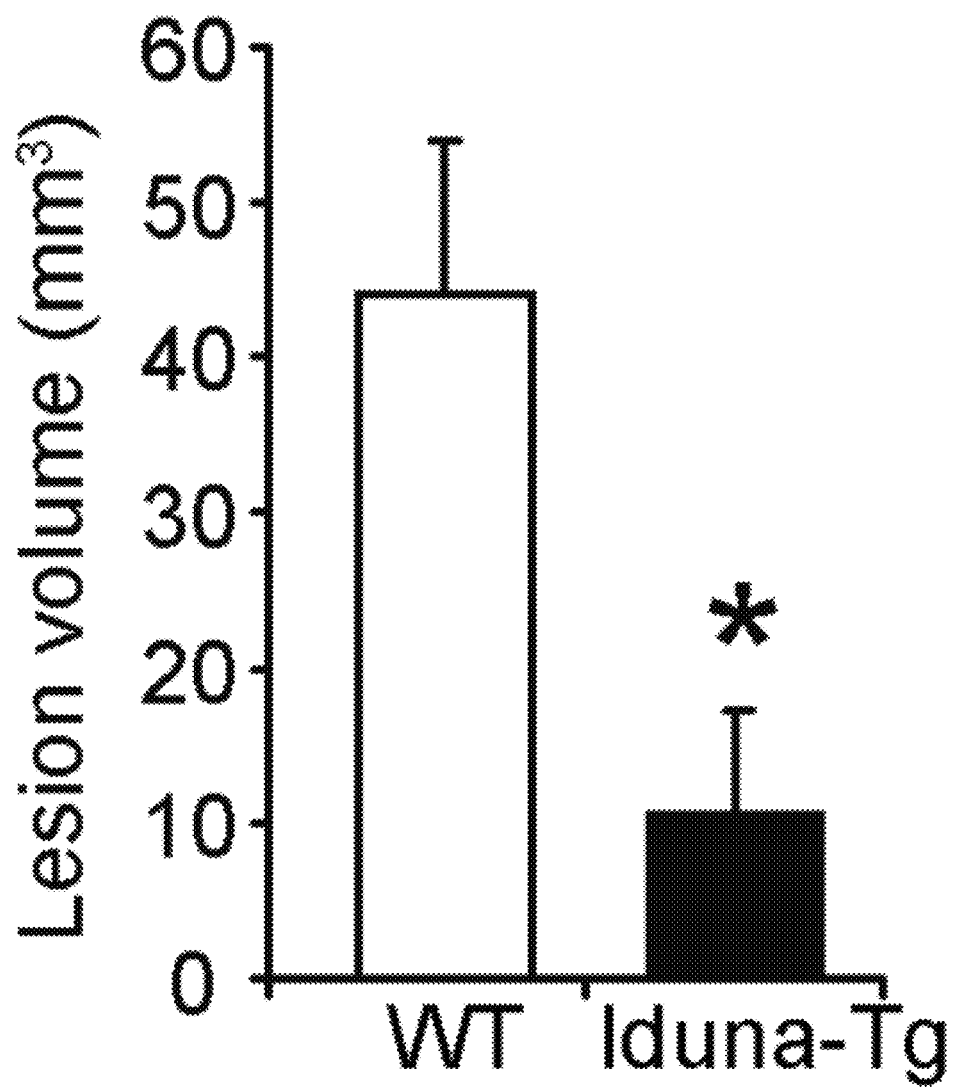

To determine whether Iduna is protective in vivo, transgenic mice overexpressing Iduna were generated by knocking in Iduna into the ROSA26 genomic locus resulting in a four-fold expression over wild type littermate mice (FIGS. 58-60). NMDA induced lesions are reduced by approximately 80% in the Iduna transgenic mice compared to littermate wild type control animals following an intrastriatal injection of NMDA (20 nmoles) (FIGS. 61 and 62).

Figure 63:
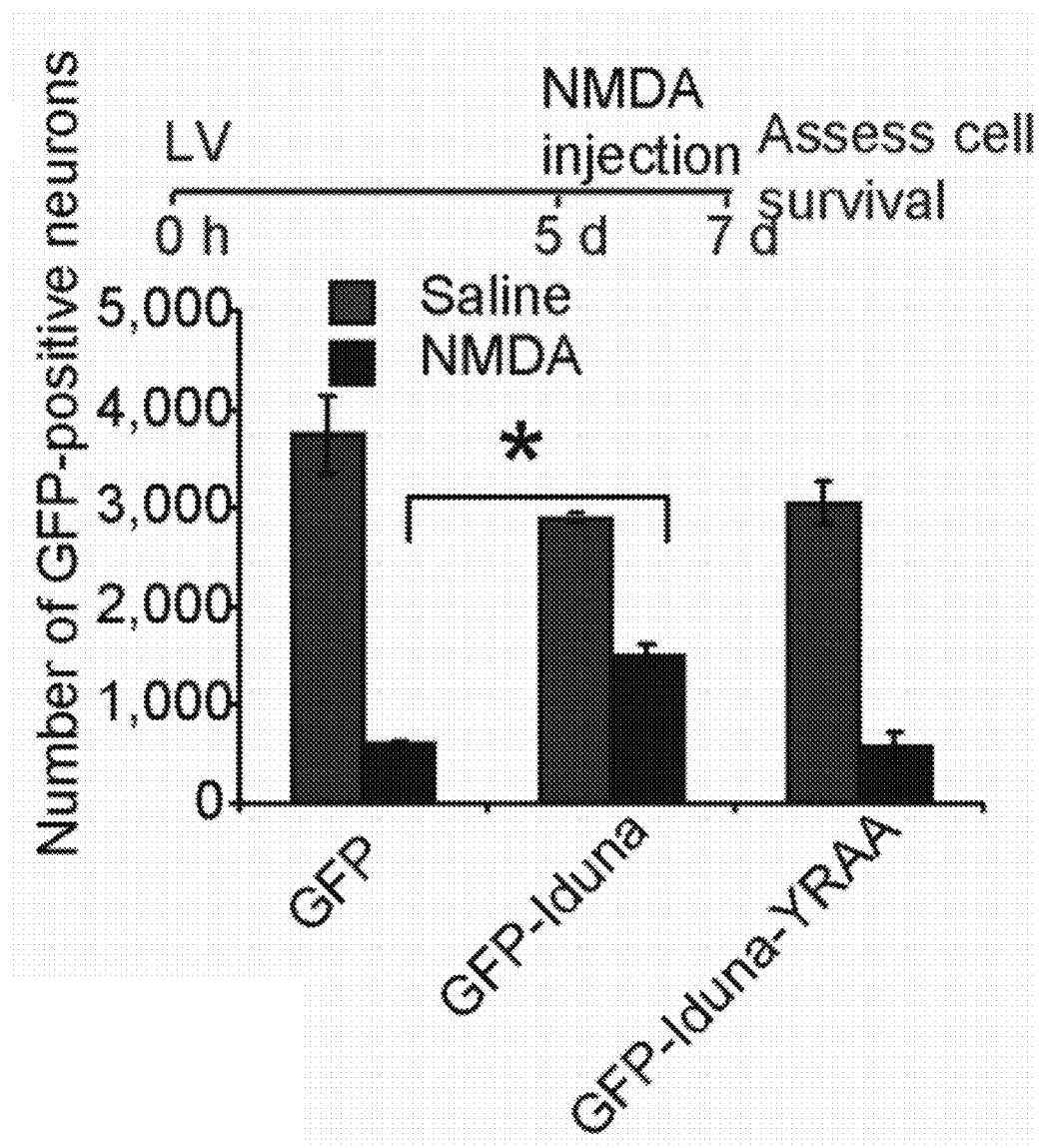
Figure 64:
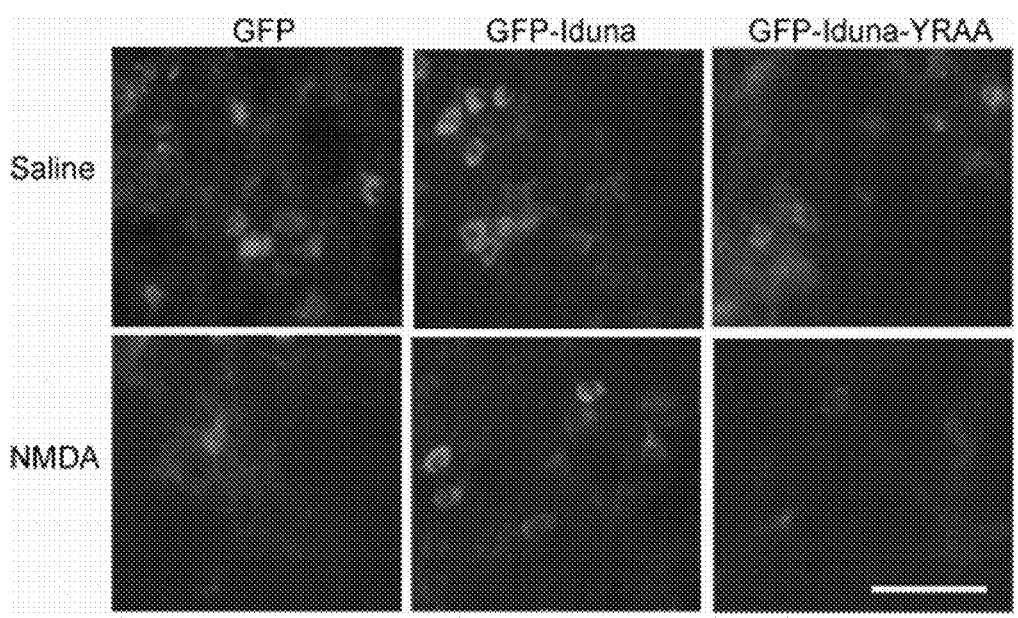
FIG. 64—Iduna protects against NMDA-induced neuronal loss in vivo. Representative pictures taken from striatum of 6 week old C57BL/6 mice showing expression of GFP, GFP-Iduna or GFP-Iduna-YRAA following lentivirus transduction. GFP positive cells are lost following injection of NMDA (20 nmoles) but not normal saline 5 days after lentiviral transduction. Magnification bar=50 µm.

Mice were injected stereotactically with GFP-Iduna, GFP-Iduna-YRAA or GFP lentiviruses, followed by intrastriatal injection of NMDA (20 nmoles) 5 days after viral injection. Cell survival was assessed by stereological cell counting of GFP-positive neurons in mouse brain sections 48 h after the NMDA injection. In GFP-injected animals, NMDA injection leads to a 90% loss of GFP positive cells whereas GFP-Iduna protects approximately 51% of the neurons against NMDA lesions (FIG. 63), similar to protection observed in vitro and in the Iduna transgenic mice. GFP-Iduna-YRAA is not able to protect against NMDA excitotoxic injections (FIGS. 63 and 64). These data indicate that either constitutive or acute overexpression of Iduna is neuroprotective in vivo. Moreover, Iduna mediated protection is dependent on PAR binding.

Figure 65:
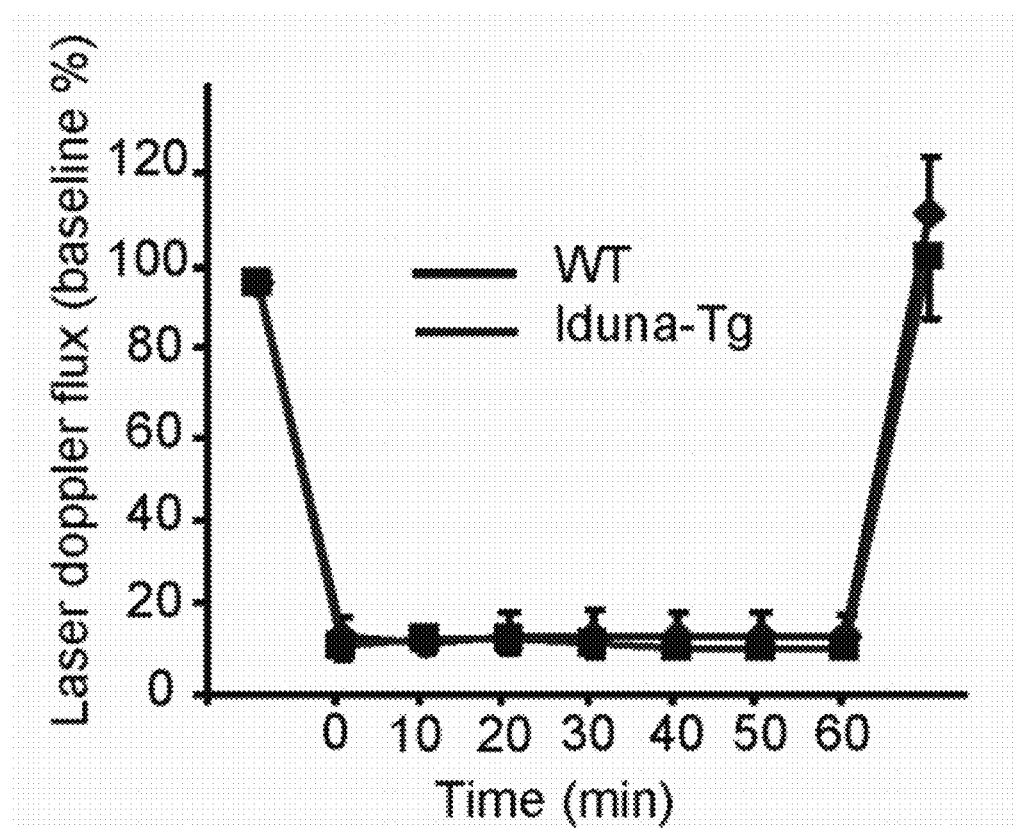
Figure 66:
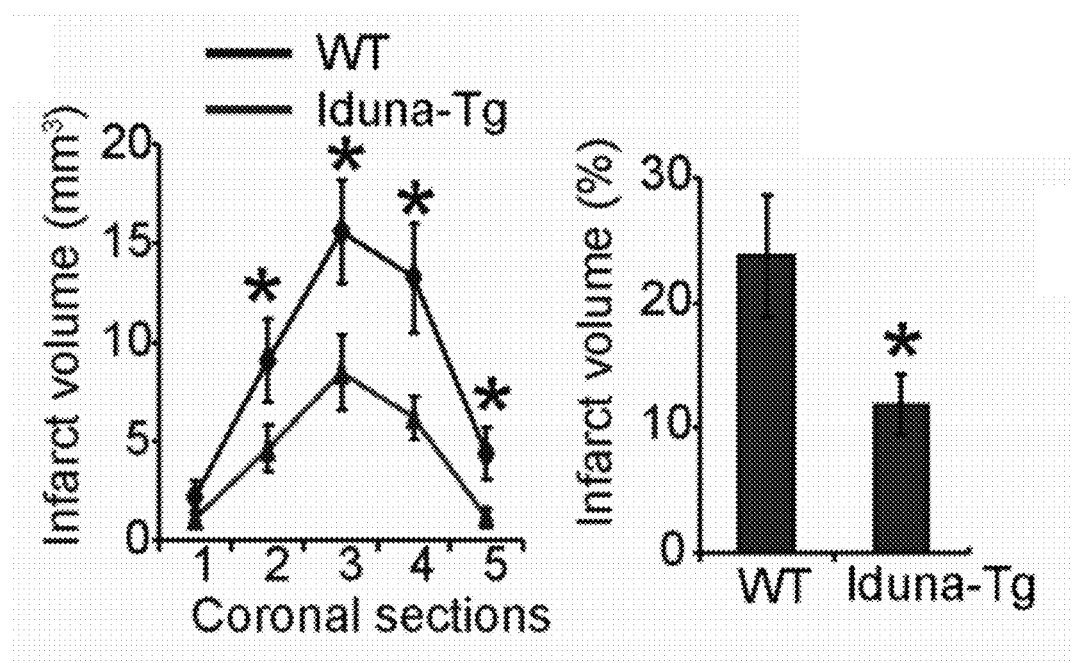
Figure 67:
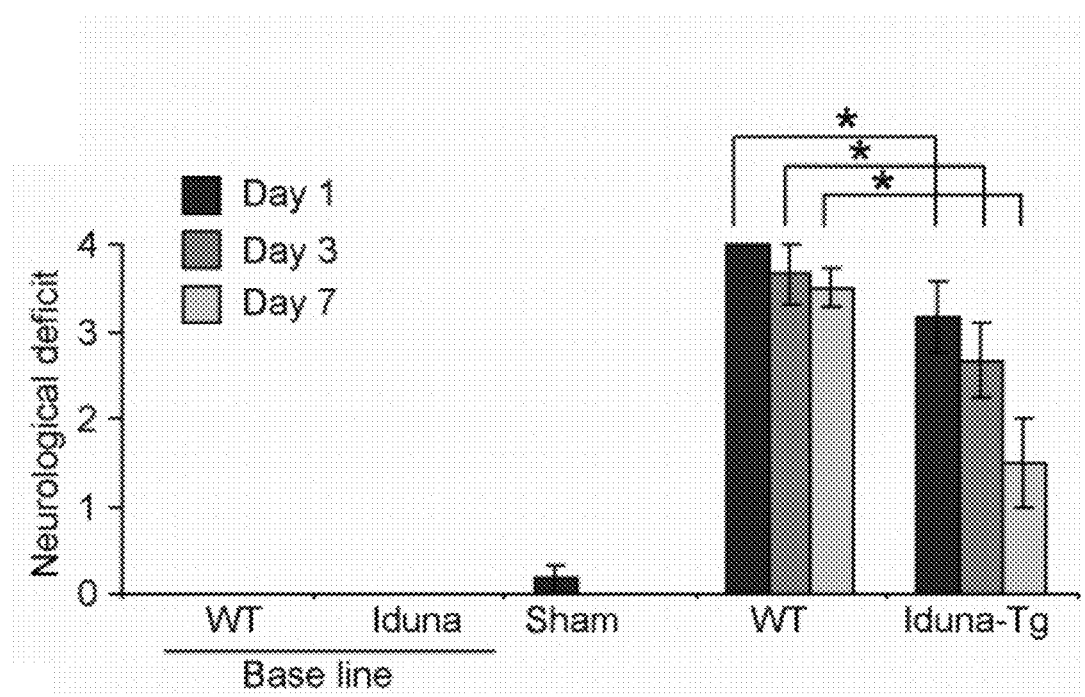
FIGS. 67 and 68—Behavioral Assessment following MCAO.
Figure 68:
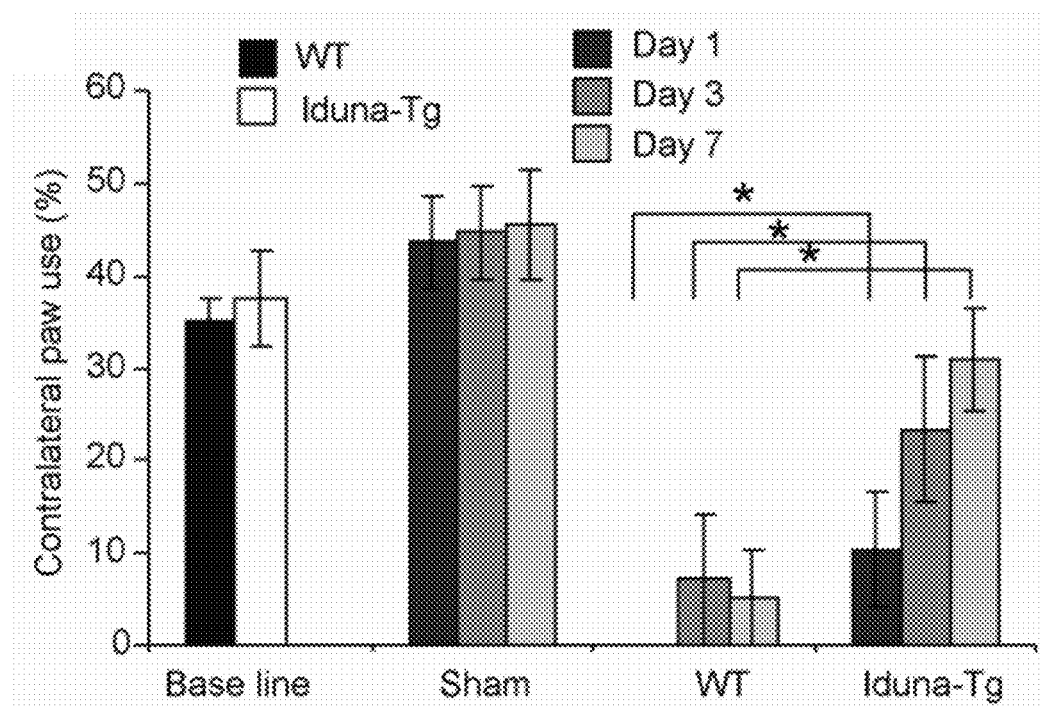

Neuroprotection against ischemic injury was determined by subjecting wild type littermates and Iduna transgenic mice to transient occlusion of the middle cerebral artery. Over the 60-min period of occlusion, cortical perfusion monitored by laser-Doppler flowmetry was reduced equivalently in wild type mice (10±1% of baseline; ±SE) and Iduna transgenic mice (12±2%). The reduction was stable throughout the occlusion period and recovered to pre-ischemic levels immediately upon removal of the filament in both groups (FIG. 65). Despite the similar intensity of the ischemic insult, infarct volume was reduced by 50% in Iduna transgenic mice compared to their wild type counterparts (FIG. 66). Moreover, the reduction in infarct size was not skewed to a particular coronal level (FIG. 66). Likewise, Iduna-Tg mice showed improved neurological function following stroke. There was no baseline neurobehavioural differences in Iduna-Tg and WT mice (FIGS. 67 and 68). Thus, Iduna overexpression protects against stroke induced neuronal injury.

Figure 69:
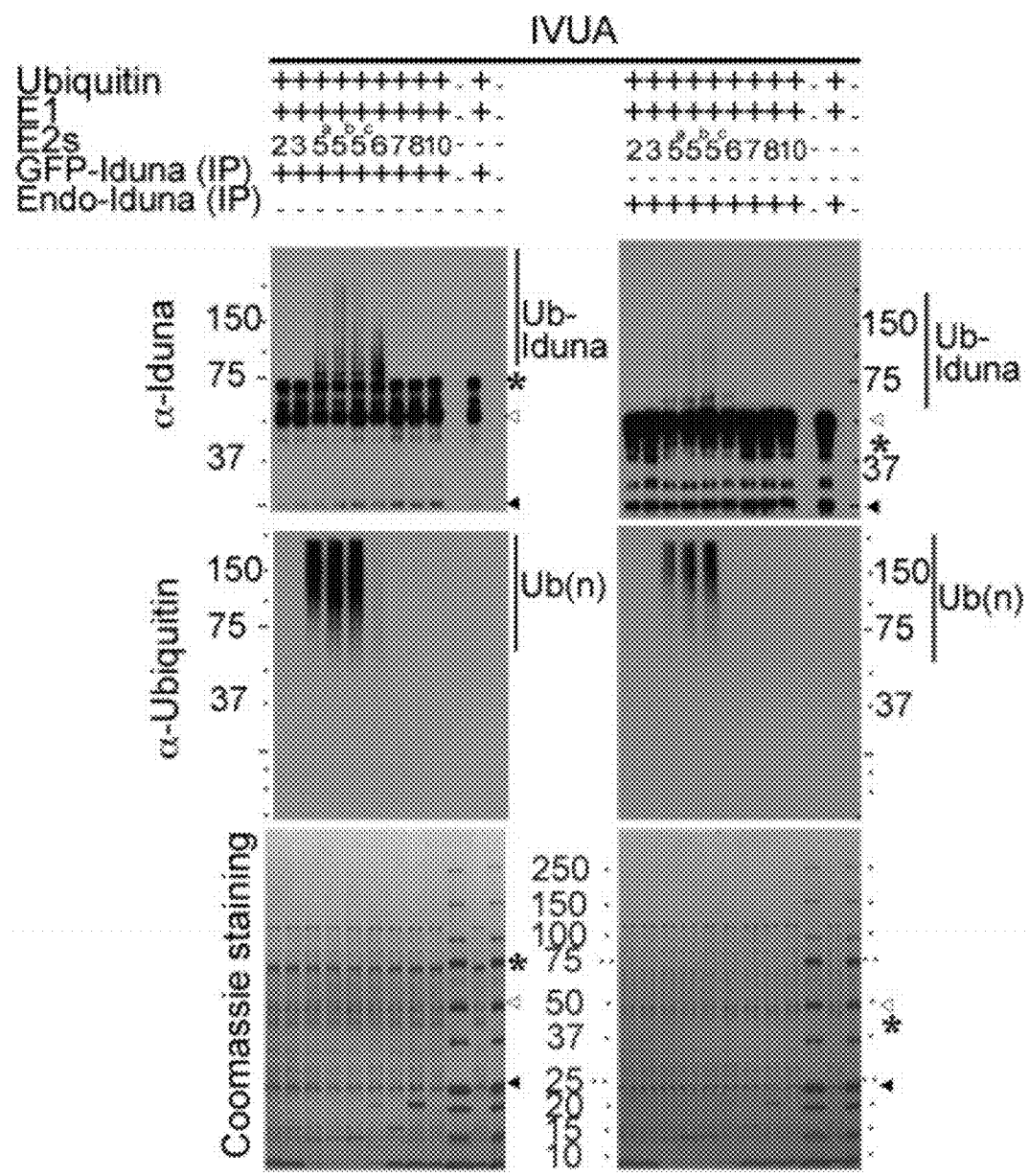
FIGS. 69 and 70—Iduna has ubiquitin E3 ligase activity. The E2s, UbCH5a, UbCH5b, UbCH5c are involved in polyubiquitination by Iduna, whereas UbCH6 is involved with monoubiquitination by Iduna.
Figure 70:
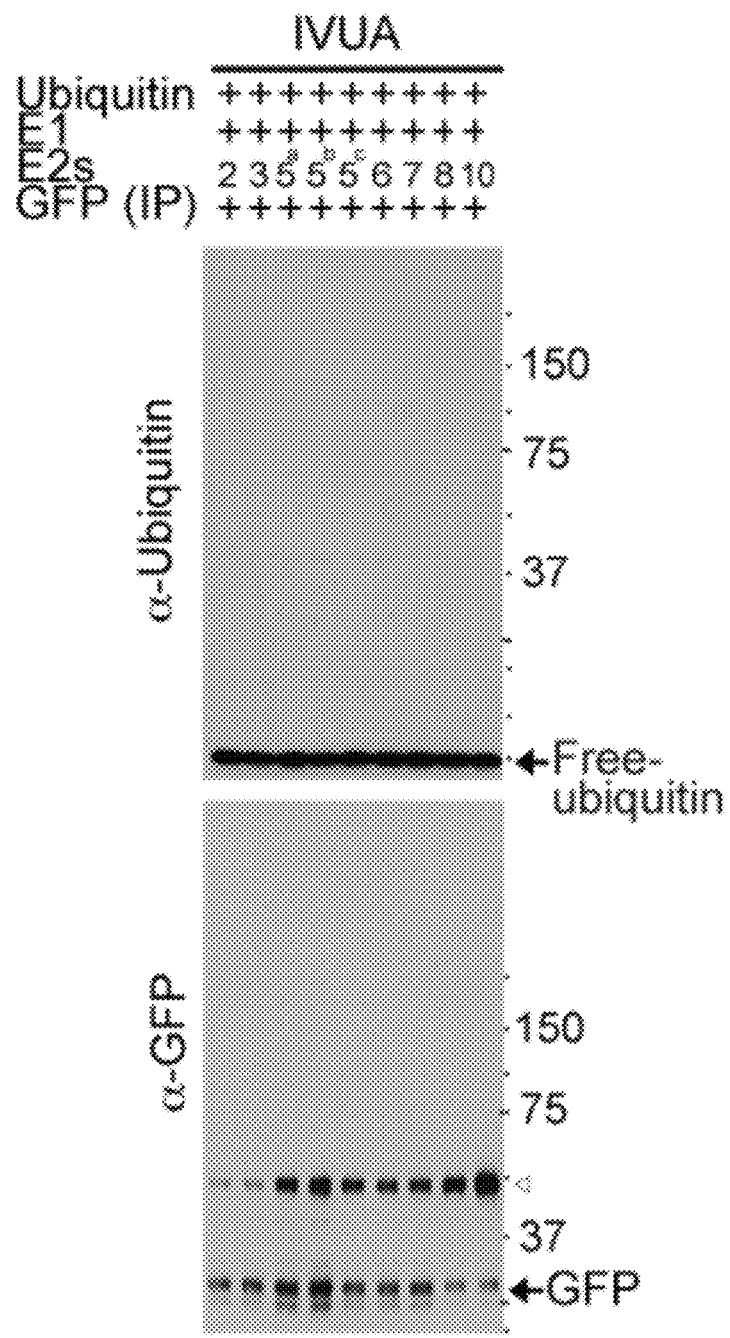
Figure 71:
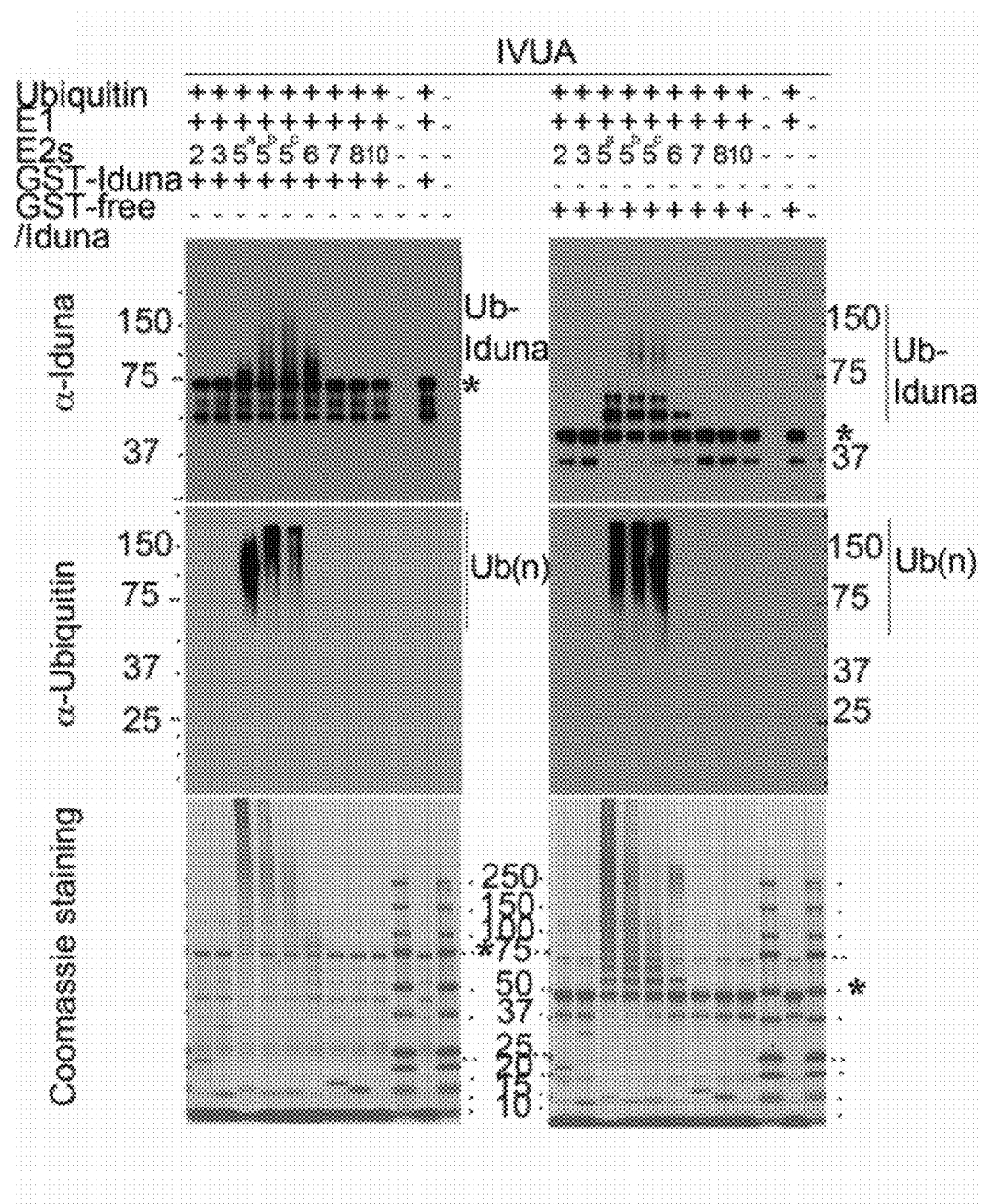
FIG. 71-74—Iduna is an ubiquitin E3 ligase that binds PARsylated proteins.

Iduna is an E3 Ubiquitin Ligase. To determine whether Iduna is an E3 ligase, cells were transfected with GFP-Iduna and compared to cells transfected with GFP alone (FIG. 69). Following immunoprecipitation of GFP-Iduna or endogenous-Iduna an in vitro ubiquitination assay was performed with recombinant E1, different recombinant E2s (UBCH2, 3, 5a, 5b, 5c, 6, 7, 8 and 10) and ubiquitin. Immunoblotting with antibodies to ubiquitin and GFP reveals that Iduna is ubiquitinated in the presence of UBCH 5a, 5b, 5c, and 6 whereas UBCH 2, 3, 7, 8, and 10 do not support Iduna mediated ubiquitination (FIG. 69). The observed ubiquitination is due to Iduna because there is no ubiquitination observed in the absence of Iduna (FIG. 70). To confirm that Iduna is autoubiquitinated an in vitro ubiquitination assay was performed with recombinant Iduna, E1, E2 (UBCH 2, 3, 5a, 5b, 5c, 6, 7, 8 and 10), and ubiquitin. In the presence of UBCH 5a, 5b, 5c, Iduna is polyubiquitinated and in the presence of UBCH 6 Iduna seems to be multi-monoubiquitinated because the polyclonal anti-ubiquitin antibody does not recognize the high molecular weight of autoubiquitinated Iduna catalyzed by UBCH6 (FIG. 71), although we cannot exclude the possibility that UBCH 6 is capable of supporting Iduna polyubiquitination. (FIG. 69).

Figure 72:
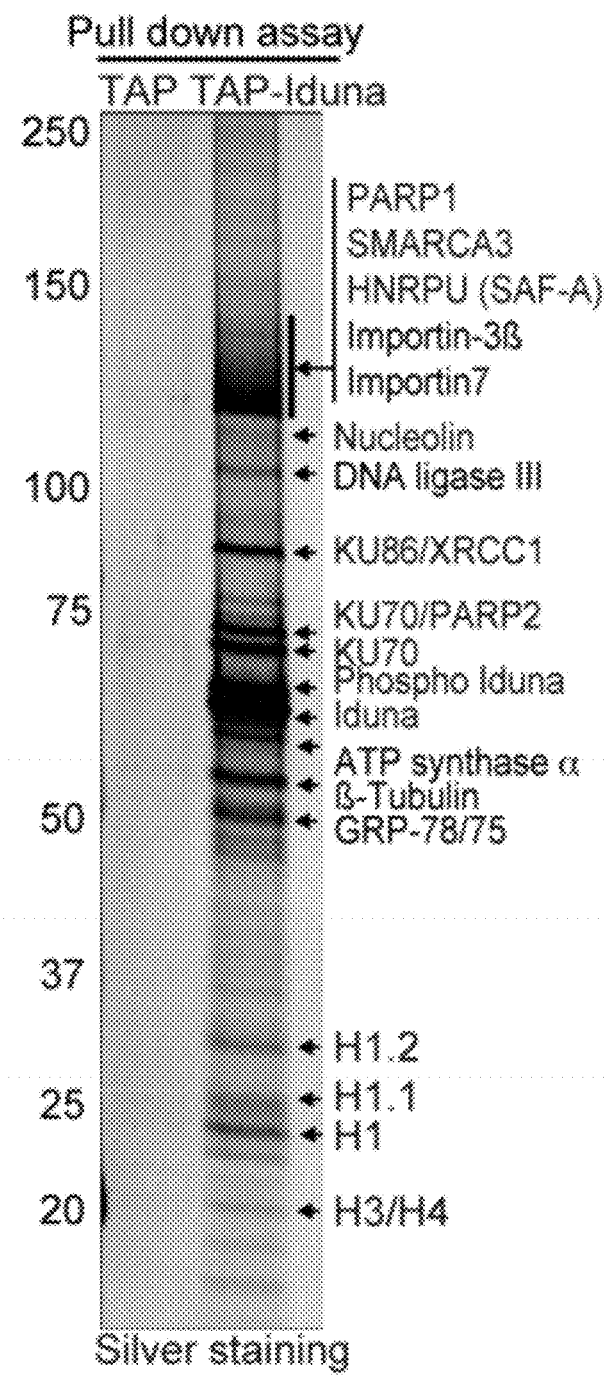
Figure 73:
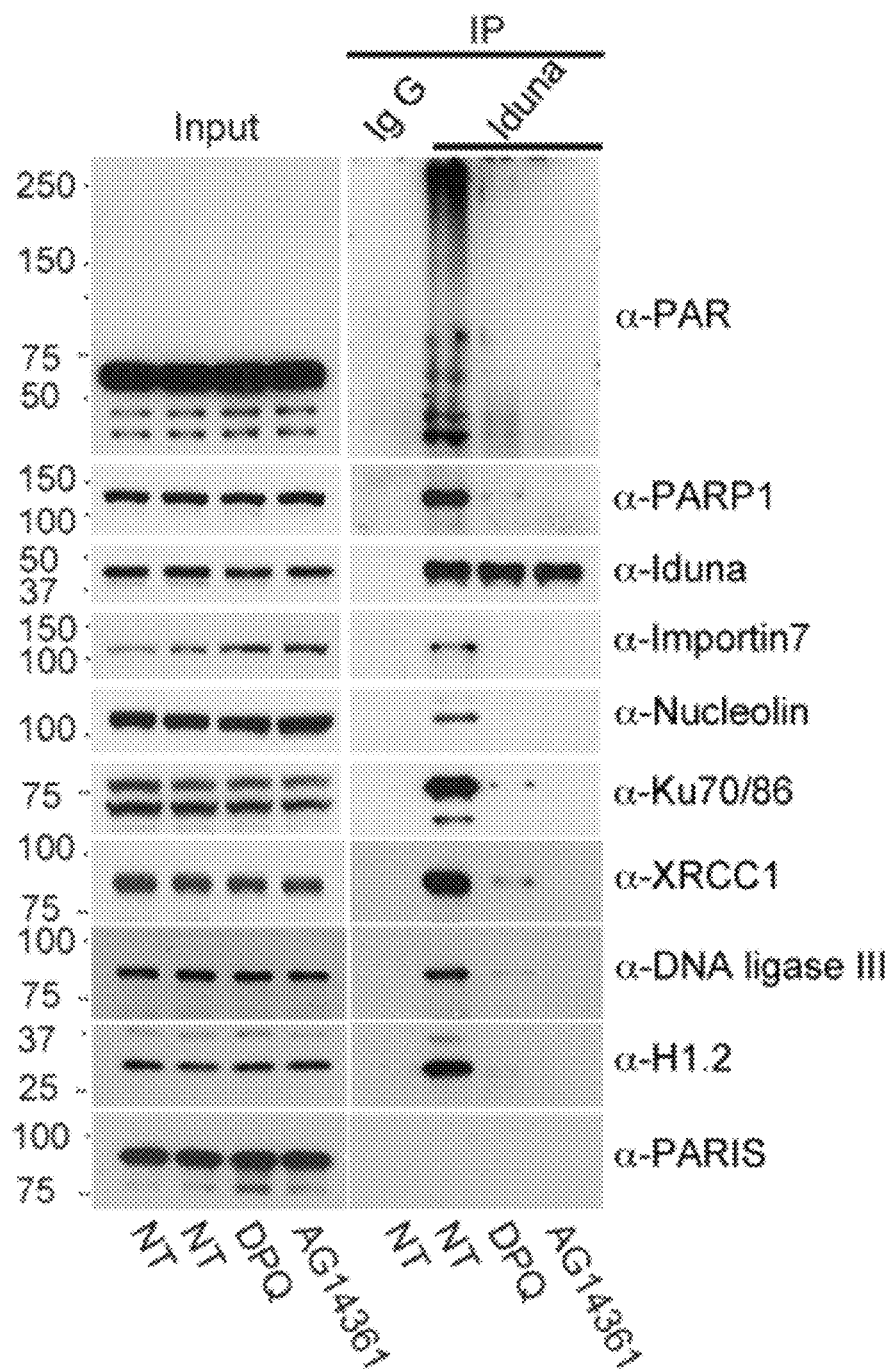
Figure 74:
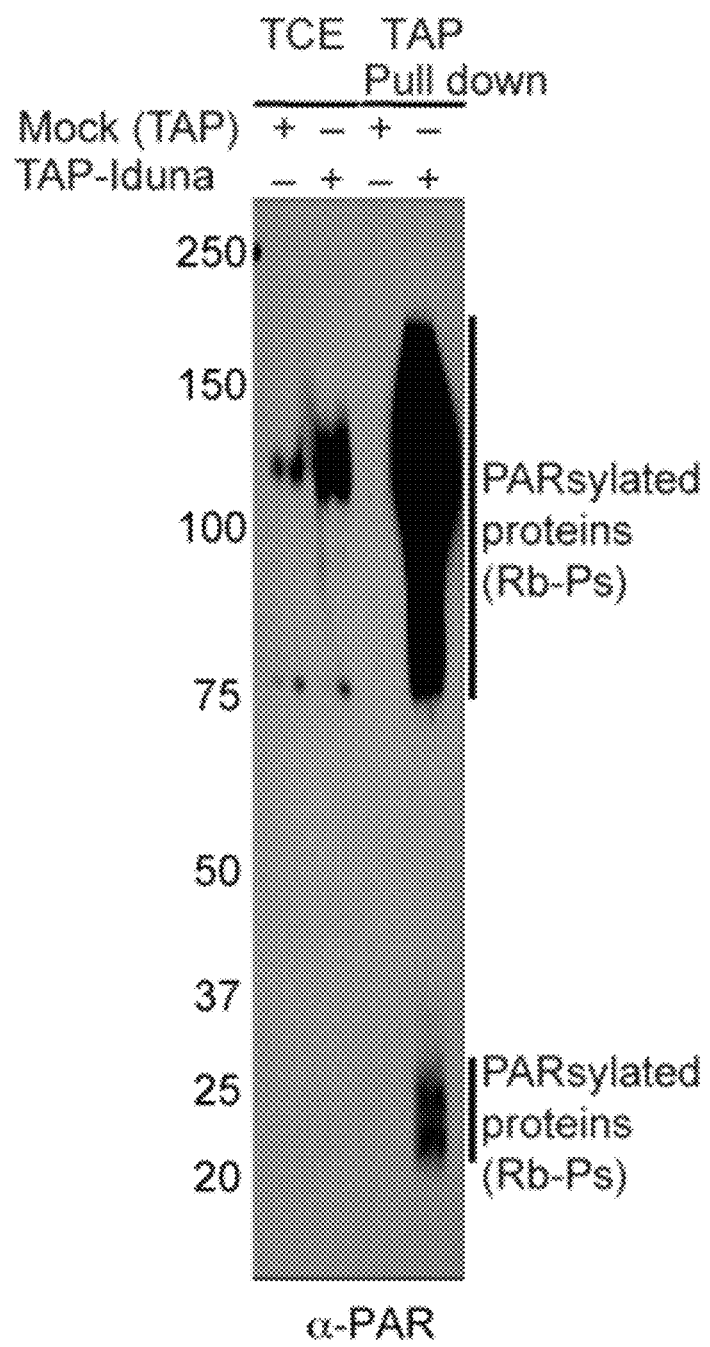

To identify potential Iduna substrates, tandem affinity purification (TAP) was performed with TAP-tagged Iduna (TAP-Iduna) composed of a streptavidin binding peptide (SBP) and calmodulin binding peptide (CBP) fused in frame to the N-terminus of Iduna in stably transfected SK-N-SH cells (FIG. 72). Following the TAP procedure, bands were excised and sequenced by mass spectrometry (Table S1). Because the TAP results reveal that most of Iduna's binding proteins are general factors involved in the DNA damage response and Iduna might be a breast cancer risk locus at 6q22.23, we elected to perform the remaining studies in the breast cancer MCF-7 cell line. Proteins identified include: PARP1, SMARCA3, HNRPU (SAF-A), Importin-β3, Importin-7, Nucleoin, DNA ligase III, KU70, KU86, XRCC1, PARP2, Phospho-Iduna, Iduna, ATP-synthase-α, β-tubulin, GRP-78 and GRP-75, Histones 1.2, 1.1, 1, 3 and 4 (FIG. 72). Confirmation of the interaction between Iduna and these proteins was performed by immunoprecipitation followed by immunoblot analysis for which there are commercially available antibodies including: PARP1, Importin-7, Nucleoin, DNA ligase III, KU70/86, XRCC1, Histone 1.2, Iduna. PARIS (parkin interacting substrate) serves as a negative control (FIG. 73). To determine whether the interaction between Iduna and its binding partners is dependent on PAR, the PARP inhibitors DPQ or AG14361 were added to the cell culture media before harvest. Both DPQ and AG14361 treatment markedly reduce the interaction between Iduna and its binding partners (FIG. 73). To confirm that Iduna binds PAR modified proteins the TAP pull-down was probed with antibodies against PAR. TAP pull-down of Iduna markedly enriches for PAR binding proteins (FIG. 74).

Figure 75:
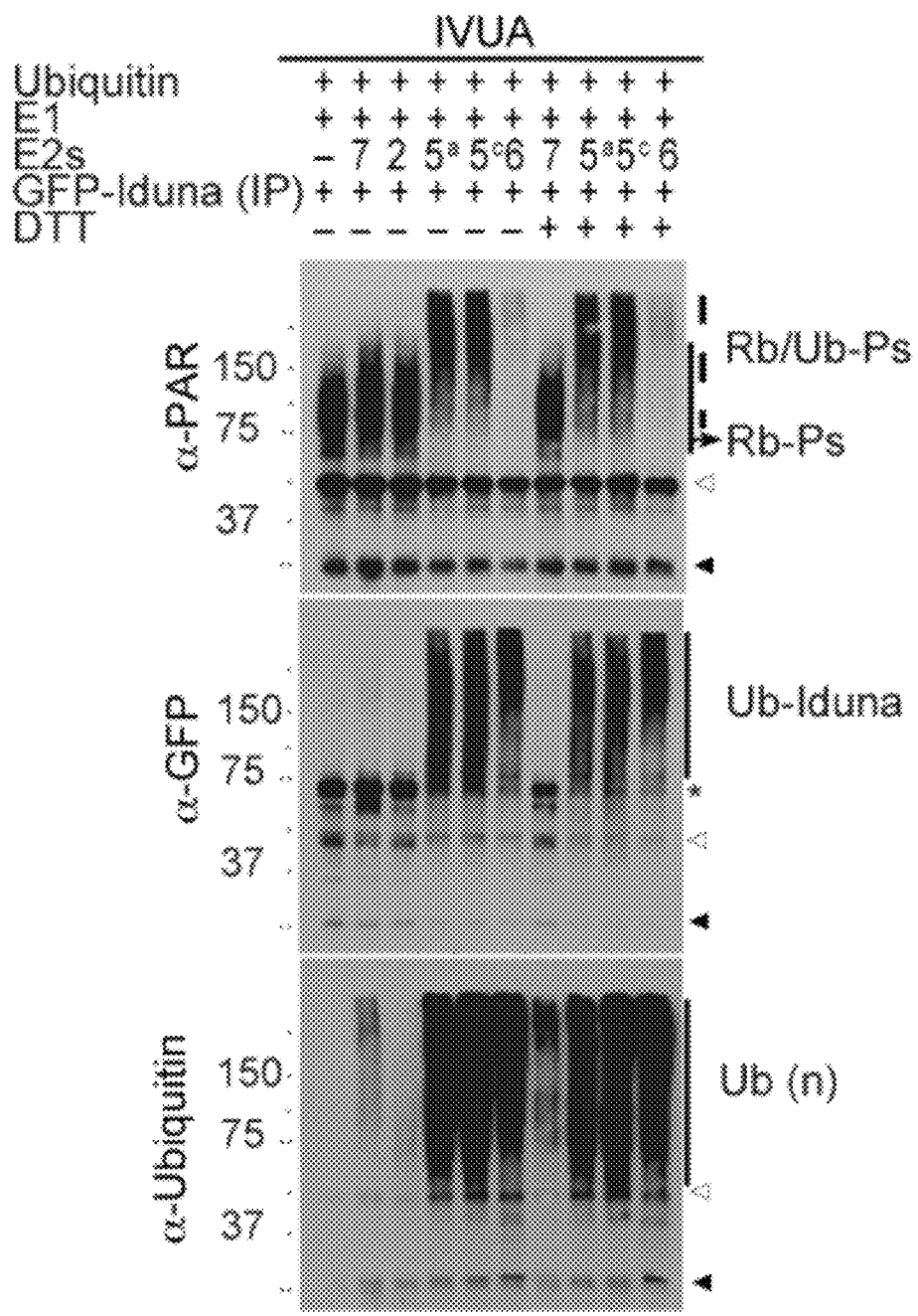
FIG. 75-78—Iduna mediates PARsylation dependent ubiquitination of its substrates.
Figure 76:
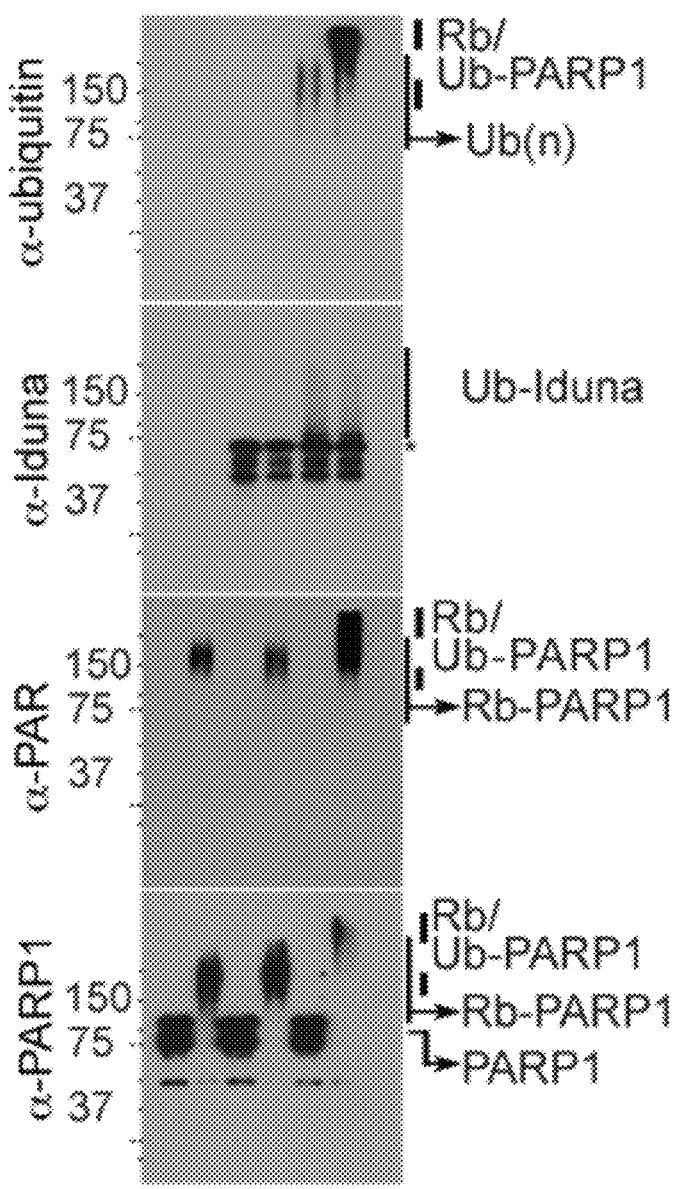
Figure 77:
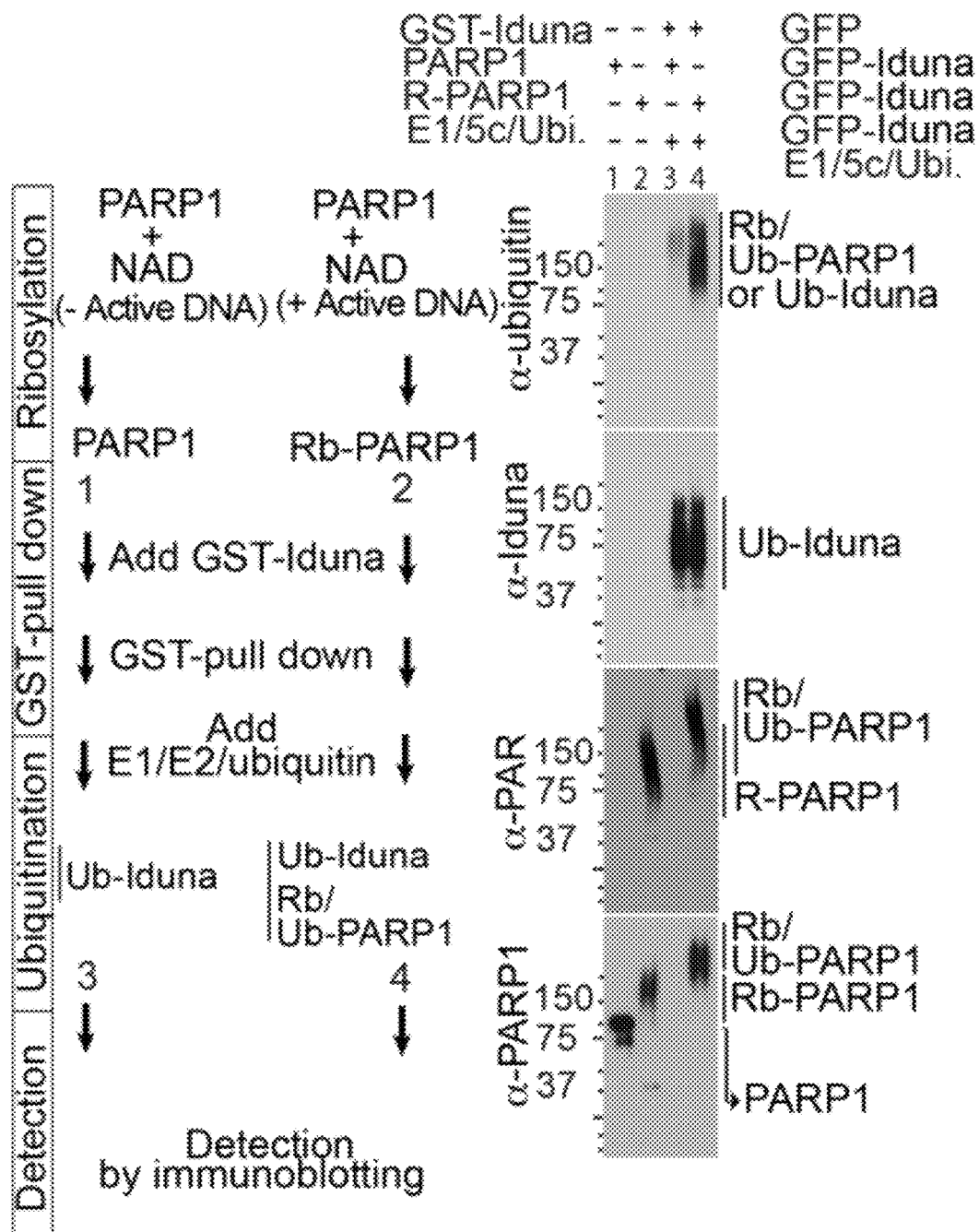
Figure 78:
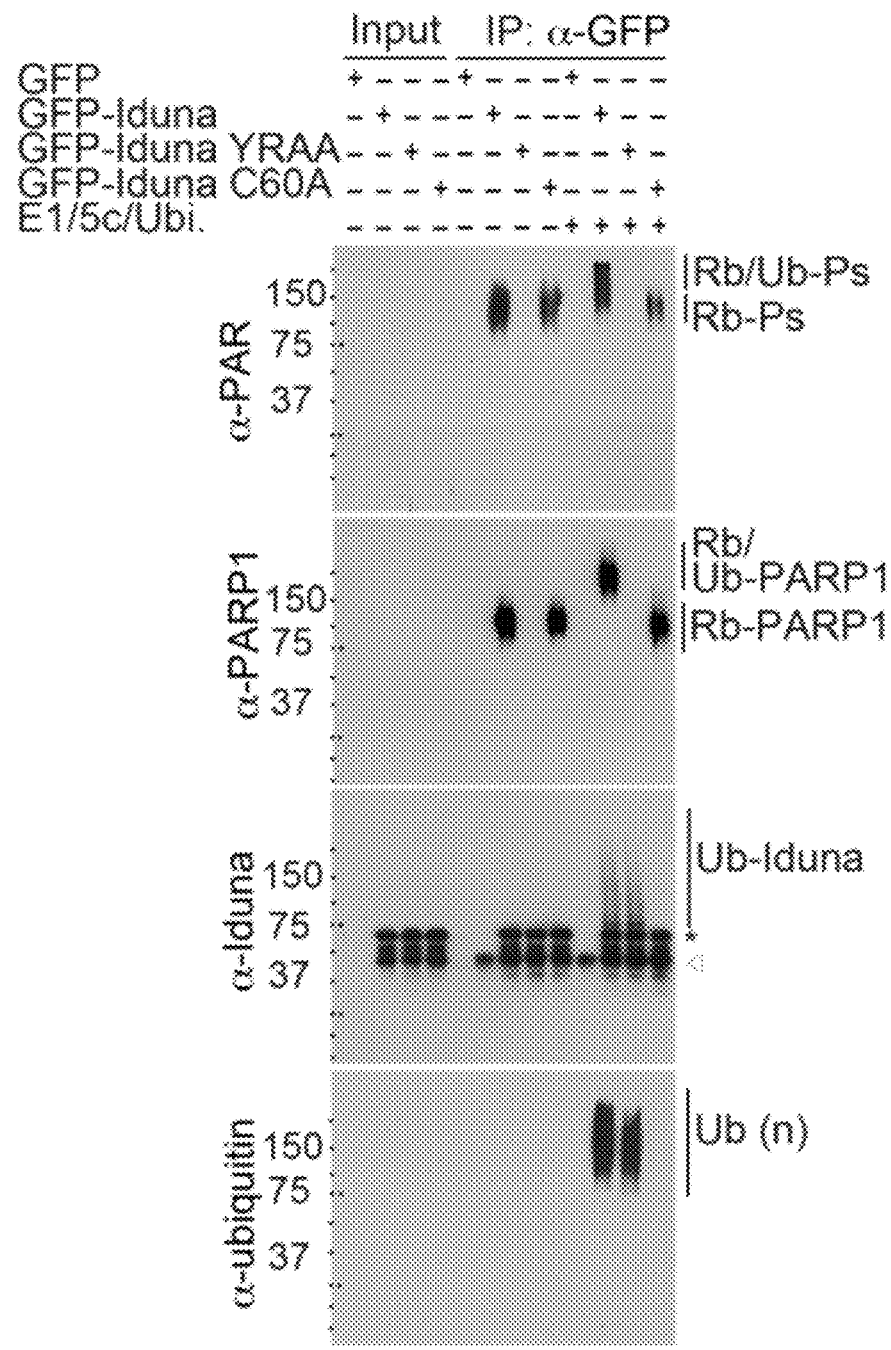
Figure 79:
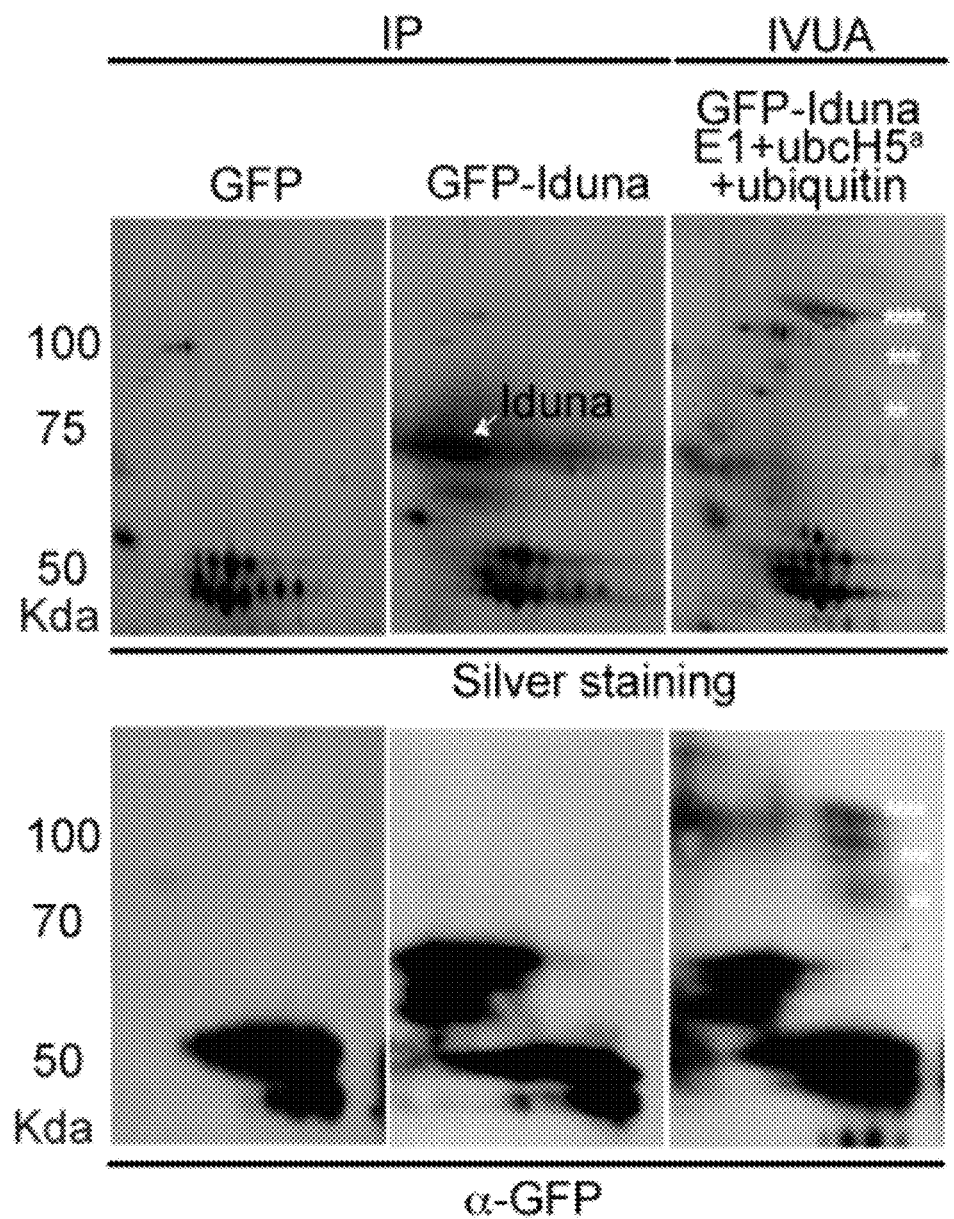
FIGS. 79 and 80—Polyubiquitination of PARP1 by Iduna.
Figure 80:
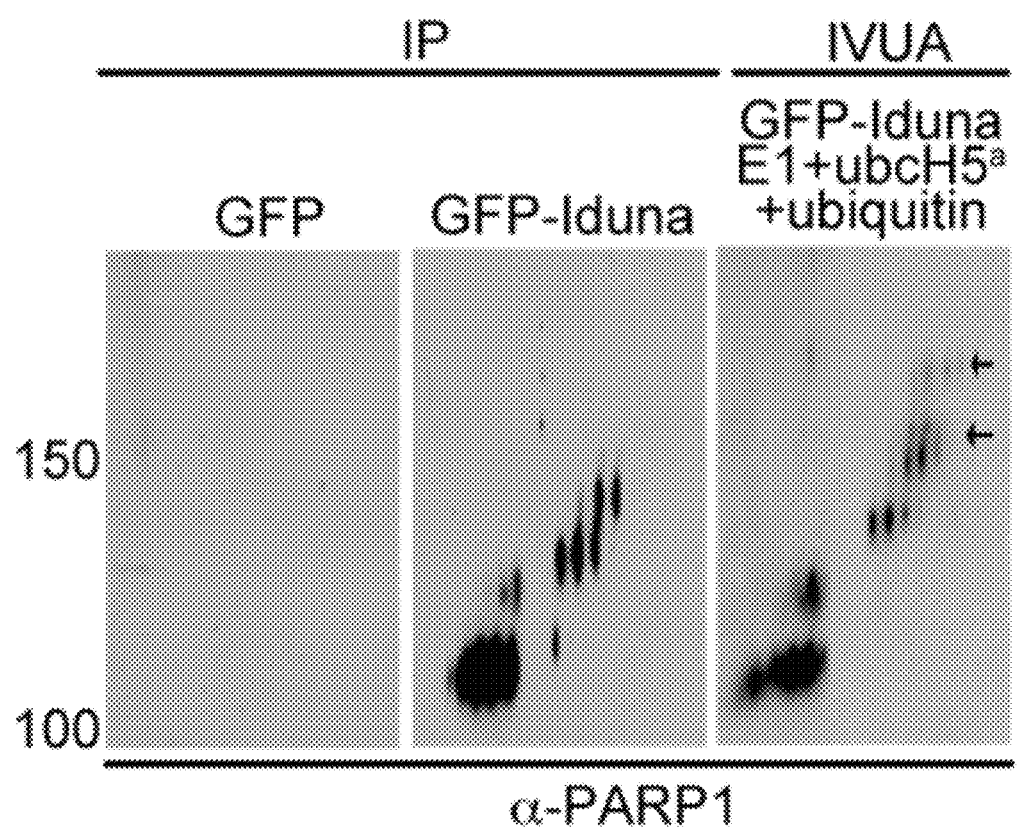

Iduna is a PAR-Dependent E3-Ligase. Because Iduna interacts with PAR modified proteins the activity of Iduna ubiquitination of PAR modified proteins was evaluated (FIGS. 75-78). MCF7 cells were transfected with GFP-Iduna, followed by immunoprecipitation with an antibody to GFP. An in vitro ubiquitination assay was performed on the precipitates in the presence of E1, E2 (UBCH 7, 2, 5a, 5c, and 6) and ubiquitin. Immunoblotting with antibodies to PAR reveals that PAR modified proteins are ubiquitinated with the E2's (UBCH 5a, 5c, and 6) whereas there is no ubiquitination with the E2 UBCH 2 or 7 (FIG. 75). GFP-Iduna is only ubiquitinated in the presence of the E2's UBCH 5a, 5c, and 6. Addition of DTT controls for non-specific ubiquitination and has no effect on Iduna PAR dependent ubiquitination. Because PARP1 is a major interacting protein with Iduna (FIG. 76) and it is the prototypic and prominently modified PAR protein, 2-D gel analysis was conducted on the in vitro ubiquitination assay of the GFP-Iduna immunoprecipitate in the presence of E1, UBCH 5a and ubiquitin to determine whether Iduna ubiquitinates PARP1. Silver staining reveals that GFP-Iduna is shifted to several high molecular weight spots consistent with polyubiqutination (FIG. 79). Immunoblot analysis with antibodies to PARP1 reveals that PARP1 is similarly shifted to high molecular weight spots consistent with polyubiqutination (FIG. 80). To ascertain whether Iduna only ubiquitinates PARsylated PARP1, an in vitro ubiquitination assay in the presence of E1, UBCH 5c and ubiquitin was utilized to monitor the ubiquitination of non-PARsylated PARP1 versus PARsylated PARP1 (FIG. 76). PARP1 was PARsylated with biotin labeled NAD in an in vitro PARsylation reaction. Only PARsylated PARP1 is ubiquitinated by GST-Iduna as revealed by immunoblot analysis with antibodies to ubiquitin (FIG. 76). A GST pull down experiment was performed to determine whether Iduna selectively binds and ubiquitinates PARsylated PARP1. Only PARsylated PARP1 binds and is ubiquitinated by Iduna (FIGS. 77 and 78).

Figure 81:
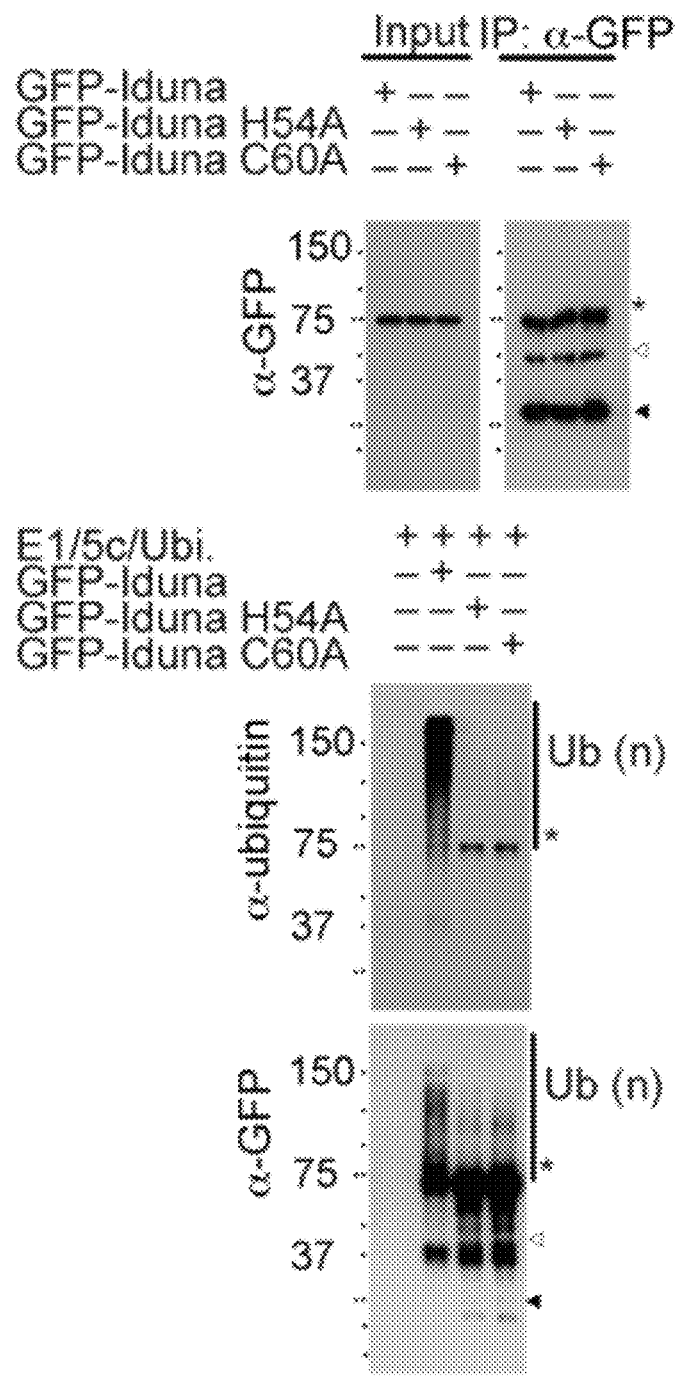
FIG. 81-83—PAR-binding and RING domains of Iduna are essential for its PAR-dependent ubiquitin E3 ligase activity.
Figure 82:
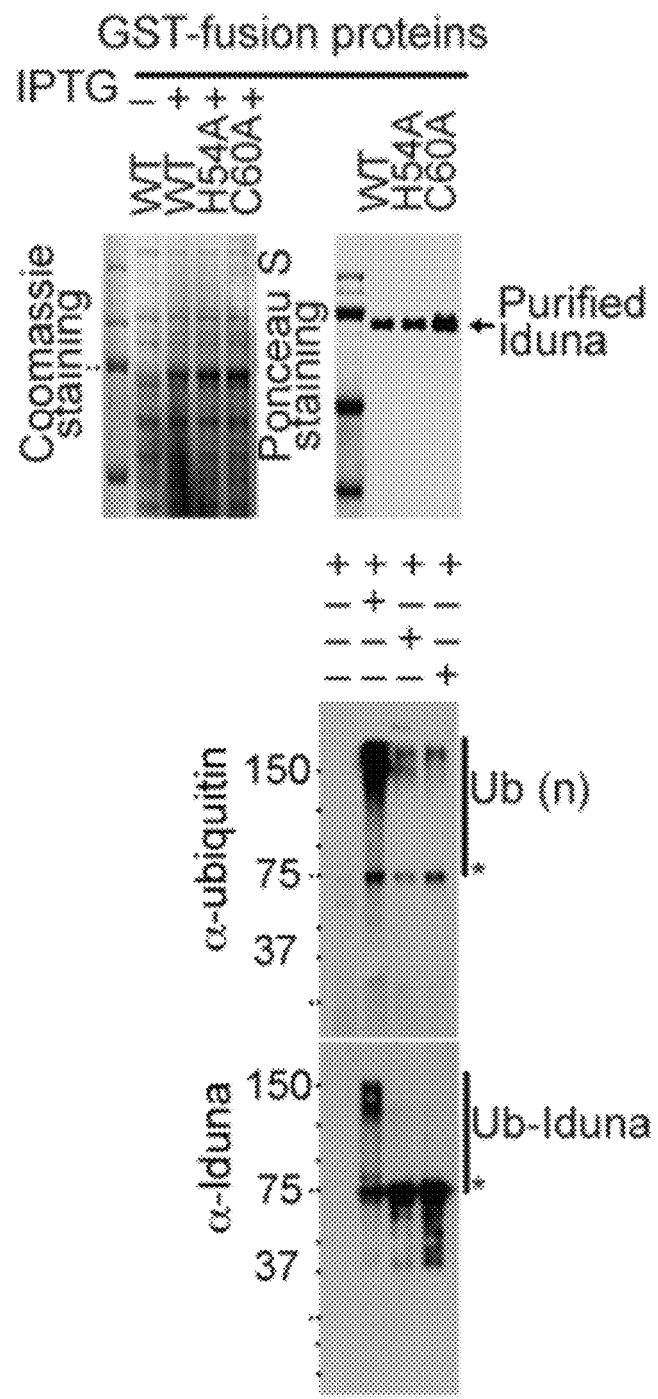

Iduna's E3 ligase activity requires its RING Domain and PBM. Two mutations were constructed to disrupt the zinc binding in the RING finger domain of Iduna (H54A and C60A). The ubiquitination activity of Iduna was monitored. MCF7 cells were transfected with GFP-Iduna, GFP-Iduna H54A or GFP-Iduna C60A, and immunoprecipitation was performed followed by in vitro ubiquitination in the presence of E1, UBCH 5c and ubiquitin. Iduna possessing point mutations at either H54A or C60A is devoid of ubiquitination activity (FIG. 81). An in vitro ubiquitination assay with recombinant GST-Iduna, GST-Iduna H54A or GST-Iduna C60A also reveals that GFP-Iduna H54A or GFP-Iduna C60A have markedly diminished ubiquitination activity (FIG. 82).

Figure 83:
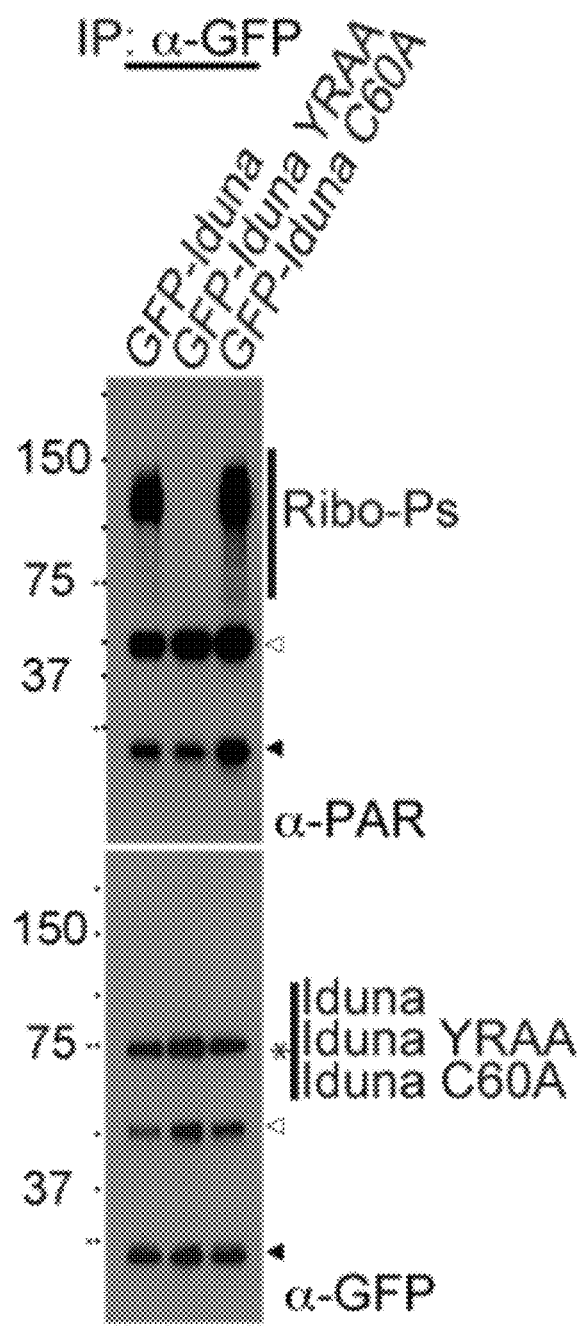
Figure 84:
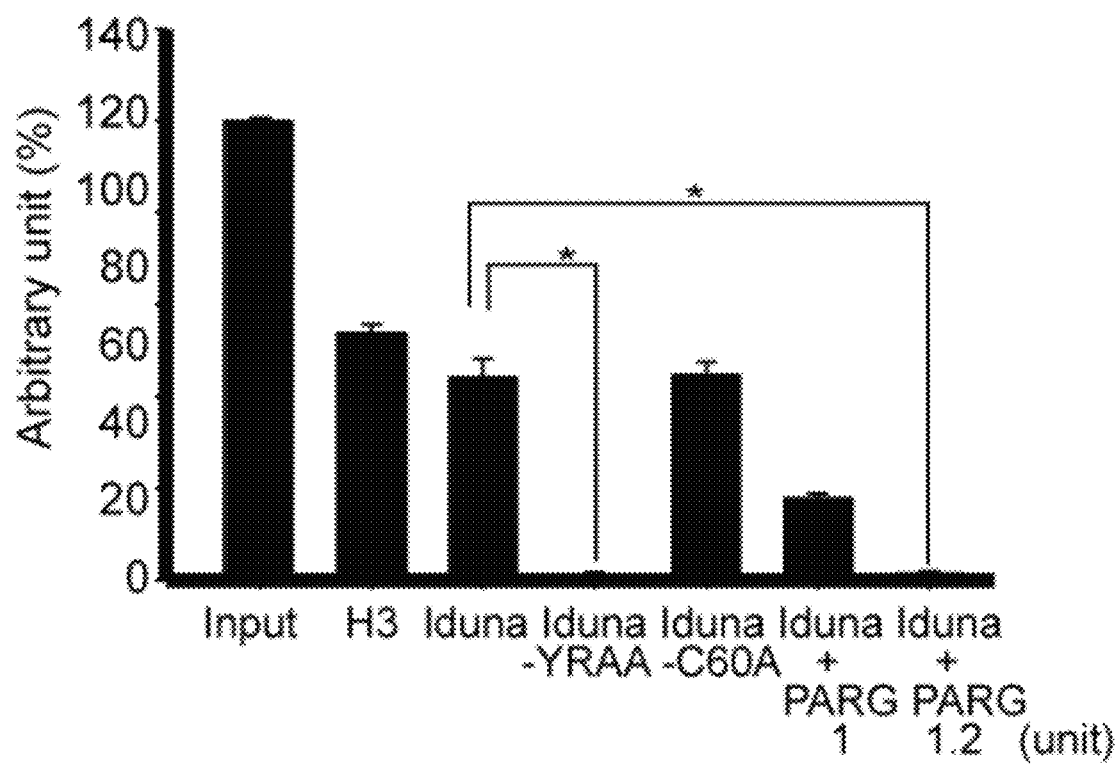
FIG. 84-87—Iduna has strong PAR binding activity.
Figure 85:
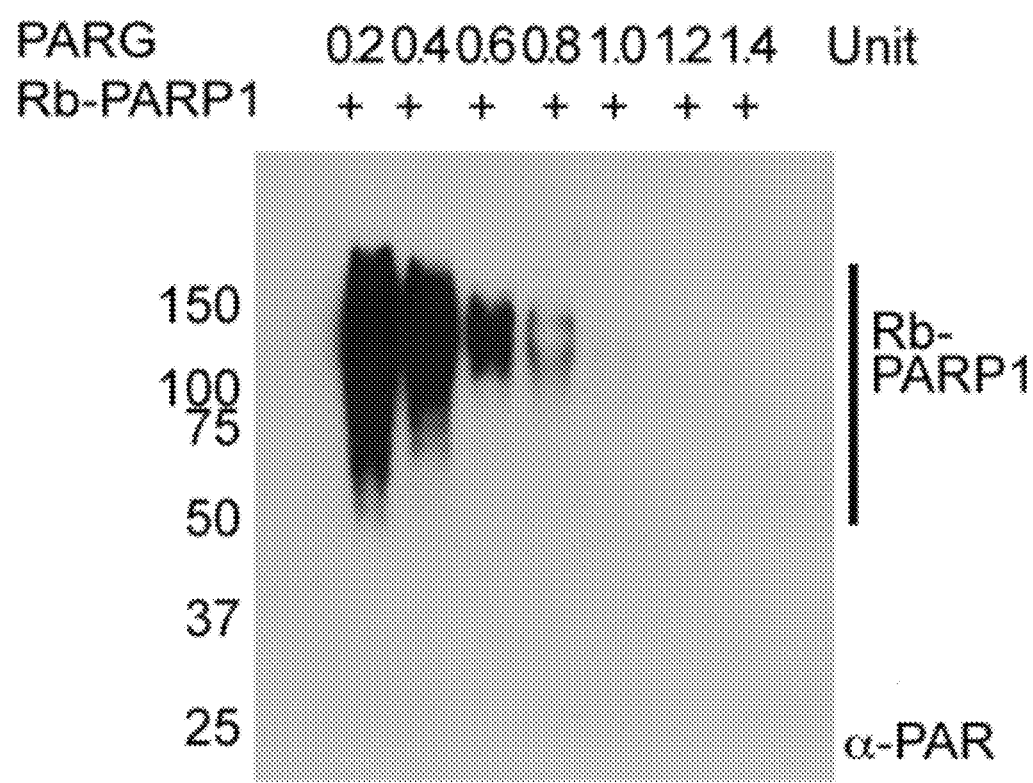
Figure 86:
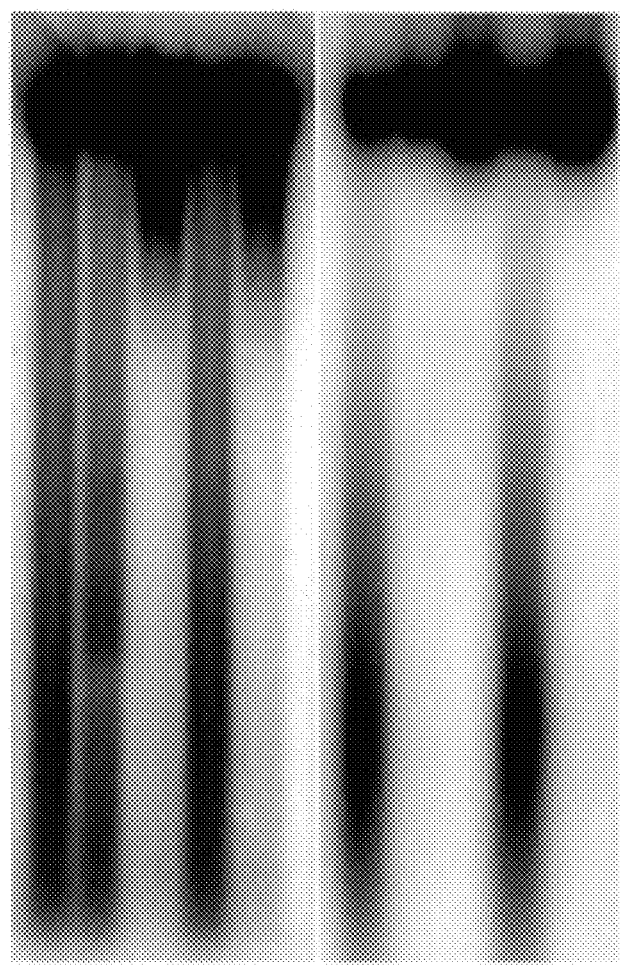
Figure 87:
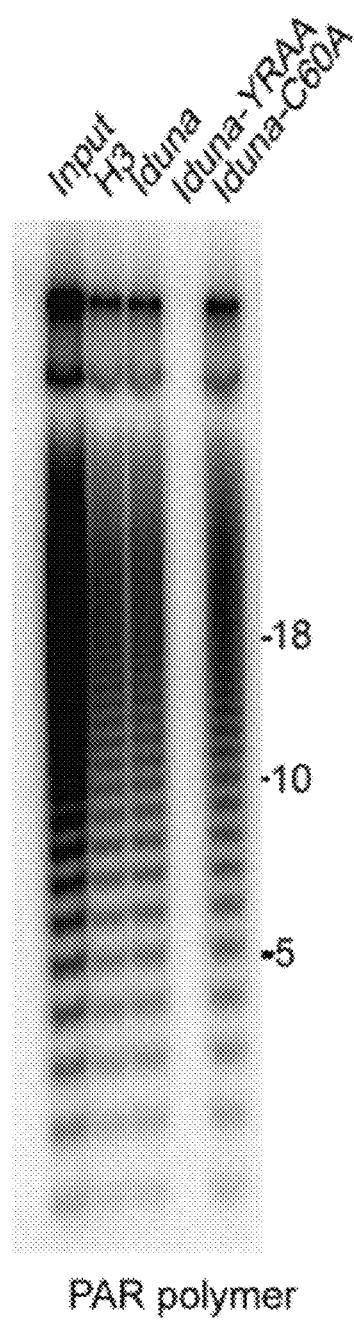

As disclosed herein, Iduna contains a consensus PBM is its WWE domain and that mutating the hydrophobic amino acids 155Y and 156R to alanine to create an Iduna YRAA mutant disrupts PAR binding to Iduna. MCF7 cells were transfected with GFP-Iduna, GFP-Iduna C60A and GFP-Iduna YRAA. 48 hours later Iduna was immunoprecipitated with antibodies to GFP followed by immunoblot analysis with antibodies to PAR. Iduna and Iduna C60A bind PAR whereas Iduna YRAA is incapable of binding PAR (FIG. 83). To confirm that Iduna binding to PARP1 is dependent on PARsylation of PARP1, binding of automodified PARP1 with $^{32}$P-NAD was monitored in a GST pull down experiment with Histone H3 as a positive control (FIGS. 84 and 85). GST-Iduna and GST-Iduna-C60A pulls down PARsylated PARP1 whereas GST-Iduna YRAA fails to pull down PARsylated PARP1. Treatment of the extract prior to GST pull down with PAR glycohydrolase (PARG), which degrades PAR, eliminates this interaction (FIG. 84). Confirmation that PARG is active is the demonstration that PARG dose dependently removes PAR from PARsylated PARP1 (FIG. 85). An electrophoretic mobility shift assay reveals that the GST tagged PAR binding proteins Histone H3, Iduna, Iduna C60A bind PAR but Iduna YRAA does not (FIG. 86). Iduna and Iduna-C60A bind to a range of PAR polymers of varying length similar to H3, whereas Iduna-YRAA fails to bind to PAR, as determined by phosphorimager detection of radiolabeled PAR polymer bound to Iduna, Iduna-C60A and H3 after separation by Tris-borate-EDTA PAGE (FIG. 87).

To determine if PAR binding is required for Iduna ubiquitination, MCF7 cells were transfected with GFP-Iduna, GFP-Iduna C60A and GFP-Iduna YRAA. Following immunoprecipitation with antibodies to GFP an in vitro ubiquitination assay was performed. Iduna YRAA fails to bind PARsylated PARP1 whereas Iduna and Iduna C60A bind PARsylated PARP1. Immunoblot analysis of the immunoprecipitates with antibodies to PAR and ubiquitin reveals that only GFP-Iduna is capable of polyubiquitination of PARsylated PARP1, whereas Iduna YRAA autoubiquitinates itself (FIG. 78). Thus, Iduna has PAR-dependent and -independent E3 ligase activity.

Figure 88:
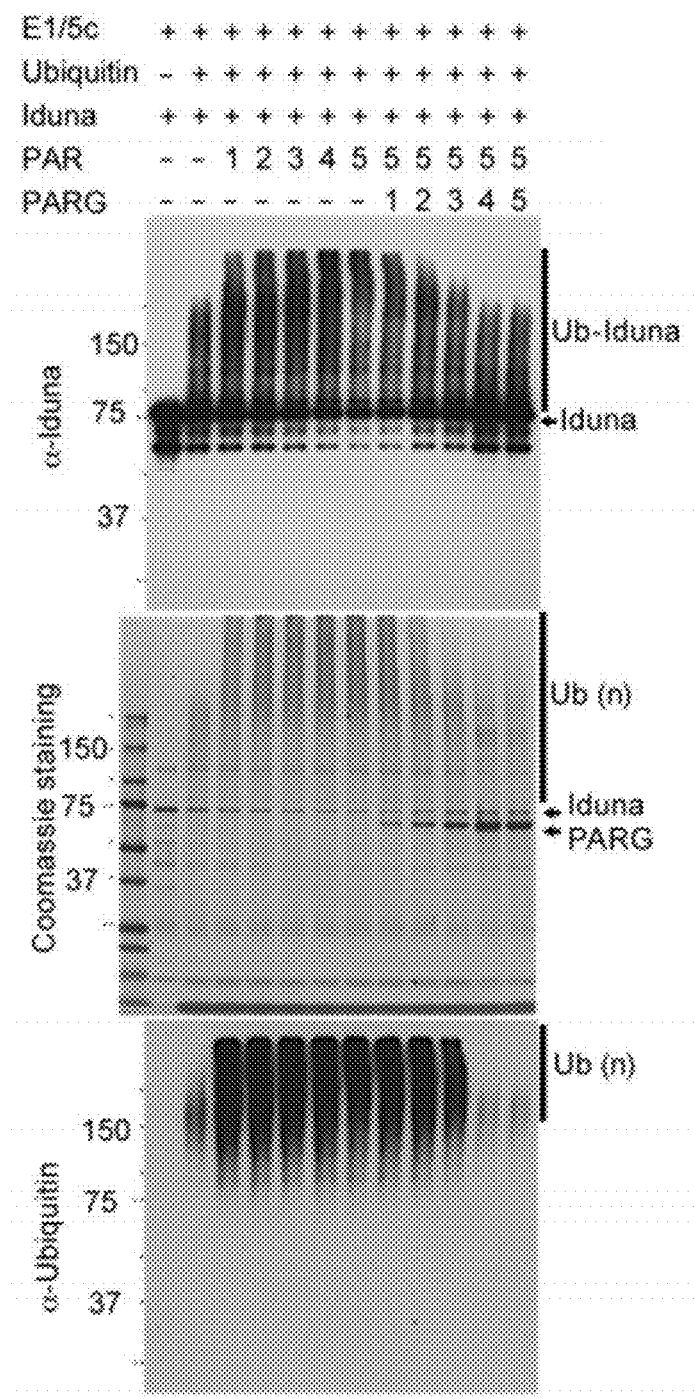
FIGS. 88 and 89—PAR and PARsylation enhance the Iduna activity.
Figure 89:
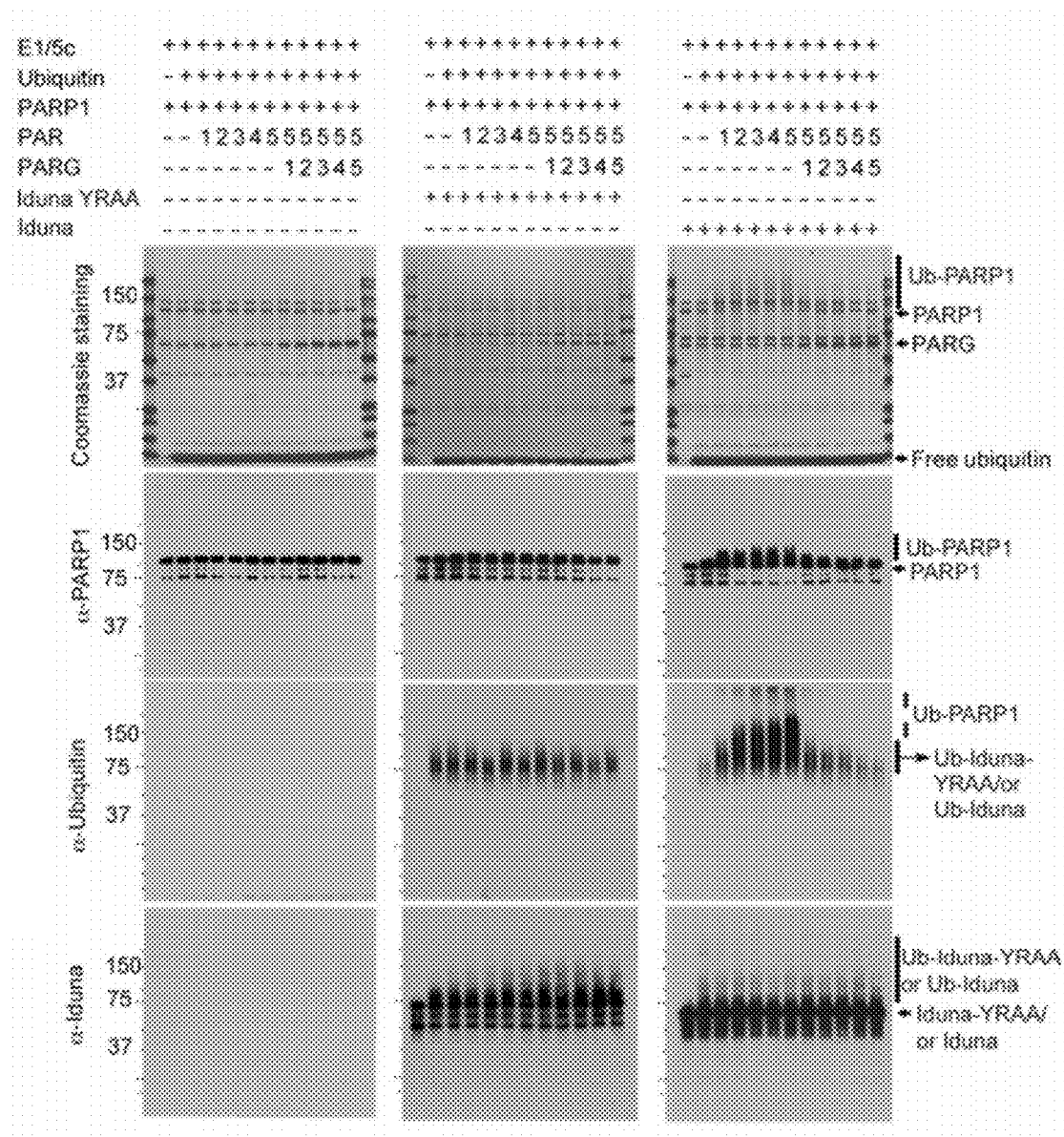

To determine whether free PAR can activate Iduna ubiquitination, an in vitro ubiquitination assay containing Iduna, E1, UBCH 5c, and ubiquitin was performed. Iduna auto-ubiquitination is increased with increasing concentrations of PAR and the addition of PARG in a dose dependent manner reduces Iduna auto-ubiquitination to baseline (FIG. 88). In the same in vitro ubiquitination reaction, PARP1 ubiquitination was monitored in the presence of Iduna and Iduna YRAA. PARP1 ubiquitination is dose dependently increased by Iduna in the presence of PAR and decreased by the addition of PARG. Iduna YRAA fails to ubiquitinate PARP1 in the presence of PAR (FIG. 89).

Mass spectrometry analysis was performed to ascertain the conjugation mode, the site of PAR dependent ubiquitination of PARP1, and auto-ubiquitination of Iduna. In the absence of PAR, Iduna auto-ubiquitination occurs on lysines 85, 95 and 176 via K11 and K48 ubiquitin linkages (Table S2) whereas in the presence of PAR, lysines 131 and 176 are ubiquitinated via K6, K33 and K48 ubiquitin linkages (Table S2). High resolution mass spectrometry also indicated that PARP1 was ubiquitinated on 24 different lysines via K11 and K48 ubiquitin linkages (Table S3).

Figure 90:
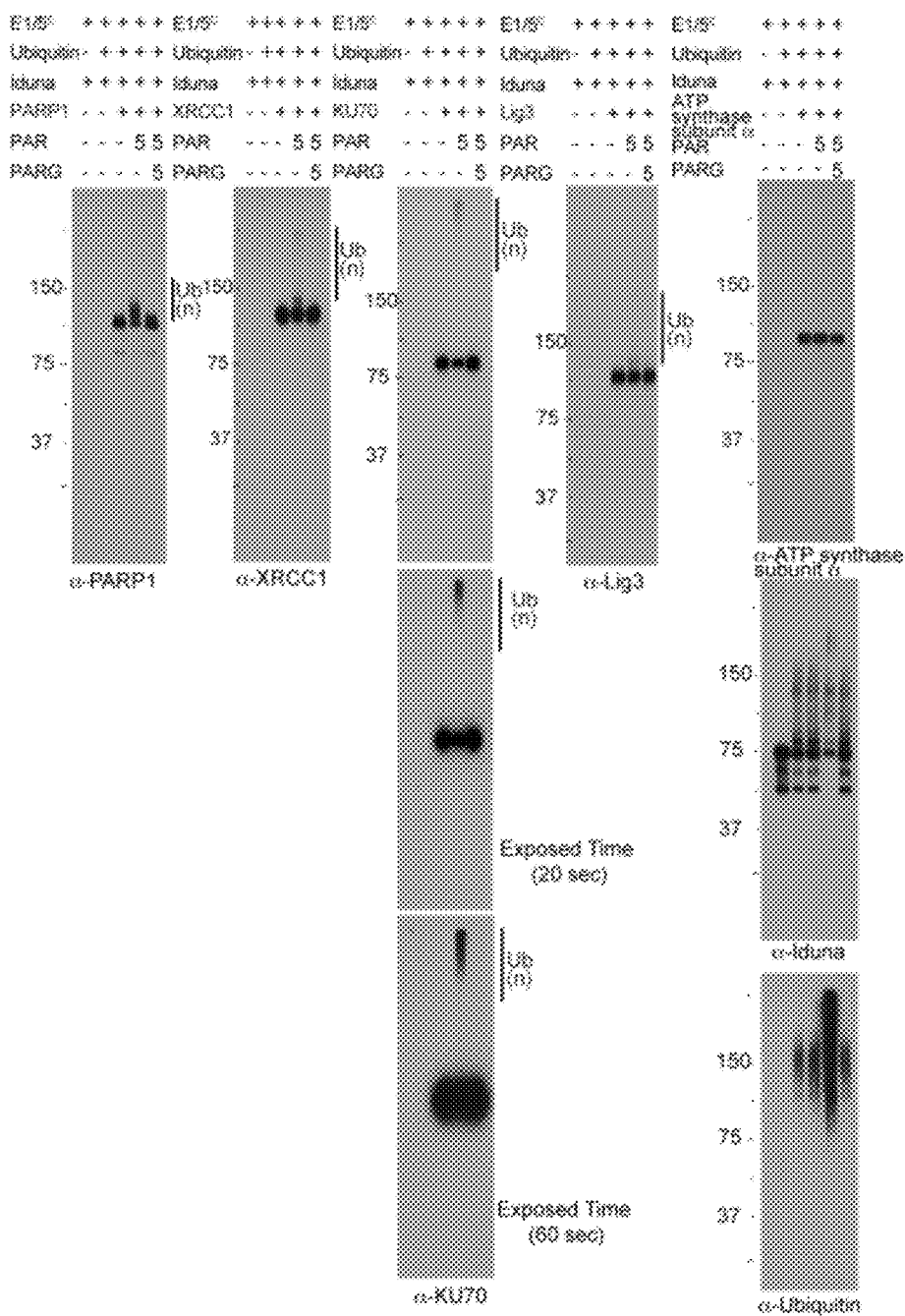
FIG. 90—PAR-dependent ubiquitination of potential Iduna substrates. PAR-dependent ubiquitination of Iduna substrates was monitored by an in vitro ubquitination assay as indicated. Ub (n), polyubiquitin chains. All experiments were repeated two times.

To ascertain if Iduna ubiquitinates other proteins in a PAR-dependent fashion, an in vitro ubiquitination assay was performed (FIG. 90). In the presence of E1, UbcH 5c, Iduna and free PAR polymer, Iduna ubiquitinates the nuclear proteins XRCC1, KU70, DNA ligase III, PARP1, but not the cytosolic ATP subunit α (FIG. 90). The ubiquitination is PAR-dependent because the addition of PARG to the reaction ablates the ubiquitination.

Figure 91:
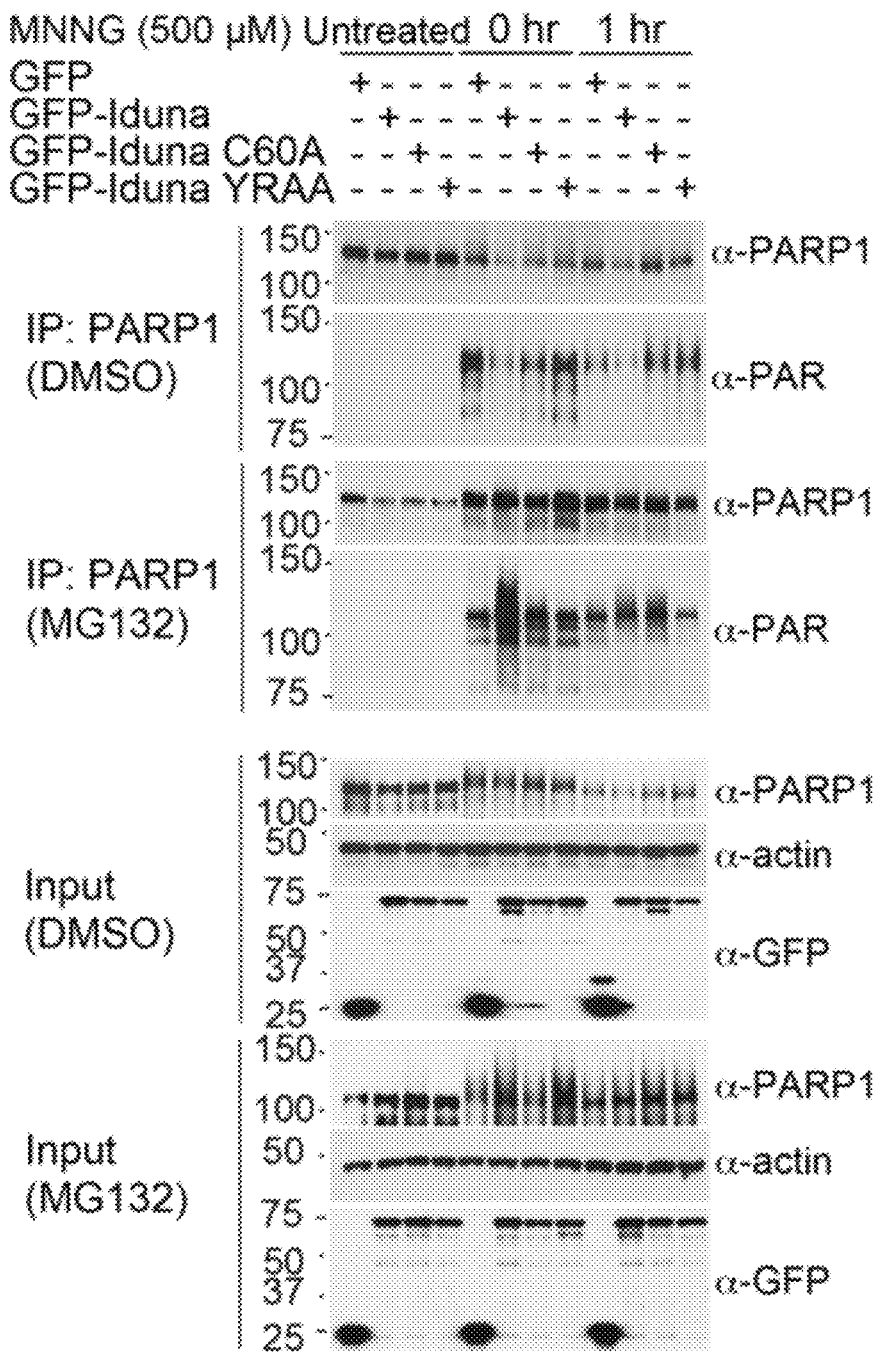
FIG. 91-96—PARsylation dependent PARP1 degradation by Iduna.
Figure 92:
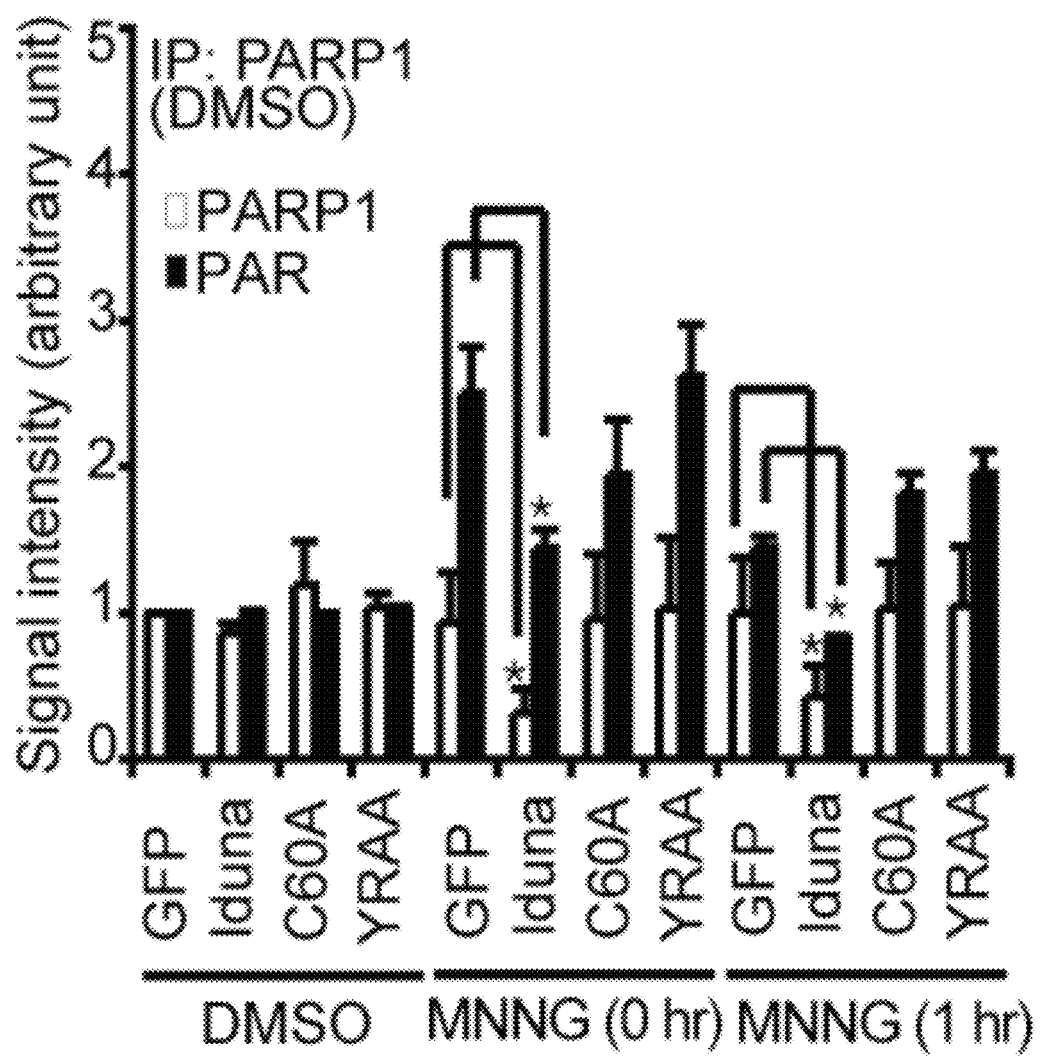
Figure 93:
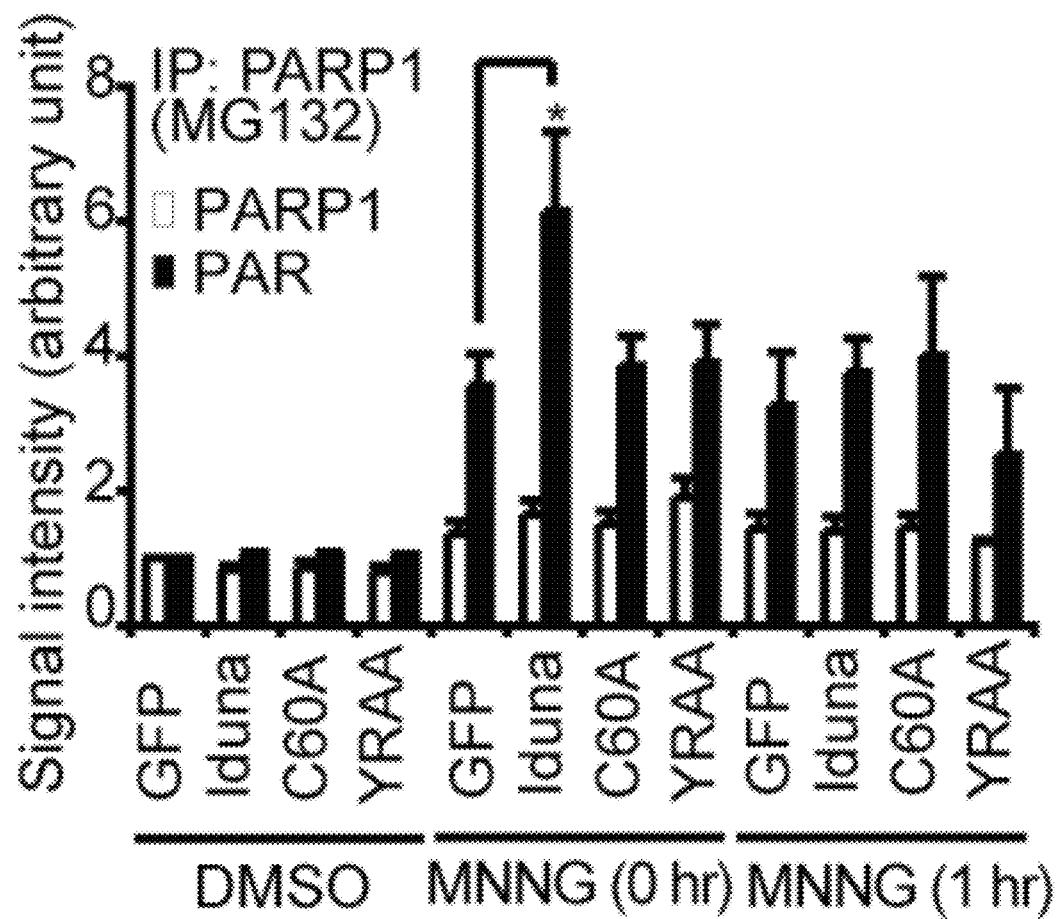
Figure 94:
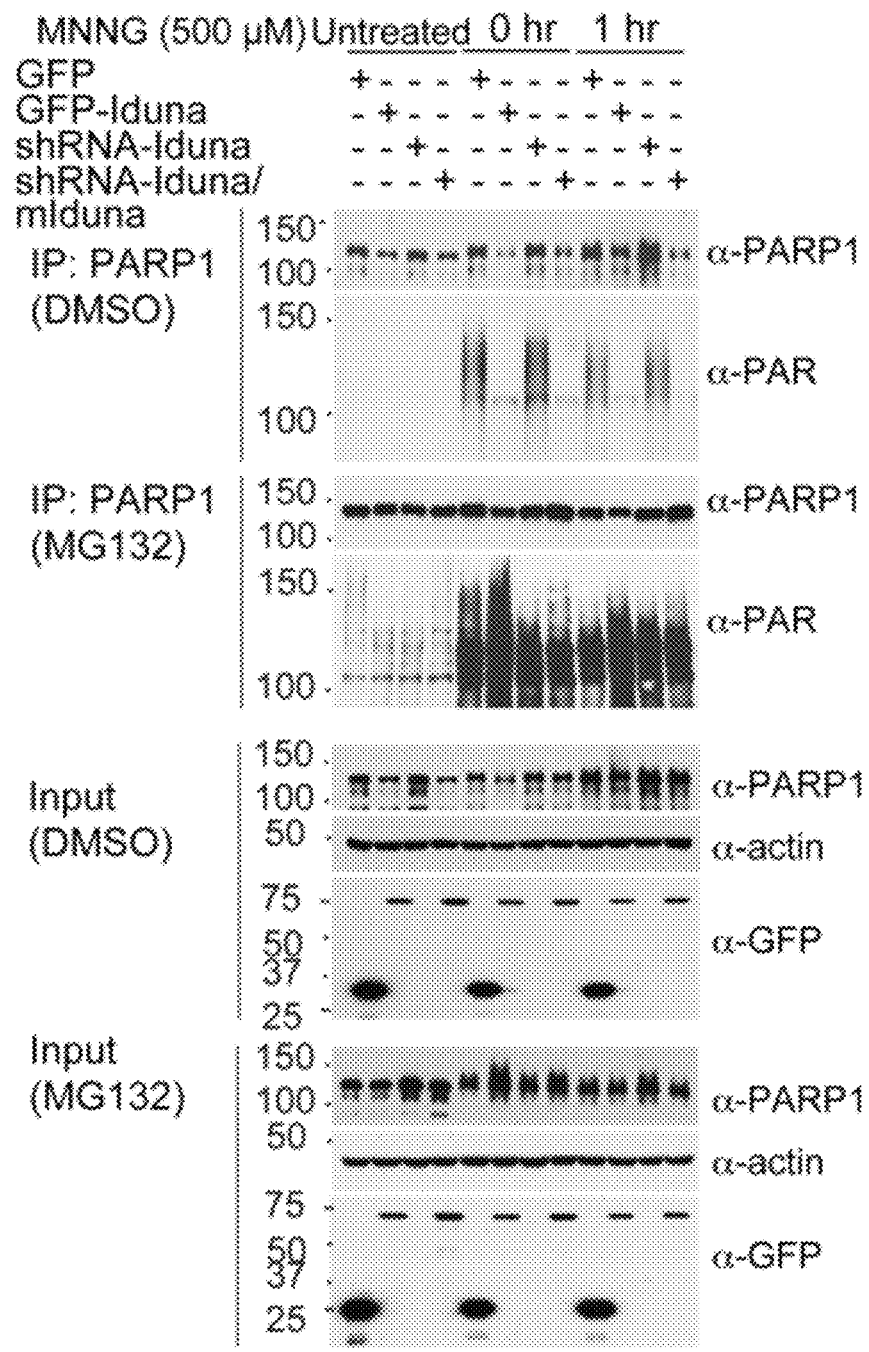
Figure 95:
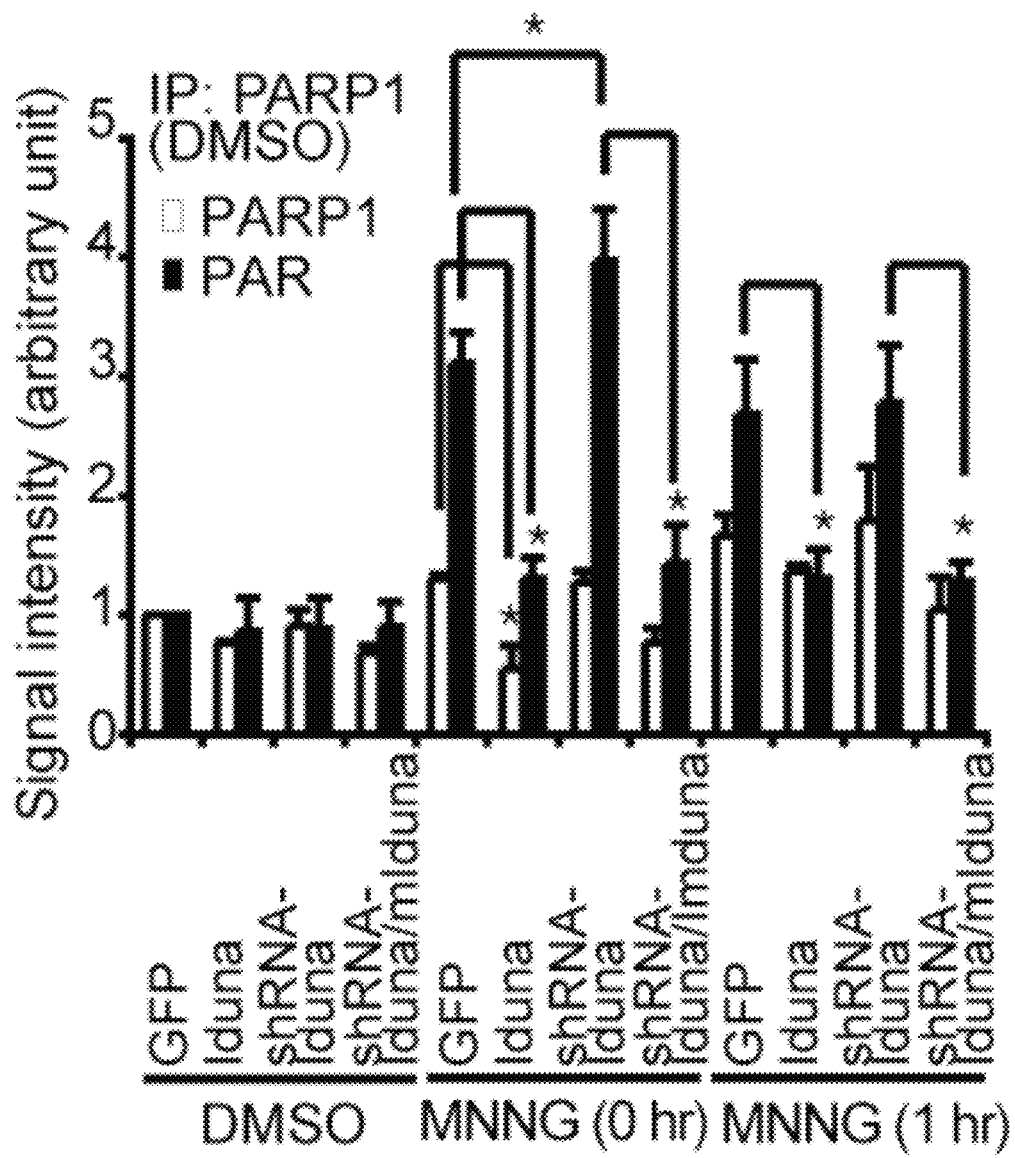
Figure 96:
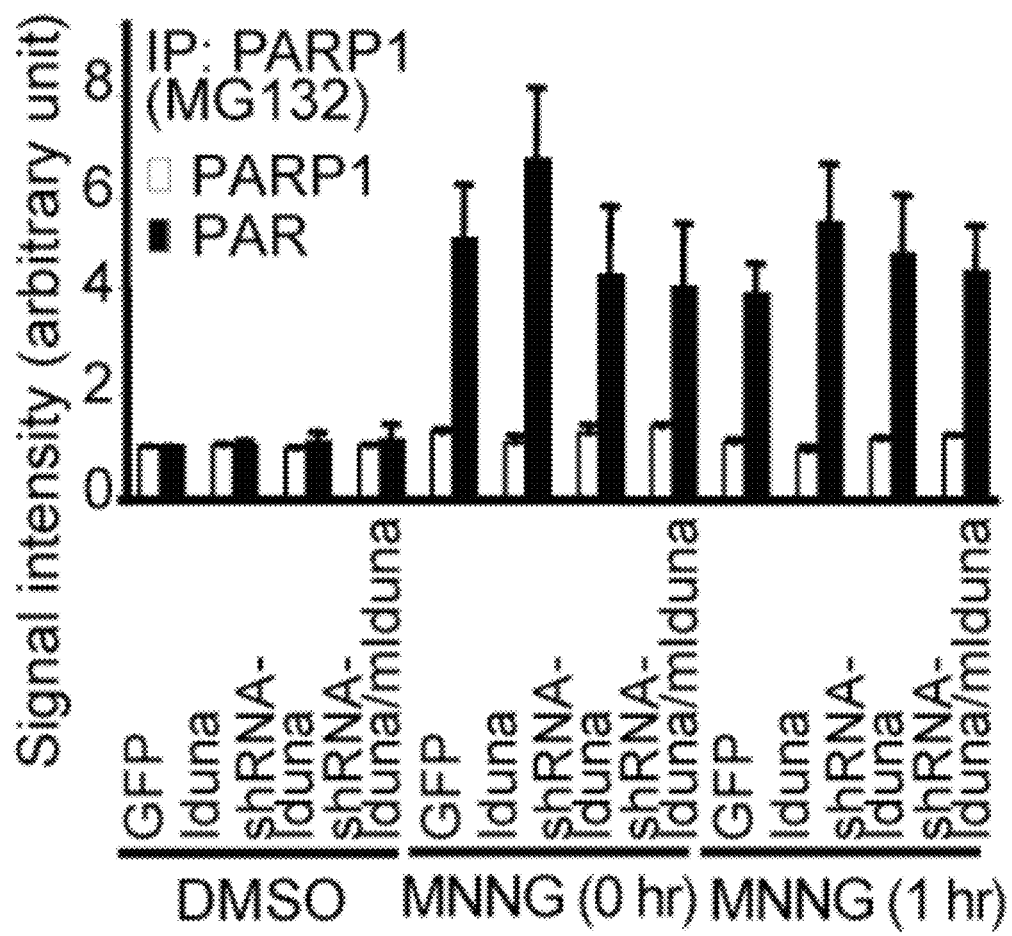
Figure 97:
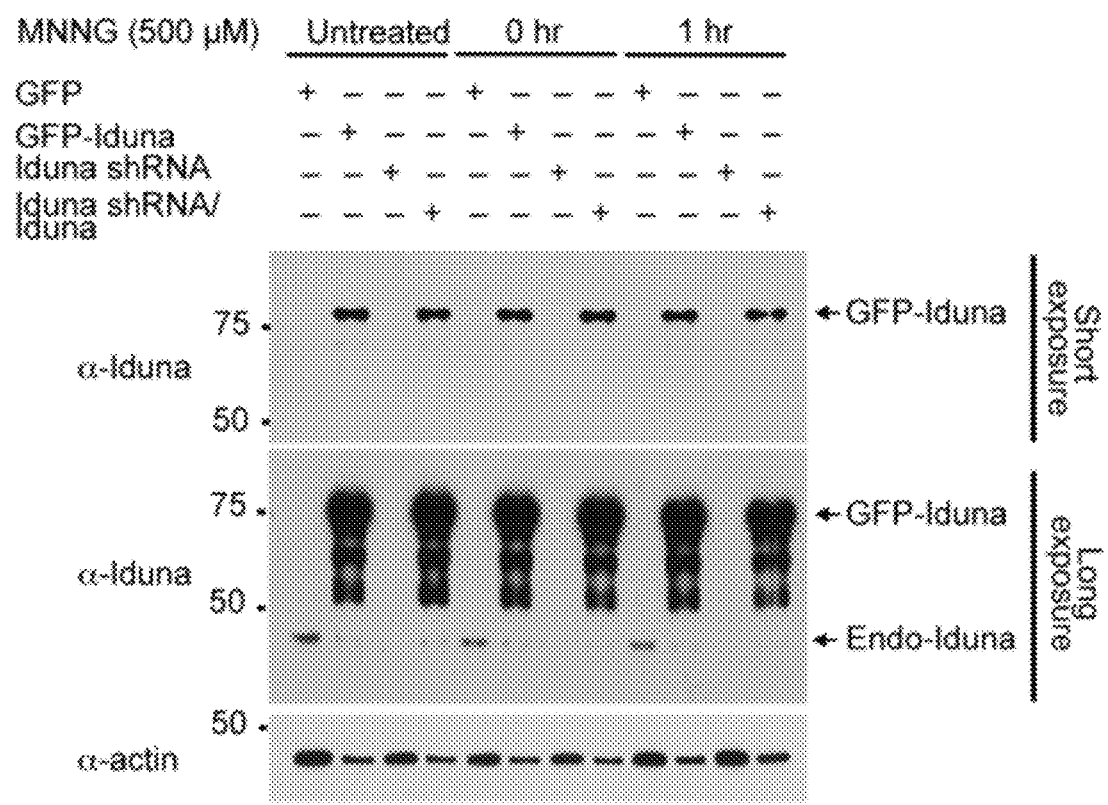
FIG. 97—Knockdown of endogenous Iduna. (A) Iduna expression by shRNA-Iduna was detected by immunoblot with anti-Iduna antibody in GFP, GFP-Iduna, shRNA-Iduna or shRNA-Iduna/mIduna stably overexpressing MCF7 cells as described in FIG. 28. Loading protein amount was diluted one-fourth for GFP-Iduna and shRNA-Iduna/mIduna. GFP-Iduna expression was detected through short time exposure (30 sec) (top), Endo-Iduna was monitored by immunoblot through long time exposure (5 min) (middle) and actin expression was analyzed as loading control (bottom). All experiments were repeated twice.

Iduna Targets PARsylated PARP1 for Ubiquitin Proteasomal Degradation. To determine whether Iduna targets PARsylated PARP1 for ubiquitin proteasomal degradation stably transfected MCF7 cells expressing GFP-Iduna, GFP-Iduna C60A and GFP-Iduna YRAA and cells stably expressing a shRNA to Iduna were examined (FIGS. 91-96). shRNA for human Iduna effectively knocks down the expression of human Iduna and mouse Iduna serves to rescue Iduna knockdown (FIG. 97). PARP1 was activated with the DNA damaging agent N-methyl-N-nitro-N-nitrosoguanidine (MNNG) followed by immunoprecipitation of PARP1. MNNG treatment did not change the overall levels of PARP1. However there is a shift in its molecular weight due to autoPARsylation and there is an almost three fold increase in PARsylated PARP1 immediately following the MNNG treatment (FIGS. 91 and 92). GFP-Iduna leads to a significant reduction in PARP1 and PARsylated PARP1. GFP-Iduna C60A or Iduna YRAA have no effect on PARP1 or PARsylated PARP1 levels (FIGS. 91 and 92). One hour post-MNNG treatment total PARP1 levels and PARsylated PARP1 levels are significantly reduced by GFP-Iduna, but not by GFP-Iduna C60A or YRAA. In the presence of the proteasome inhibitor, MG132, Iduna fails to diminish the levels of PARP1 and PARsylated PARP1 (FIGS. 90 and 92) confirming that Iduna targets PARsylated PARP1 for ubiquitin proteasomal degradation. The effect of knockdown of Iduna with shRNA on the levels of PARP1 and PARsylated PARP1 was evaluated. shRNA to Iduna prevents the reduction in PARP1 and PARsylated PARP1 following MNNG treatment (FIGS. 94 and 95). An shRNA resistant mouse Iduna decreases the levels of PARP1 and PAR modified PARP1 in the presence of the shRNA to human Iduna indicating that the effects observed with shRNA Iduna are specific (FIGS. 94 and 95). In the presence of MG132 the levels of PARP1 and PARsylated PARP1 remain elevated following MNNG treatment (FIGS. 94 and 96). These results taken together suggest that Iduna ubiquitinates PARP in a PAR-dependent manner leading to its proteasomal degradation.

Figure 98:
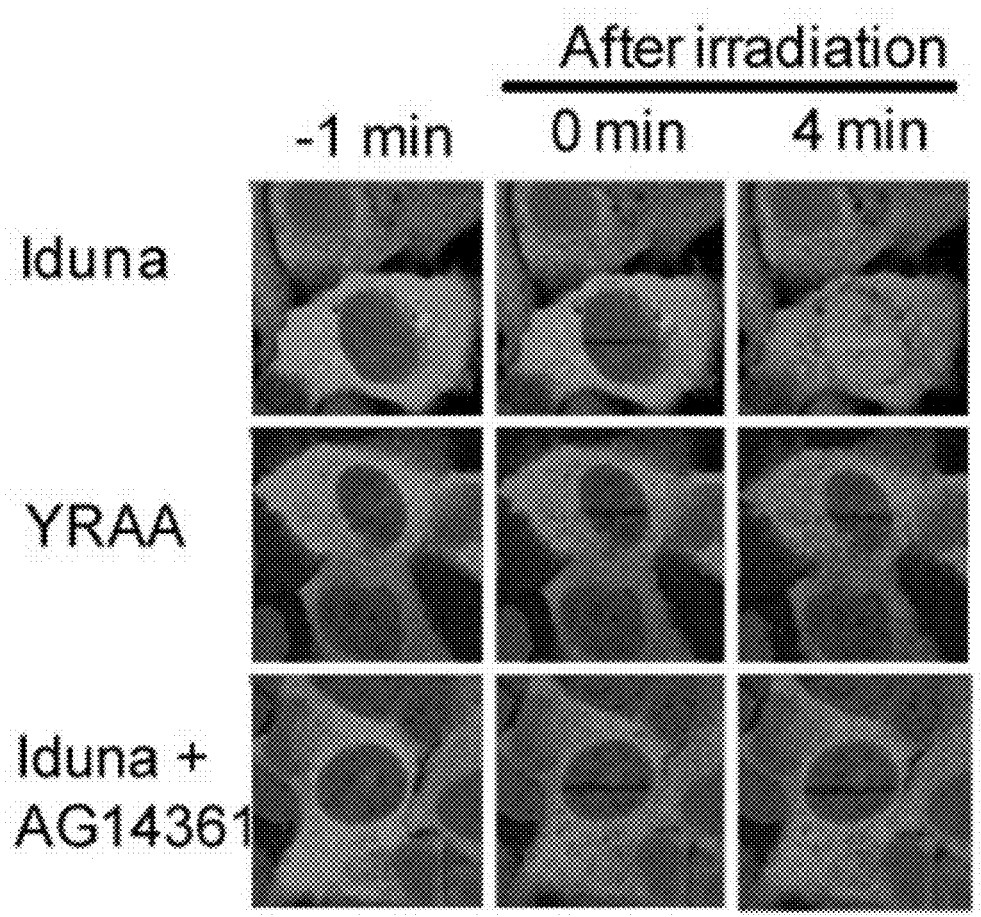
FIG. 98-106—Iduna protects against DNA damage.

Iduna Regulates the DNA Damage Response. The PAR-dependent association and ubiquitination of known DNA repair factors PARP1, PARP2, XRCC1, KU70 and DNA ligase III suggested a possible role for Iduna in the DNA damage response. To investigate the role of Iduna in the DNA damage response the recruitment of GFP-Iduna to sites of DNA damage induced by laser microirradiation was assessed (FIG. 29). GFP-Iduna begins to translocate to the nucleus and concentrate at the microirradiation site immediately after the laser microirradiation (FIGS. 98 and 99). The translocation of GFP-Iduna peaks between 3 to 4 minutes (FIGS. 98 and 99). The recruitment of GFP-Iduna to laser-induced DNA breaks requires PARP activation because the PARP inhibitor AG14361 blocks the translocation of Iduna (FIGS. 98 and 99). PAR binding to Iduna is also required for the translocation because Iduna YRAA mutant, which is defective for PAR binding is not recruited to laser-induced DNA breaks (FIGS. 98 and 99). GFP-Iduna localizes to sites of laser-induced DNA breaks, as marked by γH2AX immunostaining (FIG. 100).

The sensitivity of MCF7 cells to DNA damage induced by MNNG or γ-irradiation in the setting of Iduna overexpression and shRNA Iduna knockdown was assessed (FIGS. 101 and 102). Iduna overexpression dramatically rescues MCF7 cells from MNNG-induced cell death (FIG. 101). The rescue requires Iduna's E3 ubiquitin ligase activity because the Iduna C60A mutant that lacks E3 ligase activity is not protective (FIG. 101). Moreover, PAR binding of Iduna is also required as Iduna YRAA that lacks PAR binding is also not protective (FIG. 101). shRNA knockdown of Iduna enhances MNNG toxicity, which is reversed by overexpressing mouse Iduna that is resistant to shRNA Iduna knockdown (FIG. 101). Following γ-irradiation of MCF7 cells, Iduna overexpression rescues cells from G1 arrest in the cell cycle and promotes cell survival (FIG. 102). The rescue requires Iduna's E3 ubiquitin ligase activity because the Iduna C60A mutant that lacks E3 ligase activity is not protective (FIG. 102). Moreover, PAR binding of Iduna is also required as Iduna YRAA that lacks PAR binding is also not protective (FIG. 102). shRNA knockdown of Iduna has comparable effects to the GFP control following γ-irradiation, which is reversed by overexpression mouse Iduna that is resistant to shRNA Iduna knockdown (FIG. 102).

To ascertain if Iduna may be involved in DNA repair, the level of apurinic/apyrimidinic (AP) sites, which are one of major types of DNA lesions formed during the course of base excision and repair was assessed (FIG. 103). Following DNA damage induced by MNNG there is an 8 fold increase in the number of AP sites that is completely prevented by Iduna overexpression (FIG. 103). The prevention of the increase in AP sites by Iduna following MNNG requires PAR binding of Iduna because Iduna YRAA, which lacks PAR binding still leads to an 8 fold increase in AP sites (FIG. 103). Moreover, Iduna's E3 ubiquitin ligase activity is required for the reduction in AP sites as Iduna C60A, which is devoid of E3 ubiquitin ligase activity fails to reduce the number of AP sites induced by MNNG treatment (FIG. 103). shRNA knockdown of Iduna increases the number of AP sites by almost 14 fold after DNA damaged induced by MNNG (FIG. 103). Overexpression of mouse Iduna that is resistant to the shRNA knockdown of Iduna prevents the increase in the number of AP sites (FIG. 103).

To confirm that Iduna facilitates DNA repair, the alkaline comet assay was performed. The comet assay detects DNA fragmentation by monitoring DNA integrity by SYBR green staining during electrophoresis of cells. Cells with intact DNA have compact circular staining, whereas cells with DNA damage have bright tails that resemble comets. MCF7 cells were treated with γ-irradiation (2 Gy) in the setting of Iduna overexpression and shRNA Iduna knockdown (FIGS. 104-106). Iduna overexpression dramatically prevents the reduction in head diameter and increase in tail length in MCF7 cells treated with γ-irradiation compared to GFP control MCF7 cells (FIGS. 104-106). These effects require Iduna's E3 ubiquitin ligase activity because the Iduna C60A mutant that lacks E3 ligase activity does not prevent the reduction in head diameter and increase in tail length (FIGS. 104-106). Moreover, PAR binding of Iduna is also required as Iduna YRAA that lacks PAR binding also does not prevent the reduction in head diameter and increase in tail length (FIGS. 104-106). shRNA knockdown of Iduna enhances the reduction in head diameter and increase in tail length in MCF7 cells treated with γ-irradiation compared to GFP control MCF7 cells, which is reversed by overexpression of mouse Iduna that is resistant to shRNA Iduna knockdown (FIGS. 104-106). The data are summarized in FIG. 107.

As discussed, the identification and characterization of Iduna, a neuroprotective protein is disclosed herein. Iduna protects against parthanatos, NMDA receptor mediated glutamate excitotoxicity both in vitro and in vivo, and ischemia due to middle cerebral artery occlusion. Iduna is normally expressed at low levels in the nervous system, but expression substantially increases following a low dose of NMDA, a sub-lethal exposure to OGD, or a brief exposure to BCCAO, all of which induce neuroprotection. Thus, Iduna plays a role in the protective response to NMDA and ischemia and the subsequent development of tolerance to lethal insults. shRNA mediated knockdown of Iduna completely abolishes the protective effects of the neuroprotective dose of NMDA and overexpression of Iduna is neuroprotective. The PAR polymer binding activity of Iduna is intimately involved with its neuroprotective function. Emerging evidence reveals that PAR polymer binds to a variety of proteins in a saturable and highly specific manner. A recent unbiased proteomic screen for PAR-binding proteins identified a number of proteins including AIF. Mutation of the PAR-binding domain in AIF prevents the translocation of AIF from the mitochondria and promotes cell survival. That Iduna blocks the translocation of AIF from the mitochondria to the nucleus is consistent with these observations. The ability to interfere with PAR dependent signaling events positions Iduna as the first endogenous functional antagonist of PAR polymer death signaling.

Induction of neuroprotective proteins including Iduna is likely a result of multiple different signaling events. Low concentrations of NMDA (50 µM) or non-lethal OGD induces long-lasting neuroprotection that appears similar to that induced by dis-inhibition of GABAergic neurons by bicuculline administration, to activate calcium, nitric oxide and MEK dependent pathways, as well as, CREB dependent signaling. Different induction paradigms likely activate divergent cell survival pathways by preferential activation of synaptic and extrasynaptic receptors. Research into neuroprotective mechanisms has at its heart the goal of developing new therapeutic strategies to treat patients. Induction strategies would have use for acute injuries such as stroke or trauma, and would be extremely useful in treating patients undergoing cardiac bypass surgery, neurosurgery or other surgical cohorts where ischemia is a risk. Patients with subarachnoid hemorrhage, transient ischemic attacks, soldiers at risk for blast injury or patients suffering from chronic neurodegenerative diseases may also benefit from enhancing neuronal survival.

As disclosed herein Iduna represents a novel protein, which confers protection against parathanatos in a manner analogous to that in which Bcl-2 and IAPs prevent apoptosis. The mechanism by which Iduna protects against parthanatos unveils a previously unrecognized endogenous protective process that involves interference with PAR polymer mediated toxicity downstream of PARP-1 activation. Due to the prominent role of PARP-1 activation in many neurologic diseases and ischemia reperfusion injury in organs, therapies aimed at blocking PAR polymer induced cell death by activating Iduna or mimicking the effects of Iduna could represent novel therapeutic targets to prevent the toxic effects of PARP-1 activation and cell death.

As discussed, disclosed herein is the identification and characterization of Iduna, a novel NMDA receptor-induced survival gene that is neuroprotective against glutamate NMDA receptor mediated excitotoxicity both in vitro and in vivo and against stroke through interfering with PAR polymer induced cell death (parthanatos). Further, in certain embodiments, Iduna is protective in vivo against NMDA-induced excitotoxicity and middle cerebral artery occlusion (MCAD)-induced stroke in mice.

Ubiquitin mediated protein degradation is crucial for regulation of cell signaling and protein quality control. Poly(ADP-ribose) (PAR) is a cell-signaling molecule that mediates changes in protein function through binding at PAR binding sites. As shown, Iduna is a PAR polymer binding protein and mutations at the PAR polymer binding site abolishes the PAR binding activity of Iduna and attenuates its protective actions. Specifically, Iduna is a PAR-dependent ubiquitin E3 ligase. Iduna's E3 ligase activity invoves PAR binding because point mutations at Y156A and R157A eliminate Iduna's PAR binding and Iduna's E3 ligase activity. Iduna's E3 ligase activity also involves an intact RING domain because Iduna possessing point mutations at either H54A or C60A is devoid of ubiquitination activity. Tandem affinity purification reveals that Iduna binds to a number of proteins that are either PARsylated or bind PAR including PAR polymerase-1, 2 (PARP1, 2), nucleolin, DNA ligase III, KU70, KU86, XRCC1, DNA ligase III and histones. PAR binding to Iduna activates its E3 ligase function and PAR binding is involved with Iduna ubiquitination of PARP1, XRCC1, DNA ligase III and KU70. Iduna's PAR-dependent ubiquitination of PARP1 targets it for proteasomal degradation. Via PAR binding and ubiquitin E3 ligase activity, Iduna protects against cell death induced by the DNA damaging agent N-methyl-N-nitro-N-nitrosoguanidine (MNNG) and rescues cells from G2/M arrest and promotes cell survival after γ-irradiation. Moreover, Iduna facilitates DNA repair by reducing apurinic/apyrimidinic (AP) sites after MNNG exposure and facilitates DNA repair following γ-irradiation as assessed by the comet assay.

Further, disclosed herein are compositions and methods for treating cancers using small molecule inhibitors. For example, small molecule inhibitors of Iduna may be used to treat a variety of cancers. In addition, the techniques and compositions disclosed herein may be used to identify effective inhibitors of Iduna, such as shRNA, anti-sense, and microRNA based inhibitors. For example, shRNA Target sequences include human Iduna target sequences: 5'-CCTGTGAGATGTTTGATATTA-3' (SEQ. ID. NO.: 1) and 5'-CCTGTTCTAATACTGCACCTT-3' (SEQ. ID. NO.: 2). Further, microRNA Target sequences include: Position 104-110 of Iduna 3'UTR; 5 . . . CAUUUUGGGAGUUGGGG UGGGAA. (SEQ. ID. NO.: 3); hsa-miR-1260; and 3'ACCACCGUCUCCACCCUA (SEQ. ID. NO.: 4).

Methods and Materials

Apart from different methods specifically discussed, the following methods and techniques were generally used herein.

Plasmids and antibodies. To generate Iduna's mutant plasmids, site-directed mutagenesis were carried out using the QuickChange change site-directed mutagenesis kit (Stratagene) with following primers; C60A Forward 5'-GTT TTC TGT TAT CTG GCT GTA AAG GGT GCT T-3' (SEQ. ID. NO.: 5), C60A Reverse 5'-AAG CAC CCT TTA CAG CCA GAT AAC AGA AAA C-3' (SEQ. ID. NO.: 6), H54A Forward 5'-AGT CTG CCC TGT AAG GCT GTT TTC TGT TAT CTG-3' (SEQ. ID. NO.: 7) and H54A Reverse 5'-CAG ATA ACA GAA AAC AGC CTT ACA GGG CAG ACT-3' (SEQ. ID. NO.: 8). All mutation sites were confirmed by DNA sequencing analysis. TAP-Iduna plasmid was constructed by insertion of full-length Iduna cDNA into the EcoRI and XhoI site on pNTAPB vector. Antibodies used for immunoblot analysis were as follows: anti-Nucleolin from Novus Biologicals; anti-ATP synthase subunit α and anti-PARP1 from BD Biosciences; anti-GFP, anti-importin 7, anti-H1.2 and anti-KU70/86 from Abcam; anti-CBP from, anti-DNA ligase III, anti-H3 and anti-γH2AX from Upstate Biotech; anti-XRCC-1 and anti-actin-HRP from Sigma; Anti-ubiquitin from DAKO; secondary antibody conjugated HRP or fluorescence from Jackson Lab. Anti-Paris (clone N196/16) and anti-Iduna (clone N201/35) from NeuroMab; Anti-GST, anti-PAR and anti-Iduna antibody were previously described in the literature.

Lentiviral preparations for overexpression. Invitrogen ViraPower lentiviral packaging system was employed for high-titer viral preparations for effective transduction. All lentiviral particles were prepared as previously described (1). Briefly, lentiviral vectors were transfected into HEK 293FT cells along with viral packaging plasmids using calcium phosphate method (1). After 12 h, cells were shocked with 10% DMSO in PBS for 2 minute thereafter cells were further incubated during 18 h with fresh medium. Viral particles were precipitated by centrifugation at 25,000 g for 3 h. Pellets were dissolved with serum free medium and stored at −80° C.

Cell culture and establishment of stably overexperessing and RNAi mediated knock down cell lines. Both HEK 293FT (Human embryonic kidney cell line) and MCF7 (Human breast cancer cell line) cells were purchased from American Type Culture Collection (ATCC), and were cultured in Dulbecco's modified Eagle's medium (DMEM) and Earle's minimal essential medium (MEM) supplemented with 10% fetal bovine serum (FBS), 2 mM L-glutamine, 50 units/ml penicillin, and 50 μg/ml streptomycin, respectively. MCF7 stable cells expressing GFP, GFP-Iduna, GFP-Iduna C60A and GFP-Iduna YRAA, were established by infection using each lentiviral particles. All stably overexpressed cell lines were maintained in complete medium. To generate Iduna knockdown MCF7 cells, five RNAi TRC clones were purchased from Open Biosystem.

TRCN0000033979/1E4 (Human)
(SEQ. ID. NO.: 9)
5'-CCGGCCTGTGAGATGTTTGATATTACTCGAGTAATATCAAACATCT

CACAGGTTTTTG-3'

TRCN0000033980/1E5 (Human and Mouse)
(SEQ. ID. NO.: 10)
5'-CCGGGCAGGAAGATTAAGCGAGATACTCGAGTATCTCGCTTAATCT

TCCTGCTTTTTG-3'

TRCN0000033981/1E7 (Human)
(SEQ. ID. NO.: 11)
5'-CCGGCCTGTTCTAATACTGCACCTTCTCGAGAAGGTGCAGTATTAG

AACAGGTTTTTG-3'

TRCN0000033982/1E8 (Human and Mouse)
(SEQ. ID. NO.: 12)
5'-CCGGGCCAGTAGTGATAGTGAGGATCTCGAGATCCTCACTATCACT

ACTGGCTTTTTG-3'

TRCN0000033983/1E9 (Human, Mouse and Rat)
(SEQ. ID. NO.: 13)
5'-CCGGGCTCATTTACAACTCAGTGGACTCGAGTCCACTGAGTTGTAA

ATGAGCTTTTTG-3'

These plasmids were transfected into MCF7 cells and selected by puromycin (2 mg/ml) for 7 days. Knockdown efficiency was analyzed by immunoblotting with anti-Iduna antibody. Two clones showed significant knockdown of endogenous Iduna. These cell lines were maintained in complete medium containing puromycin (200 μg/ml). SK-N-SH cells (Human neuroblastoma cells) was purchased from ATCC and cultured in DMEM with 10% fetal bovine serum (FBS), 50 units/ml penicillin, and 50 μg/ml streptomycin. To establish a TAP-Iduna expressing cell line, pNTAP-Iduna was stably transfected to SK-N-SH cells and treated with a geneticin selection (1 mg/ml) for 3 weeks.

Tandem affinity purification. Iduna's substrates were isolated using the Interplay mammalian TAP system (Stratagene). Briefly, SK-N-SH cells expressing pNTAP or pNTAP-Iduna were harvested and collected at 500×g at 4° C. and lysed in lysis buffer (Stratagene). The TAP procedure was then performed by following the manufacturer's instructions, except that the streptavidin and calmodulin-binding reactions were incubated overnight at 4° C. Eluted proteins were boiled in SDS sample buffer and resolved on 8-16% SDS-polyacrylamide gels. The presence of TAP and TAP-Iduna was determined by immunoblot with anti-CBP (Calmodulin binding peptide) and anti-Iduna antibody.

In vitro ubiquitination assay. To measure of autoubiquitination activity of GST free Iduna, E1 (50 nM), UbcHs (50 nM) and Iduna (IP samples or recombinant protein) were incubated with recombinant ubiquitin (200 mM) at 37° C. in reaction buffer containing 50 mM Tris-Cl, pH 7.5, 2.5 mM MgCl2, 2 mM DTT, 2 mM ATP. For reducing conditions, samples were treated with SDS sample buffer and boiled supernatant were separated by 8-16% SDS-PAGE. Both polymerized ubiquitin chains and ubiquitinated proteins were detected by immunoblot with anti-ubiquitin antibody. All proteins loaded in SDS-PAGE were separately visualized by coomassie staining. Recombinant E1, UbcHs and ubiquitin were purchased from either Calbiochem or Boston Biochem.

Synthesis of [$^{32}$P] and biotin-labeled PARP1 and purification of PARP-free PAR polymer. Automodified PARP1 and free PAR polymer were purified as previously described (1). Briefly, [$^{32}$P]-labeled (PerkinElmer) or biotin-labeled NAD (Trevigen) was incubated in reaction buffer containing 100 mM Tris-cl, pH 8.0, 10 mM $MgCl_2$, 8 mM DTT, 10% glycerol, 23 ug calf thymus activated DNA, 4 mM biotin-labeled NAD or 75 uCi [$^{32}$P]-labeled NAD. 100% ethanol was added in drops for 10% concentration by volume. Sequentially, twenty units of recombinant PARP1 (Trevigen) was incubated for 30 min at 30° C. To collect automodified PARP1, 3 M $CH_3COONa$ and isopropanol were added in sample thereafter automodified PARP1 was precipitated by centrifugation at 10,000 g for 10 min. To purify PARP-free biotin-labeled or [$^{32}$P]-labeled PAR polymer, collected samples were hydrolyzed in reaction buffer containing 1 M KOH and 50 mM EDTA. Hydrolyzed PAR polymers were incubated with AAGE9 buffer (250 mM $NH_4Ac$, pH 9.0, 6 M guanidine, 10 mM EDTA) and then it was adjusted to pH 9.0 with 4N HCl. The samples were loaded on prepacked Dihydroxyboryl Bio-Rex column (DHBB) and washed with AAGE9 buffer followed by 1 M $NH_4Ac$ solution. Free biotin-labeled or [$^{32}$P]-labeled PAR polymer was eluted by water at 37° C. Polymer size distribution was analyzed by 20% TBE-PAGE (90 mM Tris-borate pH 8.0, 2 mM EDTA).

In vitro PARP1 ubiquitination assay. PARP1 or biotin-labelled PARP1 were incubated with Glutathione Sepharose 4B (GE-healthcare) linked-GST-Iduna for 2 h at 4° C. After Sepharose 4B pull-down, beads were washed three times, and GST was cleaved from recombinant GST-Iduna by using PreScission Protease (GE Healthcare). Elute proteins were dialyzed with binding buffer containing 50 mM Tris, pH 7.5, 150 mM NaCl, and then incubated with E1, ubCH5a and ubiquitin at 37° C. in reaction buffer containing 50 mM Tris-Cl, pH 7.5, 2.5 mM $MgCl_2$, 2 mM DTT, 2 mM ATP. Final samples were treated with SDS sample buffer and boiled supernatant were separated by 8-16% SDS-PAGE. The ubiquitination of PARP1 and Iduna was analyzed by western blot with anti-ubiquitin, anti-PARP1, anti-Iduna and anti-PAR antibodies.

In vitro PAR pull down and EMSA analysis. To PAR pull down analysis, [$^{32}$P]-labeled PAR polymer (10,000 cpm/μl) was incubated for 1 h with recombinant Histone H3 (Novus Biologicals), Iduna and various mutants. After washing with buffer containing 0.1% Triton X-100, 0.1% NP-40, protease inhibitors cocktail, and 1 mM PMSF, it was incubated with anti-histone H3 or anti-Iduna antibody (2 μg) linked to protein-G agarose slurries for 2 h at 4° C. The complex between [$^{32}$P]-labeled PAR polymer and those proteins was collected by centrifugation at 1000×g for 1 min and then each collected sample was hydrolyzed by 1 M KOH and 50 mM EDTA. To measure the PAR-binding activity, 10 μl of each sample was analyzed by LS 6500 Liquid Scintillation Counting System. For the EMSA analysis, protein free [$^{32}$P]-labeled PAR polymer from residual samples were purified by a DHBB column and then samples resolved in 20% TBE-PAGE (90 mM Tris-borate pH 8.0, 2 mM EDTA). The gel was dried and developed by autoradiography using a Typhoon 9400 Imager (GE Health Care).

Two-dimensional gel electrophoresis-western blot (2DE-WB). Each sample from in vitro ubiquitination assay was suspended in 1.5 mL of sample buffer containing 40 mM Tris, pH 7.4, 7 M urea (Sigma), 2 M thiourea (Sigma), 4%

CHAPS (3-[(3-cholamidopropyl)dimethylammonio]-1-propane-sulfonate) (Sigma), 65 mM DTT (Bio-Rad Laboratories), 1 mM EDTA, protease inhibitors cocktail (Roche) and 1 mM PMSF (Phenylmethylsulfonyl chloride). Samples were desalted and concentrated by ultracentrifugal filter (Millipore). Samples were applied on immobilized pH 3-10 non-linear gradient strips (13 cm). Focusing started at 200 V and the voltage was gradually increased to 8000 V at 3 V/min (approximately 151,358 Vhr total). After the first dimension, strips were equilibrated for 15 min in the equilibration buffer containing 6 M urea, 20% glycerol, 2% SDS, 2% DTT and then for 15 min in the same equilibration buffer containing 2.5% iodoacetamide instead of DTT. After equilibration, strips were loaded on 9-16% gradient SDS gels for second-dimensional separation. The gels (180×200×1.5 mm) were run at 40 mA per gel. Immediately after the second dimension running, the gels were fixed for 18 h in 50% methanol, 10% acetic acid solution. The gels were stained with either Colloidal Coomassie Blue (Invitrogen) or SilverQuest (Invitrogen). Molecular masses were determined by standard protein markers (Bio-Rad) covering a range of 10-250 kDa. pI value was used as given by the supplier of the immobilized pH gradient strips (GE Healthcare). The Gels were destained with water and scanned with UMAX Scanner. For 2DE-western, gels were soaked in transfer buffer for 15 min, transferred onto nitrocellulose membrane and analyzed by immunoblot.

In vivo PARP1 stability assay. GFP, GFP-Iduna, GFP-Iduna C60A, GFP-Iduna YRAA, shRNA-Iduna and shRNA-Iduna/GFP-Iduna stably overexpressing cells were treated with 500 µM MNNG for 15 min, and replaced with fresh growth media for posttreatment 0 or 1 h in presence of DMSO or of MG132 (Sigma). The cells were harvested and then lysed with immunoprecipitation (IP) lysis buffer containing 25 mM HEPES, pH 7.4, 1 mM EDTA, 10 mM NaCl, 0.5% Triton X-100, protease inhibitors cocktail (Roche) and 1 mM PMSF (Phenylmethylsulfonyl chloride). Equal amount of proteins from cell lysates was incubated overnight at 4° C. with protein-G and anti-PARP1 antibody in IP lysis buffer. After protein-G pull-down, beads were washed five times with IP wash buffer (25 mM HEPES, pH 7.4, 1 mM EDTA, 100 mM NaCl, 0.5% Triton X-100), boiled in SDS sample buffer (Bio-Rad), and proteins were separated by 8-16% SDS-PAGE and analyzed by immunoblot with anti-PARP1 and anti-PAR antibody.

Cell death assay. GFP, GFP-Iduna, GFP-Iduna C60A, GFP-Iduna YRAA, shRNA-Iduna and shRNA-Iduna/GFP-Iduna stably transfected cells were treated with 500 µM MNNG for 15 min, and replaced with fresh growth media. After 24 h, the cells were stained with 5 mM Hoechst 33342 (Invitrogen) and 2 mM propidium iodide (PI) (Invitrogen) and counted by automated computer-assisted program (Carl Zeiss). The percentage of cell death was determined as the ratio of live to dead cells compared with the percentage of cell death in control.

Immunoprecipitation of endogenous Iduna. The cells were pretreated with DMSO, DPQ or AG14361 for 1 h. Following washes with PBS, cells were lysed using an immunoprecipitation (IP) lysis buffer containing 25 mM HEPES, pH 7.4, 1 mM EDTA, 10 mM NaCl, 0.5% Triton X-100, protease inhibitors cocktail and 1 mM PMSF. Equal amount of protein was incubated overnight with protein-G sepharose beads (Amersham and mouse IgG or specific antibody in IP lysis buffer. After pull-down, protein-G beads were washed five times with IP washing buffer (25 mM HEPES, pH 7.4, 1 mM EDTA, 100 mM NaCl, 0.5% Triton X-100) and boiled with SDS sample buffer (Bio-Rad) containing 5% β-mercaptoethanol (Sigma). Proteins were separated by 8-16% SDS PAGE and transferred to nitrocellulose membrane (0.45 µm). 5% dried milk in PBST or TBST (phosphate or Tris buffered saline with 0.1% Tween 20) was incubated for blocking, and the membranes were applied with specific antibodies as described on previous material section. After washing with PBST or TBST and incubation with horseradish peroxidase-conjugated anti-rabbit or anti-mouse IgG (Amersham Bioscience), the antigen-antibody was detected by chemiluminescence (ECL) (Pierce) and X-ray film (RPI).

Comet assay. Single cell gel electrophoresis assay was performed by following the manufacturer's instructions. Briefly, established stable cell lines were irradiated (2 Gy) with a Gammacell irradiator and then further incubated for 15 min at 37° C. Cells were collected at 500×g at 4° C. and rinsed twice with ice cold PBS (Ca++ and Mg++ free). A total of $5 \times 10^5$ cells were counted and resuspended into PBS (Ca++ and Mg++ free) and then combined with LMAgarose (low melting agarose) at a ratio 1:10 (v/v). Each sample was spotted into CometSlide™ and lysed with buffer (supplied with CometAssay Kit, Trevigen) for 1 h at 4° C. After draining the excess lysis buffer, slides were immersed with alkaline unwinding solution (200 mM NaOH, pH>13, 1 mM EDTA) for 1 h at RT. To the single cell electrophoresis, each comet slide was placed in electrophoresis slide tray with 1 L of alkaline unwinding solution and applied to 21 Volts for 30 min for electrophoresis. After draining the excess electrophoresis buffer, slides were rinsed twice with dH$_2$O and then fixed with 70% ethanol for 5 min. To facilitate single cell observation, slides were dried at 40° C. and stained with SYBR Green I (supplied with CometAssay Kit) for 5 min at 4° C. Cell images were captured using a Zeiss epi-fluorescent microscope (Axiovert 200M) and image analysis was performed with a CASP software (version 1.2.2) (4). Fifty cells per slide were monitored and the DNA damage was calculated using comet tail length and head diameter parameters.

Cell cycle analysis. Studies were performed to evaluate the cell cycle response of each stable cell lines. Cells were plated onto 150 mm culture dishes and cultured for 24 h at 37° C. with fresh growth medium. Following replacement of growth medium, cells were irradiated at 2 Gy with a Gammacell irradiator. After 12 h, cells were washed once with PBS and incubated with PBS containing 0.2% EDTA for 5 min at 37° C., thereafter scraped with fresh growth medium and collected at 500×g at 4° C. Collected cells were washed once with ice cold PBS and then fixed with 70% ethanol. Cells were washed once with PBS containing 1% FBS and resuspended into propidium iodide (PI) staining buffer (PBS, pH 7.4, 50 µg/ml PI, 1% FBS, 100 µg/ml RNase) for 30 min at 37° C. Cells were monitored for DNA content by a flow cytometry (BD Biosciences) and then data were analyzed with FlowJo using Dean-Jett-Fox model for the quantification of each cell cycle phase.

Determination of apurinic/apyrimidinic (AP) sites. The amount of AP sites in genomic DNA was monitored by a DNA damage quantification kit (BioVision). Briefly, cells were treated with either DMSO or 500 µM MNNG for 15 min, and then replaced with normal growth media. After 1 h, cells were scraped and harvested at 500×g for 5 min and washed once with PBS. Genomic DNA was isolated using a Biovision Genomic DNA Isolation Kit (BioVision) and then AP sites on the 0.5 µg of genomic DNA was labeled with biotin by the Aldehyde Reactive Probe (ARP) reagent (supplied with the DNA damage quantification kit) for 1 h at 37° C. To precipitate the biotin-tagged DNA, sample was mixed with TE buffer containing 2% glycogen and then sequentially incubated with ice cold 70% ethanol for 30 min at −20° C. AP-site tagged DNA was precipitated at 12,000×g for 10 min and washed twice with 70% ethanol. To determine of the number of AP sites in DNA, samples were dissolved in TE buffer and then transferred into 96 well plate with DNA binding buffer (supplied with the DNA damage quantification kit). After 12 h, samples were washed five times with DNA washing buffer (supplied with the DNA damage quantification kit) and then biotin labeled AP sites were quantified using an avidin-biotin assay. Each sample and standards (supplied with a DNA damage quantification kit) were run in triplicate and the OD was measured at 650 nm using a 96-well plate reader (SpectraMax Plus384 Microplate Reader).

Live-cell imaging and Laser micro-irradiation-induced DNA damage: For induction of localized DNA damage, MCF 7 cells stably expressing GFP-Iduna or GFP-Iduna-YRAA were plated onto 25 mm glass bottom culture dishes for 48 h. Cells were presensitized with 10 µM 5-bromo-2'-deoxyuridine (BrdU, Sigma) for 24 h. Cells were incubated with 2 µM Hoechst (Invitrogen) for 5 min and mounted on a preheated (37° C.) stage on a Zeiss LSM 710 confocal microscope equipped with 405 nm laser source. A laser microbeam was focused on a small rectangular strip of nucleus through 63× oil objective to induce localized DNA damage. The laser setting was set to 100% power output with a scanning speed of 1 and 6-10 laser iterations. The kinetics were calculated using Zeiss Zen 2010 software. Time point before irradiation represents—1 min and the time point just after irradiation represent 0 min. Each data series was normalized with respect to base line data intensity values.

Primary Neuronal Culture Preparation: Primary cortical cell cultures were prepared from gestational day 15 mouse embryos as previously described. Experiments were performed at DIV (day in vitro) 14. Under these conditions, neurons represent 90% of the cells in the culture. Mature neurons were washed with control salt solution (CSS) containing 120 mM NaCl, 5.4 mM KCl, 1.8 mM $CaCl_2$, 25 mM Tris-HCl pH 7.4 and 15 mM D-glucose. To induce NMDA-mediated protection, 50 µM NMDA and 10 µM glycine in CSS solution was applied to the cells for 5 min, then the cells were washed and re-supplemented with minimum essential medium containing 10% horse serum. Sham treatment control was performed as above except for a 5 min treatment with CSS alone. NMDA excitotoxicity was induced by treating cultures with 100 or 500 µM NMDA and 10 µM glycine in CSS for 5 min. MNNG, 50 µM was applied to neurons for 15 min, cells were washed and re-supplemented with the normal growth media.

Oxygen-Glucose Deprivation (OGD): For oxygen-glucose deprivation the culture medium was removed and the cells were washed with glucose free media to remove the entire medium containing glucose. OGD was initiated by addition of glucose-free medium that was pre-bubbled for 20 min with a mixture of OGD gas (5% $CO_2$, 9.8% hydrogen and the rest N2, (Airgas Ltd. USA) to remove the dissolved $O_2$ from the media. The cultures were then immediately transferred into a hypoxia chamber connected to an $O_2$ sensor/monitor (Biospherix Ltd. USA) and maintained at 37° C. OGD is terminated by resupplying the normal growth media and transferring back the incubator containing 5% $CO_2$ in room air.

Cell Death Assessment: Following exposure of neuronal cultures to the various treatments neuronal survival was quantified and presented as percent of cell death. Percent cell death was determined as the ratio of live-to-dead cells compared with the percent cell death in control wells to account for cell death attributable to mechanical stimulation of the cultures. Quantification of neuronal survival was determined by staining treated cultures with 5 µM Hoechst 33342 and 2 µM propidium iodide (PI) (Invitrogen, Carlsbad, Calif.). Culture plates were placed on a mechanized stage of a Zeiss microscope and photomicrographs were collected by a blinded observer. The numbers of total and dead (PI positive) cells were counted by automated computer assisted software (Axiovision 4.6, Zeiss, Germany). The raw counts are presented in an Excel file for generation of percent cell death and statistical analysis. Glial nuclei fluoresce at a lower intensity than neuronal nuclei and were gated out by the software program. At least two separate experiments using four separate wells were performed for all data points.

Cell Death Assessment in GFP-Transfected Mouse Neuronal Cultures: GFP, GFP-Iduna or GFP-Iduna-YRAA constructs were transfected into mouse cortical neurons on DIV 11, using lipofectamine 2000 (Invitrogen). On DIV 13, the cultures were treated with NMDA (500 µM for 5 min) to induced excitotoxicity. 24 h later, images were taken from the transfected neurons using Axiovert M 200 Zeiss microscope and Axiovision 6 software. GFP expressing neurons with fragmented processes were considered as dead cells. % cell death was assessed by subtracting the number of fragmented (dead) cells to the total number of transfected (GFP-positive) cells in the cultures.

Northern Analysis: FirstChoice Mouse blot was purchased from Ambion. Each probe from Iduna cDNA, β-tubulin, and β-actin was labeled with $\gamma$-$^{32}$P dATP using Strip-EZ DNA kit (Ambion). The membrane was prehybridized in hybridization buffer and then hybridized with each probe at 55° C. overnight. The membrane was washed with 1×SSC at 37° C. and 0.5×SSC at 65° C., respectively. The membrane was exposed on storage phosphor screen (Packard) for 24 h. Signals were detected using Cyclone Storage Phosphor System (Packard).

Cloning of Iduna Genes: Iduna complementary DNAs were cloned from mouse cDNA and sequenced. Iduna PCR products were cloned into the phCMV1-Xi vector (Gene Therapy Systems), pEGFP-C2 vector (Clontech), pCMV-Tag5 vector (Stratagene) and pGEX-6p vector (GE Health Care). Deletion mutants and YRAA mutants were constructed by PCR and were verified by sequencing.

Antibody Preparation and Immunoprecipitation: The peptide $NH_2$-GCDAPVVVAQHSLTQQRPLVPN-OH (SEQ. ID. NO.: 14) was synthesized from the amino acids 298-317 of Iduna (Gly and Cys were added to the sequence). The purified peptide was injected as an antigen to raise rabbit polyclonal anti-Iduna anti-sera. Iduna antibody was purified from anti-sera using Sulfolink (Pierce) with the purified Iduna protein. GST-Iduna fusion protein was cloned into pGEX-6p vector, expressed in *E. coli*, and Iduna protein was purified with glutathione-Sepharose 4B beads after cleavage of GST by Precision protease according to the manufacturer's instruction (Amersham Biosciences).

For immunoprecipitation, neuronal cell extracts were collected in 0.5 ml IP buffer (Phosphate buffered saline containing 1 mM EDTA, 1 mM EGTA, 0.5% NP-40, 1% Triton X-100, 0.25 mM sodium orthovanadate, 0.25 mM PMSF, 2.5 µg/ml leupeptin, 2.5 µg/ml aprotinin) and incubated for 30 min at 4° C. with constant agitation. After centrifugation (16,000×g, 4° C. for 15 min), the resulting supernatants were subjected to immunoprecipitation by incubation for 1 h at 4° C. with anti-PARP-1 (BD Biosciences), anti-GFP (Abcam), anti-PAR (96-10) or anti-Iduna antibodies. Following the additions of protein G-agarose beads, the mixtures were incubated for 1 h at 4° C. After washing with IP buffer, bound proteins were subjected to immunoblot analysis.

Immunoblot Analysis: Neuronal cultures were exposed to NMDA for 5 min. Cell lysates were subjected to centrifugation at 12,000×g for 10 min at 4° C. The resulting supernatant was subjected to SDS-PAGE, and the separated proteins were transferred electrophoretically to a nitrocellulose membrane. The membrane was incubated with a Tris-buffered saline solution containing 5% nonfat milk and 0.1% Tween 20. The membrane was then incubated for 1 h at room temperature with the indicated antibodies in a Tris-buffered saline solution containing 0.1% Tween 20 and subsequently with appropriate secondary antibodies conjugated with horseradish peroxidase (Amersham Biosciences). The immunoblots were visualized in X-ray films by an enhanced chemiluminescence method (Pierce, USA). Antibodies used include: anti-c-myc (Roche Applied Sciences USA), anti-PAR$^2$, anti-PARP-1 (BD Pharmigen USA), anti-GFP, anti-COXIV (Abcam Inc Cambridge, Mass.), HRP conjugated anti-β-actin, anti-β-tubulin, and anti-biotin (Sigma, USA), anti-AIF (Epitomics, Burlingame, Calif.).

FAR Western, PAR Overlay and EMSA: Synthetic peptides, purified proteins or immunoprecipiated samples were diluted in TBS-T buffer (1 µg/µl) and loaded onto a nitrocellulose membrane (0.05 µm) using a dot blot manifold system (Life Technologies) for far western analysis. For the PAR overlay assay, immunoprecipiated samples were subjected to SDS-PAGE and transferred onto a nitrocellulose membrane. The membranes were washed once with TBS-T buffer and air-dried followed by incubation with indicated concentrations of biotin-labeled PAR polymer for 1 h at room temperature with constant shaking. After washing in TBS-T buffer at 4° C., the membranes were probed with anti-PAR or anti-biotin antibodies. Immunoblots were visualized in X-ray films by an enhanced chemiluminescence method (Pierce). For EMSA analysis, 100 ng of purified proteins (0.1 µg/µl) were incubated with [$^{32}$P]-labeled PAR polymer for 2 min at RT thereafter samples were resolved in 5% PAGE-gel. The gel was heat dried and developed using a Typhoon 9400 Imager (GE Health Care).

Biotin and [$^{32}$B]-labeled Automodified PARP-1 Synthesis and PARP-free PAR Preparation: Biotin and [$^{32}$P]-labeled automodified PARP-1 were synthesized according to Shah et al and modified as described in Gagné et al. Briefly PARP-1 purified up to the DNA-cellulose step (600 U/mg) was incubated with biotin labeled NAD and [$^{32}$P]-NAD$^+$ for 2 min at 30° C., thereafter nonlabelled/nonisotopic NAD$^+$ was added to the reaction mixture and incubated for further 28 min at 30° C. The high specific activity biotin labeled NAD$^+$ and [$^{32}$P]-labeled automodified PARP-1 (80 cpm/nmol) were precipitated as described. Biotin-labeled, non-radioactive and [$^{32}$P]-labeled free PAR was prepared and purified on a DHBB column as described. Polymer size was assessed by 20% TBE-PAGE (90 mM Tris-borate pH 8.0, 2 mM EDTA) 45 and HPLC chromatography using a DEAE-NPR column.

Nitrocellulose PAR-binding Assay: Synthetic peptides or purified proteins were diluted in TBS-T buffer (1 µg/µl) and loaded onto a nitrocellulose membrane (0.05 µm) using a dot blot manifold system (Life Technologies). The membranes were washed once with TBS-T buffer, removed from the manifold and air dried. The membranes were then incubated in 10 ml of TBS-T buffer containing an indicated concentration of both [$^{32}$P]-labeled automodified PARP-1 and [$^{32}$P]-labeled PAR polymer for 3 h at room temperature with constant shaking. The membranes were washed with TBS-T buffer at 4° C. until no radioactivity could be detected in the waste. Finally, the membrane was air dried and subjected to autoradiography on Bio-Max MR (Kodak) films or analyzed by Cerenkov counting using an Instant Imager system (Perkin Elmer).

Chemiluminescent PARP assay for poly(ADP-ribosyl) ation of Histone H1: Activity of PARP-1 was determined by Trevigen Universal chemiluminescent PARP assay kit (Trevigen, Gaithersburg, Md., USA) in the presence of Iduna or the PARP-1 inhibitor 3-aminobenzamide (3-AB). According to manufacturer's instructions, the incorporation of biotinylated NAD+ (Trevigen) into the poly(ADP-ribose) polymer primed at solid phase immobilized histone H1 (Trevigen) was detected by the chemiluminescent assay, either in the presence or absence of recombinant Iduna. Reactions were performed with 34 µM total biotinylated NAD+ for 60 min at 25° C. in triplicates. Chemiluminescence was measured using a fluorescence multi-well plate reader (SOSTmax, Sunnyvale, Calif.) with an excitation at 544 nm excitation/590 nm emission. In the parallel wells, PARP1 activity was measured after the 3-aminobenzamide treatment at the same concentration of biotinylated NAD+ (34 µM).

PARP Inhibition Assay: To evaluate the ability of Iduna to act as a PARP inhibitor, [$^{32}$P]-labeled automodified PARP-1 was synthesized in presence of GST, GST-Iduna or PARG, respectively. To purify the [$^{32}$P]-labeled automodified PARP-1, the reaction mixture was incubated with anti-PAR antibody for 4 h at 4° C. and then sequentially incubated with protein-G slurry for 1 h at 4° C. Samples were washed two times with PBS and the amount of [$^{32}$P]-labeled automodified PARP-1 was measured by LS 6500 Liquid Scintillation Counting System.

Lentiviral Preparations for Overexpression and RNAi: We used Invitrogen ViraPower lentiviral packaging system and obtained high-titer viral preparations for effective transduction in primary neuronal cultures and for intra-striatal injections. For developing efficient shRNA lentiviruses, we subcloned a siRNA oligo directed to the coding region +556-576 of Iduna into a lentiviral expression vector, cFUGw. The oligo was PCR amplified with primers flanked by PacI restriction sites. Following digestion and ligation, clones were selected and verified for the inserted sequence. The lentiviral construct co-expresses EGFP driven by the Ubiquitin C promoter, in addition to the mouse U6 Pol II promoter driving the shRNA. To control for off-target and non-specific effects of shRNA, a shRNA against dsRed was used. The over expression lentiviral system was developed by removing the EGFP open reading frame from the cFUGw construct by a BamHIH/XbaI digestion and replacing it with the cDNA of GFP-Iduna or GFP-Iduna YRAA. Near 100% neuron specific expression is observed, using either our over expression or RNAi lentiviral system. The cDNA of human Iduna was cloned from human MCF-7 cells mRNA by reverse transcription-PCR (RT-PCR) and then it was subcloned to pEGFP-C2 to create EGFP human-Iduna. The construction of cFUGW-EGFP human-Iduna, was performed by digesting the pEGFP-human-Iduna by BamHI/XbaI followed by subcloning into the same enzyme restriction sites of cFUGW. DNA sequences were verified by sequencing.

Real Time PCR: RNA was isolated from primary cortical neurons. Reverse transcription by PCR was performed using an oligo-dT primer. Following cDNA generation, quantitative PCR was performed using Iduna primers: sense-5'-tgg gtg gtg gca gta tga tga gc-3' (SEQ. ID. NO.: 15), and antisense-5'-ctt cac ctc tgt gac tcc gtt cag c-3' (SEQ. ID. NO.: 16). Actin primers: sense-5'-gct cgt cgt cga caa cgg ctc-3' (SEQ. ID. NO.: 17), and antisense-5'-caa aca tga tct ggg tca tct tct c-3' (SEQ. ID. NO.: 18) were used for normalization. 50 cycles were used for quantitative PCR, using conditions: 94° C. (30 s), 58° C. (30 s) and 72° C. (30 s).

Calcium Imaging: Neuronal cells were plated on 17 mm glass cover slips, pre-coated with poly-L-ornithine (0.1 mg/ml). On DIV 14, the cultures were loaded with calcium sensitive dye Fluo-5f (2.5 µM, dissolved in pleuronic acid/ DMSO solution) for 45 min at 37° C. and thereafter placed on a thermostatically confocal microscopic stage (Carl Zeiss). HEPES balanced salt solution (HBSS: NaCl 137 mM, KCl 5 mM, HEPES 20 mM, glucose 10 mM, $CaCl_2$ 1.4 mM, $NaHCO_3$ 3 mM, $Na_2HPO_4$ 0.6 mM, $KH_2PO_4$ 0.4 mM, pH 7.4) was superfused to the cultures for 100 s to obtain a steady base-line. NMDA (500 µM for 5 min) was used to induce intracellular calcium influx. Florescence values were monitored at every 10 s and calculated using LSM 510 Meta software and represent the changes in cellular calcium.

Mitochondrial Membrane Potential ($\Delta\psi_m$): TMRM was used to determine $\Delta\psi_m$. Mouse neuronal cultures were loaded with TMRM (100 nM) for 20 min. Thereafter, live-cell imaging was captured using LSM 510 Live Confocal microscope (Carl Zeiss, Germany) for 20 minutes and fluorescence values for TMRM were calculated using LSM 510 confocal software (Carl Zeiss). Following 50-100 seconds base-line stabilization, NMDA (500 µM for 5 min) was directly perfused during image acquisition on the confocal microscopic stage using a peristaltic pump (Gilson). Live images were acquired at an interval of 20 s using a low laser power to avoid excessive bleaching. Due to spectral overlap with GFP, plasma membrane potential could not be determined.

Mitochondrial Isolation: Mitochondria were isolated from C57B6 mice by percoll gradient. Mice were sacrificed and forebrains were rapidly removed, minced and homogenized in isolation buffer containing 225 mM mannitol, 75 mM sucrose, 5 mM HEPES/KOH (pH 7.4), 1 mM EGTA and 1 mg/ml fatty acid free bovine serum albumin (BSA). Two pooled mouse forebrain homogenates were centrifuged at 1,800 g for 5 min and the resulting the supernatant was again centrifuged at 12,000 g for 10 min. The pellet containing mitochondria was resuspended in 15% percoll solution and layered over a 23%-40% percoll gradient. Following centrifugation at 30,000 g for 10 min, the synaptosomal-free mitochondrial fraction was collected between the interface of 23% and 40% percoll layers. The mitochondrial fraction was carefully collected with minimum contamination from the lower 40% percoll layer and washed twice with isolation buffer at 12,000 g for 10 min. The resulting pellet was resuspended in 100 µl of isolation buffer without EGTA and BSA. The samples were kept on ice until use. All mitochondrial preparations were used within 3-4 h of isolation.

Measurements of Mitochondrial $Ca^{2+}$-uptake Capacity: Extramitochondrial free $Ca^{2+}$ was monitored in the presence of isolated mitochondria or digitonin-permeabilized cells, using an indicator of extramitochondrial free $Ca^{2+}$ (Calcium green-5N, Invitrogen). Isolated mitochondria (100 µg protein) were suspended in potassium chloride (KCl) media containing 125 mM KCl, 2 mM $K_2HPO_4$, 1 mM $MgCl_2$, 20 mM HEPES (pH 7.0) and 0.1 µM Calcium green-5N. Mitochondrial substrates 5 mM glutamate, 5 mM malate and 1 mM ADP were added to media at the time of assay. Fluorescence was continuously monitored at an excitation/ emission at 488/532 nm respectively. All the assays were performed at 37° C. using an attached circulating water bath.

For measurement of mitochondrial $Ca^{2+}$ uptake in digitonin-permeabilized cells, the cultures were harvested in growth media by trypsinization. Following centrifugation in growth medium at 2000×g for 3 min, the cells were re-suspended in KCl medium ($1\times10^7$ cells/ml) containing mitochondrial substrates 5 mM glutamate, 5 mM malate and 1 mM ADP in presence of 0.1 µM Calcium green-5N. The plasma membranes were then selectively permeabilized with digitonin (50 µg/ml, Sigma USA). $Ca^{2+}$ uptake was monitored by addition of 50 µM $CaCl_2$ to the assay medium using a Hamilton syringe.

Construction of the ROSA26-Iduna Targeting Vector: The plasmid pBigT, which has adenovirus splice acceptor (SA), followed by a loxp site, phosphoglycerine kinase (PGK)-neo cassette, transcriptional stop sequences (tpA), another loxp site, a multiple cloning site (MCS), and the bovine growth hormone polyadenylation sequence (bpA). Both PacI and AscI sites were 5' to the SA, and an AscI site 3' to the bpA, respectively. To generate the pBigT-Iduna construct, the Iduna cDNA was excised from pEGFP-Iduna with XhoI and NotI and inserted into the same sites in a MCS of pBigT as indicated in FIG. 58. The resulting plasmids were digested with Pac1 and Asc1 to release the SA-loxp-(PGK)Neo-tpA-loxp-iduna-bpA cassette, which was then inserted into a ROSA26 targeting vector, pROSA26PA. pROSA26PA was kindly provided by Dr. Soriano (University of Washington, Seattle, Wash., USA)

Transgenic Mice: ES cells were targeted and screened as described in Soriano et al. Briefly, the pROSA26PA-iduna plasmid was linearized with KpnI and electroporated into ES cells derived from mouse strain 129SvEv. Twelve of 277 G418-resistant colonies had undergone correct homologous recombination, as determined by Southern blot and PCR of the ROSA26-Iduna allele. Two of these ROSA26-Iduna ES clones were injected into C57BL/6 blastocysts. Resulting chimeras were bred to C57BL/6 mice and offspring were tested for germline transmission. Heterozygous mice for the Rosa26PA-Iduna allele were crossed to Nestin-Cre$^{(+/+)}$ mice (on C57BL/6 background), which were obtained from the Jackson Laboratory, to obtain ROSA26PA-Iduna$^{(+/loxP)/}$Nestin-Cre$^{(-/+)}$ mice. Nestin-cre/ROSA26PA-Iduna transgenic mice, in which Cre recombinase expression is under the control of the nestin promoter, specifically expresses Iduna in brain. Mice were genotyped by PCR analysis using primers (5'-AAAGTCGCTCTGAGTTGTTAT-3' (SEQ. ID. NO.: 19), 5'-GCGAAGAGTTTG TCCTCAACC-3' (SEQ. ID. NO.: 20) and 5'-GGAGCGGGAGAAATGGATATG-3' (SEQ. ID. NO.: 21)) to select the ROSA26PA-Iduna locus. Nestin-Cre mice were genotyped by PCR using following primers; CreA, 5'-CCCGGCAAAACAGG TAGTTA-3' (SEQ. ID. NO.: 22); CreS, 5'-CATTTGGG CCAGCTAAA CAT-3' (SEQ. ID. NO.: 23) (93° C. for 30 s, 51° C. for 30 s, 65° C. for 40 s).

Bilateral Common Carotid Artery Occlusion (BCCAO): 8 week old C57BL/6 mice were anesthetized with 3% isoflurane and kept under anesthesia with 1% isoflurane in air for the entire period of surgery. Body temperature was maintained at 37° C. with a heating pad and a rectal probe (Harvard Apparatus, USA). Skin along the midline on the throat was cleaned and swabbed 3 times with 70% ethanol and betadine. A midline incision was given to expose the common carotid arteries (CCA) on either sides of the trachea. Sterile normal saline was used on the incision and CCAs to keep the tissues and arteries moist, and avoid any tissue dehydration. Micro-vascular clamps (Fine Science Tools, USA) were used to occlude both right and left CCA (bilateral CCA occlusion, BCCAO) for 5 minutes. Blockade of blood flow to the brain through CCAs could be seen visually. After 5 minutes the micro-vascular clamps were slowly released to allow CCA reperfusion to the brain. The incision was sutured using a silk 5-0 suture (Ethicon, USA). Anesthesia was withdrawn and animals were transferred to a warm chamber to allow recovery from anesthesia. Following complete recovery from anesthesia, the animals were returned to the cages and housed individually. At 48 h following BCCAO, animals were sacrificed under decapitation and brain tissue was collected for biochemical analysis. The entire surgical procedure was performed except BCCAO in sham operated mice.

Middle Cerebral Artery Occlusion (MCAD): To occlude the middle cerebral artery, mice were anesthetized with 1.5-2% isoflurane and maintained at normothermic temperature. A 7-0 monofilament with an enlarged silicone tip was passed through the right internal carotid artery to the base of the middle cerebral artery. Occlusion was confirmed by laser-Doppler flowmetry with a probe placed on thinned skull over the lateral parietal cortex. After 60 min of occlusion, the filament was removed and reperfusion was verified. At 24 h of reperfusion, the brain was harvested, sectioned into five coronal slabs, and stained with the vital dye, triphenyltetrazolium chloride. Infarct area was measured on the anterior and posterior surfaces of each slab and integrated to obtain infarct volume with correction for tissue swelling. The investigator performing the surgery and analyzing infarct size was unaware of the genotype of the mouse.

Neurobehavioural Activity: Spontaneous motor activity was evaluated for 5 min by placing the animals in a mouse cage for 5 minutes. A video camera was fitted on top of the cage to record the activity of a mouse in the cage. Neurological deficits were evaluated by an observer blinded to the treatment and genotype of the animals with a scale of 0-4 (0 no neurological deficit, 4 severe neurological deficit). The following criteria were used to score deficits: 0=mice appeared normal, explored the cage environment and moved around in the cage freely; 1=mice hesitantly moved in cage and didn't approach all sides of the cage, 2=mice showed postural and movement abnormalities and had difficulty approaching the walls of the cage, 3=mice with postural abnormalities tried to move in the cage but did not approach the wall of the cage, 4=mice were unable to move in the cage and stayed at the center. The cylinder test was performed to assess the forelimb performance in mice. For this test, a transparent glass cylinder (9 cm in diameter and 15 cm in height) was placed in the center of a chamber containing two video cameras on opposite sides. A mouse was placed in the cylinder and the cameras on opposite sides were aligned at a straight axis with the cylinder to allow recordings of mouse forelimb movements on all sides of the cylinder. Recordings were evaluated by an observer blinded to the treatment and genotype of the animals. Forelimb use of the mouse was recorded for 10 minutes and analyzed according to the following criteria: (1) Ipsilateral (right) forelimb use (number of touches to the cylinder wall) independent of the left limb (2) Contralateral (left) forelimb use (number of touches to the cylinder wall) independent of the right limb (3) Simultaneous use of both limbs. The percent use of the contralateral (left) limb was quantified by subtracting contralateral fore paw touches from the total number of touches made by the mouse during the period of observation.

Stereotaxic Injections: Mice were anesthetized by intraperitoneal injection of sodium pentobarbital (45 mg/kg body weight) and the head was fixed in a stereotactic frame (Kopf, Tujunga, Calif.) for the intrastriatal injection. Following a midline incision on the scalp, a small hole was drilled using coordinates rostral, 0.5 mm; lateral, 1.7 mm; ventral, 3.5 mm from bregma. 2 µl of high titer virus was injected using a Digital Stereotaxic Apparatus and a Nanomite Injector Syringe Pump (Harvard Apparatus, USA) over a period of 10 min followed by 3 min needle pause to permit proper diffusion. 5 days following viral injections, NMDA (20 nmoles) was injected using the same coordinates. After the surgery, the animals were put in separate cages and the body temperature was maintained with a heating pad and rectal probe. Following full recovery from the anesthesia, the animals were placed back on the animal cage racks in the JHMI animal facility Stereology: Mice were anesthetized and perfused with ice-cold PBS and ice-cold 4% paraformaldehyde in PBS (pH 7.4). Brains were removed and post-fixed overnight in 4% PFA. Following cryoprotection in 30% sucrose/PBS (pH 7.4), brains were frozen and 40 µM thick coronal sections were cut with a microtome. Free-floating sections were blocked in blocking solution (10% donkey serum plus 0.3% Triton-X-100 in PBS) for 1 h at room temperature. A primary antibody against GFP (rabbit polyclonal; Abcam, USA) was incubated overnight at 4° C., followed by incubation with anti-rabbit alexa488 conjugated antibody (Invitrogen, USA). The sections were mounted on glass slides and cover glasses were mounted on the sections, using Immu-Mount (Thermo, USA). To evaluate protection offered by Iduna against NMDA-toxicity, an unbiased stereological methodology was employed to count GFP-positive neurons. For the stereological counts, a computer assisted optical fractionator probe, Stereo Investigator (MicroBrightField, Williston, Vt., USA) software was used to count the green cells in every fourth section throughout the entire striatal region of the brain.

REFERENCES

Aarts, M. M. & Tymianski, M. Molecular mechanisms underlying specificity of excitotoxic signaling in neurons. Curr Mol Med 4, 137-147 (2004).

Waxman, E. A. & Lynch, D. R. N-methyl-D-aspartate Receptor Subtypes: Multiple Roles in Excitotoxicity and Neurological Disease. Neuroscientist 11, 37-49 (2005).

David, K. K., Andrabi, S. A., Dawson, T. M. & Dawson, V. L. Parthanatos, a messenger of death. Front Biosci 14, 1116-1128 (2009).

Wang, Y., Dawson, V. L. & Dawson, T. M. Poly(ADP-ribose) signals to mitochondrial AIF: a key event in parthanatos. Exp Neurol 218, 193-202 (2009).

Yu, S. W., Wang, H., Dawson, T. M. & Dawson, V. L. Poly(ADP-ribose) polymerase-1 and apoptosis inducing factor in neurotoxicity. Neurobiol Dis 14, 303-317 (2003).

West, A. E., et al. Calcium regulation of neuronal gene expression. Proc Natl Acad Sci USA 98, 11024-11031 (2001).

Gnegy, M. E. Ca2+/calmodulin signaling in NMDA-induced synaptic plasticity. Crit. Rev Neurobiol 14, 91-129 (2000).

Hong, S. J., Dawson, T. M. & Dawson, V. L. Nuclear and mitochondrial conversations in cell death: PARP-1 and AIF signaling. Trends Pharmacol Sci 25, 259-264 (2004).

Lanahan, A. & Worley, P. Immediate-early genes and synaptic function. Neurobiol Learn Mem 70, 37-43 (1998).

Nedivi, E., Hevroni, D., Naot, D., Israeli, D. & Citri, Y. Numerous candidate plasticity-related genes revealed by differential cDNA cloning. Nature 363, 718-722 (1993).

Hardingham, G. E. & Bading, H. The Yin and Yang of NMDA receptor signalling. Trends Neurosci 26, 81-89 (2003).

Hong, S. J., Li, H., Becker, K. G., Dawson, V. L. & Dawson, T. M. Identification and analysis of plasticity-induced late-response genes. Proc Natl Acad Sci USA 101, 2145-2150 (2004).

Gonzalez-Zulueta, M., et al. Requirement for nitric oxide activation of p21(ras)/extracellular regulated kinase in neuronal ischemic preconditioning. Proc Natl Acad Sci USA 97, 436-441 (2000).

Faraco, G., et al. Brain ischemic preconditioning does not require PARP-1. Stroke 41, 181-183 (2010).

Andrabi, S. A., et al. Poly(ADP-ribose) (PAR) polymer is a death signal. Proc Natl Acad Sci USA 103, 18308-18313 (2006).

Gagne, J. P., et al. Proteome-wide identification of poly (ADP-ribose) binding proteins and poly(ADP-ribose)-associated protein complexes. Nucleic Acids Res 36, 6959-6976 (2008).

Pleschke, J. M., Kleczkowska, H. E., Strohm, M. & Althaus, F. R. Poly(ADP-ribose) binds to specific domains in DNA damage checkpoint proteins. J Biol Chem 275, 40974-40980 (2000).

Alvarez-Gonzalez, R. & Jacobson, M. K. Characterization of polymers of adenosine diphosphate ribose generated in vitro and in vivo. Biochemistry 26, 3218-3224 (1987).

Wang, H., et al. Apoptosis-inducing factor substitutes for caspase executioners in NMDA-triggered excitotoxic neuronal death. J Neurosci 24, 10963-10973 (2004).

Yu, S. W., et al. Mediation of poly(ADP-ribose) polymerase-1-dependent cell death by apoptosis-inducing factor. Science 297, 259-263 (2002).

Yu, S. W., et al. Apoptosis-inducing factor mediates poly(ADP-ribose) (PAR) polymer-induced cell death. Proc Natl Acad Sci USA 103, 18314-18319 (2006).

Deb, C., et al. A novel in vitro multiple-stress dormancy model for *Mycobacterium tuberculosis* generates a lipid-loaded, drug-tolerant, dormant pathogen. PLoS One 4, e6077 (2009).

Dirnagl, U., Becker, K. & Meisel, A. Preconditioning and tolerance against cerebral ischaemia: from experimental strategies to clinical use. Lancet Neurol 8, 398-412 (2009).

Ahel, D., et al. Poly(ADP-ribose)-dependent regulation of DNA repair by the chromatin remodeling enzyme ALC1. Science 325, 1240-1243 (2009).

Ahel, I., et al. Poly(ADP-ribose)-binding zinc finger motifs in DNA repair/checkpoint proteins. Nature 451, 81-85 (2008).

Chang, P., Jacobson, M. K. & Mitchison, T. J. Poly(ADP-ribose) is required for spindle assembly and structure. Nature 432, 645-649 (2004).

Gottschalk, A. J., et al. Poly(ADP-ribosyl)ation directs recruitment and activation of an ATP-dependent chromatin remodeler. Proc Natl Acad Sci USA 106, 13770-13774 (2009).

Schreiber, V., Dantzer, F., Ame, J. C. & de Murcia, G. Poly(ADP-ribose): novel functions for an old molecule. Nat Rev Mol Cell Biol 7, 517-528 (2006).

Timinszky, G., et al. A macrodomain-containing histone rearranges chromatin upon sensing PARP1 activation. Nat Struct Mol Biol 16, 923-929 (2009).

Hara, T., et al. CREB is required for acquisition of ischemic tolerance in gerbil hippocampal CA1 region. J Neurochem 86, 805-814 (2003).

Lee, H. T., et al. cAMP response element-binding protein activation in ligation preconditioning in neonatal brain. Ann Neurol 56, 611-623 (2004).

Mabuchi, T., et al. Phosphorylation of cAMP response element-binding protein in hippocampal neurons as a protective response after exposure to glutamate in vitro and ischemia in vivo. J Neurosci 21, 9204-9213 (2001).

Papadia, S., Stevenson, P., Hardingham, N. R., Bading, H. & Hardingham, G. E. Nuclear Ca2+ and the cAMP response element-binding protein family mediate a late phase of activity-dependent neuroprotection. J Neurosci 25, 4279-4287 (2005).

Zheng, S., et al. NMDA-induced neuronal survival is mediated through nuclear factor I-A in mice. J Clin Invest 120, 2446-2456 (2010).

Hardingham, G. E., Fukunaga, Y. & Bading, H. Extrasynaptic NMDARs oppose synaptic NMDARs by triggering CREB shut-off and cell death pathways. Nat Neurosci 5, 405-414 (2002).

Soriano, F. X., et al. Preconditioning doses of NMDA promote neuroprotection by enhancing neuronal excitability. J Neurosci 26, 4509-4518 (2006).

Zhang, S. J., et al. Decoding NMDA receptor signaling: identification of genomic programs specifying neuronal survival and death. Neuron 53, 549-562 (2007).

Pacher, P. & Szabo, C. Role of the peroxynitrite-poly (ADP-ribose) polymerase pathway in human disease. Am J Pathol 173, 2-13 (2008).

Ciechanover A (1998) The ubiquitin-proteasome pathway: on protein death and cell life. The EMBO journal 17(24):7151-7160.

Di Fiore P P, Polo S, & Hofmann K (2003) When ubiquitin meets ubiquitin receptors: a signalling connection. Nature reviews 4(6):491-497.

Hochstrasser M (2002) New structural clues to substrate specificity in the "ubiquitin system". Mol Cell 9(3):453-454.

Harper JW (2002) A phosphorylation-driven ubiquitination switch for cell-cycle control. Trends in cell biology 12(3):104-107.

Prudden J, et al. (2007) SUMO-targeted ubiquitin ligases in genome stability. The EMBO journal 26(18):4089-4101.

Krishnakumar R & Kraus WL (2010) The PARP side of the nucleus: molecular actions, physiological outcomes, and clinical targets. Mol Cell 39(1):8-24.

Rouleau M, Patel A, Hendzel M J, Kaufmann SH, & Poirier G G (2010) PARP inhibition: PARP1 and beyond. Nat Rev Cancer 10(4):293-301.

Schreiber V, Dantzer F, Ame J C, & de Murcia G (2006) Poly(ADP-ribose): novel functions for an old molecule. Nature reviews 7(7):517-528.

Gagne J P, et al. (2008) Proteome-wide identification of poly(ADP-ribose) binding proteins and poly(ADP-ribose)-associated protein complexes. Nucleic Acids Res 36(22): 6959-6976.

Wang Y, et al. (2011) Poly(ADP-ribose) (PAR) binding to apoptosis-inducing factor is critical for PAR polymerase-1-dependent cell death (parthanatos). Sci Signal 4(167):ra20.

Yu S W, et al. (2006) Apoptosis-inducing factor mediates poly(ADP-ribose) (PAR) polymer-induced cell death. Proc Natl Acad Sci USA 103(48):18314-18319.

Yu S W, et al. (2002) Mediation of poly(ADP-ribose) polymerase-1-dependent cell death by apoptosis-inducing factor. Science 297(5579):259-263.

Hong S J, Li H, Becker K G, Dawson V L, & Dawson T M (2004) Identification and analysis of plasticity-induced late-response genes. Proc Natl Acad Sci USA 101(7):2145-2150.

Gold B, et al. (2008) Genome-wide association study provides evidence for a breast cancer risk locus at 6q22.33. Proc Natl Acad Sci USA 105(11):4340-4345.

Kirchhoff T, et al. (2009) The 6q22.33 locus and breast cancer susceptibility. Cancer Epidemiol Biomarkers Prev 18(9):2468-2475.

The invention claimed is:

1. An in vivo method of protecting neurons against NMDA receptor mediated excitotoxicity, or against PAR mediated cell death (parthanatos), the method comprising increasing expression of Iduna in the neurons by intrastriatal injection of a viral vector encoding Iduna to lead to increased expression of Iduna in the neurons, wherein said increased levels confer protection to the neurons against NMDA receptor mediated excitotoxicity or against PAR mediated cell death (parthanatos).

* * * * *

```
                          SEQUENCE LISTING

<160> NUMBER OF SEQ ID NOS: 32

<210> SEQ ID NO 1
<211> LENGTH: 21
<212> TYPE: DNA
<213> ORGANISM: Homo sapiens

<400> SEQUENCE: 1
cctgtgagat gtttgatatt a                                         21

<210> SEQ ID NO 2
<211> LENGTH: 21
<212> TYPE: DNA
<213> ORGANISM: Homo sapiens

<400> SEQUENCE: 2
cctgttctaa tactgcacct t                                         21

<210> SEQ ID NO 3
<211> LENGTH: 23
<212> TYPE: RNA
<213> ORGANISM: Homo sapiens

<400> SEQUENCE: 3
cauuuuggga guugggugg gaa                                        23

<210> SEQ ID NO 4
<211> LENGTH: 18
<212> TYPE: RNA
<213> ORGANISM: Homo sapiens

<400> SEQUENCE: 4
accaccgucu ccacccua                                             18

<210> SEQ ID NO 5
<211> LENGTH: 31
<212> TYPE: DNA
<213> ORGANISM: Artificial Sequence
<220> FEATURE:
<223> OTHER INFORMATION: Synthesized
<220> FEATURE:
<223> OTHER INFORMATION: C60A Forward

<400> SEQUENCE: 5
gttttctgtt atctggctgt aaagggtgct t                              31

<210> SEQ ID NO 6
<211> LENGTH: 31
<212> TYPE: DNA
<213> ORGANISM: Artificial Sequence
<220> FEATURE:
<223> OTHER INFORMATION: Synthesized
<220> FEATURE:
<223> OTHER INFORMATION: C60A Reverse

<400> SEQUENCE: 6
aagcaccctt tacagccaga taacagaaaa c                              31

<210> SEQ ID NO 7
<211> LENGTH: 33
<212> TYPE: DNA
```

```
<213> ORGANISM: Artificial Sequence
<220> FEATURE:
<223> OTHER INFORMATION: Synthesized
<220> FEATURE:
<223> OTHER INFORMATION: H54A Reverse

<400> SEQUENCE: 7
agtctgccct gtaaggctgt tttctgttat ctg                              33

<210> SEQ ID NO 8
<211> LENGTH: 33
<212> TYPE: DNA
<213> ORGANISM: Artificial Sequence
<220> FEATURE:
<223> OTHER INFORMATION: Synthesized
<220> FEATURE:
<223> OTHER INFORMATION: H54A Reverse

<400> SEQUENCE: 8
cagataacag aaaacagcct tacagggcag act                              33

<210> SEQ ID NO 9
<211> LENGTH: 58
<212> TYPE: DNA
<213> ORGANISM: Homo sapiens

<400> SEQUENCE: 9
ccggcctgtg agatgtttga tattactcga gtaatatcaa acatctcaca ggttttttg   58

<210> SEQ ID NO 10
<211> LENGTH: 58
<212> TYPE: DNA
<213> ORGANISM: Homo sapiens

<400> SEQUENCE: 10
ccgggcagga agattaagcg agatactcga gtatctcgct taatcttcct gcttttttg   58

<210> SEQ ID NO 11
<211> LENGTH: 58
<212> TYPE: DNA
<213> ORGANISM: Homo sapiens

<400> SEQUENCE: 11
ccggcctgtt ctaatactgc accttctcga gaaggtgcag tattagaaca ggttttttg   58

<210> SEQ ID NO 12
<211> LENGTH: 58
<212> TYPE: DNA
<213> ORGANISM: Homo sapiens

<400> SEQUENCE: 12
ccgggccagt agtgatagtg aggatctcga gatcctcact atcactactg gcttttttg   58

<210> SEQ ID NO 13
<211> LENGTH: 58
<212> TYPE: DNA
<213> ORGANISM: Homo sapiens

<400> SEQUENCE: 13
ccgggctcat ttacaactca gtggactcga gtccactgag ttgtaaatga gcttttttg   58

<210> SEQ ID NO 14
<211> LENGTH: 22
<212> TYPE: PRT
<213> ORGANISM: Artificial Sequence
```

```
<220> FEATURE:
<223> OTHER INFORMATION: Synthesized
<220> FEATURE:
<223> OTHER INFORMATION: amino acids 298 - 317 of Iduna

<400> SEQUENCE: 14

Gly Cys Asp Ala Pro Val Val Val Ala Gln His Ser Leu Thr Gln Gln
1               5                   10                  15

Arg Pro Leu Val Pro Asn
            20

<210> SEQ ID NO 15
<211> LENGTH: 23
<212> TYPE: DNA
<213> ORGANISM: Artificial Sequence
<220> FEATURE:
<223> OTHER INFORMATION: Synthesized
<220> FEATURE:
<223> OTHER INFORMATION: Iduna primer: sense

<400> SEQUENCE: 15
tgggtggtgg cagtatgatg agc                                        23

<210> SEQ ID NO 16
<211> LENGTH: 25
<212> TYPE: DNA
<213> ORGANISM: Artificial Sequence
<220> FEATURE:
<223> OTHER INFORMATION: Synthesized
<220> FEATURE:
<223> OTHER INFORMATION: Iduna primer: antisense

<400> SEQUENCE: 16
cttcacctct gtgactccgt tcagc                                      25

<210> SEQ ID NO 17
<211> LENGTH: 21
<212> TYPE: DNA
<213> ORGANISM: Artificial Sequence
<220> FEATURE:
<223> OTHER INFORMATION: Synthesized
<220> FEATURE:
<223> OTHER INFORMATION: Actin primer: sense

<400> SEQUENCE: 17
gctcgtcgtc gacaacggct c                                          21

<210> SEQ ID NO 18
<211> LENGTH: 25
<212> TYPE: DNA
<213> ORGANISM: Artificial Sequence
<220> FEATURE:
<223> OTHER INFORMATION: Synthesized
<220> FEATURE:
<223> OTHER INFORMATION: Actin primer: antisense

<400> SEQUENCE: 18
caaacatgat ctgggtcatc ttctc                                      25

<210> SEQ ID NO 19
<211> LENGTH: 21
<212> TYPE: DNA
<213> ORGANISM: Artificial Sequence
<220> FEATURE:
<223> OTHER INFORMATION: Synthesized
<220> FEATURE:
<223> OTHER INFORMATION: Primer
```

-continued

<400> SEQUENCE: 19
aaagtcgctc tgagttgtta t					21

<210> SEQ ID NO 20
<211> LENGTH: 21
<212> TYPE: DNA
<213> ORGANISM: Artificial Sequence
<220> FEATURE:
<223> OTHER INFORMATION: Synthesized
<220> FEATURE:
<223> OTHER INFORMATION: Primer

<400> SEQUENCE: 20
gcgaagagtt tgtcctcaac c					21

<210> SEQ ID NO 21
<211> LENGTH: 21
<212> TYPE: DNA
<213> ORGANISM: Artificial Sequence
<220> FEATURE:
<223> OTHER INFORMATION: Synthesized
<220> FEATURE:
<223> OTHER INFORMATION: Primer

<400> SEQUENCE: 21
ggagcgggag aaatggatat g					21

<210> SEQ ID NO 22
<211> LENGTH: 20
<212> TYPE: DNA
<213> ORGANISM: Artificial Sequence
<220> FEATURE:
<223> OTHER INFORMATION: Synthesized
<220> FEATURE:
<223> OTHER INFORMATION: CreA primer

<400> SEQUENCE: 22
cccggcaaaa caggtagtta					20

<210> SEQ ID NO 23
<211> LENGTH: 20
<212> TYPE: DNA
<213> ORGANISM: Artificial Sequence
<220> FEATURE:
<223> OTHER INFORMATION: Synthesized
<220> FEATURE:
<223> OTHER INFORMATION: CreS primer

<400> SEQUENCE: 23
catttgggcc agctaaacat					20

<210> SEQ ID NO 24
<211> LENGTH: 359
<212> TYPE: PRT
<213> ORGANISM: Mus musculus

<400> SEQUENCE: 24

Met Glu Met Ala Gly Cys Gly Glu Ile Asp His Ser Ile Asn Met Leu
1               5                   10                  15

Pro Thr Asn Lys Lys Ala Asn Glu Ser Cys Ser Asn Thr Ala Pro Ser
            20                  25                  30

Leu Thr Val Pro Glu Cys Ala Ile Cys Leu Gln Thr Cys Val His Pro
        35                  40                  45

Val Ser Leu Pro Cys Lys His Val Phe Cys Tyr Leu Cys Val Lys Gly
    50                  55                  60

```
Ala Ser Trp Leu Gly Lys Arg Cys Ala Leu Cys Arg Gln Glu Ile Pro
 65                  70                  75                  80

Glu Asp Phe Leu Asp Lys Pro Thr Leu Leu Ser Pro Glu Glu Leu Lys
                 85                  90                  95

Ala Ala Ser Arg Gly Asn Gly Glu Tyr Ala Trp Tyr Tyr Glu Gly Arg
            100                 105                 110

Asn Gly Trp Trp Gln Tyr Asp Glu Arg Thr Ser Arg Glu Leu Glu Asp
        115                 120                 125

Ala Phe Ser Lys Gly Lys Lys Asn Thr Glu Met Leu Ile Ala Gly Phe
130                 135                 140

Leu Tyr Val Ala Asp Leu Glu Asn Met Val Gln Tyr Arg Arg Asn Glu
145                 150                 155                 160

His Gly Arg Arg Arg Lys Ile Lys Arg Asp Ile Ile Asp Ile Pro Lys
                165                 170                 175

Lys Gly Val Ala Gly Leu Arg Leu Asp Cys Asp Thr Asn Thr Val Asn
            180                 185                 190

Leu Ala Arg Glu Ser Ser Ala Asp Gly Ala Asp Ser Gly Ser Ala Gln
        195                 200                 205

Thr Gly Ala Ser Val Gln Leu Ala Val Pro Ser Thr Arg Pro Leu
210                 215                 220

Thr Ser Val Asp Gly Gln Leu Thr Ser Pro Val Thr Pro Ser Pro Asp
225                 230                 235                 240

Ala Gly Ile Ser Leu Glu Asp Ser Phe Ala His Leu Gln Leu Ser Gly
                245                 250                 255

Asp Ser Ile Ala Glu Arg Ser His Arg Gly Glu Gly Glu Glu Asp His
            260                 265                 270

Glu Ser Pro Ser Ser Gly Arg Val Pro Asp Thr Ser Val Glu Glu Thr
        275                 280                 285

Glu Ser Asp Ala Ser Ser Asp Ser Glu Asp Ala Pro Val Val Val Ala
290                 295                 300

Gln His Ser Leu Thr Gln Gln Arg Pro Leu Val Pro Asn Gly Asn Gln
305                 310                 315                 320

Thr Val Ala Asp Gln Ser Asp Arg Ser Gly Thr Asp Arg Ser Val Ala
                325                 330                 335

Gly Gly Gly Thr Met Ser Val Asn Val Arg Ser Arg Arg Pro Asp Gly
            340                 345                 350

Gln Cys Thr Val Ile Glu Val
        355

<210> SEQ ID NO 25
<211> LENGTH: 352
<212> TYPE: PRT
<213> ORGANISM: Rattus norvegicus

<400> SEQUENCE: 25

Met Ala Gly Cys Gly Glu Ile Asp His Ser Leu Asn Met Leu Pro Thr
 1               5                  10                  15

Asn Lys Lys Ala Ser Glu Thr Cys Ser Asn Thr Ala Pro Ser Leu Thr
             20                  25                  30

Val Pro Glu Cys Ala Ile Cys Leu Gln Thr Cys Val His Pro Val Ser
         35                  40                  45

Leu Pro Cys Lys His Val Phe Cys Tyr Leu Cys Val Lys Gly Ala Ser
     50                  55                  60

Trp Leu Gly Lys Arg Cys Ala Leu Cys Arg Gln Glu Ile Pro Glu Asp
```

```
                65                  70                  75                  80
        Phe Leu Asp Lys Pro Thr Leu Leu Ser Pro Glu Glu Leu Lys Ala Ala
                        85                  90                  95

Ser Arg Gly Asn Gly Glu Tyr Val Trp Tyr Tyr Glu Gly Arg Asn Gly
                        100                 105                 110

Trp Trp Gln Tyr Asp Glu Arg Thr Ser Arg Glu Leu Glu Asp Ala Phe
                        115                 120                 125

Ser Lys Gly Lys Lys Asn Thr Glu Met Leu Ile Ala Gly Phe Leu Tyr
                        130                 135                 140

Val Ala Asp Leu Glu Asn Met Val Gln Tyr Arg Arg Asn Glu His Gly
        145                 150                 155                 160

Arg Arg Arg Lys Ile Lys Arg Asp Ile Ile Asp Pro Lys Lys Gly
                        165                 170                 175

Val Ala Gly Leu Arg Leu Asp Cys Asp Ser Asn Thr Val Asn Leu Ala
                        180                 185                 190

Arg Glu Ser Ser Ala Asp Gly Ala Asp Ser Gly Ser Ala His Thr Gly
                        195                 200                 205

Ala Ser Val Gln Leu Pro Val Pro Ser Ser Thr Arg Pro Leu Thr Ser
        210                 215                 220

Val Asp Gly Gln Leu Thr Ser Pro Val Thr Pro Ser Pro Asp Ala Gly
        225                 230                 235                 240

Ala Ser Leu Glu Asp Ser Phe Ala His Leu Gln Leu Ser Gly Asp Ser
                        245                 250                 255

Ile Ala Glu Arg Ser His Arg Gly Glu Gly Glu Glu Asp His Glu Ser
                        260                 265                 270

Pro Ser Ser Gly Arg Val Pro Asp Thr Ser Thr Glu Glu Thr Glu Ser
                        275                 280                 285

Asp Ala Ser Ser Asp Ile Glu Asp Ala Pro Val Val Val Ala Gln His
                        290                 295                 300

Ser Leu Thr Gln Gln Arg Leu Leu Val Ser Ser Ala Asn Gln Thr Val
        305                 310                 315                 320

Ala Glu Arg Ser Asp Arg Ser Val Ala Gly Gly Thr Met Ser Val
                        325                 330                 335

Asn Val Arg Ser Arg Arg Pro Asp Gly Gln Cys Thr Val Ile Glu Val
                        340                 345                 350

<210> SEQ ID NO 26
<211> LENGTH: 358
<212> TYPE: PRT
<213> ORGANISM: Homo sapiens

<400> SEQUENCE: 26

Met Ala Gly Cys Gly Glu Ile Asp His Ser Ile Asn Met Leu Pro Thr
        1               5                   10                  15

Asn Lys Lys Ala Asn Glu Ser Cys Ser Asn Thr Ala Pro Ser Leu Thr
                        20                  25                  30

Val Pro Glu Cys Ala Ile Cys Leu Gln Thr Cys Val His Pro Val Ser
                        35                  40                  45

Leu Pro Cys Lys His Val Phe Cys Tyr Leu Cys Val Lys Gly Ala Ser
                        50                  55                  60

Trp Leu Gly Lys Arg Cys Ala Leu Cys Arg Gln Glu Ile Pro Glu Asp
        65                  70                  75                  80

Phe Leu Asp Lys Pro Thr Leu Leu Ser Pro Glu Glu Leu Lys Ala Ala
                        85                  90                  95
```

-continued

```
Ser Arg Glu Asn Gly Glu Tyr Ala Trp Tyr Glu Gly Arg Asn Gly
            100                 105                 110

Trp Trp Gln Tyr Asp Glu Arg Thr Ser Arg Glu Leu Asp Ala Phe
        115                 120                 125

Ser Lys Gly Lys Lys Asn Thr Glu Met Leu Ile Ala Gly Phe Leu Tyr
    130                 135                 140

Val Ala Asp Leu Glu Asn Met Val Gln Tyr Arg Arg Asn Glu His Gly
145                 150                 155                 160

Arg Arg Arg Lys Val Lys Arg Asp Ile Ile Asp Ile Pro Lys Lys Gly
                165                 170                 175

Val Ala Gly Leu Arg Leu Asp Cys Asp Ala Asn Thr Val Asn Leu Ala
            180                 185                 190

Arg Glu Ser Ser Ala Asp Gly Ala Asp Ser Val Ser Ala Gln Ser Gly
        195                 200                 205

Ala Ser Val Gln Pro Leu Val Ser Ser Val Arg Pro Leu Thr Ser Val
    210                 215                 220

Asp Gly Gln Leu Thr Ser Pro Ala Thr Pro Ser Pro Asp Ala Ser Thr
225                 230                 235                 240

Ser Leu Glu Asp Ser Phe Ala His Leu Gln Leu Ser Gly Asp Asn Thr
                245                 250                 255

Ala Glu Arg Ser His Arg Gly Glu Gly Glu Asp His Glu Ser Pro
            260                 265                 270

Ser Ser Gly Arg Val Pro Ala Pro Asp Thr Ser Ile Glu Glu Thr Glu
        275                 280                 285

Ser Asp Ala Ser Ser Asp Ser Glu Asp Val Ser Ala Val Val Ala Gln
    290                 295                 300

His Ser Leu Thr Gln Gln Arg Leu Leu Val Ser Asn Ala Asn Gln Thr
305                 310                 315                 320

Val Pro Asp Arg Ser Asp Arg Ser Gly Thr Asp Arg Ser Val Ala Gly
                325                 330                 335

Gly Gly Thr Val Ser Val Ser Val Arg Ser Arg Arg Pro Asp Gly Gln
            340                 345                 350

Cys Thr Val Ile Glu Val
            355

<210> SEQ ID NO 27
<211> LENGTH: 364
<212> TYPE: PRT
<213> ORGANISM: Danio rerio

<400> SEQUENCE: 27

Met Ala Ser Cys Gly Glu Val Asn Leu Thr Val Asp Ser Leu Thr Ser
1               5                   10                  15

Gly Lys Lys Val Ser Gly Glu Ala Val Pro Glu Gly Ser Gly Ser Pro
            20                  25                  30

Ser Ser Pro Ser Leu Pro Val Pro Glu Cys Pro Ile Cys Leu Gln Ser
        35                  40                  45

Cys Val His Pro Val Arg Leu Pro Cys Arg His Ile Phe Cys Phe Leu
    50                  55                  60

Cys Val Lys Gly Ala Ser Trp His Ser Lys Arg Cys Ala Leu Cys Arg
65                  70                  75                  80

Arg Glu Val Pro Glu Asp Phe Leu Glu Arg Pro Thr Leu Leu Ser Pro
                85                  90                  95

Glu Glu Leu Lys Ala Ser Ala Thr Gly Gly Cys Gly Thr Gly Ser Ser
            100                 105                 110
```

Gly His Ala Trp Tyr Tyr Glu Gly Arg Asn Gly Trp Trp Gln Tyr Asp
            115                 120                 125

Glu Arg Thr Ser Arg Glu Leu Glu Asp Ala Phe Ser Lys Gly Lys Lys
        130                 135                 140

Ser Ala Glu Met Leu Ile Ala Gly Phe Leu Tyr Val Ala Asp Leu Glu
145                 150                 155                 160

Asn Met Val Gln Tyr Arg Arg Asn Glu His Gly Arg Arg Arg Arg Met
                165                 170                 175

Lys Arg Asp Val Val Asp Ile Pro Lys Lys Gly Val Ala Gly Leu Arg
                180                 185                 190

Leu Asp Pro Asp Pro Asn Ser Ser Ala Gly Ala Val Pro Ala Pro Ala
            195                 200                 205

Val Val Asp Val Ser Val Asp Gly Ala Ala Glu Arg Glu Ser Ser
            210                 215                 220

Ala Asp Gly Ala Asp Thr Gly Val Ser Gly Gly Arg Pro Gln Gly Thr
225                 230                 235                 240

Phe Val Pro Ala Pro Ile Arg Pro Thr Ile Leu Gly Gly His Leu
                245                 250                 255

Thr Ser Pro Ala Ser Ser Ser Asp Ile Gln Leu Val Gln Thr Leu Ala
            260                 265                 270

Gln Leu Asn Ile Ser Pro Asn Glu Gln Glu Pro Glu Glu Glu Asp Ala
        275                 280                 285

Glu Asp Glu Asp Asp Ser Ala Ala Pro Asp Ala Ser Gly Tyr Asp Ser
        290                 295                 300

Glu Ser Gly Thr Ser Asp Asp Glu Gln Val Glu Asp Glu Asp Glu
305                 310                 315                 320

Asn Glu His Thr Asp Gly Ser Gln Gly Lys His Arg Leu Gln Gln Leu
                325                 330                 335

Asn Arg Pro Pro Pro Gly Gly Gly Pro Ala Asn Ser Gly Asp Arg Ser
            340                 345                 350

Gly Cys Pro Asp Gly Gln Cys Thr Val Thr Lys Val
        355                 360

<210> SEQ ID NO 28
<211> LENGTH: 214
<212> TYPE: PRT
<213> ORGANISM: Caenorhabditis elegans
<220> FEATURE:
<221> NAME/KEY: misc_feature
<222> LOCATION: (10)..(10)
<223> OTHER INFORMATION: Xaa is Pyrrolysine
<220> FEATURE:
<221> NAME/KEY: misc_feature
<222> LOCATION: (11)..(11)
<223> OTHER INFORMATION: Xaa is Pyrrolysine
<220> FEATURE:
<221> NAME/KEY: misc_feature
<222> LOCATION: (13)..(13)
<223> OTHER INFORMATION: Xaa is Pyrrolysine
<220> FEATURE:
<221> NAME/KEY: misc_feature
<222> LOCATION: (14)..(14)
<223> OTHER INFORMATION: Xaa is Pyrrolysine

<400> SEQUENCE: 28

Met Asn Ala Ser Thr Ser Ser Pro Ser Xaa Xaa Leu Xaa Xaa Ala Ile
1               5                   10                  15

Asn Ser Thr Ile Asp Lys Glu Cys Ala Val Cys Tyr Ser Glu Met Ile
            20                  25                  30

```
Leu Pro Thr Thr Ile Pro Ser Cys Gly His Lys Phe Cys Phe Ile Cys
             35                  40                  45

Leu Lys Gly Val Ser Val Ser Asn Asn Gly Asp Cys Pro Ile Cys Arg
 50                  55                  60

Gly Pro Ile Asp Ser Gln Ile Phe Lys Lys Pro Leu Gln Ala Val Asp
 65                  70                  75                  80

Leu Lys Met Asp Ile Pro Gly Thr Pro Ser Ala Ala Ala Pro Asp Pro
                     85                  90                  95

Val Val Lys Gln Glu Val Asp Asp Glu Asp Val Lys Pro Asp Val Lys
                100                 105                 110

Lys Leu Gln Glu Glu Leu Lys Lys Gln Gln Ala Ala Ala Ala Ala Gln
                115                 120                 125

Lys Met Phe Trp Leu Tyr Arg Gly Arg His Gln Gly Trp Trp Arg Phe
            130                 135                 140

Asp Pro Arg Ile Glu Lys Glu Ile Glu Glu Ala Phe Thr His Gln Met
145                 150                 155                 160

Pro Met Thr Glu Val Thr Ile Cys Gly Asn Pro Tyr Ile Val Asp Phe
                165                 170                 175

Ser Gln Met Cys Gln Tyr Pro Lys Asn Gln Ser Asn Tyr Ser Arg Asn
            180                 185                 190

Val Lys Tyr Gly Ser Arg Leu Lys Val Leu Lys Ile Leu Ala Lys Ile
            195                 200                 205

Asp Arg Lys Ser Ala Phe
            210

<210> SEQ ID NO 29
<211> LENGTH: 17
<212> TYPE: PRT
<213> ORGANISM: Homo sapiens

<400> SEQUENCE: 29

Lys Ser Thr Glu Leu Leu Ile Arg Lys Leu Pro Phe Gln Arg Leu Val
1               5                   10                  15

Arg

<210> SEQ ID NO 30
<211> LENGTH: 24
<212> TYPE: PRT
<213> ORGANISM: Homo sapiens

<400> SEQUENCE: 30

Phe Leu Tyr Val Ala Asp Leu Glu Asn Met Val Gln Tyr Arg Arg Asn
1               5                   10                  15

Glu His Gly Arg Arg Arg Lys Ile
            20

<210> SEQ ID NO 31
<211> LENGTH: 24
<212> TYPE: PRT
<213> ORGANISM: Homo sapiens

<400> SEQUENCE: 31

Phe Leu Tyr Val Ala Asp Leu Glu Asn Met Val Gln Ala Ala Arg Asn
1               5                   10                  15

Glu His Gly Arg Arg Arg Lys Ile
            20

<210> SEQ ID NO 32
```

```
<211> LENGTH: 13
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 32

Xaa His Xaa Asx Xaa His His Asx Asx His His Asx Xaa
 1               5                   10
```